US012758532B2

(12) United States Patent
Wang et al.

(10) Patent No.: US 12,758,532 B2
(45) Date of Patent: Oct. 13, 2026

(54) SUBSTITUTED HETEROARYL COMPOUNDS AND USE THEREOF

(71) Applicant: HELIOS HUAMING BIOPHARMA CO., LTD., Suzhou (CN)

(72) Inventors: Yanming Wang, Suzhou (CN); Yan Xia, Suzhou (CN); Jinquan Sun, Suzhou (CN); Mingde Xia, Suzhou (CN)

(73) Assignee: HELIOS HUAMING BIOPHARMA CO., LTD., Suzhou (CN)

( * ) Notice: Subject to any disclaimer, the term of this patent is extended or adjusted under 35 U.S.C. 154(b) by 630 days.

(21) Appl. No.: 18/248,750

(22) PCT Filed: Oct. 11, 2021

(86) PCT No.: PCT/CN2021/123088

§ 371 (c)(1),
(2) Date: Apr. 12, 2023

(87) PCT Pub. No.: WO2022/078294

PCT Pub. Date: Apr. 21, 2022

(65) Prior Publication Data

US 2023/0381146 A1 Nov. 30, 2023

(30) Foreign Application Priority Data

Oct. 12, 2020 (WO) ................ PCT/CN2020/120319

(51) Int. Cl.

| | |
|---|---|
| ***A61K 31/421*** | (2006.01) |
| ***A61K 31/417*** | (2006.01) |
| ***A61K 31/422*** | (2006.01) |
| ***A61K 31/4245*** | (2006.01) |
| ***A61K 31/4439*** | (2006.01) |
| ***A61K 31/496*** | (2006.01) |
| ***A61K 31/5377*** | (2006.01) |
| ***A61K 39/395*** | (2006.01) |
| ***C07D 233/64*** | (2006.01) |
| ***C07D 263/32*** | (2006.01) |
| ***C07D 271/06*** | (2006.01) |
| ***C07D 271/10*** | (2006.01) |
| ***C07D 413/12*** | (2006.01) |
| ***C07D 495/04*** | (2006.01) |

(52) U.S. Cl.

CPC .......... *A61K 31/421* (2013.01); *A61K 31/417* (2013.01); *A61K 31/422* (2013.01); *A61K 31/4245* (2013.01); *A61K 31/4439* (2013.01); *A61K 31/496* (2013.01); *A61K 31/5377* (2013.01); *A61K 39/3955* (2013.01); *C07D 233/64* (2013.01); *C07D 263/32* (2013.01); *C07D 271/06* (2013.01); *C07D 271/10* (2013.01); *C07D 413/12* (2013.01); *C07D 495/04* (2013.01)

(58) Field of Classification Search

CPC .. C07D 233/64; C07D 263/32; C07D 271/10; A61K 31/421; A61K 31/417; A61K 31/496; A61K 31/5539

See application file for complete search history.

(56) References Cited

FOREIGN PATENT DOCUMENTS

| | | | |
|---|---|---|---|
| CN | 103189063 | A | 7/2013 |
| CN | 108391432 | A | 8/2018 |
| WO | 2015116896 | A1 | 8/2015 |
| WO | 2017007405 | A1 | 1/2017 |
| WO | 2018102262 | A1 | 6/2018 |

OTHER PUBLICATIONS

International Search Report and Written Opinion for PCT/CN2021/123088 dated Jan. 13, 2022.

Muth et al. "Development of a Selective Inhibitor of Protein Arginine Deiminase 2" Mar. 22, 2017, J. Med. Chem., vol. 60(7), pp. 3198-3211.

Subramanian et al. "Design, Synthesis and Biological Evaluation of Tetrazole Analogs of CI-Amidine as Protein Arginine Deiminase Inhibitors" Jan. 5, 2015, J. Med. Chem., vol. 58(3), pp. 1337-1344.

Extended European Search Report for European Patent Application No. 21879338.8 issued Sep. 11, 2024, 11 pages.

Hamada et al., "The application of bioisosteres in drug design for novel drug discovery: focusing on acid protease inhibitors", Expert Opinion on Drug Discovery, vol. 7, No. 10, Aug. 8, 2012 (Aug. 8, 2012), pp. 903-922, XP093199627, London, GB ISSN: 1746-0441, DOI: 10.1517/17460441.2012.712513.

Subramanian et al., "Design, Synthesis, and Biological Evaluation of Tetrazole Analogs of CI-Amidine as Protein Arginine Deiminase Inhibitors", Journal of Medicinal Chemistry, vol. 58, No. 3, Feb. 12, 2015 (Feb. 12, 2015), pp. 1337-1344 XP055922617, US ISSN: 0022-2623, DOI:10.1021/jm501636x.

Chinese Office Action for Application No. 202180069931.5 dated Feb. 27, 2025, pp. 1-12.

*Primary Examiner* — Kamal A Saeed

(74) *Attorney, Agent, or Firm* — DLA Piper LLP (US)

(57) ABSTRACT

The present disclosure provides substituted heteroaryl compounds and use thereof, also provides compounds or pharmaceutically acceptable salts or solvates thereof as PAD inhibitors and their use in treatment of a disease or disorder.

29 Claims, No Drawings

SUBSTITUTED HETEROARYL COMPOUNDS AND USE THEREOF

CROSS-REFERENCE TO RELATED APPLICATIONS

This application is a National Stage entry of International Application No. PCT/CN2021/123088 filed Oct. 11, 2021, which claims the benefit of International Application No. PCT/CN2020/120319 filed Oct. 12, 2020, each of which are hereby incorporated by reference in its entirety.

BACKGROUND OF THE INVENTION

Peptidylarginine deiminase (PAD) citrullinates arginine (Arg) and mono-methyl Arg residues in substrate proteins such as transcription factors and histones. PAD affects diseases via its role in cancer, immune responses and other cellular events. There is a continuing need for PAD inhibitors in the treatment of diseases.

SUMMARY OF THE INVENTION

The present disclosure provides a compound or a pharmaceutically acceptable salt or solvate thereof and use thereof, which is used as a PAD inhibitor. The compound, pharmaceutically acceptable salt or solvate thereof is used for treating a disease or disorder. The compound or the present disclosure reveals effect in PAD4 inhibition.

The present disclosure provides a compound of formula (I):

(I)

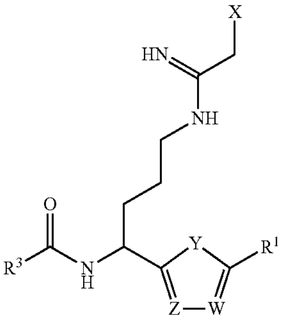

wherein, X is halogen; W is N, C—$R^2$; each Y and Z is independently selected from N, NH, O and S; $R^3$ is selected from ($C_6$-$C_{10}$) aryl, and ($C_1$-$C_9$) heteroaryl; each $R^1$ and $R^2$ is independently selected from H, ($C_1$-$C_8$) alkyl, ($C_3$-$C_{10}$) cycloalkyl, ($C_6$-$C_{10}$) aryl, and ($C_1$-$C_9$) heteroaryl, provided that $R^1$ and $R^2$ are not both H, and that $R^1$ and $R^2$ are not bonded to one another by one or more chemical bonds; when $R^1$ is ($C_3$-$C_{10}$) cycloalkyl or ($C_6$-$C_{10}$) aryl, said $R^1$ is unsubstituted or substituted with one or more substituents $R^4$, said $R^4$ is independently selected from H, halogen, ($C_1$-$C_8$) alkyl, ($C_1$-$C_8$) haloalkyl, ($C_1$-$C_8$) alkoxy, ($C_1$-$C_8$) alkylamino, and the groups (Sub A)

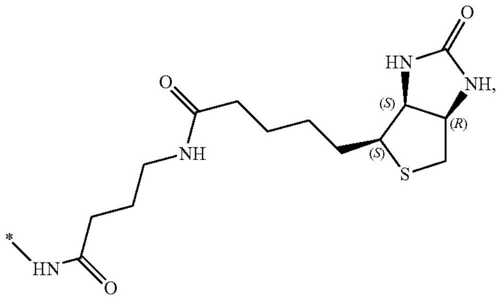

(Sub B)

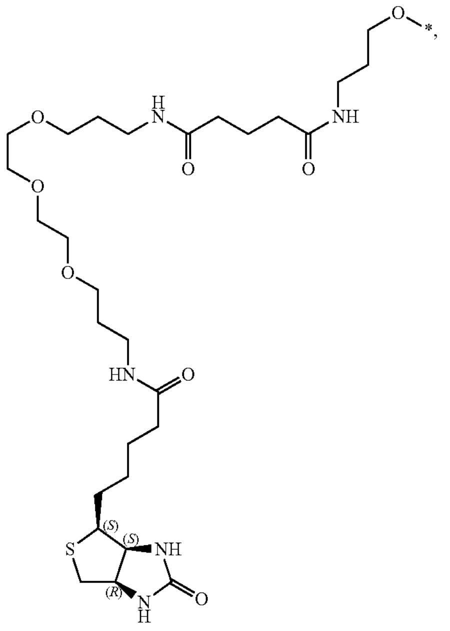

wherein, the asterisk "*" in the structure formulas indicates the available radical ends to be connected; when $R^3$ is ($C_6$-$C_{10}$) aryl or ($C_1$-$C_9$) heteroaryl, said $R^3$ is unsubstituted or substituted with one or more substituents $R^5$, said $R^5$ is independently selected from H, halogen, ($C_1$-$C_8$) alkyl, ($C_2$-$C_8$) alkenyl, ($C_2$-$C_8$) alkynyl, ($C_1$-$C_8$) alkoxy, ($C_1$-$C_8$) haloalkyl, ($C_1$-$C_8$) alkylamino, ($C_2$-$C_9$) heterocycloalkyl, ($C_6$-$C_{10}$) aryl, ($C_1$-$C_9$) heteroaryl, Sub A and Sub B; when $R^5$ is ($C_2$-$C_9$) heterocycloalkyl, ($C_6$-$C_{10}$) aryl or ($C_1$-$C_9$) heteroaryl, said $R^5$ is unsubstituted or substituted with one or more substituents $R^6$, said $R^6$ is independently selected from H, halogen, ($C_1$-$C_8$) alkyl, ($C_1$-$C_8$) alkoxy, ($C_1$-$C_8$) hydroxyalkyl; or a pharmaceutically acceptable salt or solvate thereof.

In some embodiments, wherein said $R^1$ is a phenyl.

In some embodiments, wherein said $R^1$ is substituted with one or more substituents $R^4$, said $R^4$ is independently selected from H, halogen, ($C_1$-$C_8$) alkyl, ($C_1$-$C_8$) haloalkyl, ($C_1$-$C_8$) alkoxy, ($C_1$-$C_8$) alkylamino, Sub A and Sub B.

In some embodiments, wherein said $R^3$ is a ($C_6$-$C_{10}$) aryl, and said $R^3$ is substituted with one or more substituents $R^5$, said $R^5$ is independently selected from H, halogen, ($C_1$-$C_8$) alkyl, ($C_2$-$C_5$) alkenyl, ($C_2$-$C_8$) alkynyl, ($C_1$-$C_8$) alkoxy, ($C_1$-$C_8$) haloalkyl, ($C_1$-$C_8$) alkylamino, ($C_2$-$C_9$) heterocycloalkyl, ($C_6$-$C_{10}$) aryl, ($C_1$-$C_9$) heteroaryl, Sub A and Sub B.

In some embodiments, wherein said $R^3$ is a phenyl or naphthyl.

In some embodiments, wherein said $R^3$ is substituted with one or more substituents $R^5$, said $R^5$ is independently selected from H, halogen, ($C_1$-$C_8$) alkyl, ($C_2$-$C_8$) alkenyl, ($C_2$-$C_8$) alkynyl, ($C_1$-$C_8$) alkoxy, ($C_1$-$C_8$) haloalkyl, ($C_1$-$C_8$) alkylamino, ($C_2$-$C_9$) heterocycloalkyl, ($C_6$-$C_{10}$) aryl, ($C_1$-$C_9$) heteroaryl, Sub A and Sub B.

In some embodiments, wherein said X is Cl or F.

In one aspect, the present disclosure provides a compound of formula (II):

(II)

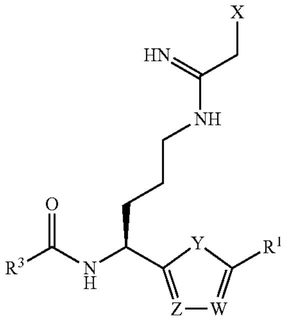

wherein, X is halogen; W is N, C—$R^2$; each Y and Z is independently selected from N, NH, O and S; $R^3$ is selected from ($C_6$-$C_{10}$) aryl, and ($C_1$-$C_9$) heteroaryl; each $R^1$ and $R^2$ is independently selected from H, ($C_1$-$C_8$) alkyl, ($C_3$-$C_{10}$) cycloalkyl, ($C_6$-$C_{10}$) aryl, and ($C_1$-$C_9$) heteroaryl, provided that $R^1$ and $R^2$ are not both H, and that $R^1$ and $R^2$ are not bonded to one another by one or more chemical bonds; when $R^1$ is ($C_3$-$C_{10}$) cycloalkyl or ($C_6$-$C_{10}$) aryl, said $R^1$ is unsubstituted or substituted with one or more substituents $R^4$, said $R^4$ is independently selected from H, halogen, ($C_1$-$C_8$) alkyl, ($C_1$-$C_8$) haloalkyl, ($C_1$-$C_8$) alkoxy, ($C_1$-$C_8$) alkylamino, and the groups (Sub A)

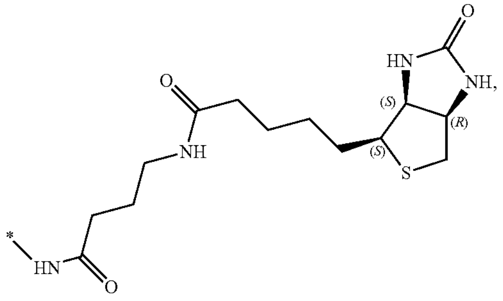

-continued (Sub B)

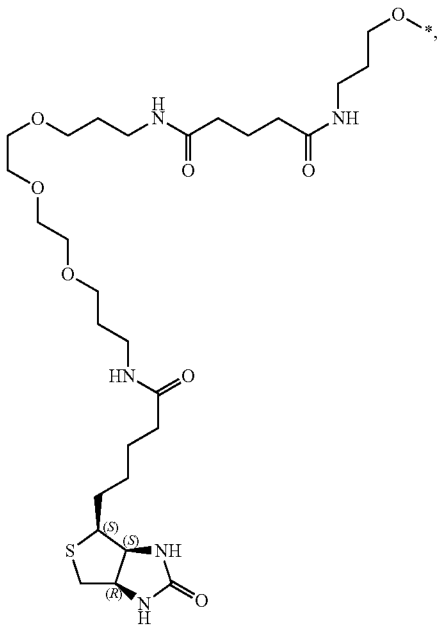

wherein, the asterisk "*" in the structure formulas indicates the available radical ends to be connected; when $R^3$ is ($C_6$-$C_{10}$) aryl or ($C_1$-$C_9$) heteroaryl, said $R^3$ is unsubstituted or substituted with one or more substituents $R^5$, said $R^5$ is independently selected from H, halogen, ($C_1$-$C_8$) alkyl, ($C_2$-$C_8$) alkenyl, ($C_2$-$C_8$) alkynyl, ($C_1$-$C_8$) alkoxy, ($C_1$-$C_8$) haloalkyl, ($C_1$-$C_8$) alkylamino, ($C_2$-$C_9$) heterocycloalkyl, ($C_6$-$C_{10}$) aryl, ($C_1$-$C_9$) heteroaryl, Sub A and Sub B; when $R^5$ is ($C_2$-$C_9$) heterocycloalkyl, ($C_6$-$C_{10}$) aryl or ($C_1$-$C_9$) heteroaryl, said $R^5$ is unsubstituted or substituted with one or more substituents $R^6$, said $R^6$ is independently selected from H, halogen, ($C_1$-$C_8$) alkyl, ($C_1$-$C_8$) alkoxy, ($C_1$-$C_8$) hydroxyalkyl; or a pharmaceutically acceptable salt or solvate thereof.

In some embodiments, wherein said $R^1$ is a phenyl.

In some embodiments, wherein said $R^1$ is substituted with one or more substituents $R^4$, said $R^4$ is independently selected from H, halogen, ($C_1$-$C_8$) alkyl, ($C_1$-$C_8$) haloalkyl, ($C_1$-$C_8$) alkoxy, ($C_1$-$C_8$) alkylamino, Sub A and Sub B.

In some embodiments, wherein said $R^3$ is a ($C_6$-$C_{10}$) aryl, and said $R^3$ is substituted with one or more substituents $R^5$, said $R^5$ is independently selected from H, halogen, ($C_1$-$C_8$) alkyl, ($C_2$-$C_8$) alkenyl, ($C_2$-$C_8$) alkynyl, ($C_1$-$C_8$) alkoxy, ($C_1$-$C_8$) haloalkyl, ($C_1$-$C_8$) alkylamino, ($C_2$-$C_9$) heterocycloalkyl, ($C_6$-$C_{10}$) aryl, ($C_1$-$C_9$) heteroaryl, Sub A and Sub B.

In some embodiments, wherein said $R^3$ is a phenyl or naphthyl.

In some embodiments, wherein said $R^3$ is substituted with one or more substituents $R^5$, said $R^5$ is independently selected from H, halogen, ($C_1$-$C_8$) alkyl, ($C_2$-$C_8$) alkenyl, ($C_2$-$C_8$) alkynyl, ($C_1$-$C_8$) alkoxy, ($C_1$-$C_8$) haloalkyl, ($C_1$-$C_8$) alkylamino, ($C_2$-$C_9$) heterocycloalkyl, ($C_6$-$C_{10}$) aryl, ($C_1$-$C_9$) heteroaryl, Sub A and Sub B.

In some embodiments, wherein said X is Cl or F.

In some embodiments, wherein said compound is selected from:

EX-1
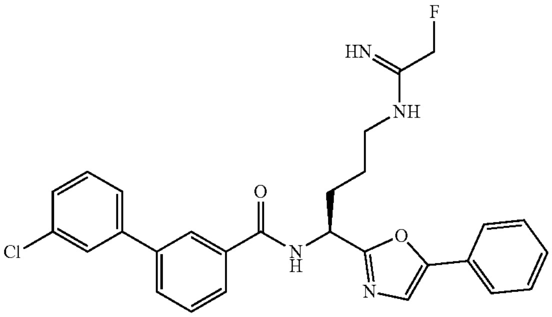
,
EX-2
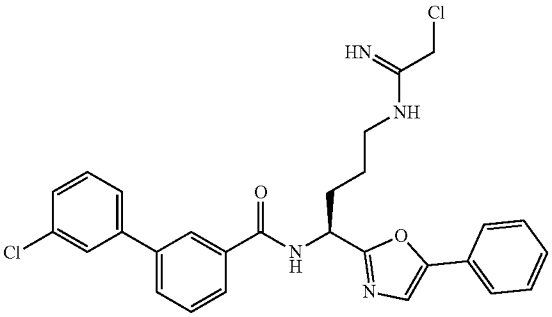
,
EX-3
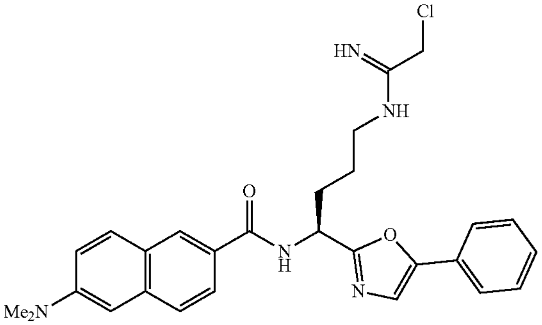
,
EX-4
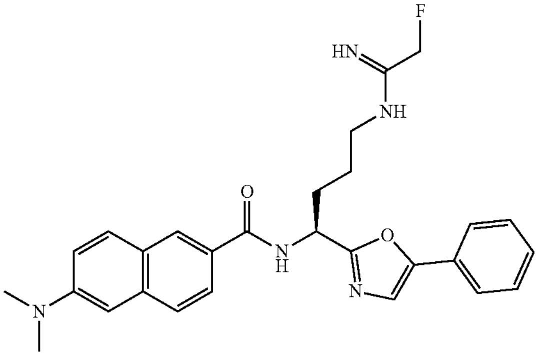
,
EX-5
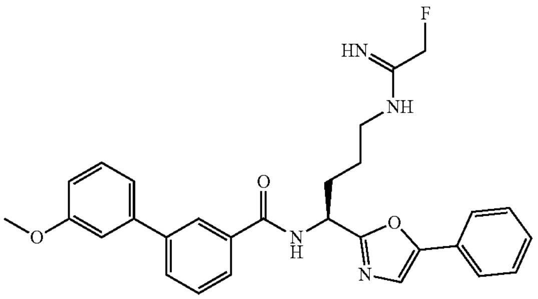
,
EX-6
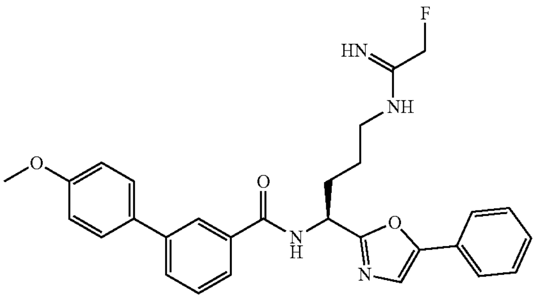
,
EX-7
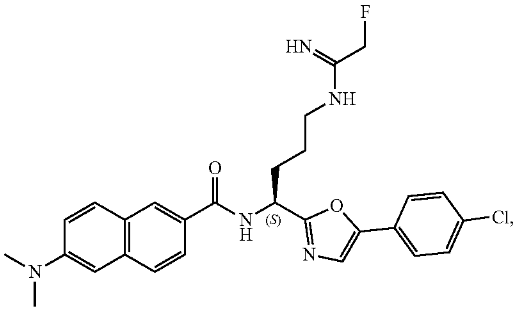
,
EX-8
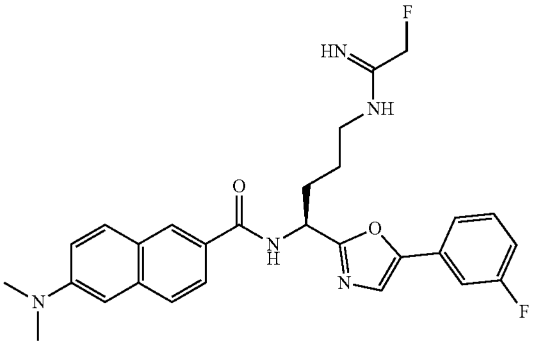
, -continued
EX-9
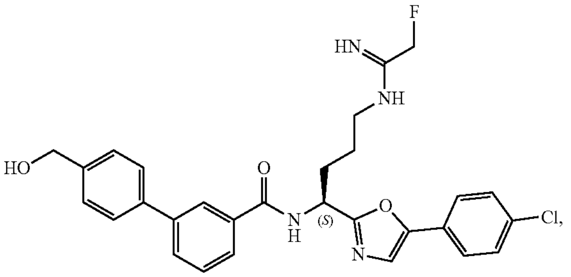
,
EX-10
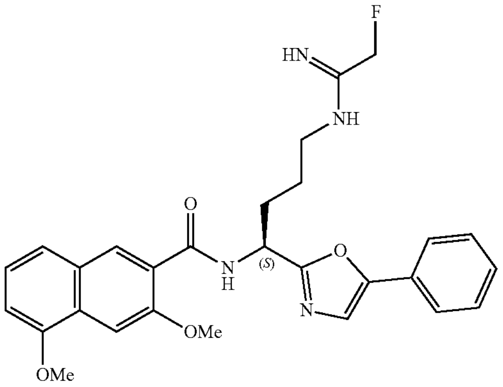
,
EX-11
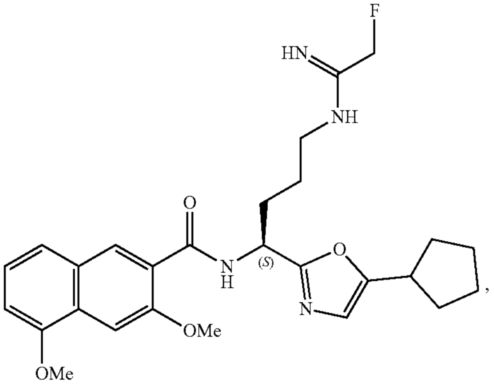
,
EX-12
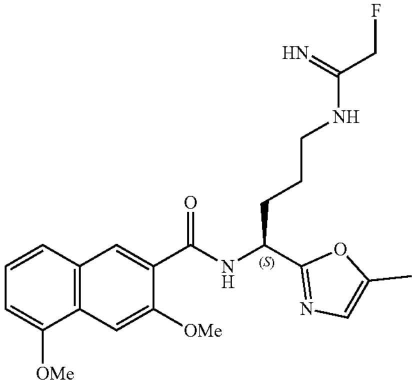
,
EX-13
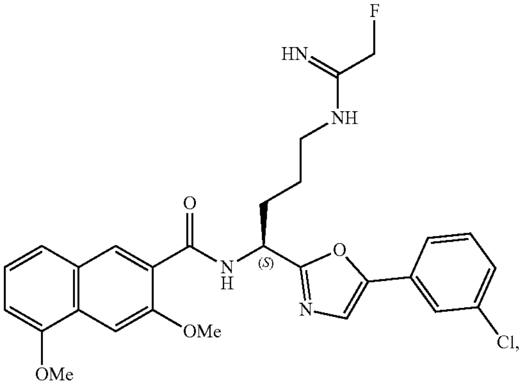
,
EX-14
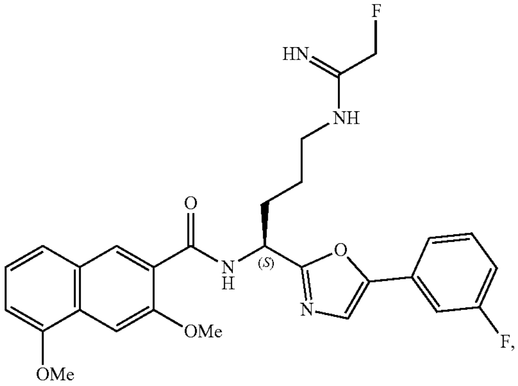
,
EX-15
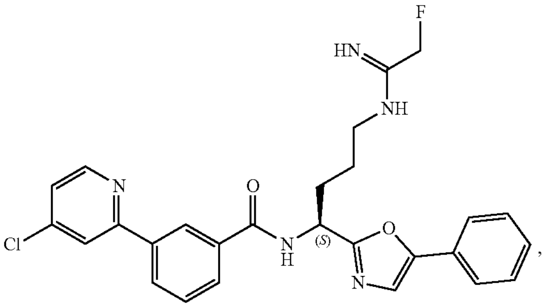
,
EX-16
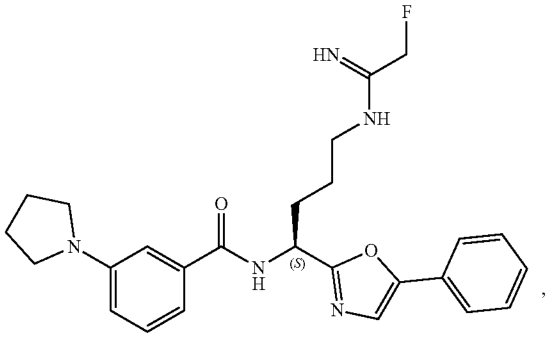
, -continued
EX-17
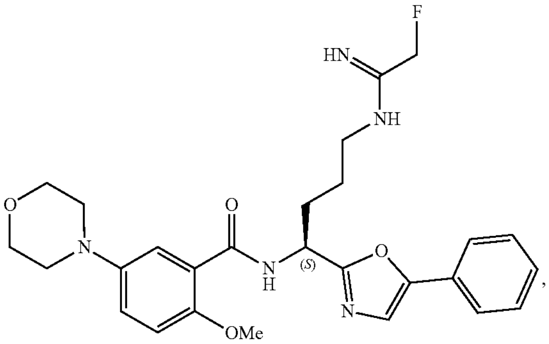
,
EX-18
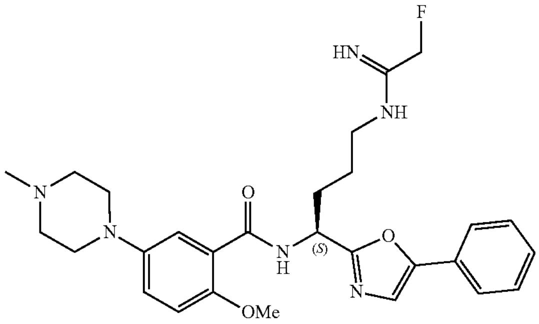
,
EX-19
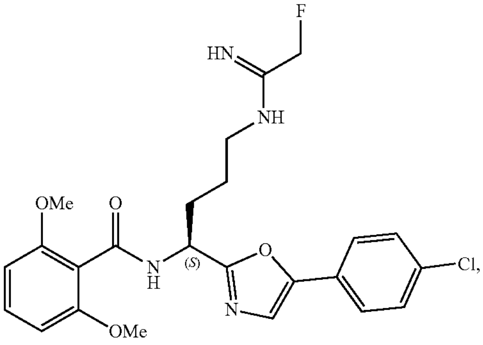
,
EX-20
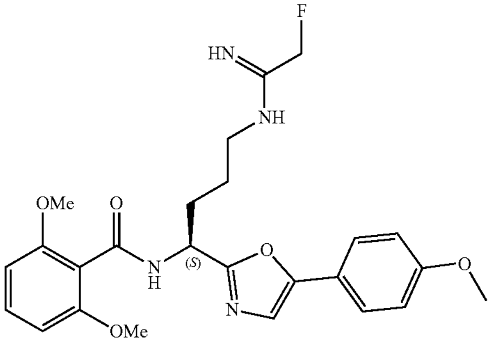
,
EX-21
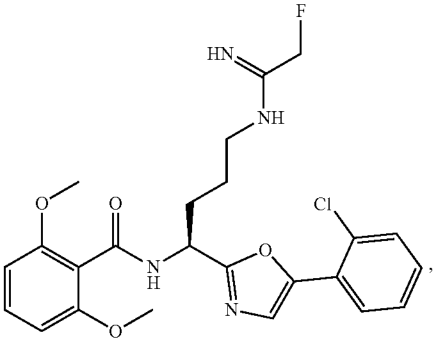
,
EX-22
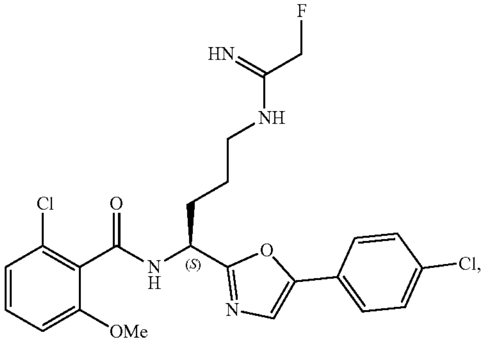
,
EX-23
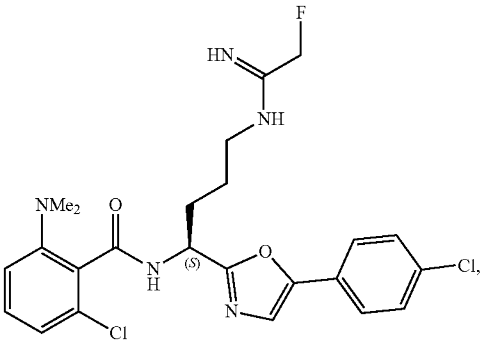
,
EX-24
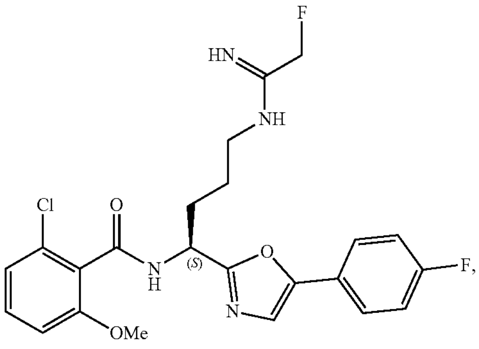
, -continued
EX-25
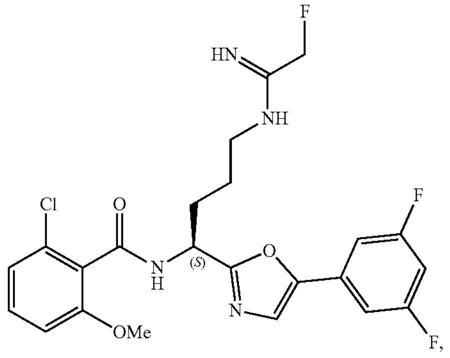
EX-26
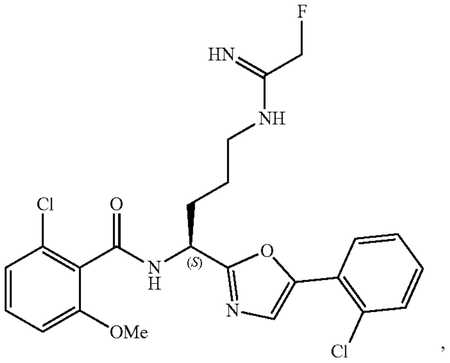
EX-27
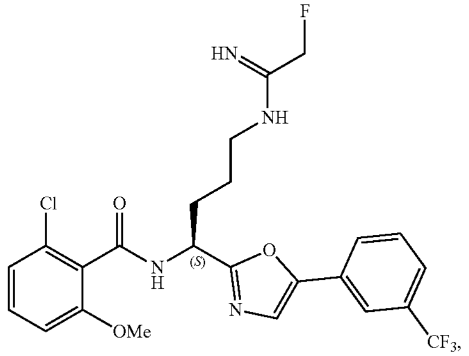
EX-28
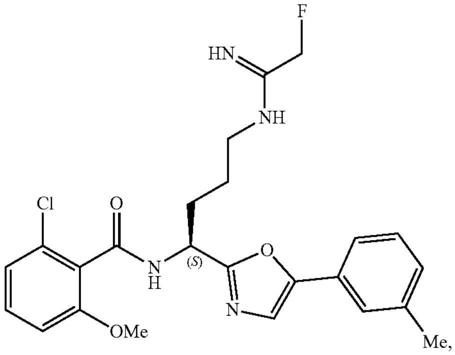
EX-29
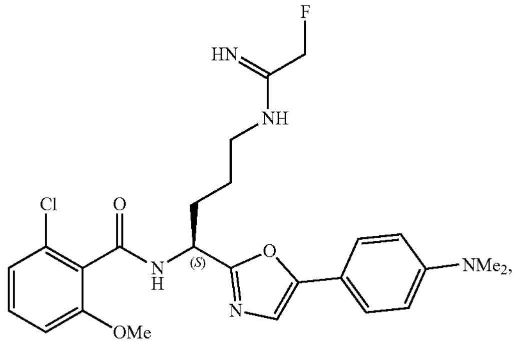
EX-30
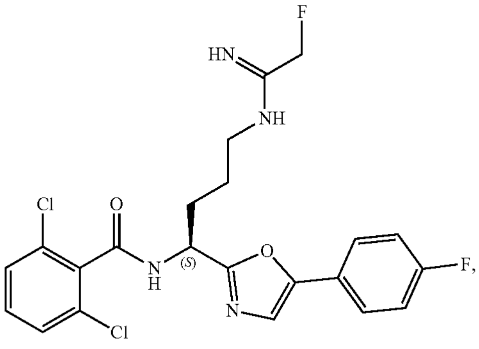
EX-31
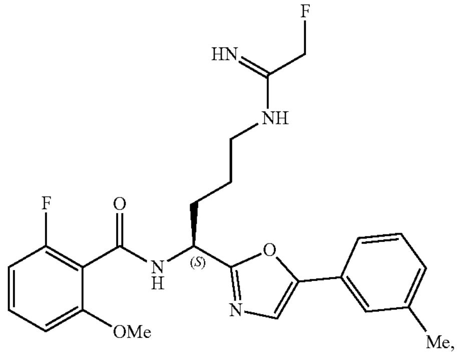
EX-32
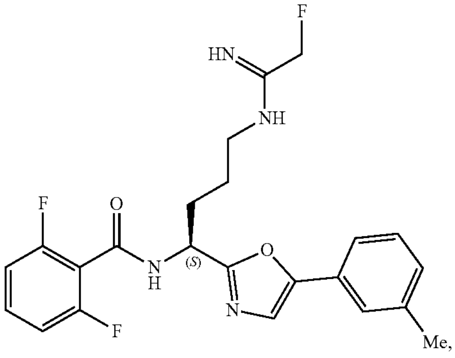

-continued
EX-33
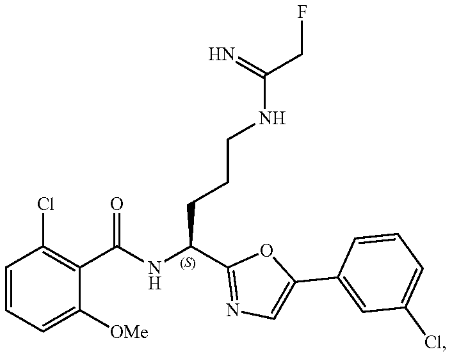
EX-34
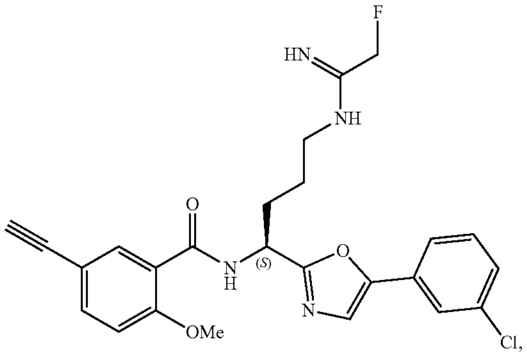
EX-35
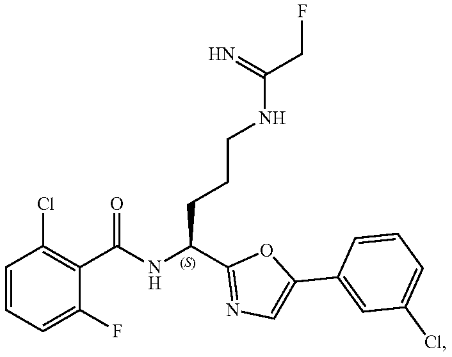
EX-36
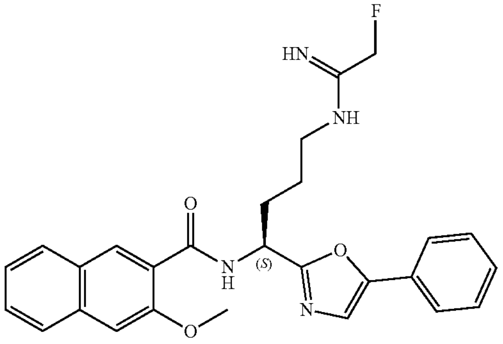
,
EX-37
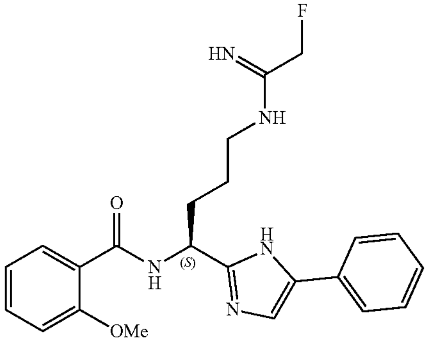
,
EX-38
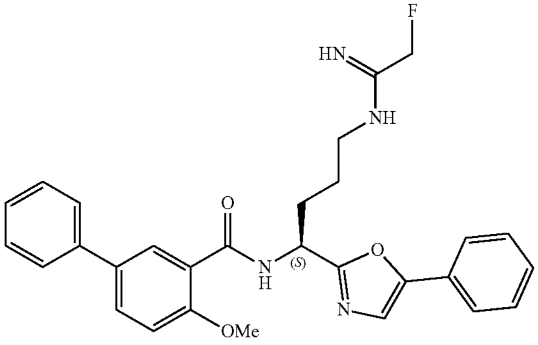
,
EX-39
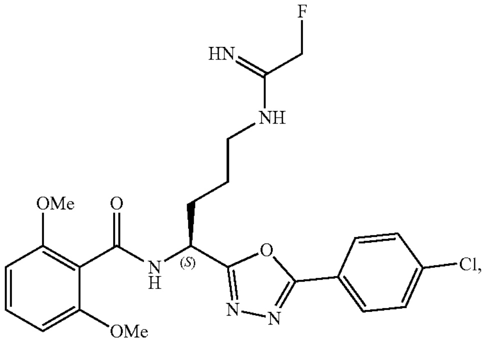
EX-40
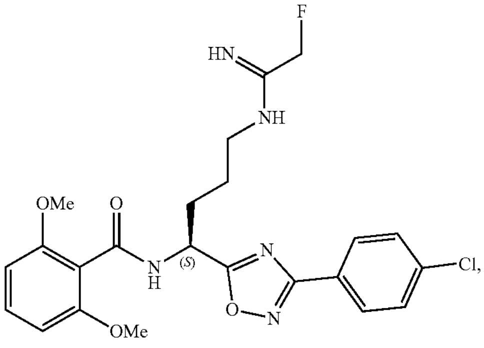

-continued

EX-41

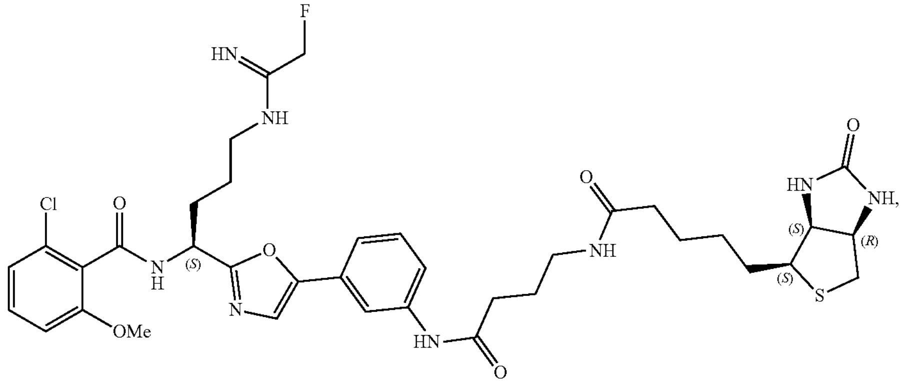

and

EX-42

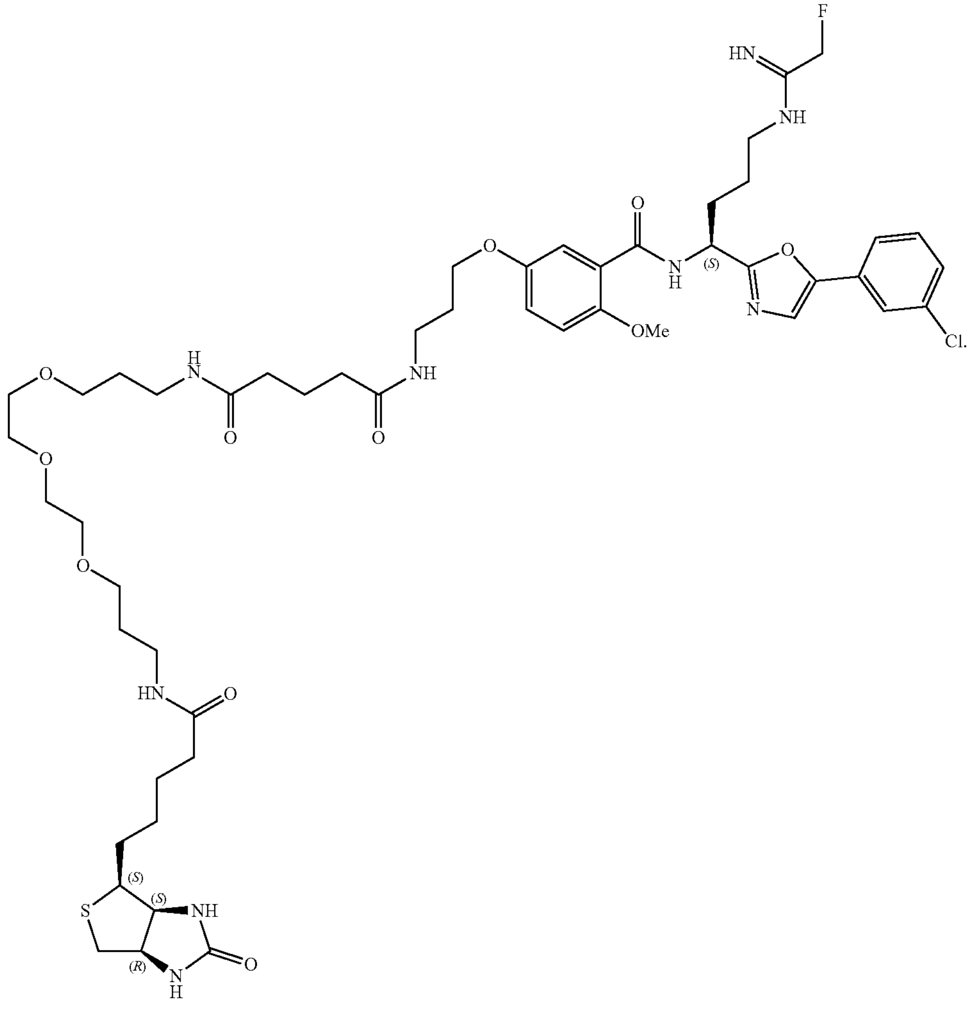

In one aspect, the present disclosure provides a composition comprising a compound, or a pharmaceutically acceptable salt or solvate thereof.

In some embodiments, wherein said salt is the hydrochloride salt.

In some embodiments, further comprising a pharmaceutically acceptable carrier.

In some embodiments, wherein said composition comprises a therapeutically effective amount of said compound, or a pharmaceutically acceptable salt or solvate thereof.

In some embodiments, wherein said composition is suitable for parenteral, transdermal, mucosal, nasal, buccal, sublingual, or oral administration to a patient.

In one aspect, the present disclosure provides a use of a compound, or a pharmaceutically acceptable salt or solvate thereof, in the preparation of a PAD inhibitor.

In some embodiments, wherein said PAD inhibitor is a PAD2 or PAD4 inhibitor.

In some embodiments, wherein said PAD inhibitor is a PAD4 inhibitor.

In one aspect, the present disclosure provides a method of treating a disease or disorder, the method comprising administering to a patient a therapeutically effective amount of the compound, or a pharmaceutically acceptable salt, prodrug, or metabolite thereof.

In some embodiments, wherein said diseases or disorders are various diseases or disorders in oncology or immunology associated with PAD4, The method according to above paragraph, wherein said diseases or disorders are described in detail, herein, and include, cancers and their related metastatic cancers for example lung cancer, liver cancer, blood cancer, esophageal cancer, breast cancer, colon cancer, as well as rheumatoid arthritis, multiple sclerosis, vasculitis, systemic lupus erythematosus, ulcerative colitis, cystic fibrosis, asthma, cutaneous lupus erythematosis, psoriasis. ischemia-reperfusion injury, and immune responses induced during transplant rejection.

In some embodiments, further comprising administering to the subject one or more additional therapeutics including radiotherapy, chemotherapy, cell therapy, or immune checkpoint inhibitors.

In some embodiments, further comprising administering to the subject one or more additional therapeutics including PD-1 inhibitor, PD-L1 inhibitor, CTLA-4 inhibitor, B7-H3 inhibitor, LAG3 inhibitor, TIM3 inhibitor, TIGIT inhibitor, anti-PDL1/TGFβ bispecific antibody, anti-EpCAM-CD3 bispecific antibody, and/or CD40 agonists, etc.

In some embodiments, wherein said compound attenuates activity of a protein arginine deiminase (PAD).

In some embodiments, wherein said PAD is PAD2 or PAD4.

In some embodiments, wherein said PAD is PAD4.

In some embodiments, wherein said activity is measured by inhibition of formation of neutrophil extracellular traps (NETs).

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "halogen", as used herein, generally refers to chloro (Cl), iodo (I), fluoro (F) and bromo (Br). For example, "halogen" groups may be fluoro, chloro, bromo, iodo or the like.

The term "hydroxyalkyl", as used herein, generally refers to an alkyl group of from 1 to 8 carbon atoms substituted with one or more hydroxy groups, wherein the alkyl group is as defined herein. Some non-limiting examples may comprise hydroxyethyl, 2-hydroxypropyl, hydroxymethyl or the like.

The term "alkyl", as used herein, generally refers to a hydrocarbon radical of from 1 to 8 carbon atoms which can be linear or branched, with single or multiple branching. For example, methyl (Me), ethyl (Et), propyl, isopropyl (i-propyl), n-butyl, i-butyl (isobutyl), 2-butyl (sec-butyl), t-butyl (tert-butyl), isopentyl, 2-ethyl-propyl, 1,2-dimethyl-propyl, 1-hexy, 1-heptyl, 1-octyl or the like.

The term "haloalkyl", as used herein, generally refers to an alkyl radical of from 1 to 8 carbon atoms having the meaning as defined above wherein one or more hydrogens are replaced with a halogen. For example, monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. For example, haloalkyl radicals may comprise fluoromethyl, difluoromethyl, trifluoromethyl, chloromethyl, dichloromethyl, trichloromethyl, trichloroethyl, pentafluoroethyl, heptafluoropropyl, difluorochloromethyl, dichlorofluoromethyl, difluoroethyl, difluoropropyl, dichloroethyl, dichloropropyl or the like.

The term "alkenyl", as used herein, generally refers to a monovalent linear or branched saturated hydrocarbon group of from 2 to 8 carbon atoms, and comprising one, two or three double bonds. For example, $(C_2-C_8)$ alkenyl may comprise ethenyl, 1-propenyl, 2-propenyl (allyl), iso-propenyl, 2-methyl-1-propenyl, 1-butenyl, 2-butenyl or the like.

The term "alkynyl", as used herein, generally refers to a monovalent linear or branched saturated hydrocarbon group of from 2 to 8 carbon atoms, and comprising one or two triple bonds. For example, $(C_2-C_8)$ alkynyl may comprise ethynyl, 1-propynyl, 2-propynyl, 1-butynyl, 2-butynyl, 3-butynyl or the like.

The term "cycloalkyl", as used herein, generally refers to a monovalent saturated monocyclic or bicyclic hydrocarbon group of 3 to 10 carbon atoms, for example, a monovalent saturated monocyclic hydrocarbon group of 3 to 10 carbon atoms. Bicyclic means consisting of two saturated carbocycles having two carbon atoms in common, i.e. the bridge separating the two rings is either a single bond or a chain of one or two carbon atoms. Examples may be cyclopropyl, cyclobutanyl, cyclopentyl, cyclohexyl, cycloheptyl, cyclooctyl, cyclononyl, and cyclodecyl. For example, bicyclic cycloalkyl may be bicyclo[2.2.1]heptanyl, bicyclo[2.2.2]octanyl, adamantanyl or the like.

The terms "heterocycloalkyl" and, interchangeably, "heterocycle", as used herein, generally refers to a saturated, partially unsaturated, or fully unsaturated monocyclic, bicyclic, or tricyclic heterocyclic radical comprising one or more heteroatoms as ring members, wherein each said heteroatom may be independently selected from the group consisting of nitrogen, oxygen, and sulfur, and wherein there are typically 3 to 10 ring members in each ring. In some embodiments of this invention heterocyclic rings may comprise 1 to 4 heteroatoms. "Heterocycloalkyl" and "heterocycle" are intended to comprise sulfones, sulfoxides, N-oxides of tertiary nitrogen ring members, and carbocyclic fused and benzo fused ring systems; additionally, both terms may also comprise systems where a heterocycle ring is fused to an aryl group, as defined herein, or an additional heterocycle group.

Heterocycle groups of the invention may be exemplified by aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. For example, 1-pyrrolinyl, pyrrolinyl, 3-pyrrolinyl, pyrrolidino, 2-pyrrolidinyl, 3-pyrrolidinyl, 1-imidazolinyl, 2-imidazolinyl, 4-imidazolinyl, 1-imidazolidinyl, 2-imidazolidinyl, 4-imidazolidinyl, 1-pyrazolinyl, 3-pyrazolinyl, 4-pyrazolinyl, 1-pyrazolidinyl, 3-pyrazolidinyl, 4-pyrazolidinyl, piperidino, 2-piperidyl, 3-piperidyl, 4-piperidyl, piperazino, 2-piperazinyl, 2-morpholinyl, 3-morpholinyl, morpholino, tetrahydropyranyl or the like.

The terms "oxy" or "oxa", as used herein, generally refers to —O—.

The term "alkyloxy" or "alkoxy", as used herein, generally refers to an alkylether substituent, i.e., —O-alkyl. For example, such a substituent may comprise methoxy (—O—$CH_3$), ethoxy, n-propoxy, isopropoxy, n-butoxy, iso-butoxy, sec-butoxy, tert-butoxy, n-pentyloxy, n-hexyloxy, n-heptyloxy, n-octyloxy or the like.

The term "alkylamino", as used herein, generally refers to amino groups which have been substituted with one or two alkyl radicals of 1 to 8 carbon atoms. For example, "alkylamino" groups may be mono- or dialkylated, forming groups such as, for example, N-methylamino, N-ethylamino, N, N-dimethylamino, N, N-diethylamino or the like. For example, methylamino, ethylamino, n-propylamino, isopropylamino, n-butylamino, isobutylamino, sec-butylamino, tert-butylamino, n-pentylamino, n-hexylamino or the like.

The term "aryl", as used herein, generally refers to a monovalent aromatic carbocyclic mono- or bicyclic ring system comprising 6 to 10 carbon ring atoms. For example, aryl moieties may comprise phenyl, indenyl, dihydroindenyl, naphthyl, tetrahydronaphthyl, anthracenyl, phenanthrenyl or the like.

The term "heteroaryl" or, alternatively, "heteroaromatic", as used herein, generally refers to a 5- to 10-membered aromatic radical comprising 1 to 9 carbon ring atoms (e.g., $C_1$-$C_9$ heteroaryl) that may comprise one or more ring heteroatoms selected from nitrogen, oxygen and sulfur, and which may be a monocyclic or bicyclic ring system. Whenever it appears herein, a numerical range such as "5 to 10" refers to each integer in the given range; e.g., "5 to 10 ring atoms" means that the heteroaryl group may comprise 5 ring atoms, 6 ring atoms, 7 ring atoms, 8 ring atoms, 9 ring atoms or 10 ring atoms. An N-containing "heteroaromatic" or "heteroaryl" moiety refers to an aromatic group in which at least one of the skeletal atoms of the ring may be a nitrogen atom. The heteroaryl may be attached to the rest of the molecule through any atom of the ring(s). For example, "heteroaryl" groups may comprise benzofuryl, benzoimidazolyl, 1H-benzoimidazolyl, benzooxazinyl, benzoxazolyl, benzothiazinyl, benzothiazolyl, benzothienyl, benzotriazolyl, furyl, imidazolyl, indazolyl, 1H-indazolyl, indolyl, isoquinolinyl, isothiazolyl, isoxazolyl, oxazolyl, pyrazinyl, pyrazolyl (pyrazyl), 1H-pyrazolyl, pyrazolo[1,5-a]pyridinyl, pyridazinyl, pyridinyl, pyrimidinyl, pyrrolyl, quinolinyl, tetrazolyl, thiazolyl, thienyl, triazolyl, 6,7-dihydro-5H-[1]pyrindinyl or the like.

The term "aromatic", as used herein, generally refers to the conventional idea of aromaticity as defined in the literature, for example, in IUPAC-Compendium of Chemical Terminology, 2nd, A. D. McNaught & A. Wilkinson (Eds). Blackwell Scientific Publications, Oxford (1997).

The term "optionally substituted", as used herein, generally refers to the anteceding group may be substituted or unsubstituted. When substituted, the hydrogen atoms bound to the carbon, nitrogen, sulfur, or oxygen atoms may be replaced by "substituents" which may comprise H, protium, deuterium, tritium, halogen, an alkyl group, an aryl group, a heteroaryl group, an alkyloxy group and an alkylamino group.

The term "independently selected", as used herein, generally refers to each substituent is selected independent of the other(s). Each substituent therefore may be identical to or different from the other substituent(s).

The term "pharmaceutically acceptable", as used herein, generally refers to those compounds, materials, compositions, carriers, and/or dosage forms which are, within the scope of sound medical judgment, suitable for use in contact with the tissues of human beings and animals. In addition, the compounds, material, compositions, carriers, and/or dosage forms may have no excessive toxicity, irritation, allergic response, or other problem or complication, commensurate with a reasonable benefit/risk ratio.

The term "pharmaceutically acceptable salt", as used herein, generally refers to those modified parent compound which are within the scope of sound medical judgment, suitable for use in contact with the tissues of human beings and animals. For example, the parent compound could be modified by making acid or base salts thereof.

Pharmaceutically acceptable salts may include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates, fumarates and organic sulfonates.

The term "solvate", as used herein, generally refers to solvent addition forms that contain either stoichiometric or non stoichiometric amounts of solvent. Some compounds or salts have a tendency to trap a fixed molar ratio of solvent molecules in the crystalline solid state, thus forming a solvate. For example, if the solvent is water, the solvate formed is a hydrate, and if the solvent is alcohol, the solvate formed is an alcoholate. For example, hydrates are formed by the combination of one or more molecules of water with one molecule of the substance in which the water retains its molecular state as $H_2O$.

The term "substituted", as used herein, generally refers to that any one or more atoms on the designated atom is replaced with a selection from the indicated group. In some embodiments, the designated atom's normal valency is not exceeded, and that the substitution results in a stable compound.

The term "pharmaceutically acceptable carrier" as used herein, generally refers to any preparation or supported media that can deliver effective amount of active substance of the disclosure. In addition, the preparation or supported media may don't interfere biological activity of active substance and is non-toxic to hosts or patients. For example, pharmaceutically acceptable carriers may include water, oil, vegetable oil and mineral, cream base, lotion base, ointment base and the like. Additional component may include suspending agent, tackifier and penetration enhancer and the like. Their preparations are known to technicians in cosmetic and topical medication fields.

The term "therapeutically effective amount", as used herein, generally refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

The term "PAD" or "peptidylarginine deiminase", as used herein, generally refers to the human peptidylarginine deiminase (PAD) family consists of five proteins, including PAD1, PAD2, PAD3, PAD4, and PAD6. For example, PAD4 has a nuclear localization signal and is nuclear localized among PAD family members. PAD family members express in specific tissues. For example, PAD4 is expressed in bone marrow and myeloid lineage cells, such as neutrophils, monocytes and macrophages. PAD4 regulates a unique type of cell death termed NETOSIS wherein neutrophils release chromatin to form neutrophil extracellular traps (NETs). NETs are composed of nuclear chromatin associated with antibacterial proteins such as neutrophil elastase and myeloperoxidase. For example, Both PAD4 and PAD4-mediated protein citrullination can produce self-reacting antibodies under autoimmune conditions. PAD4 regulates gene expression in cancer cells to foster tumorigenesis. For example, PAD4 affects cancer and immune cells [Yuzhalin, A. E., et al. (2018). Nat. Commun., 9(1).].

One of ordinary skill in the art would appreciate that compounds of the invention may exhibit the phenomena of tautomerism, conformational isomerism, geometric isomerism, and/or optical isomerism. For example, the compounds of the invention may include one or more chiral centers and/or double bonds and as a consequence can exist as stereoisomers, such as double-bond isomers (such as, geometric isomers), enantiomers, diastereomers, and mixtures thereof, such as racemic mixtures. As another example, the compounds of the invention may exist in several tautomeric forms, including the enol form, the keto form, and mixtures thereof. As the various compound names, formulae and compound drawings within the specification and claims can represent only one of the possible tautomeric, conformational isomeric, optical isomeric, or geometric isomeric forms, it would be understood that the invention encompasses any tautomeric, conformational isomeric, optical isomeric, and/or geometric isomeric forms of the compounds described herein, as well as mixtures of these various different isomeric forms. It is intended that the compounds encompassed herein are, with the exception of forms of isomerism, chemically stable and isolable.

As is understood by one of ordinary skill in the art, certain atoms may occur in more than one isotopic form. For example, hydrogen may occur as protium (H), deuterium (2H) and tritium ($^3$H), and carbon may occur naturally as three different isotopes, $^{12}$C, $^{13}$C and $^{14}$C. Examples of isotopes that may be incorporated into the compounds disclosed herein also include, but are not limited to, $^{15}$N, $^{18}$O, $^{17}$O, $^{18}$F, $^{32}$P, $^{33}$P, $^{129}$I, $^{131}$I, $^{123}$I, $^{124}$I, $^{125}$I, or the like. Thus, the disclosed compounds may be enriched in one or more of these isotopes relative to the natural abundance of such isotope. As is known to those of skill in the art, such isotopically enriched compounds may be useful for a variety of purposes. For example, substitution with heavier isotopes such as deuterium ($^2$H) may afford certain therapeutic advantages that result from greater metabolic stability. Substitution with positron emitting isotopes, such as $^{18}$F may be useful in Positron Emission Tomography (PET) studies. By way of example, deuterium ($^2$H) has a natural abundance of about 0.015%. Accordingly, for approximately every 6,500 hydrogen atoms occurring in nature, there is one deuterium atom. Thus, deuterium containing compounds of the disclosure have deuterium at one or more positions (as the case may be) in an abundance of greater than 0.015%.

Compound of Formula (I)

In one aspect, the present disclosure provides a compound of formula (I):

(I)

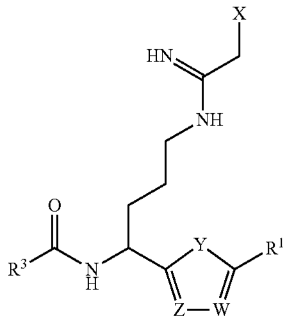

wherein, X may be halogen; W may be N or C—$R^2$; each Y and Z may be independently selected from N, NH, O and S; $R^3$ may be selected from ($C_6$-$C_{10}$) aryl, and ($C_1$-$C_9$) heteroaryl; each $R^1$ and $R^2$ may be independently selected from H, ($C_1$-$C_8$) alkyl, ($C_3$-$C_{10}$) cycloalkyl, ($C_6$-$C_{10}$) aryl, and ($C_1$-$C_9$) heteroaryl, provided that $R^1$ and $R^2$ may be not both H, and that $R^1$ and $R^2$ may be not bonded to one another by one or more chemical bonds; when $R^1$ may be ($C_3$-$C_{10}$) cycloalkyl or ($C_6$-$C_{10}$) aryl, said $R^1$ may be unsubstituted or substituted with one or more substituents $R^4$, said $R^4$ may be independently selected from H, halogen, ($C_1$-$C_8$) alkyl, ($C_1$-$C_8$) haloalkyl, ($C_1$-$C_8$) alkoxy, ($C_1$-$C_8$) alkylamino, and the groups (Sub A)

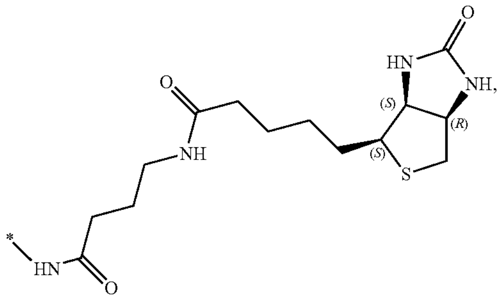

(Sub B)

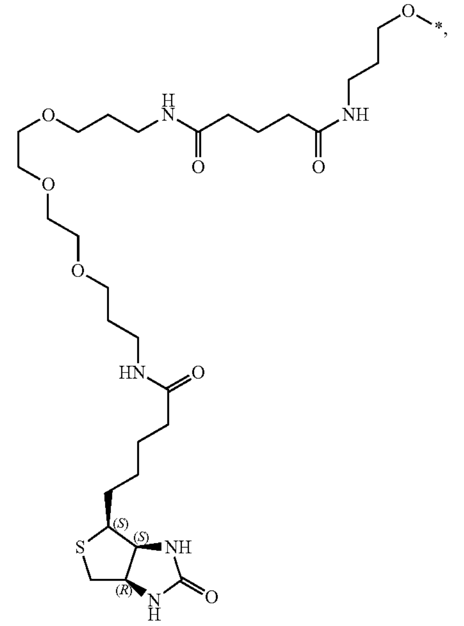

wherein, the asterisk "*" in the structure formulas indicates the available radical ends to be connected; when $R^3$ may be ($C_6$-$C_{10}$) aryl or ($C_1$-$C_9$) heteroaryl, said $R^3$ may be unsubstituted or substituted with one or more substituents $R^5$, said $R^5$ may be independently selected from H, halogen, ($C_1$-$C_8$) alkyl, ($C_2$-$C_8$) alkenyl, ($C_2$-$C_8$) alkynyl, ($C_1$-$C_8$) alkoxy, ($C_1$-$C_8$) haloalkyl, ($C_1$-$C_8$) alkylamino, ($C_2$-$C_9$) heterocycloalkyl, ($C_6$-$C_{10}$) aryl, ($C_1$-$C_9$) heteroaryl, Sub A and Sub B; when $R^5$ is ($C_2$-$C_9$) heterocycloalkyl, ($C_6$-$C_{10}$) aryl or ($C_1$-$C_9$) heteroaryl, said $R^5$ may be unsubstituted or substituted with one or more substituents $R^6$, said $R^6$ may be independently selected from H, halogen, ($C_1$-$C_8$) alkyl, ($C_1$-$C_8$) alkoxy, ($C_1$-$C_8$) hydroxyalkyl; or a pharmaceutically acceptable salt or solvate thereof.

For example, the X may be flouro, chloro, bromo, or iodo.

For example, $R^1$ and $R^2$ may be independently selected from H, ($C_1$-$C_8$) alkyl, ($C_3$-$C_{10}$) cycloalkyl, ($C_6$-$C_{10}$) aryl, and ($C_1$-$C_9$) heteroaryl, provided that $R^1$ and $R^2$ are not both H, and that $R^1$ and $R^2$ are not bonded to one another by one or more chemical bonds.

For example, the alkyl may include, but not limited to methyl (Me), ethyl (Et), propyl, isopropyl (i-propyl), n-butyl, i-butyl (isobutyl), 2-butyl (sec-butyl), t-butyl (tert-butyl), isopentyl, 2-ethyl-propyl, 1,2-dimethyl-propyl, 1-hexy, 1-heptyl, 1-octyl or the like.

For example, the cycloalkyl may include, but not limited to cyclopropyl, cyclobutanyl, cyclopentyl, cyclohexyl, cycloheptyl, cyclooctyl, cyclononyl, cyclodecyl. bicyclo[2.2.1]heptanyl, bicyclo[2.2.2]octanyl, adamantanyl or the like.

For example, the aryl may include, but not limited to phenyl, 2-naphthyl, halogen substituted phenyl, N-linked aliphatic substituted 2-naphthyl and the like; the ($C_6$-$C_{10}$) aryl may include, but not limited to phenyl, halogen substituted phenyl, aliphatic substituted phenyl, aromatic substituted phenyl and the like; the ($C_6$-$C_{10}$) aryl may include, but not limited to 2-naphthyl, substituted 2-naphthyl and the like.

For example, the heteroaryl may include, but not limited to pyridinyl, furanyl halogen substituted pyridinyl and the like.

For example, the pharmaceutically acceptable salt in the disclosure may comprise salts of the compound that modified by non-toxic acids or alkalis and the like.

For example, the pharmaceutical acceptable acid-additive salts of the compound in the disclosure may include, but not limited to inorganic acid salts, such as, hydrochloric acid, hydrobromic acid, nitric acid, carbonic acid, phosphorous acid and the like; organic acid salts, such as, maleic acid, benzenesulfonic acid, p-methyl benzenesulfonic acid, citric acid, tartaric acid, and the like.

For another example, the pharmaceutical acceptable alkali-additive salts of the compound in the disclosure may include, but not limited to sodium, potassium, calcium, ammonium or magnesium salts.

For example, the solvate of the compound in the disclosure may comprise the hydrate compound which the compound molecule trap different molar ratio of water molecules, the alcoholate compound which the compound molecule trap different molar ratio of alcohol molecule and the like.

For example, the ($C_6$-$C_{10}$) aryl of $R^1$ may be substituted with one or more substituents selected from $R^4$, said $R^4$ may be independently selected from H, halogen, ($C_1$-$C_8$) alkyl, ($C_1$-$C_8$) haloalkyl, ($C_1$-$C_8$) alkoxy, ($C_1$-$C_8$) alkylamino, Sub A and Sub B.

The substituted ($C_6$-$C_{10}$) aryl may include, but not limited to, phenyl, halogen substituted phenyl, ($C_1$-$C_8$) alkyl substituted phenyl, ($C_1$-$C_8$) haloalkyl substituted phenyl, ($C_1$-$C_8$) alkoxy substituted phenyl, ($C_1$-$C_8$) alkylamino substituted phenyl, Sub A or Sub B substituted phenyl. For example, the ($C_1$-$C_9$) heteroaryl of $R^1$ may be substituted with one or more substituents $R^4$, said $R^4$ may be independently selected from H, halogen, ($C_1$-$C_8$) alkyl, ($C_1$-$C_8$) haloalkyl, ($C_1$-$C_8$) alkoxy, ($C_1$-$C_8$) alkylamino, Sub A and Sub B.

For example, the phenyl of $R^1$ in formula (I) may be substituted with one or more substituents $R^4$, said $R^4$ may be independently selected from H, halogen, ($C_1$-$C_8$) alkyl, ($C_1$-$C_8$) haloalkyl, ($C_1$-$C_8$) alkoxy, ($C_1$-$C_8$) alkylamino, Sub A and Sub B.

For example, the ($C_6$-$C_{10}$) aryl of $R^2$ may be substituted with one or more substituents $R^4$, said $R^4$ may be independently selected from H, halogen, ($C_1$-$C_8$) alkyl, ($C_1$-$C_8$) haloalkyl, ($C_1$-$C_8$) alkoxy, ($C_1$-$C_8$) alkylamino, Sub A and Sub B.

For example, the ($C_1$-$C_9$) heteroaryl of $R^2$ may be substituted with one or more substituents $R^4$, said $R^4$ may be independently selected from H, halogen, ($C_1$-$C_8$) alkyl, ($C_1$-$C_8$) haloalkyl, ($C_1$-$C_8$) alkoxy, ($C_1$-$C_8$) alkylamino, Sub A and Sub B.

For example, the phenyl of $R^2$ in formula (I) may be substituted with one or more substituents $R^4$, said $R^4$ may be independently selected from H, halogen, ($C_1$-$C_8$) alkyl, ($C_1$-$C_8$) haloalkyl, ($C_1$-$C_8$) alkoxy, ($C_1$-$C_8$) alkylamino, Sub A and Sub B.

For example, the ($C_6$-$C_{10}$) aryl of $R^3$ may be substituted with one or more substituents $R^5$, said $R^5$ may be independently selected from H, halogen, ($C_1$-$C_8$) alkyl, ($C_2$-$C_8$) alkenyl, ($C_2$-$C_8$) alkynyl, ($C_1$-$C_8$) alkoxy, ($C_1$-$C_8$) haloalkyl, ($C_1$-$C_8$) alkylamino, ($C_2$-$C_9$) heterocycloalkyl, ($C_6$-$C_{10}$) aryl, ($C_1$-$C_9$) heteroaryl, Sub A and Sub B.

For example, $R^5$ may be ($C_2$-$C_9$) heterocycloalkyl, ($C_6$-$C_{10}$) aryl or ($C_1$-$C_9$) heteroaryl and the like.

For example, $R^5$ may be ($C_2$-$C_9$) heterocycloalkyl, ($C_6$-$C_{10}$) aryl or ($C_1$-$C_9$) heteroaryl, said $R^5$ may be unsubstituted or substituted with one or more substituents $R^6$, said $R^6$ is independently selected from H, halogen, ($C_1$-$C_8$) alkyl, ($C_1$-$C_8$) alkoxy, ($C_1$-$C_8$) hydroxyalkyl.

For example, the X in compound of formula (I) may be Cl or F.

For example, the X in compound of formula (I) may be Cl or F, the $R^1$ may be a group selected from ($C_6$-$C_{10}$) aryl and ($C_1$-$C_9$) heteroaryl, which include, but not limited to phenyl, halogen substituted phenyl and the like; $R^2$ may be a group selected from H, ($C_6$-$C_{10}$) aryl and ($C_1$-$C_9$) heteroaryl, which include, but not limited to H, phenyl, halogen substituted phenyl and the like; the $R^3$ may be a group selected from ($C_6$-$C_{10}$) aryl and ($C_1$-$C_9$) heteroaryl which include, but not limited to phenyl, halogen substituted phenyl, ($C_1$-$C_8$) alkyl substituted phenyl, ($C_2$-$C_8$) alkenyl substituted phenyl, ($C_2$-$C_8$) alkynyl substituted phenyl, ($C_1$-$C_8$) alkoxy substituted phenyl, ($C_1$-$C_8$) haloalkyl substituted phenyl, ($C_1$-$C_8$) alkylamino substituted phenyl, ($C_2$-$C_9$) heterocycloalkyl substituted phenyl, ($C_6$-$C_{10}$) aryl substituted phenyl, ($C_1$-$C_9$) heteroaryl substituted phenyl and, Sub A or Sub B substituted phenyl and the like.

For example, the X in compound of formula (I) may be Cl or F, the $R^1$ may be a group selected from substituted ($C_6$-$C_{10}$) aryl and substituted ($C_1$-$C_9$) heteroaryl, in which the substituent is selected from H, halogen, ($C_1$-$C_8$) alkyl, ($C_1$-$C_8$) haloalkyl, ($C_1$-$C_8$) alkoxy, ($C_1$-$C_8$) alkylamino, Sub A and Sub B, and the $R^1$ may include, but not limited to phenyl, halogen substituted phenyl and the like; $R^2$ may be a group selected from H, substituted ($C_6$-$C_{10}$) aryl and substituted ($C_1$-$C_9$) heteroaryl, in which, the substituent is selected from H, halogen, ($C_1$-$C_8$) alkyl, ($C_1$-$C_8$) haloalkyl, ($C_1$-$C_8$) alkoxy, ($C_1$-$C_8$) alkylamino, Sub A and Sub B, and the $R^2$ may include, but not limited to H, phenyl, halogen substituted phenyl and the like; $R^3$ may be a group selected from substituted ($C_6$-$C_{10}$) aryl and substituted ($C_1$-$C_9$) heteroaryl, in which, the substituent is selected from H, halogen, ($C_1$-$C_8$) alkyl, ($C_2$-$C_8$) alkenyl, ($C_2$-$C_8$) alkynyl, ($C_1$-$C_8$) alkoxy, ($C_1$-$C_8$) haloalkyl, ($C_1$-$C_8$) alkylamino, ($C_2$-$C_9$) heterocycloalkyl, ($C_6$-$C_{10}$) aryl, ($C_1$-$C_9$) heteroaryl, Sub A and Sub B, and the $R^3$ may include, but not limited to phenyl, halogen substituted phenyl, ($C_1$-$C_8$) alkyl substituted phenyl, ($C_2$-$C_8$) alkenyl substituted phenyl, ($C_2$-$C_8$) alkynyl substituted phenyl, ($C_1$-$C_8$) alkoxy substituted phenyl, ($C_1$-$C_8$) haloalkyl substituted phenyl, ($C_1$-$C_8$) alkylamino substituted phenyl, ($C_2$-$C_9$) heterocycloalkyl substituted phenyl, ($C_6$-$C_{10}$) aryl substituted phenyl, ($C_1$-$C_9$) heteroaryl substituted phenyl and, Sub A or Sub B substituted phenyl, and the and the $R^3$ may include, but not limited to naphthyl, halogen substituted naphthyl, ($C_1$-$C_8$) alkyl substituted naphthyl, ($C_2$-$C_8$) alkenyl substituted naphthyl, ($C_2$-$C_8$) alkynyl substituted naphthyl, ($C_1$-$C_8$) alkoxy substituted naphthyl, ($C_1$-$C_8$) haloalkyl substituted naphthyl, ($C_1$-$C_8$) alkylamino substituted naphthyl, ($C_2$-$C_9$) heterocycloalkyl substituted naphthyl, ($C_6$-$C_{10}$) aryl substituted naphthyl, ($C_1$-$C_9$) heteroaryl substituted naphthyl, Sub A or Sub B substituted naphthyl, and the like.

For example, the X in compound of formula (I) may be Cl or F, the $R^1$ may be phenyl, the $R^2$ may be a group selected from H, substituted ($C_6$-$C_{10}$) aryl and substituted ($C_1$-$C_9$) heteroaryl, in which, the substituent is selected from H, halogen, ($C_1$-$C_8$) alkyl, ($C_1$-$C_8$) haloalkyl, ($C_1$-$C_8$) alkoxy, ($C_1$-$C_8$) alkylamino, Sub A and Sub B, and the $R^2$ may include, but not limited to H, phenyl, halogen substituted phenyl and the like; the $R^3$ may be a group selected from substituted ($C_6$-$C_{10}$) aryl and substituted ($C_1$-$C_9$) heteroaryl, in which, the substituent is selected from H, halogen, ($C_1$-$C_8$) alkyl, ($C_2$-$C_8$) alkenyl, ($C_2$-$C_8$) alkynyl, ($C_1$-$C_8$) alkoxy, ($C_1$-$C_8$) haloalkyl, ($C_1$-$C_8$) alkylamino, ($C_2$-$C_9$) heterocycloalkyl, ($C_6$-$C_{10}$) aryl, ($C_1$-$C_9$) heteroaryl, Sub A and Sub B, and the $R^3$ may include, but not limited to phenyl, halogen substituted phenyl, ($C_1$-$C_8$) alkyl substituted phenyl, ($C_2$-$C_8$) alkenyl substituted phenyl, ($C_2$-$C_8$) alkynyl substituted phenyl, ($C_1$-$C_8$) alkoxy substituted phenyl, ($C_1$-$C_8$) haloalkyl substituted phenyl, ($C_1$-$C_8$) alkylamino substituted phenyl, ($C_2$-$C_9$) heterocycloalkyl substituted phenyl, ($C_6$-$C_{10}$) aryl substituted phenyl, ($C_1$-$C_9$) heteroaryl substituted phenyl, Sub A or Sub B substituted phenyl, and the like.

For example, the X in compound of formula (I) may be Cl or F, the $R^1$ may be substituted phenyl, in which the substituent is selected from H, halogen, ($C_1$-$C_8$) alkyl, ($C_1$-$C_8$) haloalkyl, ($C_1$-$C_8$) alkoxy, ($C_1$-$C_8$) alkylamino, Sub A and Sub B, and the $R^1$ may include, but not limited to phenyl, halogen substituted phenyl and the like; the $R^2$ may be a group selected from H, halogen, ($C_1$-$C_8$) alkyl, ($C_1$-$C_8$) haloalkyl, ($C_1$-$C_8$) alkoxy, ($C_1$-$C_8$) alkylamino, Sub A and Sub B, and the $R^2$ may include, but not limited to H, phenyl, halogen substituted phenyl and the like; the $R^3$ may be a group selected from substituted ($C_6$-$C_{10}$) aryl and substituted ($C_1$-$C_9$) heteroaryl, in which, the substituent is selected from H, halogen, ($C_1$-$C_8$) alkyl, ($C_2$-$C_8$) alkenyl, ($C_2$-$C_8$) alkynyl, ($C_1$-$C_8$) alkoxy, ($C_1$-$C_8$) haloalkyl, ($C_1$-$C_8$) alkylamino, ($C_2$-$C_9$) heterocycloalkyl, ($C_6$-$C_{10}$) aryl, ($C_1$-$C_9$) heteroaryl, Sub A and Sub B, and the $R^3$ may include, but not limited to phenyl, halogen substituted phenyl, ($C_1$-$C_8$) alkyl substituted phenyl, ($C_2$-$C_8$) alkenyl substituted phenyl, ($C_2$-$C_8$) alkynyl substituted phenyl, ($C_1$-$C_8$) alkoxy substituted phenyl, ($C_1$-$C_8$) haloalkyl substituted phenyl, ($C_1$-$C_8$) alkylamino substituted phenyl, ($C_2$-$C_9$) heterocycloalkyl substituted phenyl, ($C_6$-$C_{10}$) aryl substituted phenyl, ($C_1$-$C_9$) heteroaryl substituted phenyl and, Sub A or Sub B substituted phenyl, and the $R^3$ may include, but not limited to naphthyl, halogen substituted naphthyl, ($C_1$-$C_8$) alkyl substituted naphthyl, ($C_2$-$C_8$) alkenyl substituted naphthyl, ($C_2$-$C_8$) alkynyl substituted naphthyl, ($C_1$-$C_8$) alkoxy substituted naphthyl, ($C_1$-$C_8$) haloalkyl substituted naphthyl, ($C_1$-$C_8$) alkylamino substituted naphthyl, ($C_2$-$C_9$) heterocycloalkyl substituted naphthyl, ($C_6$-$C_{10}$) aryl substituted naphthyl, ($C_1$-$C_9$) heteroaryl substituted naphthyl, Sub A or Sub B substituted naphthyl, and the like.

In one aspect, the present disclosure provides a compound of formula (II):

(II)

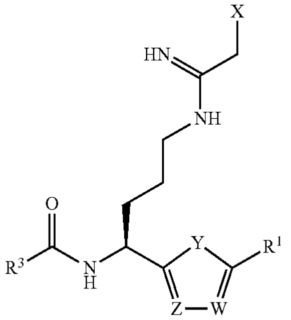

wherein, X is halogen; W is N, C—$R^2$; each Y and Z is independently selected from N, NH, O and S; $R^3$ is selected from ($C_6$-$C_{10}$) aryl, and ($C_1$-$C_9$) heteroaryl; each $R^1$ and $R^2$ is independently selected from H, ($C_1$-$C_8$) alkyl, ($C_3$-$C_{10}$) cycloalkyl, ($C_6$-$C_{10}$) aryl, and ($C_1$-$C_9$) heteroaryl, provided that $R^1$ and $R^2$ are not both H, and that $R^1$ and $R^2$ are not bonded to one another by one or more chemical bonds; when $R^1$ is ($C_3$-$C_{10}$) cycloalkyl or ($C_6$-$C_{10}$) aryl, said $R^1$ is unsubstituted or substituted with one or more substituents $R^4$, said $R^4$ is independently selected from H, halogen, ($C_1$-$C_8$) alkyl, ($C_1$-$C_8$) haloalkyl, ($C_1$-$C_8$) alkoxy, ($C_1$-$C_8$) alkylamino, and the groups (Sub A)

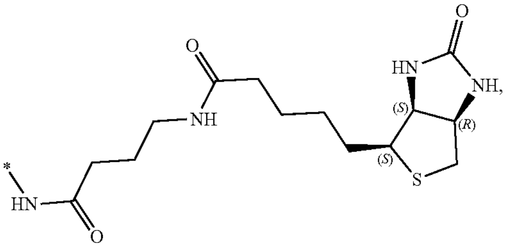

(Sub B)

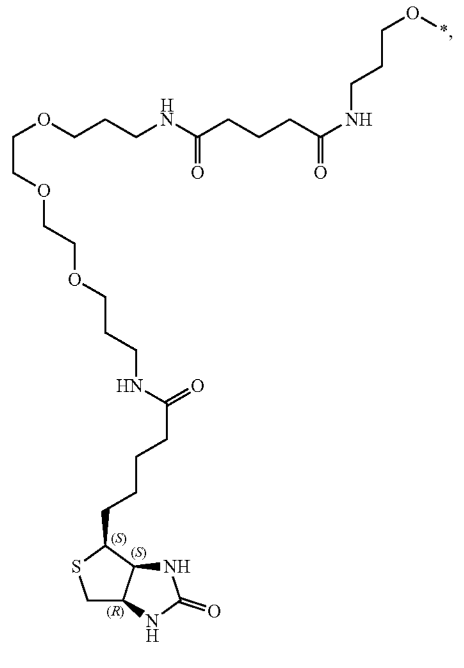

wherein, the asterisk "*" in the structure formulas indicates the available radical ends to be connected; when $R^3$ is ($C_6$-$C_{10}$) aryl or ($C_1$-$C_9$) heteroaryl, said $R^3$ is unsubstituted or substituted with one or more substituents $R^5$, said $R^5$ is independently selected from H, halogen, ($C_1$-$C_8$) alkyl, ($C_2$-$C_5$) alkenyl, ($C_2$-$C_5$) alkynyl, ($C_1$-$C_8$) alkoxy, ($C_1$-$C_8$) haloalkyl, ($C_1$-$C_8$) alkylamino, ($C_2$-$C_9$) heterocycloalkyl, ($C_6$-$C_{10}$) aryl, ($C_1$-$C_9$) heteroaryl, Sub A and Sub B; when $R^5$ is ($C_2$-$C_9$) heterocycloalkyl, ($C_6$-$C_{10}$) aryl or ($C_1$-$C_9$) heteroaryl, said $R^5$ is unsubstituted or substituted with one or more substituents $R^6$, said $R^6$ is independently selected from H, halogen, ($C_1$-$C_8$) alkyl, ($C_1$-$C_8$) alkoxy, ($C_1$-$C_8$) hydroxyalkyl; or a pharmaceutically acceptable salt or solvate thereof.

For example, the X may be flouro, chloro, bromo, or iodo.

For example, $R^1$ and $R^2$ may be independently selected from H, ($C_1$-$C_8$) alkyl, ($C_3$-$C_{10}$) cycloalkyl, ($C_6$-$C_{10}$) aryl, and ($C_1$-$C_9$) heteroaryl, provided that $R^1$ and $R^2$ are not both H, and that $R^1$ and $R^2$ are not bonded to one another by one or more chemical bonds.

For example, the alkyl may include, but not limited to methyl (Me), ethyl (Et), propyl, isopropyl (i-propyl), n-butyl, i-butyl (isobutyl), 2-butyl (sec-butyl), t-butyl (tert-butyl), isopentyl, 2-ethyl-propyl, 1,2-dimethyl-propyl, 1-hexy, 1-heptyl, 1-octyl or the like.

For example, the cycloalkyl may include, but not limited to cyclopropyl, cyclobutanyl, cyclopentyl, cyclohexyl, cycloheptyl, cyclooctyl, cyclononyl, cyclodecyl. bicyclo [2.2.1]heptanyl, bicyclo[2.2.2]octanyl, adamantanyl or the like.

For example, the aryl may include, but not limited to phenyl, 2-naphthyl, halogen substituted phenyl, N-linked aliphatic substituted 2-naphthyl and the like; the ($C_6$-$C_{10}$) aryl may include, but not limited to phenyl, halogen substituted phenyl, aliphatic substituted phenyl, aromatic substituted phenyl and the like; the ($C_6$-$C_{10}$) aryl may include, but not limited to 2-naphthyl, substituted 2-naphthyl and the like.

For example, the heteroaryl may include, but not limited to pyridinyl, furanyl, halogen substituted pyridinyl and the like.

For example, the pharmaceutically acceptable salt in the disclosure may comprise salts of the compound that modified by non-toxic acids or alkalis and the like.

For example, the pharmaceutical acceptable acid-additive salts of the compound in the disclosure may include, but not limited to inorganic acid salts, such as, hydrochloric acid, hydrobromic acid, nitric acid, carbonic acid, phosphorous acid and the like; organic acid salts, such as, maleic acid, benzenesulfonic acid, p-methyl benzenesulfonic acid, citric acid, tartaric acid, and the like.

For another example, the pharmaceutical acceptable alkali-additive salts of the compound in the disclosure may include, but not limited to sodium, potassium, calcium, ammonium or magnesium salts.

For example, the solvate of the compound in the disclosure may comprise the hydrate compound which the compound molecule trap different molar ratio of water molecules, the alcoholate compound which the compound molecule trap different molar ratio of alcohol molecule and the like.

For example, the ($C_6$-$C_{10}$) aryl of $R^1$ may be substituted with one or more substituents selected from $R^4$, said $R^4$ may be independently selected from H, halogen, ($C_1$-$C_8$) alkyl, ($C_1$-$C_8$) haloalkyl, ($C_1$-$C_8$) alkoxy, ($C_1$-$C_8$) alkylamino, Sub A and Sub B. The substituted ($C_6$-$C_{10}$) aryl may include, but not limited to, phenyl, halogen substituted phenyl, ($C_1$-$C_8$)

alkyl substituted phenyl, $(C_1-C_8)$ haloalkyl substituted phenyl, $(C_1-C_8)$ alkoxy substituted phenyl, $(C_1-C_8)$ alkylamino substituted phenyl, Sub A or Sub B substituted phenyl and the like.

For example, the $(C_1-C_9)$ heteroaryl of $R^1$ may be substituted with one or more substituents $R^4$, said $R^4$ may be independently selected from H, halogen, $(C_1-C_8)$ alkyl, $(C_1-C_8)$ haloalkyl, $(C_1-C_8)$ alkoxy, $(C_1-C_8)$ alkylamino, Sub A and Sub B.

For example, the phenyl of $R^1$ in formula (II) may be substituted with one or more substituents $R^4$, said $R^4$ may be independently selected from H, halogen, $(C_1-C_8)$ alkyl, $(C_1-C_8)$ haloalkyl, $(C_1-C_8)$ alkoxy, $(C_1-C_8)$ alkylamino, Sub A and Sub B.

For example, the $(C_6-C_{10})$ aryl of $R^2$ may be substituted with one or more substituents $R^4$, said $R^4$ may be independently selected from H, halogen, $(C_1-C_8)$ alkyl, $(C_1-C_8)$ haloalkyl, $(C_1-C_8)$ alkoxy, $(C_1-C_8)$ alkylamino, Sub A and Sub B.

For example, the $(C_1-C_9)$ heteroaryl of $R^2$ may be substituted with one or more substituents $R^4$, said $R^4$ may be independently selected from H, halogen, $(C_1-C_8)$ alkyl, $(C_1-C_8)$ haloalkyl, $(C_1-C_8)$ alkoxy, $(C_1-C_8)$ alkylamino, Sub A and Sub B.

For example, the phenyl of $R^2$ in formula (II) may be substituted with one or more substituents $R^4$, said $R^4$ may be independently selected from H, halogen, $(C_1-C_8)$ alkyl, $(C_1-C_8)$ haloalkyl, $(C_1-C_8)$ alkoxy, $(C_1-C_8)$ alkylamino, Sub A and Sub B.

For example, the $(C_6-C_{10})$ aryl of $R^3$ may be substituted with one or more substituents $R^5$, said $R^5$ may be independently selected from H, halogen, $(C_1-C_8)$ alkyl, $(C_2-C_8)$ alkenyl, $(C_2-C_8)$ alkynyl, $(C_1-C_8)$ alkoxy, $(C_1-C_8)$ haloalkyl, $(C_1-C_8)$ alkylamino, $(C_2-C_9)$ heterocycloalkyl, $(C_6-C_{10})$ aryl, $(C_1-C_9)$ heteroaryl, Sub A and Sub B.

For example, $R^5$ may be $(C_2-C_9)$ heterocycloalkyl, $(C_6-C_{10})$ aryl or $(C_1-C_9)$ heteroaryl and the like.

For example, $R^5$ may be $(C_2-C_9)$ heterocycloalkyl, $(C_6-C_{10})$ aryl or $(C_1-C_9)$ heteroaryl, said $R^5$ may be unsubstituted or substituted with one or more substituents $R^6$, said $R^6$ is independently selected from H, halogen, $(C_1-C_8)$ alkyl, $(C_1-C_8)$ alkoxy, $(C_1-C_8)$ hydroxyalkyl.

For example, the X in compound of formula (II) may be Cl or F.

For example, the X in compound of formula (II) may be Cl or F, the $R^1$ may be a group selected from $(C_6-C_{10})$ aryl and $(C_1-C_9)$ heteroaryl, which include, but not limited to phenyl, halogen substituted phenyl and the like; $R^2$ may be a group selected from H, $(C_6-C_{10})$ aryl and $(C_1-C_9)$ heteroaryl, which include, but not limited to H, phenyl, halogen substituted phenyl and the like; the $R^3$ may be a group selected from $(C_6-C_{10})$ aryl and $(C_1-C_9)$ heteroaryl which include, but not limited to phenyl, halogen substituted phenyl, $(C_1-C_8)$ alkyl substituted phenyl, $(C_2-C_8)$ alkenyl substituted phenyl, $(C_2-C_8)$ alkynyl substituted phenyl, $(C_1-C_8)$ alkoxy substituted phenyl, $(C_1-C_8)$ haloalkyl substituted phenyl, $(C_1-C_8)$ alkylamino substituted phenyl, $(C_2-C_9)$ heterocycloalkyl substituted phenyl, $(C_6-C_{10})$ aryl substituted phenyl, $(C_1-C_9)$ heteroaryl substituted phenyl and, Sub A or Sub B substituted phenyl, and the like.

For example, the X in compound of formula (II) may be Cl or F, the $R^1$ may be a group selected from substituted $(C_6-C_{10})$ aryl and substituted $(C_1-C_9)$ heteroaryl, in which the substituent is selected from H, halogen, $(C_1-C_8)$ alkyl, $(C_1-C_8)$ haloalkyl, $(C_1-C_8)$ alkoxy, $(C_1-C_8)$ alkylamino, Sub A and Sub B, and the $R^1$ may include, but not limited to phenyl, halogen substituted phenyl and the like; $R^2$ may be a group selected from H, substituted $(C_6-C_{10})$ aryl and substituted $(C_1-C_9)$ heteroaryl, in which, the substituent is selected from H, halogen, $(C_1-C_8)$ alkyl, $(C_1-C_8)$ haloalkyl, $(C_1-C_8)$ alkoxy, $(C_1-C_8)$ alkylamino, Sub A and Sub B, and the $R^2$ may include, but not limited to H, phenyl, halogen substituted phenyl and the like; $R^3$ may be a group selected from substituted $(C_6-C_{10})$ aryl and substituted $(C_1-C_9)$ heteroaryl, in which, the substituent is selected from H, halogen, $(C_1-C_8)$ alkyl, $(C_2-C_8)$ alkenyl, $(C_2-C_8)$ alkynyl, $(C_1-C_8)$ alkoxy, $(C_1-C_8)$ haloalkyl, $(C_1-C_8)$ alkylamino, $(C_2-C_9)$ heterocycloalkyl, $(C_6-C_{10})$ aryl, $(C_1-C_9)$ heteroaryl, Sub A and Sub B, and the $R^3$ may include, but not limited to phenyl, halogen substituted phenyl, $(C_1-C_8)$ alkyl substituted phenyl, $(C_2-C_8)$ alkenyl substituted phenyl, $(C_2-C_8)$ alkynyl substituted phenyl, $(C_1-C_8)$ alkoxy substituted phenyl, $(C_1-C_8)$ haloalkyl substituted phenyl, $(C_1-C_8)$ alkylamino substituted phenyl, $(C_2-C_9)$ heterocycloalkyl substituted phenyl, $(C_6-C_{10})$ aryl substituted phenyl, $(C_1-C_9)$ heteroaryl substituted phenyl and, Sub A or Sub B substituted phenyl, and the and the $R^3$ may include, but not limited to naphthyl, halogen substituted naphthyl, $(C_1-C_8)$ alkyl substituted naphthyl, $(C_2-C_8)$ alkenyl substituted naphthyl, $(C_2-C_8)$ alkynyl substituted naphthyl, $(C_1-C_8)$ alkoxy substituted naphthyl, $(C_1-C_8)$ haloalkyl substituted naphthyl, $(C_1-C_8)$ alkylamino substituted naphthyl, $(C_2-C_9)$ heterocycloalkyl substituted naphthyl, $(C_6-C_{10})$ aryl substituted naphthyl, $(C_1-C_9)$ heteroaryl substituted naphthyl and, Sub A or Sub B substituted naphthyl, and the like.

For example, the X in compound of formula (II) may be Cl or F, the $R^1$ may be phenyl, the $R^2$ may be a group selected from H, substituted $(C_6-C_{10})$ aryl and substituted $(C_1-C_9)$ heteroaryl, in which, the substituent is selected from H, halogen, $(C_1-C_8)$ alkyl, $(C_1-C_8)$ haloalkyl, $(C_1-C_8)$ alkoxy, $(C_1-C_8)$ alkylamino, Sub A and Sub B, and the $R^2$ may include, but not limited to H, phenyl, halogen substituted phenyl and the like; the $R^3$ may be a group selected from substituted $(C_6-C_{10})$ aryl and substituted $(C_1-C_9)$ heteroaryl, in which, the substituent is selected from H, halogen, $(C_1-C_8)$ alkyl, $(C_2-C_8)$ alkenyl, $(C_2-C_8)$ alkynyl, $(C_1-C_8)$ alkoxy, $(C_1-C_8)$ haloalkyl, $(C_1-C_8)$ alkylamino, $(C_2-C_9)$ heterocycloalkyl, $(C_6-C_{10})$ aryl, $(C_1-C_9)$ heteroaryl and, Sub A and Sub B, and the $R^3$ may include, but not limited to phenyl, halogen substituted phenyl, $(C_1-C_8)$ alkyl substituted phenyl, $(C_2-C_8)$ alkenyl substituted phenyl, $(C_2-C_8)$ alkynyl substituted phenyl, $(C_1-C_8)$ alkoxy substituted phenyl, $(C_1-C_8)$ haloalkyl substituted phenyl, $(C_1-C_8)$ alkylamino substituted phenyl, $(C_2-C_9)$ heterocycloalkyl substituted phenyl, $(C_6-C_{10})$ aryl substituted phenyl, $(C_1-C_9)$ heteroaryl substituted phenyl and, Sub A or Sub B substituted phenyl, and the like.

For example, the X in compound of formula (II) may be Cl or F, the $R^1$ may be substituted phenyl, in which the substituent is selected from H, halogen, $(C_1-C_8)$ alkyl, $(C_1-C_8)$ haloalkyl, $(C_1-C_8)$ alkoxy, $(C_1-C_8)$ alkylamino, Sub A and Sub B, and the $R^1$ may include, but not limited to phenyl, halogen substituted phenyl and the like; the $R^2$ may be a group selected from H, halogen, $(C_1-C_8)$ alkyl, $(C_1-C_8)$ haloalkyl, $(C_1-C_8)$ alkoxy, $(C_1-C_8)$ alkylamino, Sub A and Sub B, and the $R^2$ may include, but not limited to H, phenyl, halogen substituted phenyl and the like; the $R^3$ may be a group selected from substituted $(C_6-C_{10})$ aryl and substituted $(C_1-C_9)$ heteroaryl, in which, the substituent is selected from H, halogen, $(C_1-C_8)$ alkyl, $(C_2-C_8)$ alkenyl, $(C_2-C_8)$ alkynyl, $(C_1-C_8)$ alkoxy, $(C_1-C_8)$ haloalkyl, $(C_1-C_8)$ alkylamino, $(C_2-C_9)$ heterocycloalkyl, $(C_6-C_{10})$ aryl, $(C_1-C_9)$ heteroaryl, Sub A and Sub B, and the $R^3$ may include, but not limited to phenyl, halogen substituted phenyl, $(C_1-C_8)$ alkyl substituted phenyl, $(C_2$-$C_8)$ alkenyl substituted phenyl, $(C_2$-$C_8)$ alkynyl substituted phenyl, $(C_1$-$C_8)$ alkoxy substituted phenyl, $(C_1$-$C_8)$ haloalkyl substituted phenyl, $(C_1$-$C_8)$ alkylamino substituted phenyl, $(C_2$-$C_9)$ heterocycloalkyl substituted phenyl, $(C_6$-$C_{10})$ aryl substituted phenyl, $(C_1$-$C_9)$ heteroaryl substituted phenyl, Sub A or Sub B substituted phenyl, and the $R^3$ may include, but not limited to naphthyl, halogen substituted naphthyl, $(C_1$-$C_8)$ alkyl substituted naphthyl, $(C_2$-$C_8)$ alkenyl substituted naphthyl, $(C_2$-$C_8)$ alkynyl substituted naphthyl, $(C_1$-$C_8)$ alkoxy substituted naphthyl, $(C_1$-$C_8)$ haloalkyl substituted naphthyl, $(C_1$-$C_8)$ alkylamino substituted naphthyl, $(C_2$-$C_9)$ heterocycloalkyl substituted naphthyl, $(C_6$-$C_{10})$ aryl substituted naphthyl, $(C_1$-$C_9)$ heteroaryl substituted naphthyl and, Sub A or Sub B substituted naphthyl, and the like.

For example, the compound of the disclosure may be selected from:

EX-1

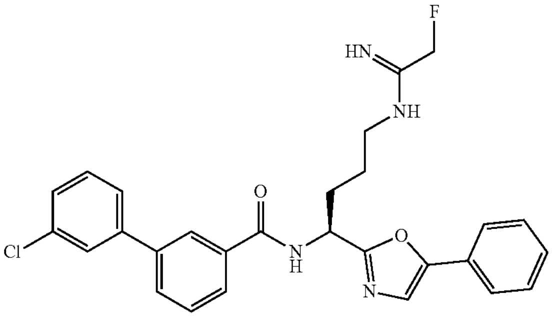

,

EX-2

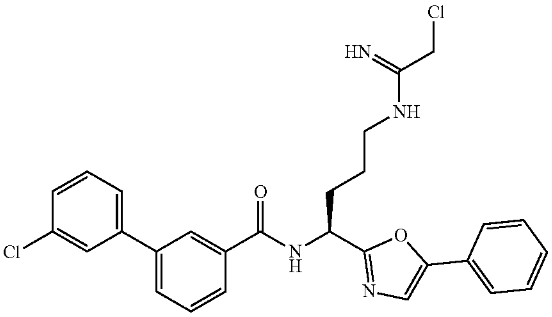

,

EX-3

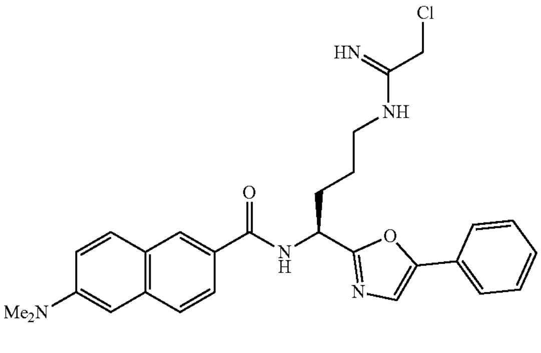

,

EX-4

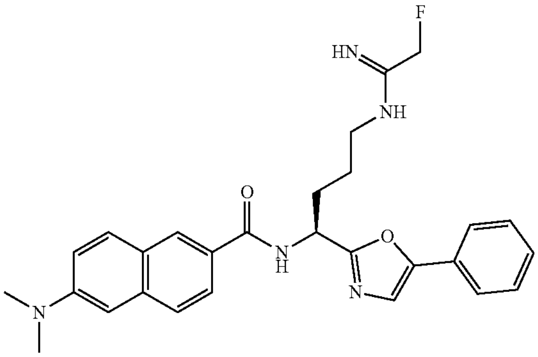

,

EX-5

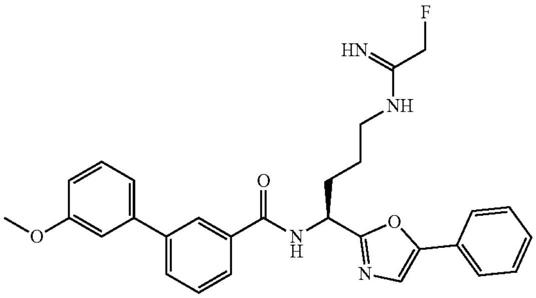

,

EX-6

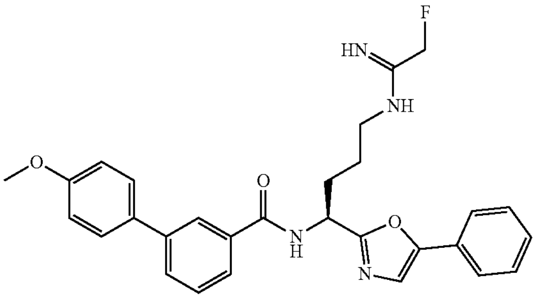

,

EX-7

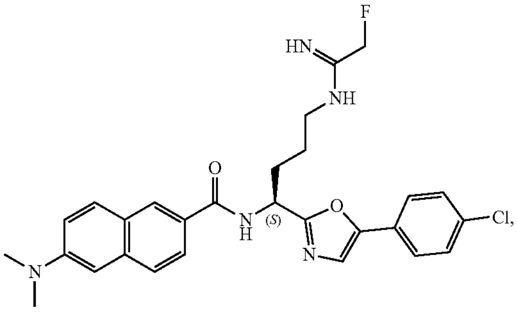

,

EX-8

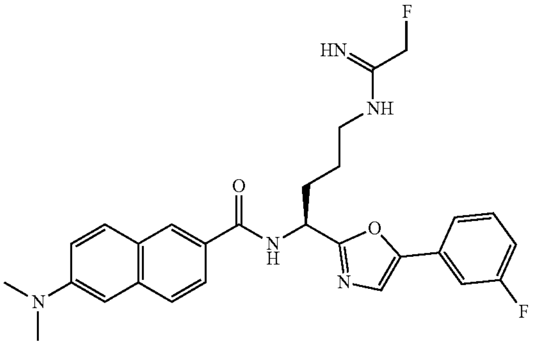

,

-continued
EX-9
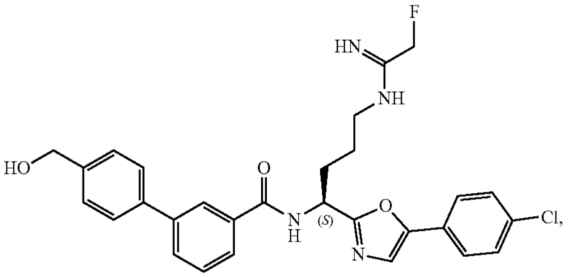
EX-10
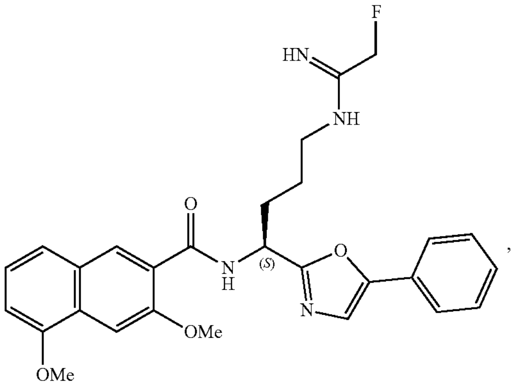
EX-11
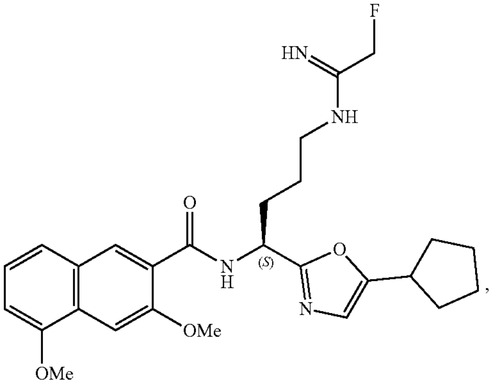
EX-12
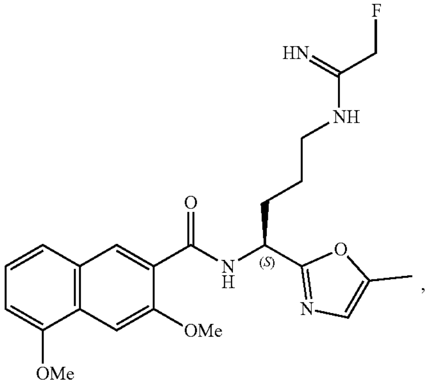
EX-13
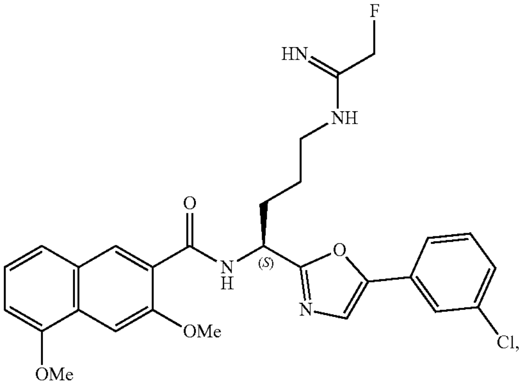
EX-14
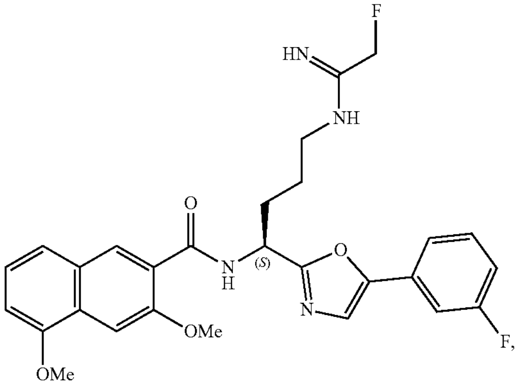
EX-15
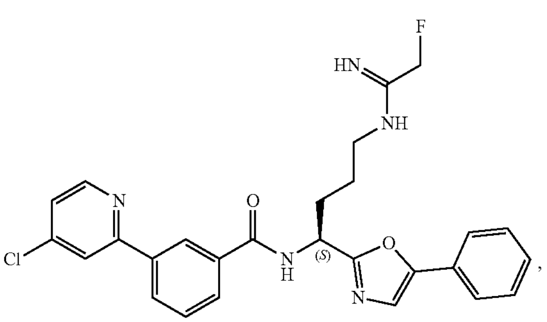
EX-16
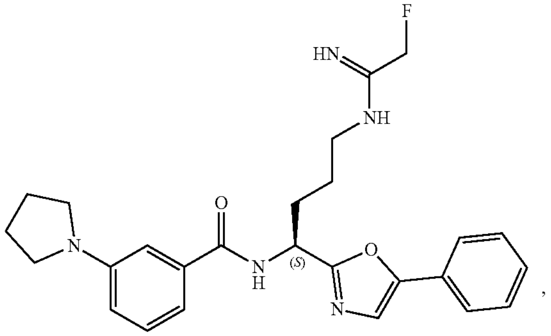

-continued
EX-17
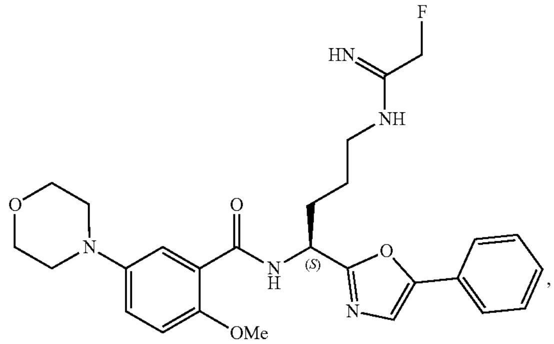
,
EX-18
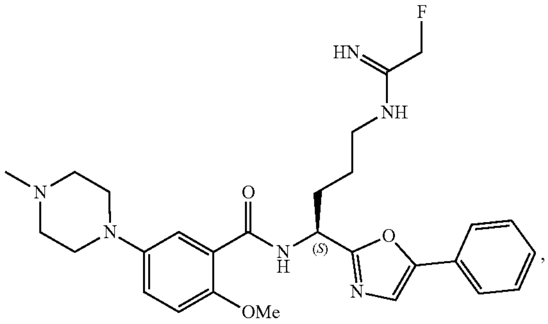
,
EX-19
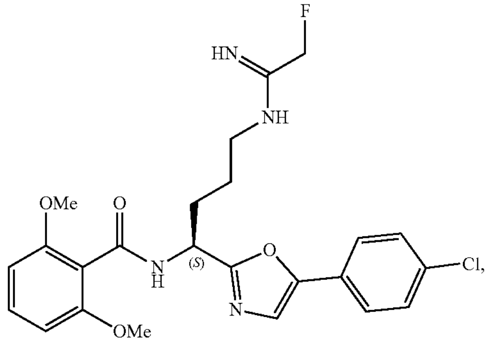
EX-20
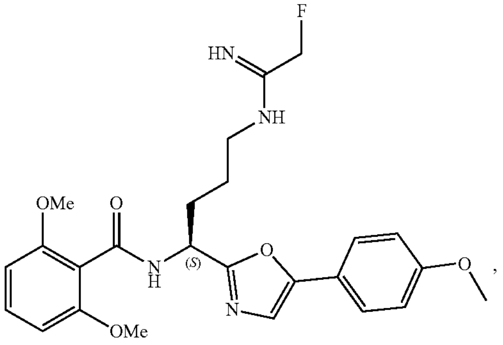
,
EX-21
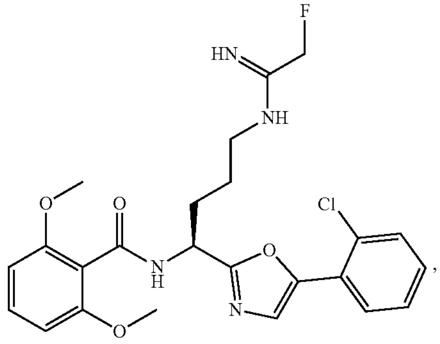
,
EX-22
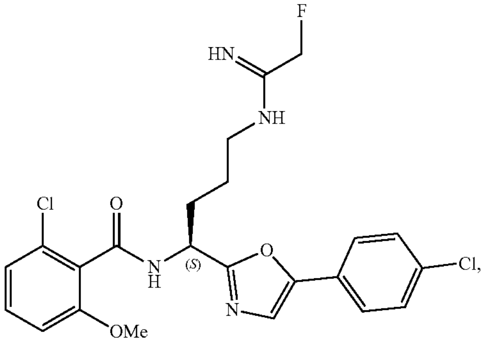
EX-23
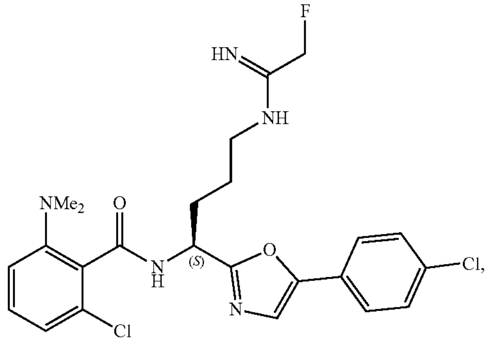
EX-24
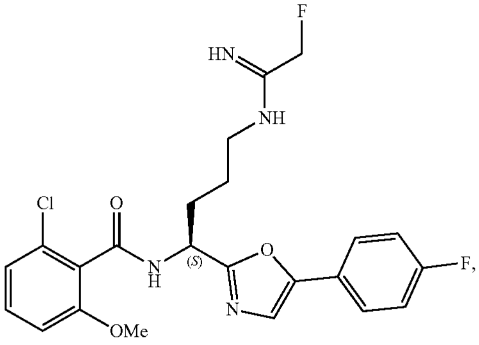

-continued
EX-25
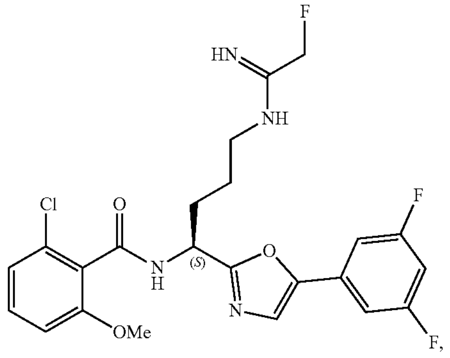
EX-26
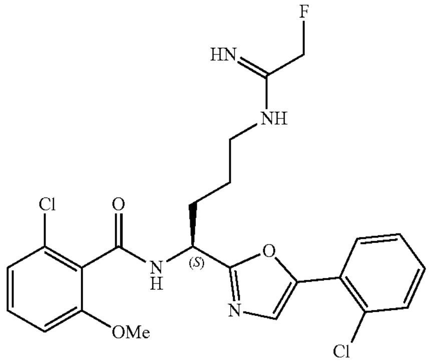
,
EX-27
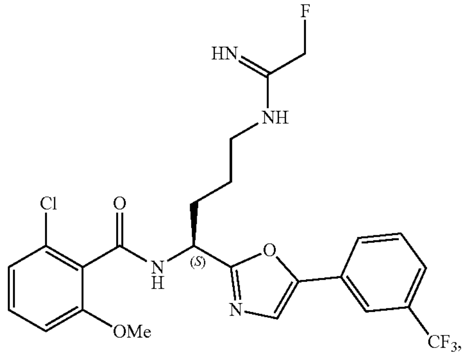
EX-28
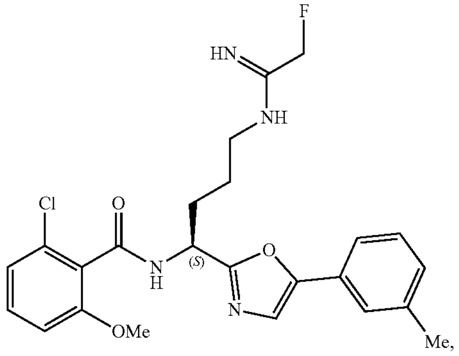
EX-29
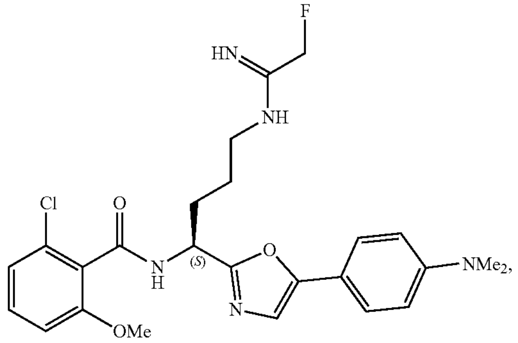
EX-30
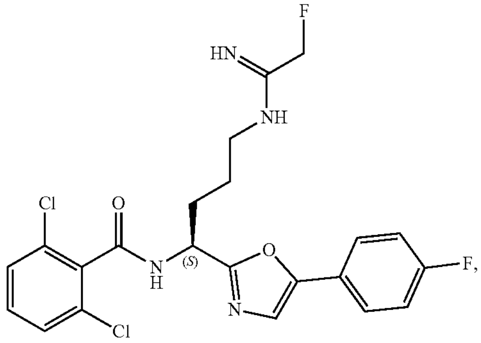
EX-31
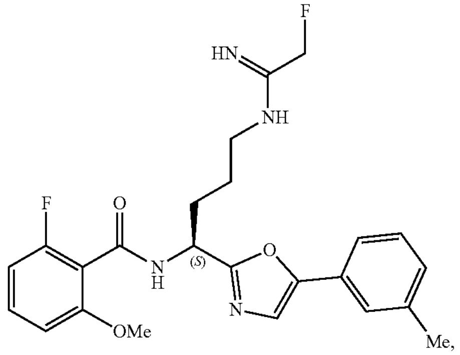
EX-32
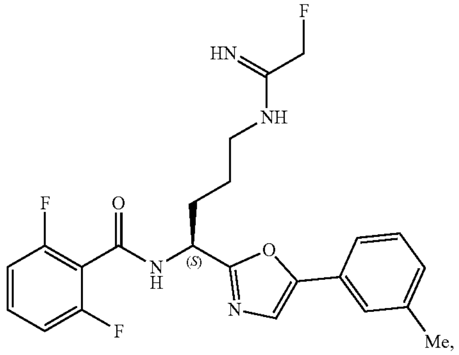

-continued
EX-33
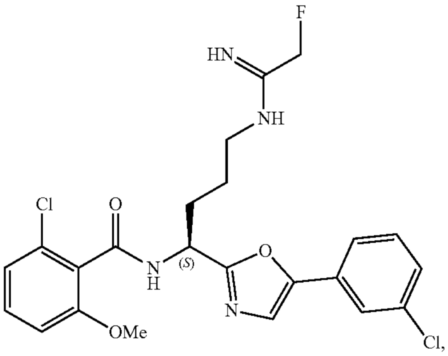
,
EX-34
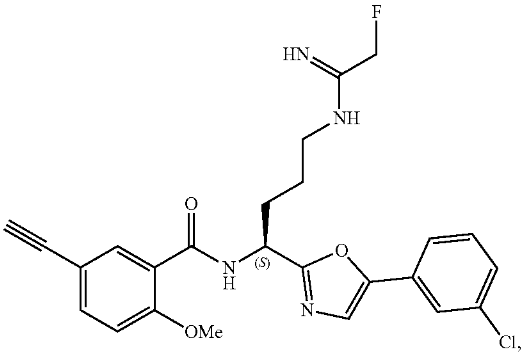
,
EX-35
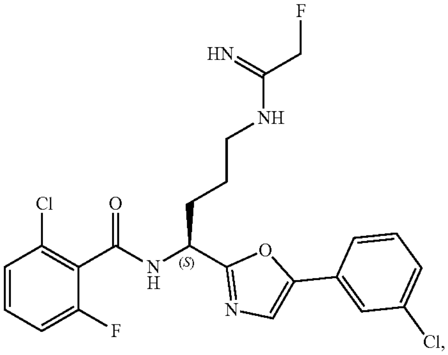
,
EX-36
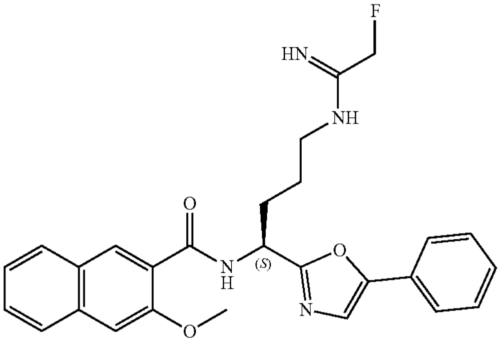
,
EX-37
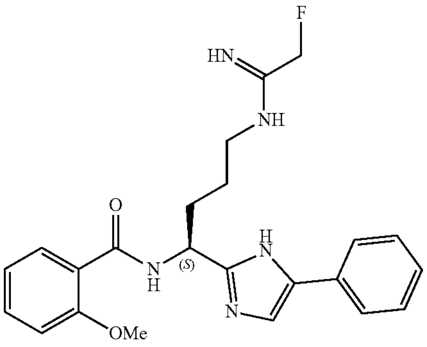
,
EX-38
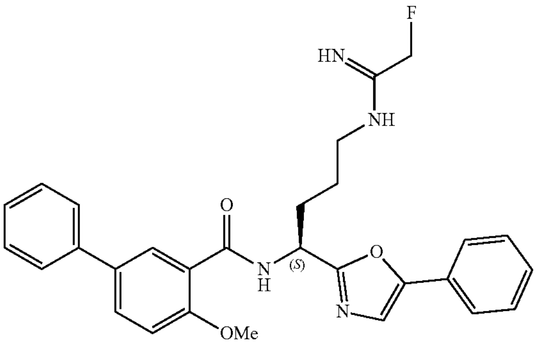
,
EX-39
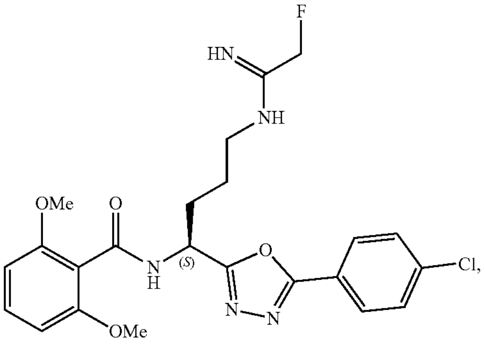
,
EX-40
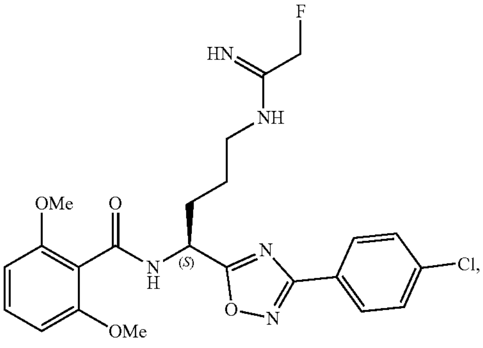
, -continued

EX-41

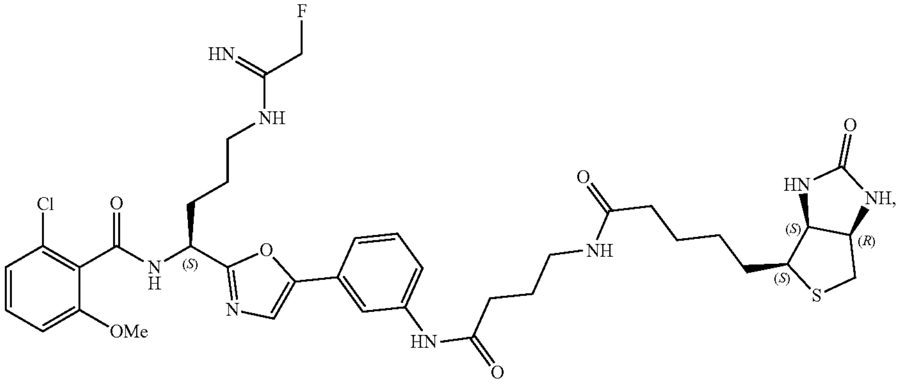

, and

EX-42

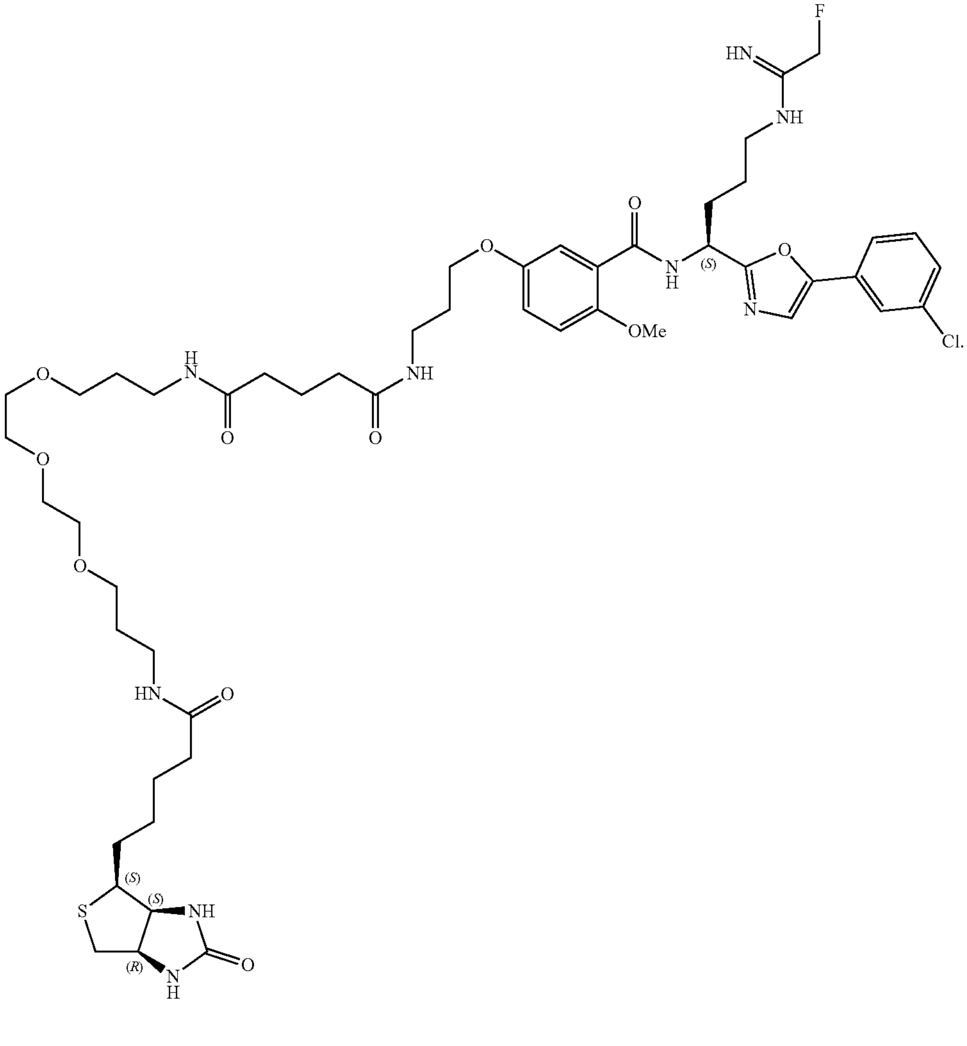

Cl.

For example, the compound of the disclosure may be compound EX-1.

For example, the compound of the disclosure may be compound EX-4.

In one aspect, the present disclosure provides a composition comprising the compound of the disclosure, or a pharmaceutically acceptable salt or solvate thereof.

For example, the composition may include compound of formula (I), compound of formula (II), compound selected from EX-1 to EX-42.

For example, the composition may include the pharmaceutically acceptable salt of compound (I), the pharmaceutically acceptable salt of compound (II), the pharmaceutically acceptable salt of compound selected from EX-1 to EX-42.

For example, the composition may include the solvate compound of formula (I), the solvate compound of formula (II), the solvate compound selected from EX-1 to EX-42.

The composition further comprising a pharmaceutically acceptable carrier. For example, the carrier may include, but not limited to sugars, such as lactose, glucose and sucrose; starches, such as corn starch and potato starch; cellulose, and its derivatives, such as sodium carboxymethyl cellulose, ethyl cellulose and cellulose acetate; powdered tragacanthin; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

The composition comprises a therapeutically effective amount of the compound of the disclosure, or a pharmaceutically acceptable salt of the compound of the disclosure or solvate compound of the disclosure.

The therapeutically effective amount means an amount of the subject composition that is enough to treat, ameliorate, or prevent an identified disease or condition, or to exhibit a detectable therapeutic or inhibitory effect. The specific amount/concentration of the active agent comprised may vary according to the method of administration and the need of a patient, and can be determined based on e.g., volume, viscosity, and/or body weight of a patient etc. It shall be understood that the specific doses may be conveniently adjusted by a skilled person in the art (e.g., a doctor or a pharmacist) based on conditions of a specific patient, formulation, and/or disease.

In one aspect, the present disclosure provides a method for preparing a PAD inhibitor, comprising providing a compound of formula (I), compound of formula (II), compound selected from EX-1 to EX-42, the pharmaceutically acceptable salt of compound (I), the pharmaceutically acceptable salt of compound (II), the pharmaceutically acceptable salt of compound selected from EX-1 to EX-42 or the solvate compound of formula (I), the solvate compound of formula (II), the solvate compound selected from EX-1 to EX-42.

The PAD inhibitor may be an inhibitor which could inhibit the function of PAD, such as PAD1, PAD2, PAD3, PAD4, PAD6 and the like. The function of PAD may be catalyzing the conversion of arginine residues to citrulline residues.

For example, the PAD inhibitor may be a PAD2 or PAD4 inhibitor.

In one aspect, the present disclosure provides the compound, or a pharmaceutically acceptable salt of solvate thereof, for use in treating a disease or disorder. In one aspect, the present disclosure a method of treating a disease or disorder comprising administering to a subject in need thereof the compound, or a pharmaceutically acceptable salt of solvate thereof. In some embodiments, wherein said diseases or disorders are various diseases or disorders in oncology or immunology associated with PAD4, The method according to this, wherein said diseases or disorders are described in detail, herein, and include, cancers and their related metastatic cancers for example lung cancer, liver cancer, blood cancer, esophageal cancer, breast cancer, colon cancer, as well as rheumatoid arthritis, multiple sclerosis, vasculitis, systemic lupus erythematosus, ulcerative colitis, cystic fibrosis, asthma, cutaneous lupus erythematosis, psoriasis. ischemia-reperfusion injury, and immune responses induced during transplant rejection.

In one aspect, the present disclosure provides a use of the compound of the disclosure, or a pharmaceutically acceptable salt or solvate thereof, in the preparation of a medicament for treating diseases or disorders in oncology or immunology associated with PAD4. For example, the diseases or disorders wherein said are described in detail, herein, and include cancers and their related metastatic cancers for example lung cancer, liver cancer, blood cancer, esophageal cancer, breast cancer, colon cancer, as well as rheumatoid arthritis, multiple sclerosis, vasculitis, systemic lupus erythematosus, ulcerative colitis, cystic fibrosis, asthma, cutaneous lupus erythematosis, psoriasis. ischemia-reperfusion injury, and immune responses induced during transplant rejection.

In one aspect, the present disclosure provides a method for treating a disease or disorder, comprising administering to a subject in need thereof a compound of the disclosure, or a pharmaceutically acceptable salt or solvate thereof. In some embodiments, wherein said diseases or disorders are described in detail, herein, and include, cancers and their related metastatic cancers for example lung cancer, liver cancer, blood cancer, esophageal cancer, breast cancer, colon cancer, as well as rheumatoid arthritis, multiple sclerosis, vasculitis, systemic lupus erythematosus, ulcerative colitis, cystic fibrosis, asthma, cutaneous lupus erythematosis, psoriasis. ischemia-reperfusion injury, and immune responses induced during transplant rejection. For example, the administration form may comprise oral administration as a tablet, capsule, pill, powder, sustained release formulations, solution, suspension and the like; parenteral injection as a sterile solution, suspension or emulsion and the like; topical administration as an ointment or cream and like; or rectal administration as a suppository and the like.

In one aspect, the present disclosure provides a method for synthesizing the compound of the disclosure. The specific synthesis procedure of the compounds of the disclosure is illustrated in the examples, where the terms, such as I-1, I-2, I-3, I-4, I-5, I-6, I-7, I-8 I-2a, I-3a and the like, refers to the intermediates during the synthesis procedure.

For example, the intermediate I-5, I-5a, I-5b, I-5c may be a compound of formula:

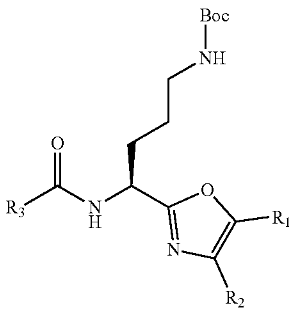

wherein, $R^1$ may be a ($C_6$-$C_{10}$) aryl such as phenyl, halogen substituted phenyl and the like, $R^2$ may be H, $R^3$ may be a ($C_6$-$C_{10}$) aryl such as halogen substituted phenyl, aromatic substituted phenyl and the like.

For example, the inter mediate I-7, I-7a, I-7d may be a compound of formula:

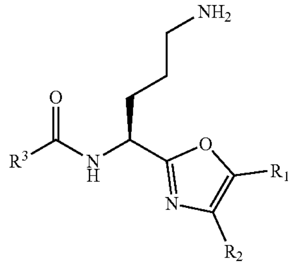

wherein, $R^1$ may be a ($C_6$-$C_{10}$) aryl such as phenyl, halogen substituted phenyl and the like, $R^2$ may be H, $R^3$ may be a ($C_6$-$C_{10}$) aryl such as aromatic substituted phenyl, N-linked aliphatic substituted 2-naphthyl and the like.

Compound EX-1 is synthesized by a method of 8 steps starting from tert-butyl (2S)-2-amino-5-[[(benzyloxy)carbonyl]amino]pentanoate hydrochloride. As illustrated in the synthesis procedure, step 1 is a acylation between n-tert-butyl (2S)-2-amino-5-[[(benzyloxy)carbonyl]amino]pentanoate hydrochloride and 3-bromobenzoic acid which resulted in intermediate I-1. Step 2 is a hydrolysis reaction of intermediate I-1 which result in intermediate I-2. Step 3 is an acylation of I-2 which resulted in I-3. Step 4 is an intramolecular cyclization of I-3 which resulted in I-4. Step 5 is an acylation to result in intermediate I-5. Step 6 is the Suzuki coupling reaction between I-5 and 3-chlorophenylboronic acid which resulted in I-6. Step 7 is the hydrolysis reaction of intermediate I-6 to result in I-7. Step 8 is the synthesis of substrate I-8. Step 9 is the reaction between I-7 and I-8 which result in the compound EX-1.

Compound EX-2 is synthesized by the reaction between I-7 and I-8a, wherein the I-8a is synthesized in the same way of synthesizing I-8.

The method of synthesizing compound EX-3 is similar to the synthesis of compound EX-2, wherein the step 6 in the synthesis of compound EX-1 is not needed in this procedure.

The method of synthesizing compound EX-54, EX-7 is similar to the synthesis of compound EX-3.

The method of synthesizing compound EX-5, EX-6, EX-9 is similar to compound EX-1.

Compound EX-10 is synthesized by a method of 9 steps starting from tert-butyl (S)-2-amino-5-(((benzyloxy)carbonyl)amino)pentanoate. Step 1 is the reaction between tert-butyl (S)-2-amino-5-(((benzyloxy)carbonyl)amino)pentanoate and phthalic anhydride which resulted in intermediate I-11. Step 2 is a hydrolysis reaction of intermediate I-11 which result in intermediate I-12. Step 3 is acylation of I-12 which resulted in I-13. Step 4 is an intramolecular cyclization of I-13 which resulted in I-14. Step 5 is an acylation to result in intermediate I-15. Step 6 is a deprotection of I-15 to result in I-16. Step 7 is an acylation to result in intermediate I-17. Step 8 is the hydrolysis reaction of intermediate I-17 to result in I-18. Step 9 is the reaction between I-18 and I-8 which resulted in compound EX-10.

Compound EX-15 is synthesized from intermediate I-5. The first two steps are Suzuki coupling reactions, and step 3 is an acylation to result in intermediate I-7e. The last step is the reaction between I-7e and 18 which resulted in compound EX-15.

Abbreviations

AcOH Acetic acid
aq. Aqueous
br broad
Bn Benzyl
d doublet
CDI Carbonyldiimidazole
DBU 1,8-Diazabicyclo[5.4.0]undec-7-ene
DCC N,N'-Dicyclohexylcarbodiimide
DCE 1,2-Dichloroethane
DCM Dichloromethane
DIEA, DIPEA N,N-diisopropylethylamine
DME Dimethoxyethane
DMF N,N-Dimethylformamide
DMSO Dimethyl sulphoxide
EA, EtOAc Ethyl Acetate
EDCI 1,3-Propanediamine, N3-(ethylcarbonimidoyl)-N1,N1-dimethyl-, hydrochloride
eq., equiv. Equivalent
HATU N,N,N',N'-Tetramethyl-O-(7-azabenzotriazol-1-yl)uronium-hexafluorophospate
HOBT Hydroxybenzotriazole
IPA Isopropanol
NBS N-Bromosuccinimide
NMR Nuclear magnetic resonance
PE Petroleum ether
prep-HPLC Preparative High Pressure Liquid Chromatography
prep-TLC Preparation Thin-layer chromatography
RT, rt Room temperature
s singlet
t triplet
TEA Triethylamine
TLC Thin-layer chromatography
THF Tetrahydrofuran
TFA Trifluoroacetic acid
V, v Volume

EXAMPLES

The following examples are set forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); nt, nucleotide(s); i.m., intramuscular(ly); i.p., intraperitoneal(ly); s.c., subcutaneous(ly); and the like.

Example 1 Synthesis of (S)-3'-chloro-N-(4-(2-fluoroacetimidamido)-1-(5-phenyloxazol-2-yl)butyl)-[1,1'-biphenyl]-3-carboxamide (EX-1)
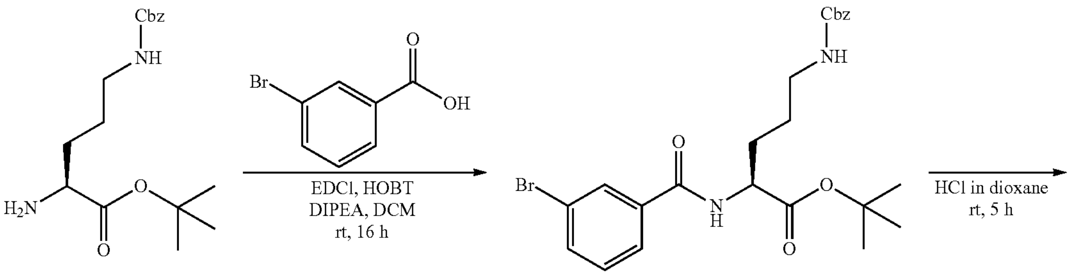
1-1
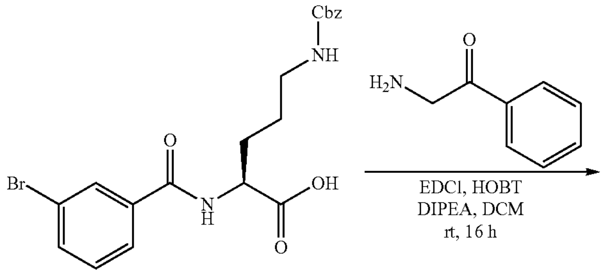
1-2
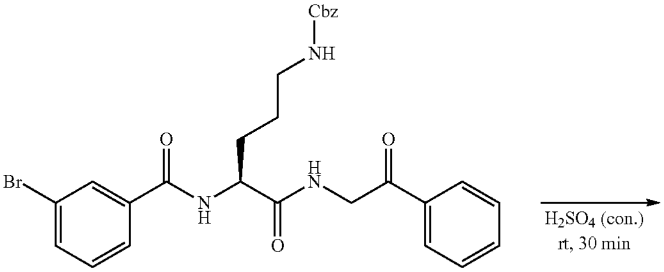
1-3
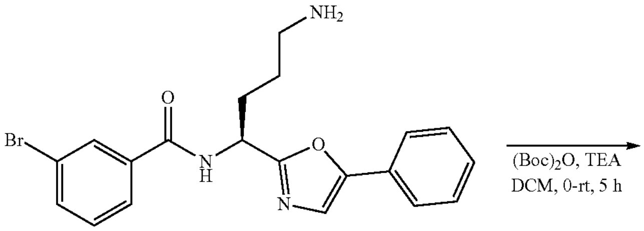
1-4
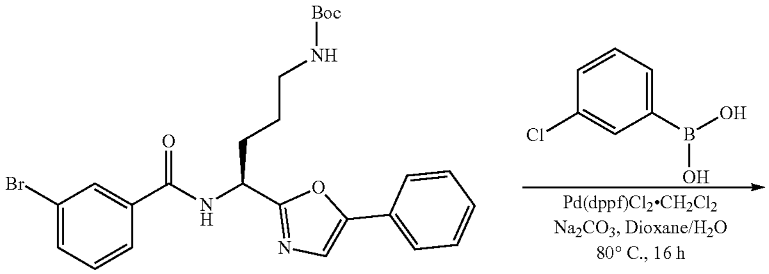
1-5

-continued
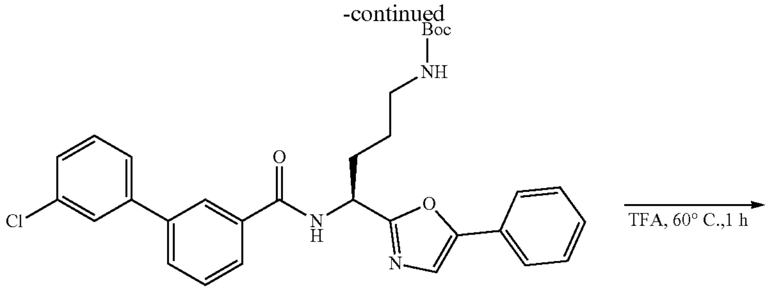
1-6
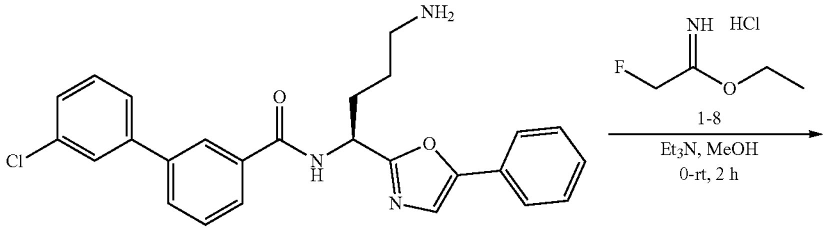
1-7
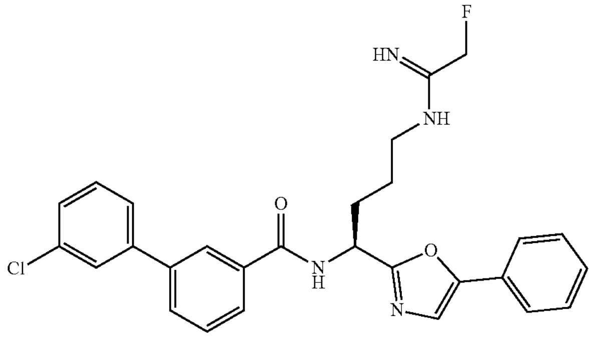
EX-1
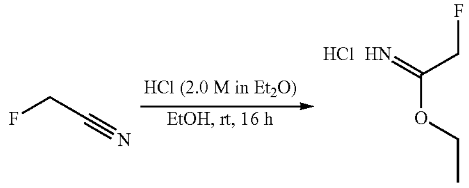
1-8
Step 1: tert-Butyl (2S)-5-[[(benzyloxy)carbonyl]amino]-2-[(3-bromophenyl)formamido]pentanoate (1-1)
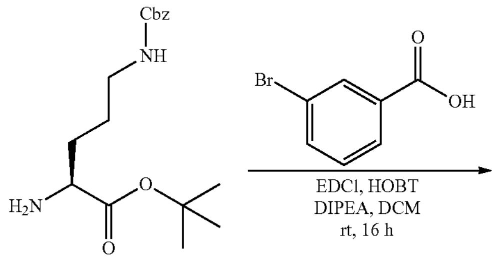
-continued
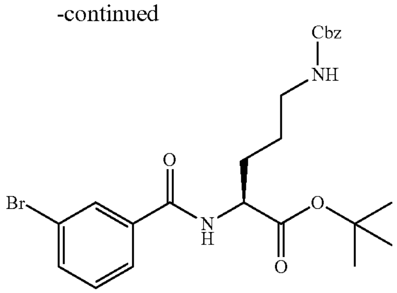
1-1
Into a 250-mL round-bottom flask purged and maintained with an inert atmosphere of nitrogen, was placed tert-butyl (2S)-2-amino-5-[[(benzyloxy)carbonyl]amino]pentanoate hydrochloride (5.00 g, 13.9 mmol, 1.00 equiv.), 3-bromobenzoic acid (2.94 g, 14.6 mmol, 1.05 equiv.), HOBT (2.82 g, 20.9 mmol, 1.50 equiv.), EDCI·HCl (4.01 g, 20.9 mmol, 1.50 equiv.) in DCM (20 mL). DIPEA (7.19 g, 55.6 mmol, 3.99 equiv.) was added at 0° C. The resulting solution was stirred at room temperature for 16 hours. The resulting mixture was concentrated under vacuum. The residue was purified by silica gel column chromatography to afford the product (1-1, 5.3 g, 75%). $^1$H NMR (300 MHz, DMSO-$d_6$): δ=8.74 (d, J=7.4 Hz, 1H), 8.07 (t, J=1.8 Hz, 1H), 7.87 (dt, J=7.8, 1.3 Hz, 1H), 7.76 (ddd, J=8.0, 2.1, 1.0 Hz, 1H), 7.46 (t, J=7.9 Hz, 1H), 7.40-7.25 (m, 6H), 5.00 (s, 2H), 4.34-4.21 (m, 1H), 3.03 (q, J=6.6 Hz, 2H), 1.74 (d, J=7.4 Hz, 1H), 1.56-1.47 (m, 2H), 1.40 (s, 9H), 1.21 (d, J=13.6 Hz, 1H). MS (ESI): m/z=505 [M+H]$^+$.

Step 2: (2S)-5-[[(Benzyloxy)carbonyl]amino]-2-[(3-bromophenyl)formamido]pentanoic acid (1-2)

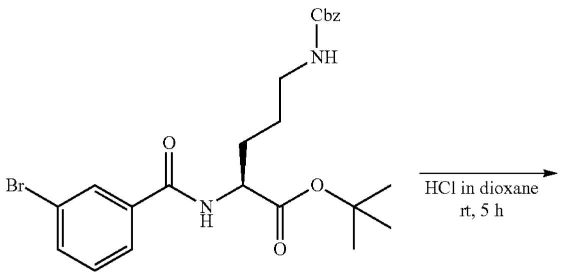

1-1

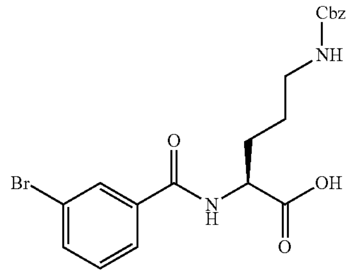

1-2

Into a 100-mL round-bottom flask was placed tert-butyl (2S)-5-[[(benzyloxy)carbonyl]amino]-2-[(3-bromophenyl) formamido]pentanoate (1-1, 2.00 g, 3.96 mmol, 1.00 equiv.) in 4N HCl in 1,4-dioxane (70 mL, 280 mmol, 70 equiv.). The resulting solution was stirred at room temperature for 5 hours. The resulting mixture was concentrated under vacuum. This resulted in 2 g of crude (2S)-5-[[(benzyloxy) carbonyl]amino]-2-[(3-bromophenyl)formamido]pentanoic acid (1-2) and used directly for the next step without further purification. MS (ESI): m/z=505 [M+H]$^+$.

Step 3: Benzyl N-[(4S)-4-[(3-bromophenyl)formamido]-4-[(2-oxo-2-phenylethyl)carbamoyl]butyl] carbamate (1-3)

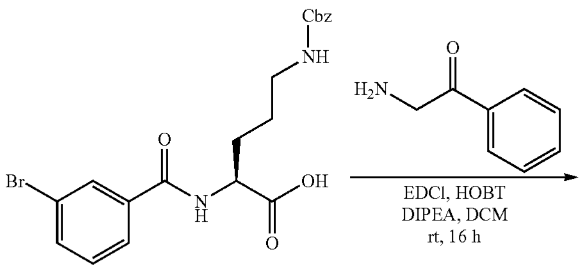

1-2

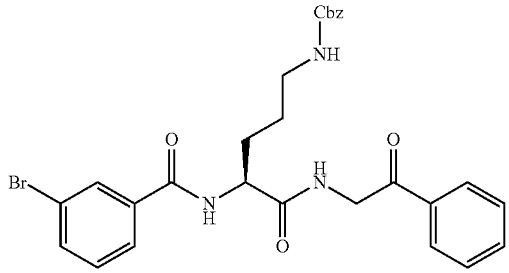

1-3

Into a 40-mL sealed tube purged and maintained with an inert atmosphere of nitrogen, was placed (2S)-5-[[(benzyloxy)carbonyl]amino]-2-[(3-bromophenyl)formamido]pentanoic acid (1-2, 1.00 g, 2.22 mmol, 1.00 equiv.), 2-amino-1-phenylethan-1-one hydrochloride (419 mg, 2.44 mmol, 1.10 equiv.), EDCI·HCl (641 mg, 3.34 mmol, 1.50 equiv.) and HOBT (451 mg, 3.33 mmol, 1.50 equiv.) in $CH_2Cl_2$ (20 mL). DIPEA (1.14 g, 8.89 mmol, 3.99 equiv.) was added at 0° C. The resulting solution was stirred overnight at room temperature. After completion, the resulting mixture was purified by prep-TLC to provide the product (1-3, 1.03 g, 81.7%). $^1$H NMR (300 MHz, DMSO-$d_6$): δ=8.68 (d, J=8.0 Hz, 1H), 8.33 (t, J=5.5 Hz, 1H), 8.13 (t, J=1.8 Hz, 1H), 7.99 (dt, J=7.1, 1.3 Hz, 2H), 7.91 (dt, J=7.8, 1.3 Hz, 1H), 7.75 (ddd, J=8.0, 2.0, 1.0 Hz, 1H), 7.71-7.61 (m, 1H), 7.54 (dd, J=8.4, 7.0 Hz, 2H), 7.45 (t, J=7.9 Hz, 1H), 7.39-7.26 (m, 6H), 5.01 (s, 2H), 4.74-4.57 (m, 2H), 4.53 (d, J=8.4 Hz, 1H), 3.04 (q, J=6.5 Hz, 2H), 1.52 (d, J=8.4 Hz, 2H), 1.23 (s, 1H). MS (ESI): m/z=566 [M+H]$^+$.

Step 4: N-[(1S)-4-Amino-1-(5-phenyl-1,3-oxazol-2-yl)butyl]-3-bromobenzamide (1-4)

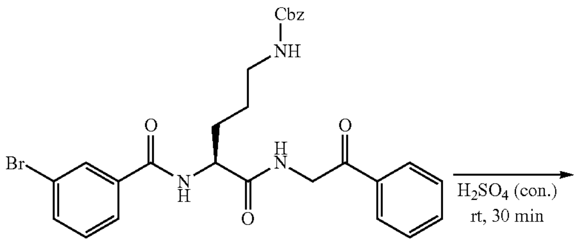

1-3

-continued

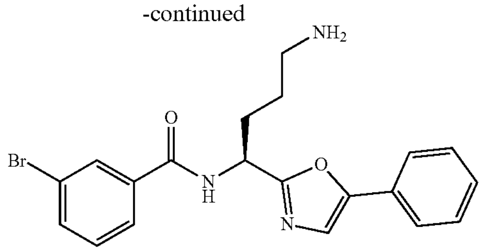

1-4

Into a 40-mL sealed tube, was placed benzyl N-[(4S)-4-[(3-bromophenyl)formamido]-4-[(2-oxo-2-phenylethyl)carbamoyl]butyl]carbamate (1-3, 1.00 g, 1.76 mmol, 1.00 equiv) in concentrated $H_2SO_4$ (20 mL, 375 mmol, 212 equiv.). The resulting solution was stirred for 30 min at room temperature. The resulting solution was diluted with water-ice. The pH was adjusted to 9 with NaOH (0.5 M). The solids were collected by filtration. The filtrate was extracted with ethyl acetate and dried over anhydrous sodium sulfate. The solids were filtered out. The filtrate was concentrated under vacuum. The residue was purified by Prep-TLC resulting in 560 mg (76%) of product (1-4). $^1H$ NMR (300 MHz, DMSO-$d_6$): δ=8.12 (s, 1H), 7.92 (d, J=7.8 Hz, 1H), 7.77 (s, 1H), 7.72-7.60 (m, 2H), 7.52-7.41 (m, 2H), 7.37 (d, J=8.2 Hz, 1H), 2.64 (s, 1H), 1.98 (s, 1H), 1.84 (s, 2H), 1.52 (s, 1H), 1.23 (s, 1H). MS (ESI): m/z=414 $[M+H]^+$.

Step 5: tert-Butyl N-[(4S)-4-[(3-bromophenyl)formamido]-4-(5-phenyl-1,3-oxazol-2-yl)butyl]carbamate (1-5)

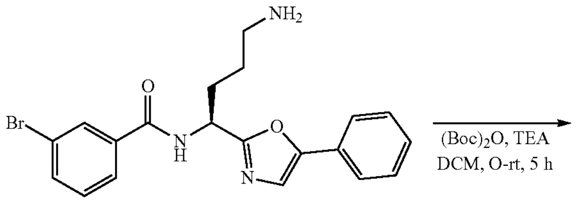

1-4

-continued

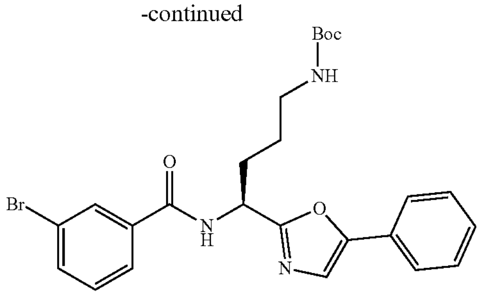

1-5

Into a 40-mL sealed tube purged and maintained with an inert atmosphere of nitrogen, was placed N-[(1S)-4-amino-1-(5-phenyl-1,3-oxazol-2-yl)butyl]-3-bromobenzamide (1-4, 500 mg, 1.20 mmol, 1.00 equiv) and $NEt_3$ (610 mg, 6.02 mmol, 5.00 equiv.) in $CH_2Cl_2$ (20 mL), $(Boc)_2O$ (263 mg, 1.20 mmol, 1.00 equiv) in $CH_2Cl_2$ (2 mL) was added dropwise with stirring at 0° C. The resulting solution was stirred for 5 hours at room temperature. The resulting solution was quenched with $H_2O$ (50 mL) and extracted with $CH_2Cl_2$ (3×10 mL). Then, the organic layer was washed with NaCl solution and dried over anhydrous sodium sulfate. The solution was concentrated under vacuum. This resulted in 500 mg (80%) of product (1-5). $^1H$ NMR (400 MHz, Methanol-d4): δ=8.10 (t, J=1.9, 1H), 7.86-7.91 (m, 1H), 7.68-7.76 (m, 3H), 7.33-7.49 (m, 5H), 5.39 (dd, J=5.9, 9.0, 1H), 3.16 (q, J=6.4, 2H), 2.05-2.28 (m, 2H), 1.58-1.73 (m, 2H), 1.44 (s, 9H). MS (ESI): m/z=514 $[M+H]^+$.

Step 6: tert-Butyl (S)-(4-(3'-chloro-[1,1'-biphenyl]-3-carboxamido)-4-(5-phenyloxazol-2-yl)butyl)carbamate (1-6)

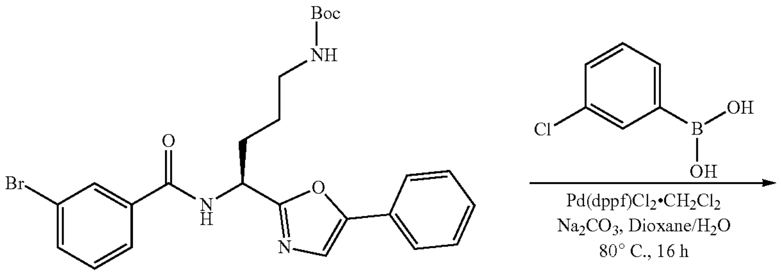

1-5

-continued

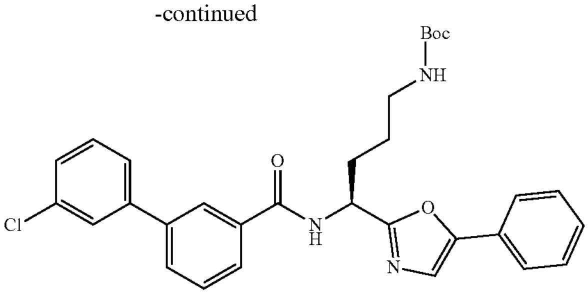

1-6

Into a 40-mL sealed tube purged and maintained with an inert atmosphere of nitrogen, was placed tert-butyl N-[(4S)-4-[(3-bromophenyl)formamido]-4-(5-phenyl-1,3-oxazol-2-yl)butyl]carbamate (1-5, 500 mg, 0.972 mmol, 1.00 equiv.), 3-chlorophenylboronic acid (167 mg, 1.06 mmol, 1.10 equiv.), $Na_2CO_3$ (412 mg, 3.88 mmol, 4.00 equiv.) and $Pd(dppf)Cl_2 \cdot CH_2Cl_2$ (50 mg, 0.061 mmol, 0.06 equiv.) in 1,4-dioxane/$H_2O$ (20 mL, v/v=5:1). The resulting solution was stirred at 80° C. for 16 hours. To the resulting solution was added $H_2O$ (20 mL) and extracted with ethyl acetate (3×50 mL). The organic layers were combined and dried over anhydrous sodium sulfate and concentrated under vacuum. The residue was purified by Prep-TLC providing 330 mg of product (1-6, 62%). $^1H$ NMR (300 MHz, DMSO-$d_6$): δ=9.15 (d, J=8.2 Hz, 1H), 8.21 (t, J=1.8 Hz, 1H), 7.92 (ddt, J=14.3, 7.8, 1.4 Hz, 2H), 7.83 (t, J=1.9 Hz, 1H), 7.76-7.59 (m, 6H), 7.57 (d, J=4.9 Hz, 1H), 7.55-7.41 (m, 5H), 7.41-7.28 (m, 2H), 6.87 (t, J=5.7 Hz, 1H), 5.33 (q, J=7.8 Hz, 1H), 3.69-3.47 (m, 1H), 3.01 (d, J=6.6 Hz, 2H), 2.21-1.86 (m, 3H), 1.66-1.43 (m, 3H), 1.36 (s, 10H), 1.19 (dd, J=15.2, 8.0 Hz, 1H). MS (ESI): m/z=546 $[M+H]^+$.

Step 7: (S)—N-(4-Amino-1-(5-phenyloxazol-2-yl)butyl)-3'-chloro-[1,1'-biphenyl]-3-carboxamide (1-7)

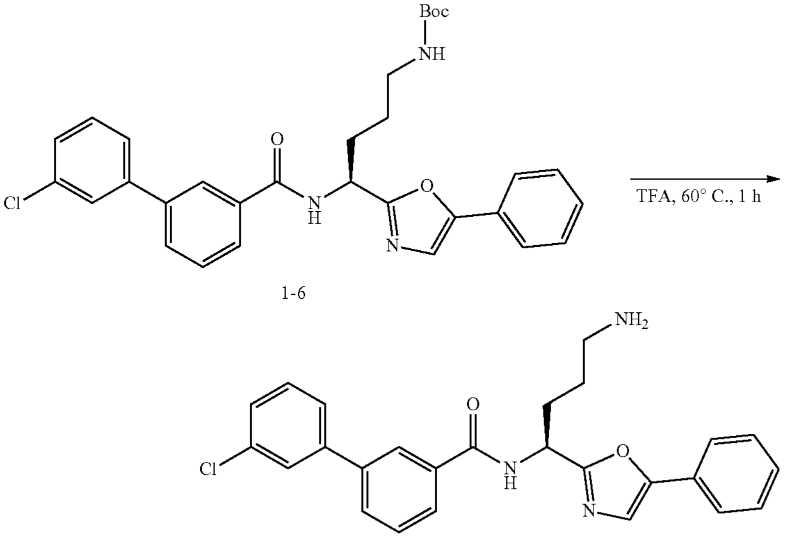

1-6

1-7

Into a 40-mL sealed tube purged and maintained with an inert atmosphere of nitrogen, was placed tert-butyl (S)-(4-(3'-chloro-[1,1'-biphenyl]-3-carboxamido)-4-(5-phenyloxazol-2-yl)butyl)carbamate (1-6, 330 mg, 0.604 mmol, 1.00 equiv.) in $CH_2Cl_2$ (10 mL). Trifluoroacetic acid (10 mL) was added at room temperature. The resulting solution was stirred for 60 min at room temperature. The resulting mixture was concentrated under vacuum. This resulted in 400 mg of crude product (1-7), which used directly for the next step without further purification. MS (ESI): m/z=446 $[M+H]^+$.

Step 8: Ethyl 2-fluoroethanimidate hydrochloride (1-8)

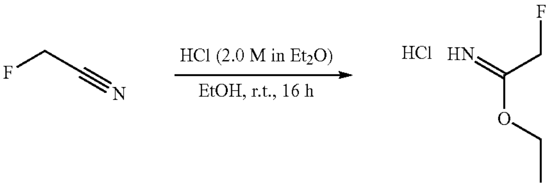

1-8

Ino a 100-mL round-bottom flask, was placed hydrogen chloride (2.0 M in $Et_2O$, 60 mL, 120 mmol, 4.72 equiv.), 2-fluoroacetonitrile (1.5 g, 25 mmol, 1 equiv.) and ethanol (1.29 g, 27.9 mmol, 1.1 equiv.). The resulting solution was stirred for 16 hours at room temperature. The solids were collected by filtration and the solid was dried in an oven under reduced pressure. This resulted in 2.8 g (78%) of ethyl 2-fluoroethanimidate hydrochloride (1-8).

Step 9: (S)-3'-Chloro-N-(4-(2-fluoroacetimidamido)-1-(5-phenyloxazol-2-yl)butyl)-[1,1'-biphenyl]-3-carboxamide (EX-1)

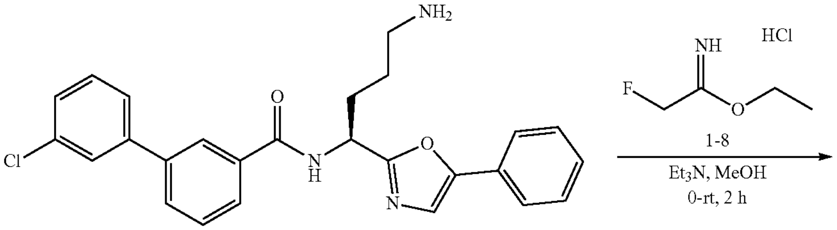

1-7

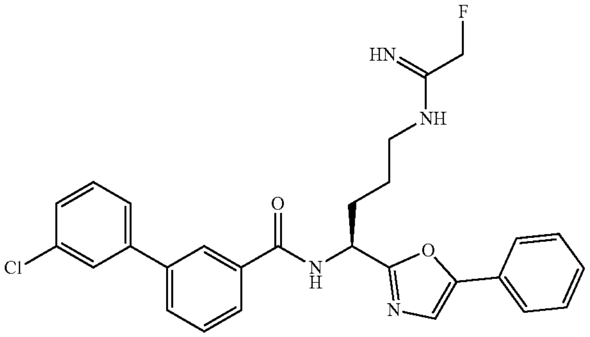

EX-1

Into a 40-mL sealed tube purged and maintained with an inert atmosphere of nitrogen, was placed (S)—N-(4-amino-1-(5-phenyloxazol-2-yl)butyl)-3'-chloro-[1,1'-biphenyl]-3-carboxamide (1-7, 400 mg, 0.897 mmol, 1.00 equiv), ethyl 2-fluoroethanimidate hydrochloride (1-8, 800 mg, 5.65 mmol, 6.30 equiv.) in MeOH (20 mL). TEA (0.6 mL) was added dropwise at 0° C. The resulting solution was stirred for 2 h at rt. The reaction was quenched by the addition of 4 mL of 2 M HCl in $Et_2O$ solution. The resulting mixture was concentrated under vacuum. The crude product was purified by Prep-HPLC yielding (S)-3'-chloro-N-(4-(2-fluoroacetimidamido)-1-(5-phenyloxazol-2-yl)butyl)-[1,1'-biphenyl]-3-carboxamide (EX-1) as the hydrochloride (71.5 mg, 14.7%). $^1H$ NMR (300 MHz, Methanol-$d_4$): δ=8.19 (t, J=1.7 Hz, 1H), 7.99-7.90 (m, 1H), 7.89-7.80 (m, 1H), 7.72 (dt, J=5.4, 1.5 Hz, 3H), 7.68-7.55 (m, 3H), 7.51-7.32 (m, 5H), 5.54 (t, J=7.5 Hz, 1H), 5.35 (s, 1H), 5.20 (s, 1H), 3.49 (t, J=7.1 Hz, 2H), 2.45-2.12 (m, 2H), 1.91 (s, 2H). MS (ESI): m/z=505 $[M+H]^+$.-

Example 2 Synthesis of (S)-3'-chloro-N-(4-(2-chloroacetimidamido)-1-(5-phenyloxazol-2-yl)butyl)-[1,1'-biphenyl]-3-carboxamide (EX-2)
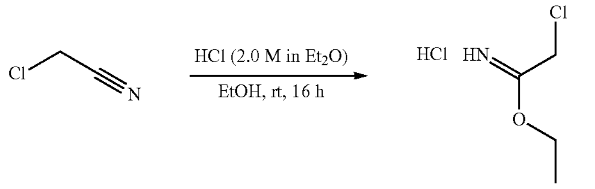
2-1
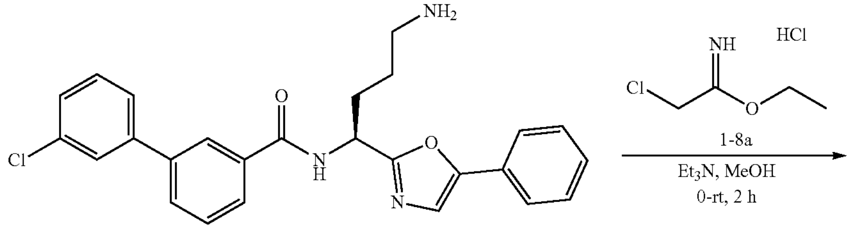
1-7
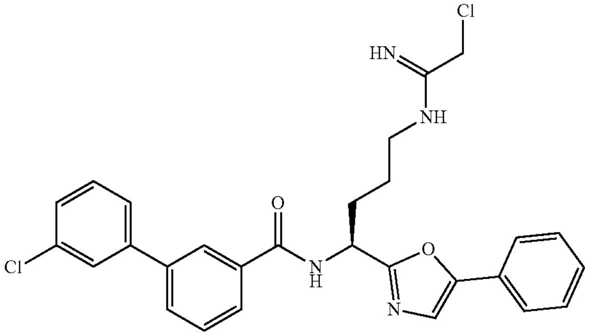
EX-2
Step 1: Ethyl 2-chloroacetimidate hydrochloride (2-1)
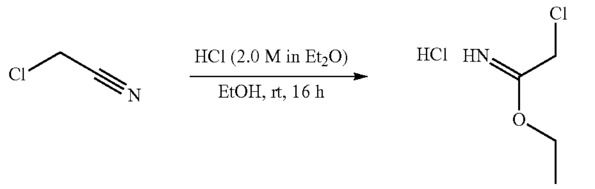
2-1
Ethyl 2-chloroacetimidate hydrochloride (2-1) was synthesized similarly to Example 1, Step 8, replacing 2-fluoroacetonitrile with 2-chloroacetonitrile.

Step 2: (S)-3'-Chloro-N-(4-(2-chloroacetimidamido)-1-(5-phenyloxazol-2-yl)butyl)-[1,1'-biphenyl]-3-carboxamide (EX-2)

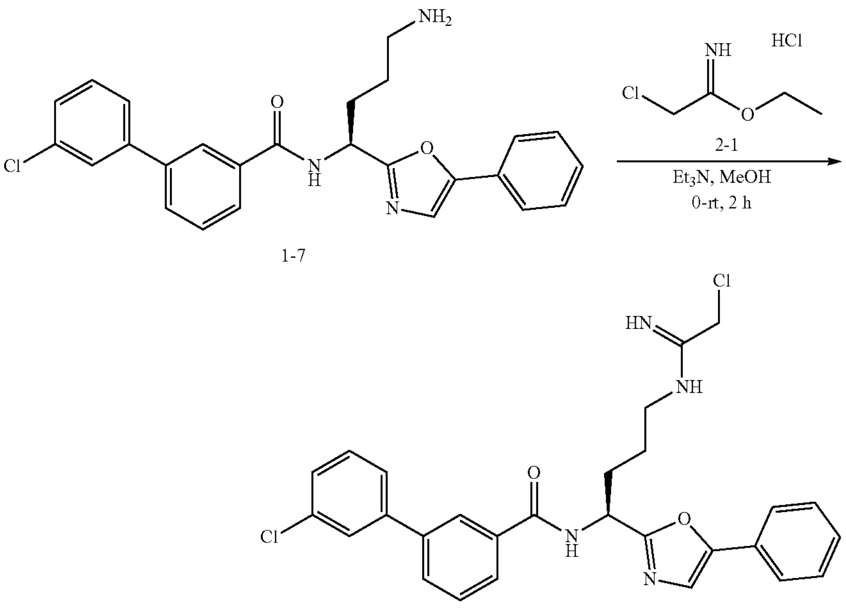

1-7

EX-2

(S)-3'-Chloro-N-(4-(2-chloroacetimidamido)-1-(5-phenyloxazol-2-yl)butyl)-[1,1'-biphenyl]-3-carboxamide (EX-2) was synthesized as the hydrochloride from (S)—N-(4-amino-1-(5-phenyloxazol-2-yl)butyl)-3'-chloro-[1,1'-biphenyl]-3-carboxamide (1-7, 400 mg, 0.897 mmol, 1.00 equiv) similarly to Example 1, Step 9, replacing ethyl 2-fluoroethanimidate hydrochloride (1-8) with ethyl 2-chloroacetimidate hydrochloride (2-1). $^1$H NMR ((300 MHz, Methanol-$d_4$): δ=1.86-1.94 (m, 2H), 2.09-2.48 (m, 2H), 3.40-3.56 (m, 2H), 4.39 (s, 2H), 5.53 (dd, J=5.9, 8.8, 1H), 7.32-7.48 (m, 5H), 7.51 (d, J=6.5, 1H), 7.57-7.67 (m, 2H), 7.68-7.77 (m, 3H), 7.86 (dt, J=1.4, 7.9, 1H), 7.95 (dt, J=1.4, 7.6, 1H), 8.19 (t, J=1.8, 1H). MS (ESI) m/z=521 $[M+H]^+$.

Example 3 Synthesis of N-[(1S)-4-(2-chloroethanimidamido)-1-(5-phenyl-1,3-oxazol-2-yl)butyl]-6-(dimethylamino)naphthalene-2-carboxamide (EX-3)

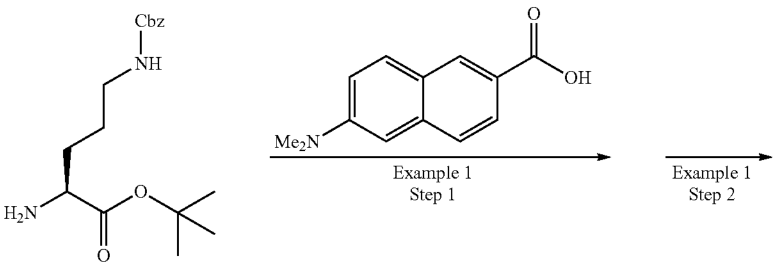

-continued
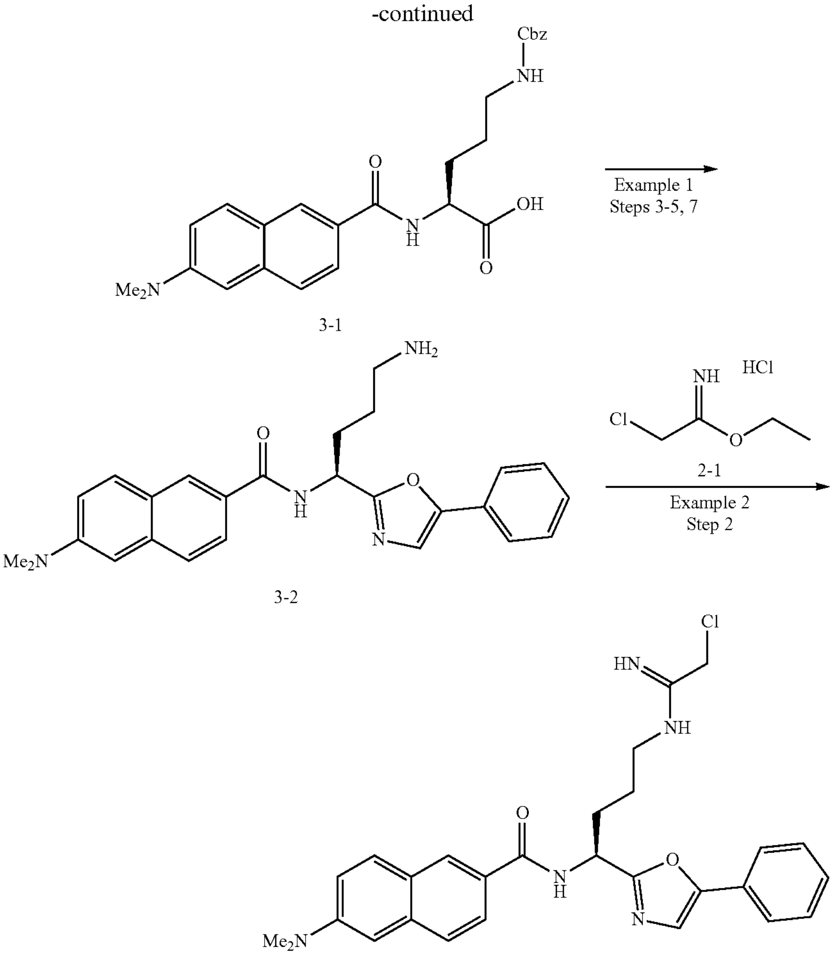
3-1
3-2
EX-3
Step 1: (2S)-5-[[(Benzyloxy)carbonyl]amino]-2-[[6-(dimethylamino)naphthalen-2-yl]formamido]pentanoic acid (3-1)
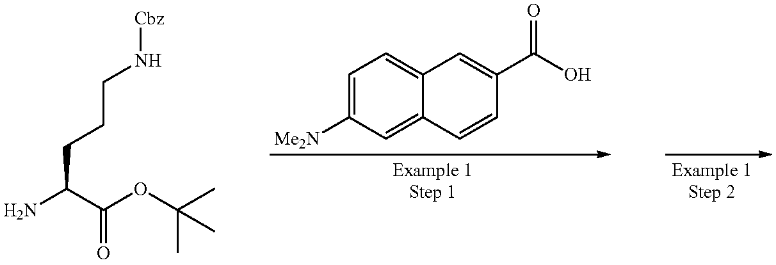

-continued

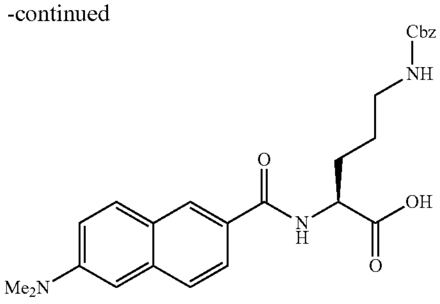

3-1

(2S)-5-[[(Benzyloxy)carbonyl]amino]-2-[[6-(dimethylamino)naphthalen-2-yl]formamido]pentanoic acid (3-1) was synthesized similarly to Example 1, Steps 1 and 2, replacing 3-bromobenzoic acid with 6-(dimethylamino)-2-naphthoic acid in Step 1.

Step 2: (2S)-5-[[(Benzyloxy)carbonyl]amino]-2-[[6-(dimethylamino)naphthalen-2-yl]formamido]pentanoic acid (3-2)

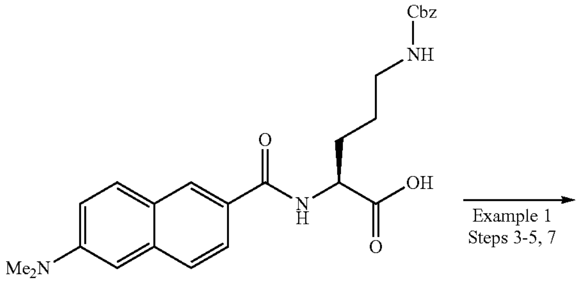

3-1

-continued

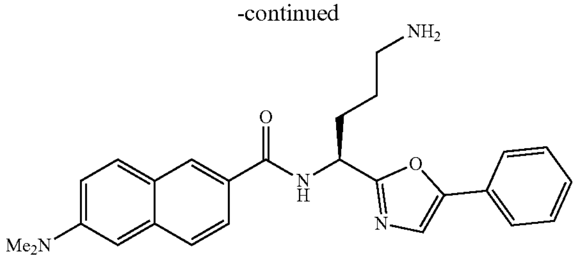

3-2

N-[(1S)-4-Amino-1-(5-phenyl-1,3-oxazol-2-yl)butyl]-6-(dimethylamino)naphthalene-2-carboxamide (3-2) was synthesized as a white solid from (2S)-5-[[(benzyloxy)carbonyl]amino]-2-[[6-(dimethylamino)naphthalen-2-yl]formamido]pentanoic acid (3-1) similarly to Example 1, Steps 3-5 and 7. MS (ESI) m/z=429 [M+H]$^+$.

Step 3: N-[(1S)-4-(2-Chloroethanimidamido)-1-(5-phenyl-1,3-oxazol-2-yl)butyl]-6-(dimethylamino)naphthalene-2-carboxamide (EX-3)

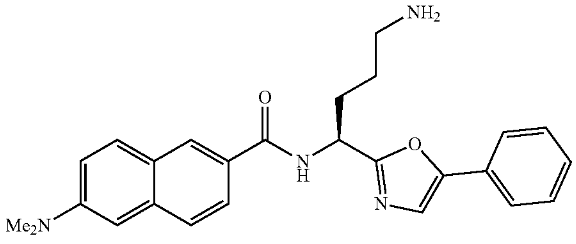

3-2

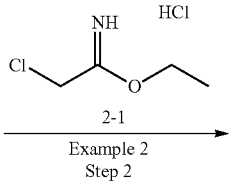

-continued

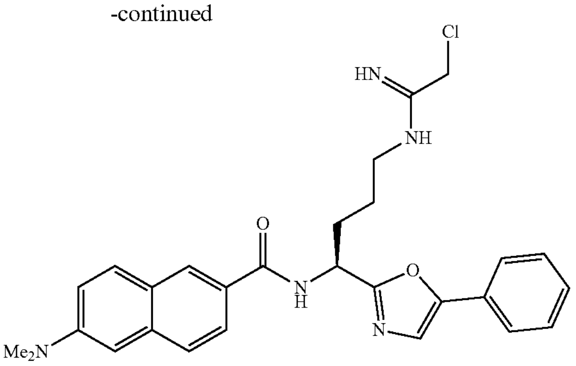

EX-3

N-[(1S)-4-(2-Chloroethanimidamido)-1-(5-phenyl-1,3-oxazol-2-yl)butyl]-6-(dimethylamino)naphthalene-2-carboxamide (EX-3) was synthesized as a off-white solid from N-[(1S)-4-amino-1-(5-phenyl-1,3-oxazol-2-yl)butyl]-6-(dimethylamino)naphthalene-2-carboxamide (3-2) similarly to Example 2, Step 2. $^1$H NMR (400 MHz, DMSO-$d_6$): δ=1.74 (t, J=10.1, 2H), 2.01-2.30 (m, 3H), 3.09 (s, 6H), 3.37 (d, J=6.7, 2H), 4.45 (s, 2H), 5.28-5.44 (m, 1H), 7.12-7.55 (m, 6H), 7.60-7.73 (m, 3H), 7.78 (d, J=8.7, 1H), 7.87-8.00 (m, 2H), 8.46 (s, 1H), 9.11 (d, J=8.0, 1H), 9.26 (s, 1H), 9.65 (s, 1H), 10.26 (s, 1H). MS (ESI) m/z=504 $[M+H]^+$.

Example 4 Synthesis of (S)-6-(Dimethylamino)-N-(4-(2-fluoroacetimidamido)-1-(5-phenyloxazol-2-yl)butyl)-2-naphthamide (EX-4)

(S)-6-(Dimethylamino)-N-(4-(2-fluoroacetimidamido)-1-(5-phenyloxazol-2-yl)butyl)-2-naphthamide (EX-4) was synthesized from N-[(1S)-4-amino-1-(5-phenyl-1,3-oxazol-2-yl)butyl]-6-(dimethylamino)naphthalene-2-carboxamide (3-2) similarly to Example 1, Step 9, replacing (S)—N-(4-amino-1-(5-phenyloxazol-2-yl)butyl)-3'-chloro-[1,1'-biphenyl]-3-carboxamide (1-7) with N-[(1S)-4-amino-1-(5-phenyl-1,3-oxazol-2-yl)butyl]-6-(dimethylamino)naphthalene-2-carboxamide (3-2). $^1$H NMR (400 MHz, DMSO-$d_6$): δ ppm 1.71-1.79 (m, 2H), 2.08-2.15 (m, 2H), 3.12 (s, 6H), 3.39-3.41 (m, 2H), 5.26 (s, 1H), 5.33-5.38 (m, 2H), 7.34-7.37 (m, 1H), 7.44-7.48 (m, 2H), 7.58 (s, 1H), 7.65-7.69 (m, 3H), 7.85-7.87 (m, 1H), 7.87-8.02 (m, 2H), 8.53 (s, 1H), 9.20 (d, J=7.6 HZ, 1H), 9.35 (s, 1H), 9.50 (s, 1H), 10.00 (s, 1H). MS (ESI) m/z=487.9 $[M+H]^+$.

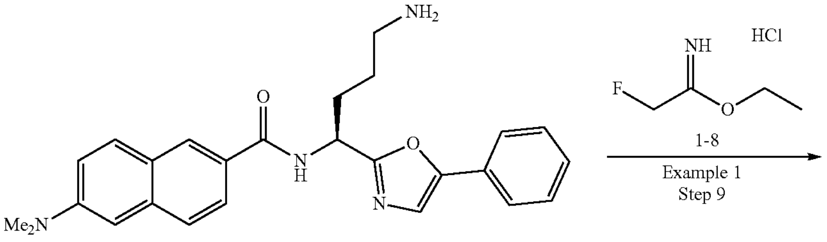

3-2

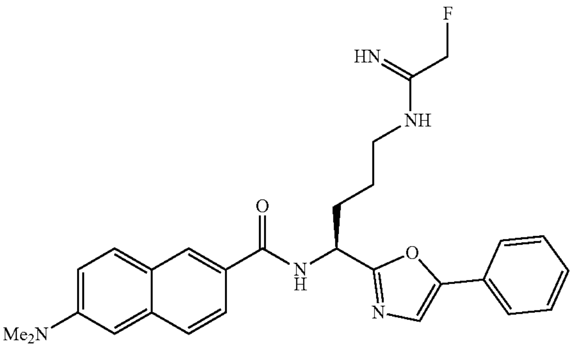

EX-4

Example 5 Synthesis of (S)—N-(4-(2-fluoro-acetimidamido)-1-(5-phenyloxazol-2-yl)butyl)-3'-methoxy-[1,1'-biphenyl]-3-carboxamide (EX-5)

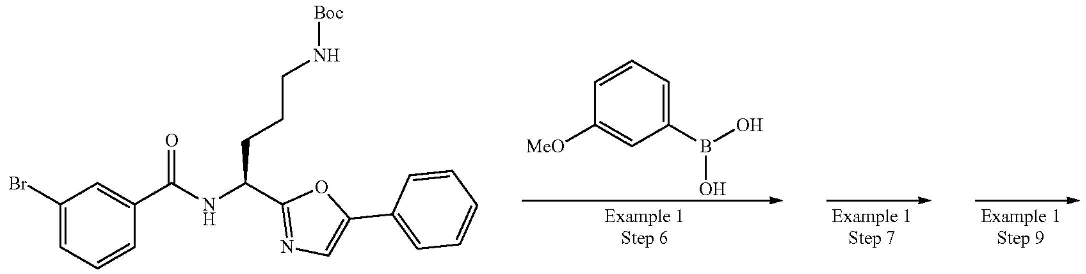

1-5

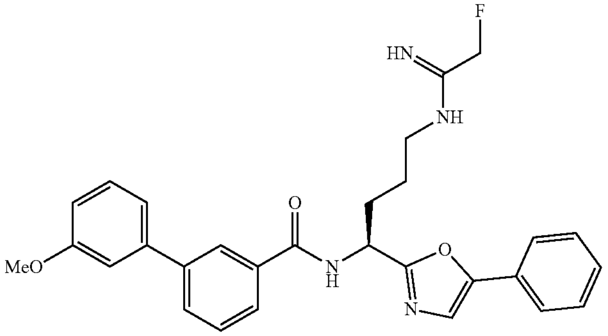

EX-5

(S)—N-(4-(2-Fluoroacetimidamido)-1-(5-phenyloxazol-2-yl)butyl)-3'-methoxy-[1,1'-biphenyl]-3-carboxamide (EX-5) hydrochloride was synthesized as a white solid from tert-butyl N-[(4S)-4-[(3-bromophenyl)formamido]-4-(5-phenyl-1,3-oxazol-2-yl)butyl]carbamate (1-5) similarly to Example 1, Steps 6, 7, and 9, replacing 3-chlorophenylboronic acid with 3-methoxyphenylboronic acid in Step 6. $^1$H NMR (400 MHz, DMSO-$d_6$): δ ppm 1.62-1.88 (m, 2H), 2.03-2.27 (m, 2H), 3.30-3.50 (m, 2H), 3.84 (s, 3H), 5.26 (s, 1H), 5.31-5.44 (m, 2H), 6.99 (dd, J=8.0, 2.0 Hz, 1H), 7.30-7.39 (m, 3H), 7.40-7.49 (m, 7H), 7.59 (t, J=8.0 Hz, 1H), 7.65-7.75 (m, 3H), 7.87 (d, J=7.6 Hz, 1H), 7.95 (d, J=7.6 Hz, 1H), 8.24 (s, 1H), 9.25-9.40 (m, 2H), 9.48 (s, 1H), 9.98 (s, 1H). MS (ESI) m/z=500.8 $[M+H]^+$.

Example 6 Synthesis of (S)—N-(4-(2-fluoro-acetimidamido)-1-(5-phenyloxazol-2-yl)butyl)-4'-methoxy-[1,1'-biphenyl]-3-carboxamide (EX-6)

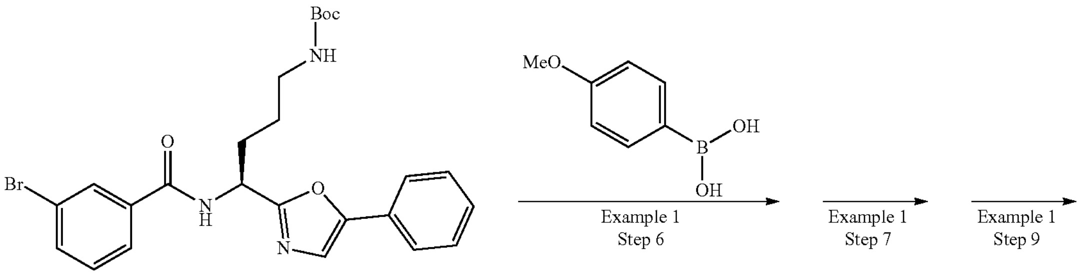

1-5

-continued

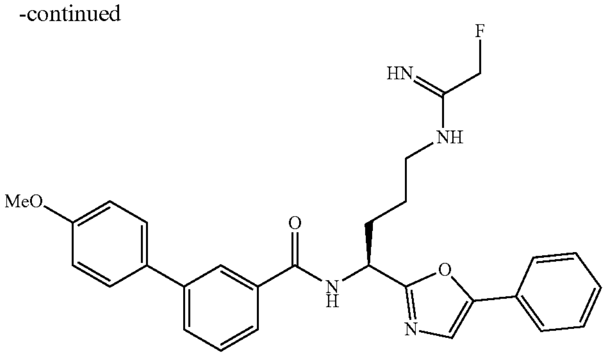

EX-6

(S)—N-(4-(2-Fluoroacetimidamido)-1-(5-phenyloxazol-2-yl)butyl)-4'-methoxy-[1,1'-biphenyl]-3-carboxamide (EX-6) hydrochloride was synthesized as a white solid from tert-butyl N-[(4S)-4-[(3-bromophenyl)formamido]-4-(5-phenyl-1,3-oxazol-2-yl)butyl]carbamate (1-5) similarly to Example 1, Steps 6, 7, and 9, replacing 3-chlorophenylboronic acid with 4-methoxyphenylboronic acid in Step 6. $^1$H NMR (400 MHz, DMSO-$d_6$): δ ppm 1.62-1.85 (m, 2H), 2.02-2.27 (m, 2H), 3.34-3.43 (m, 2H), 3.81 (s, 3H), 5.24-5.42 (m, 3H), 7.01-7.10 (m, 2H), 7.33-7.58 (m, 4H), 7.65-7.73 (m, 5H), 7.78-7.92 (m, 2H), 8.19 (s, 1H), 9.26 (d, J=8.0 Hz, 1H), 9.32 (s, 1H), 9.47 (s, 1H), 9.96 (s, 1H). MS (ESI) m/z=500.8 $[M+H]^+$.

Example 7 Synthesis of (S)—N-(1-(5-(4-chlorophenyl)oxazol-2-yl)-4-(2-fluoroacetimidamido)butyl)-6-(dimethylamino)-2-naphthamide (EX-7)

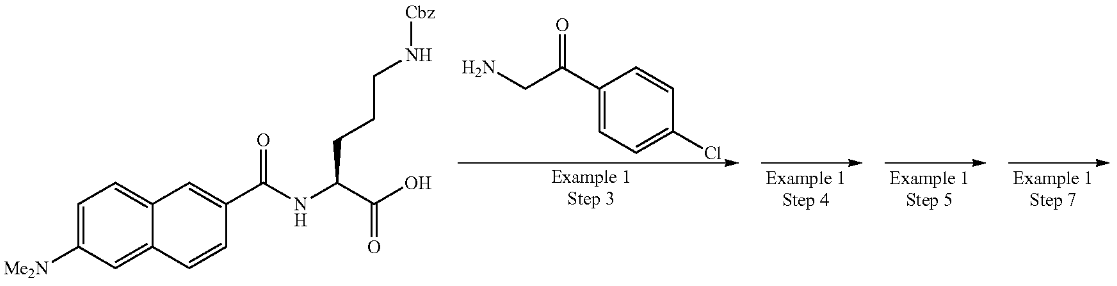

3-1

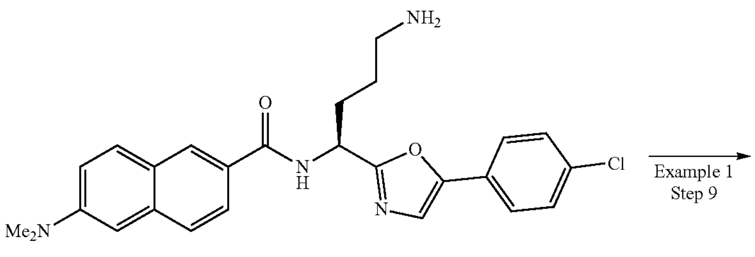

7-1

-continued

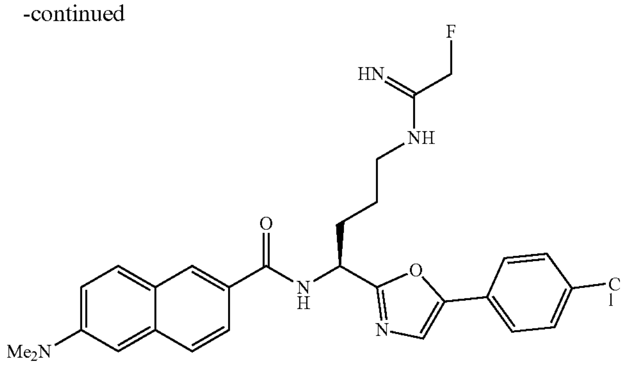

EX-7

Step 1: (S)—N-(4-Amino-1-(5-(4-chlorophenyl)oxazol-2-yl)butyl)-6-(dimethylamino)-2-naphthamide (7-1)

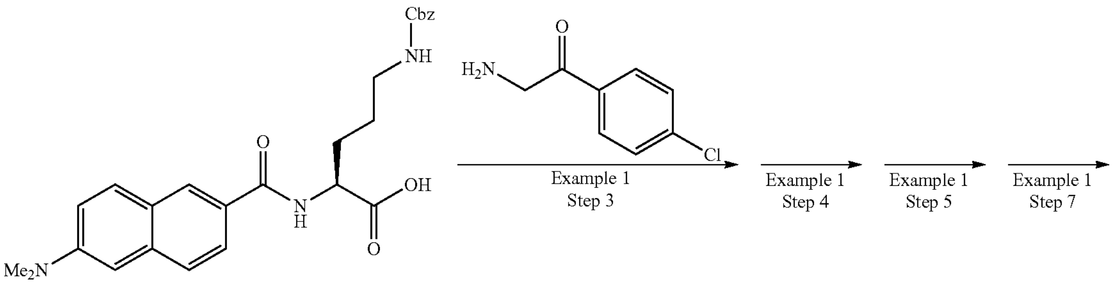

3-1

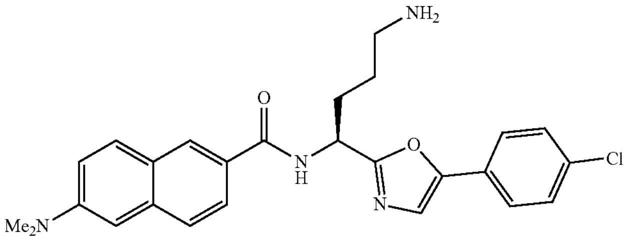

7-1

(S)—N-(4-Amino-1-(5-(4-chlorophenyl)oxazol-2-yl)butyl)-6-(dimethylamino)-2-naphthamide (7-1) was synthesized from (2S)-5-[[(benzyloxy)carbonyl]amino]-2-[[6-(dimethylamino)naphthalen-2-yl]formamido]pentanoic acid (3-1) similarly to Example 1, Steps 3, 4, 5, and 7, replacing 2-amino-1-phenylethan-1-one with 2-amino-1-(4-chlorophenyl)ethan-1-one in Step 3.

Step 2: (S)—N-(1-(5-(4-Chlorophenyl)oxazol-2-yl)-4-(2-fluoroacetimidamido)butyl)-6-(dimethylamino)-2-naphthamide (EX-7)

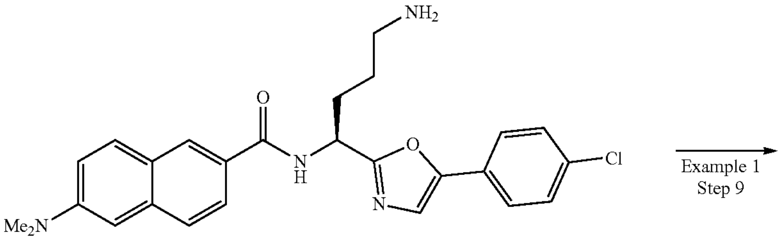

7-1

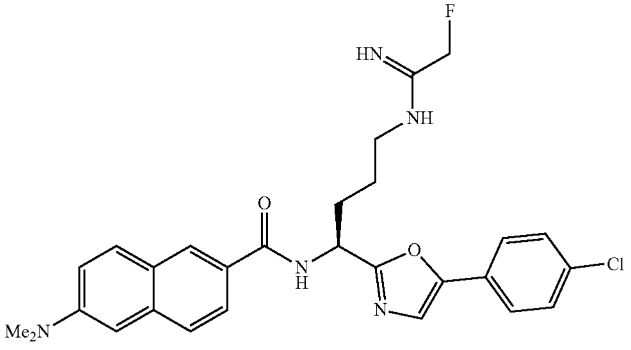

EX-7

S)—N-(1-(5-(4-Chlorophenyl)oxazol-2-yl)-4-(2-fluoroacetimidamido)butyl)-6-(dimethylamino)-2-naphthamide (EX-7) hydrochloride was synthesized as a white solid from (S)—N-(4-amino-1-(5-(4-chlorophenyl)oxazol-2-yl)butyl)-6-(dimethylamino)-2-naphthamide (7-1) similarly to Example 1, Step 9. $^1$H NMR (400 MHz, DMSO-$d_6$): δ ppm 1.69-1.75 (m, 2H), 2.06-2.16 (m, 2H), 3.05 (s, 6H), 3.35-3.37 (m, 2H), 5.23 (s, 1H), 5.34-5.37 (m, 2H), 6.96-6.97 (m, 1H), 7.27-7.30 (m, 1H), 7.53-7.55 (m, 2H), 7.69-7.72 (m, 4H), 7.82-7.87 (m, 2H), 8.37 (s, 1H), 9.03 (d, J=8.0 Hz, 1H), 9.65 (br. s, 3H). MS (ESI) m/z=521.8 $[M+H]^+$.

Example 8 Synthesis of (S)-6-(Dimethylamino)-N-(4-(2-fluoroacetimidamido)-1-(5-(3-fluorophenyl)oxazol-2-yl)butyl)-2-naphthamide (EX-8)

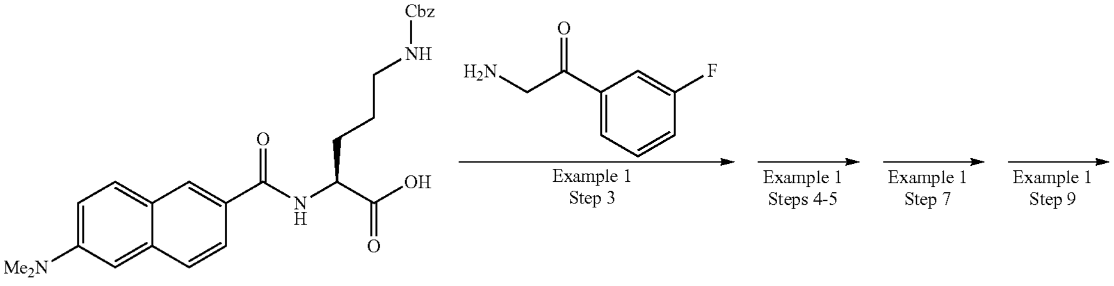

3-1

-continued

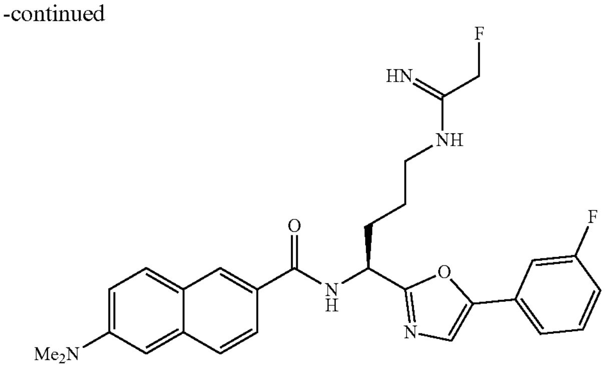

EX-8

(S)-6-(Dimethylamino)-N-(4-(2-fluoroacetimidamido)-1-(5-(3-fluorophenyl)oxazol-2-yl)butyl)-2-naphthamide hydrochloride (EX-8) hydrochloride was synthesized as a white solid from (2S)-5-[[(benzyloxy)carbonyl]amino]-2-[[6-(dimethylamino)naphthalen-2-yl]formamido]pentanoic acid (3-1) and 2-amino-1-(3-fluorophenyl)ethan-1-one similarly to Example 7 using appropriate starting materials and reagents. $^1$H NMR (400 MHz, DMSO-$d_6$): δ ppm 1.69-1.79 (m, 2H), 2.10-2.14 (m, 2H), 3.12 (s, 6H), 3.38-3.43 (m, 2H), 5.31 (d, J=45 Hz, 2H), 5.31-5.38 (m, 1H), 7.18-7.23 (m, 1H), 7.48-7.52 (m, 4H), 7.85-7.87 (m, 2H), 7.96-8.00 (m, 2H), 8.51 (s, 1H), 9.19 (d, J=8 Hz, 1H), 9.34 (br. s, 1H), 9.49 (br. s, 1H), 9.99 (br. s, 1H). MS (ESI) m/z=506.1 [M+H]$^+$.

Example 9 Synthesis of (S)—N-(1-(5-(4-chlorophenyl)oxazol-2-yl)-4-(2-fluoroacetimidamido)butyl)-4'-(hydroxymethyl)-[1,1'-biphenyl]-3-carboxamide (EX-9)

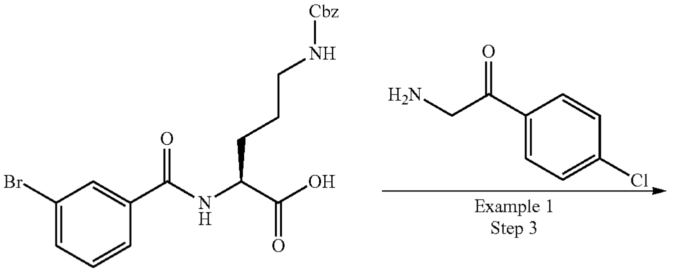

1-2

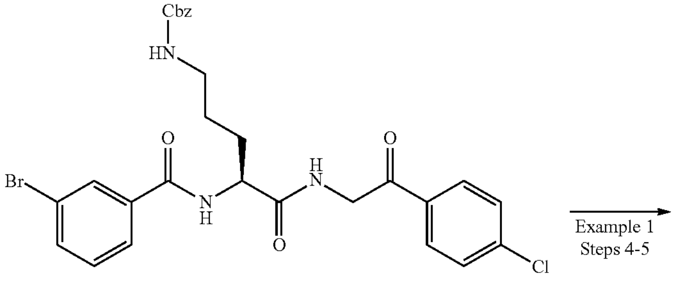

9-1

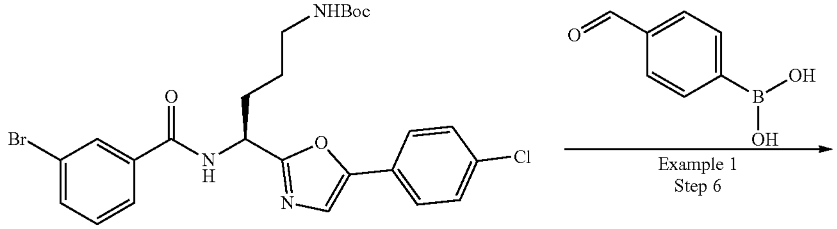

9-2

-continued

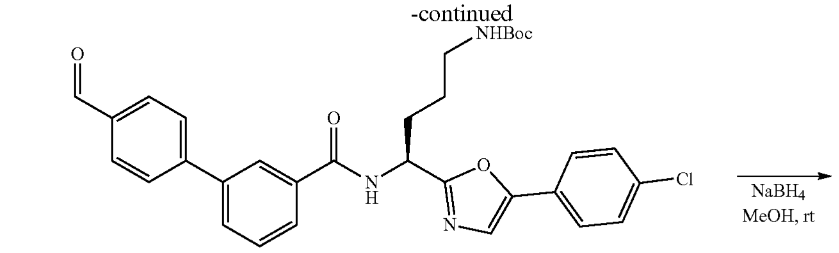

9-3

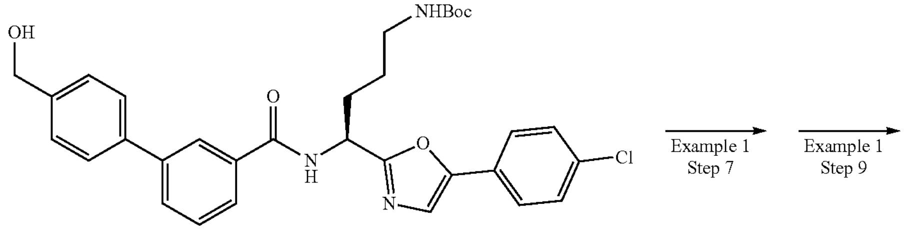

9-4

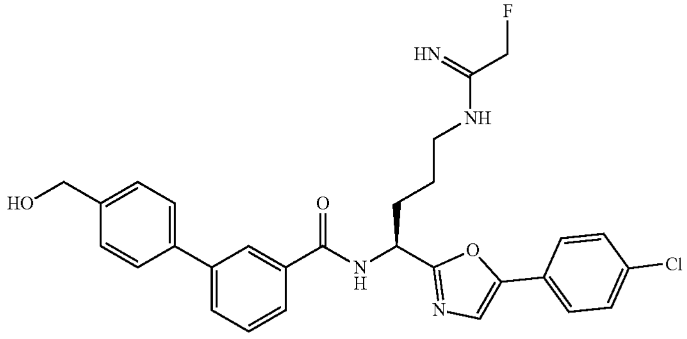

EX-9

Step 1: Benzyl (S)-(4-(3-bromobenzamido)-5-((2-(4-chlorophenyl)-2-oxoethyl)amino)-5-oxopentyl)carbamate (9-1)

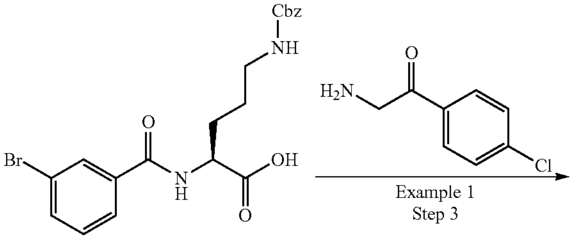

1-2

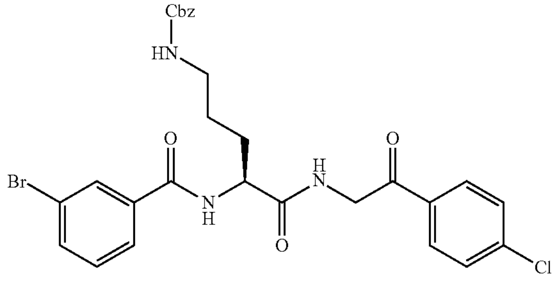

9-1

Benzyl (S)-(4-(3-bromobenzamido)-5-((2-(4-chlorophenyl)-2-oxoethyl)amino)-5-oxopentyl)carbamate (9-1) was synthesized from (2S)-5-[[(benzyloxy)carbonyl]amino]-2-[(3-bromophenyl)formamido]pentanoic acid (1-2) similarly to Example 1, Step 3 replacing 2-amino-1-phenylethan-1-one with 2-amino-1-(4-chlorophenyl)ethan-1-one. MS (ESI) m/z=621.6 $[M+Na]^+$.

Step 2: tert-Butyl (S)-(4-(3-bromobenzamido)-4-(5-(4-chlorophenyl)oxazol-2-yl)butyl)carbamate (9-2)

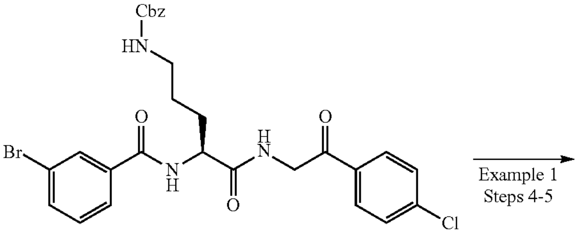

9-1

-continued

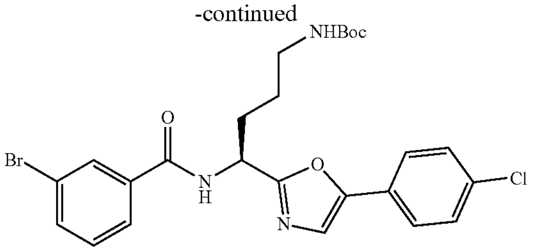

9-2 tert-Butyl (S)-(4-(3-bromobenzamido)-4-(5-(4-chlorophenyl)oxazol-2-yl)butyl)carbamate (9-2) was synthesized from benzyl (S)-(4-(3-bromobenzamido)-5-((2-(4-chlorophenyl)-2-oxoethyl)amino)-5-oxopentyl)carbamate (9-1) similarly to Example 1, Steps 4 and 5.

Step 3: tert-Butyl (S)-(4-(5-(4-chlorophenyl)oxazol-2-yl)-4-(4'-formyl-[1,1'-biphenyl]-3-carboxamido)butyl)carbamate (9-3)

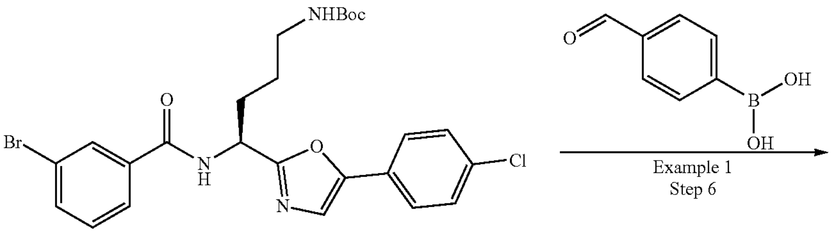

9-2

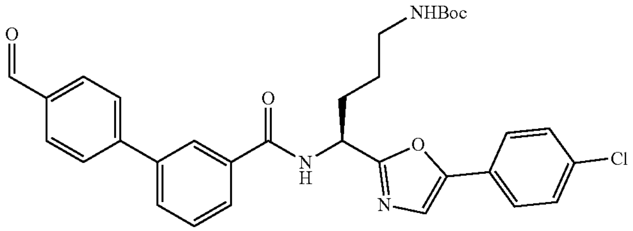

9-3 tert-Butyl (S)-(4-(5-(4-chlorophenyl)oxazol-2-yl)-4-(4'-formyl-[1,1'-biphenyl]-3-carboxamido)butyl)carbamate (9-3) was synthesized from tert-Butyl (S)-(4-(3-bromobenzamido)-4-(5-(4-chlorophenyl)oxazol-2-yl)butyl)carbamate (9-2) similarly to Example 1, Step 6, replacing 3-chlorophenylboronic acid with 4-formylphenylboronic acid.

Step 4: tert-Butyl (S)-(4-(5-(4-chlorophenyl)oxazol-2-yl)-4-(4'-(hydroxymethyl)-[1,1'-biphenyl]-3-carboxamido)butyl)carbamate (9-4)

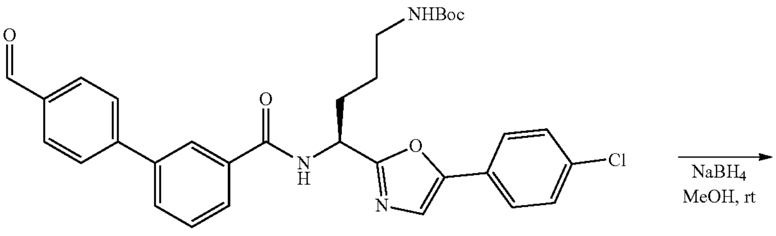

9-3

-continued

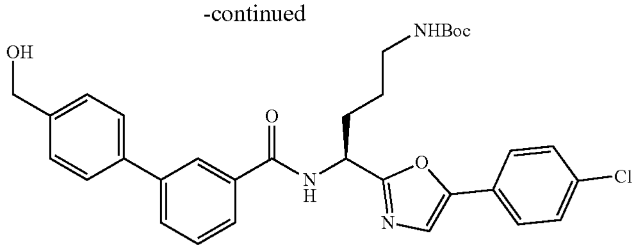

9-4

To a solution of tert-Butyl (S)-(4-(5-(4-chlorophenyl) oxazol-2-yl)-4-(4'-formyl-[1,1'-biphenyl]-3-carboxamido) butyl)carbamate (9-3) (1 g, 1.74 mmol) in methanol (10 mL) was added sodium borohydride (129 mg, 3.49 mmol). The mixture was stirred at room temperature for 2 hours. The mixture was quenched with water (20 mL). The product was extracted with ethyl acetate (200 mL×2). The organic layers were washed with brine (100 mL), dried over anhydrous $Na_2SO_4$ and concentrated under vacuum to afford the crude product which was purified by silica gel chromatography (elution gradient: DCM/MeOH, 20/1, v/v). Pure fractions were evaporated to dryness to afford tert-butyl (S)-(4-(5-(4-chlorophenyl)oxazol-2-yl)-4-(4'-(hydroxymethyl)-[1,1'-biphenyl]-3-carboxamido)butyl)carbamate (9-4, 700 mg) as a yellow solid. MS (ESI) m/z=575.8 $[M+H]^+$.

Step 5: (S)—N-(1-(5-(4-Chlorophenyl)oxazol-2-yl)-4-(2-fluoroacetimidamido)butyl)-4'-(hydroxymethyl)-[1,1'-biphenyl]-3-carboxamide (EX-9)

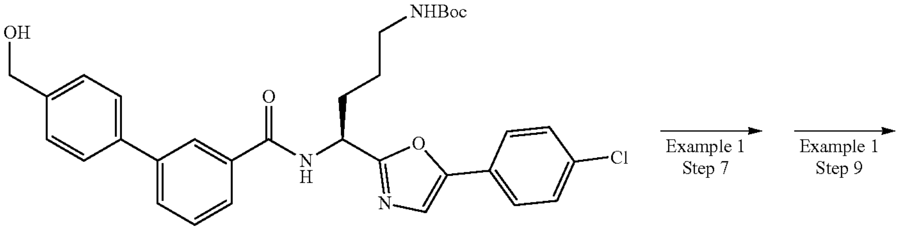

9-4

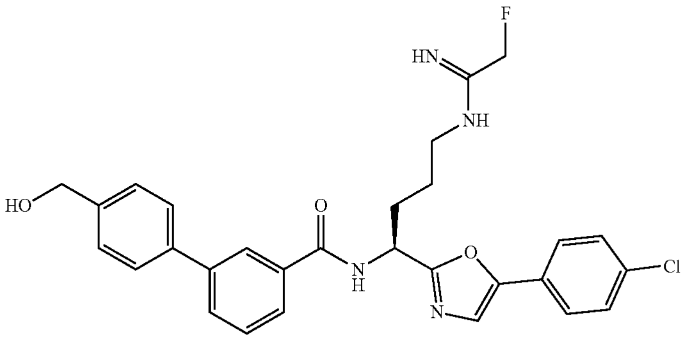

EX-9

(S)—N-(1-(5-(4-Chlorophenyl)oxazol-2-yl)-4-(2-fluoroacetimidamido)butyl)-4'-(hydroxymethyl)-[1,1'-biphenyl]-3-carboxamide (EX-9) was synthesized as the hydrochloride from tert-butyl (S)-(4-(5-(4-chlorophenyl)oxazol-2-yl)-4-(4'-(hydroxymethyl)-[1,1'-biphenyl]-3-carboxamido)butyl) carbamate (9-4) similarly to Example 1, Steps 7 and 9. $^1H$ NMR (400 MHz, DMSO-$d_6$): δ ppm 1.68-1.75 (m, 2H), 2.08-2.21 (m, 2H), 3.36-3.41 (m, 2H), 4.56 (s, 2H), 5.25 (s, 1H), 5.33-5.39 (m, 2H), 7.43-7.45 (m, 2H), 7.53-7.60 (m, 3H), 7.70-7.74 (m, 5H), 7.85-7.96 (m, 2H), 8.23-8.25 (m, 1H), 9.25-9.29 (m, 2H), 9.45 (s, 1H), 9.93 (s, 1H). MS (ESI) m/z=534.7 $[M+H]^+$.

Example 10 Synthesis of (S)—N-(1-(5-(4-chlorophenyl)oxazol-2-yl)-4-(2-fluoroacetimidamido)butyl)-4'-(hydroxymethyl)-[1,1'-biphenyl]-3-carboxamide (EX-10)

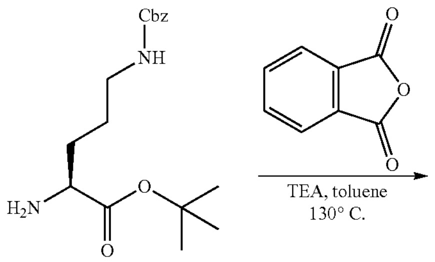

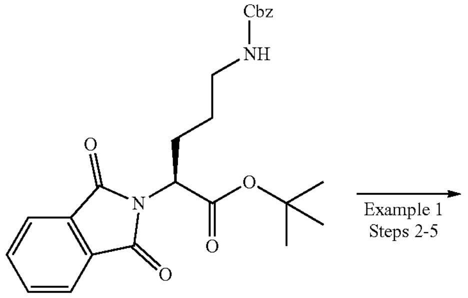

10-1

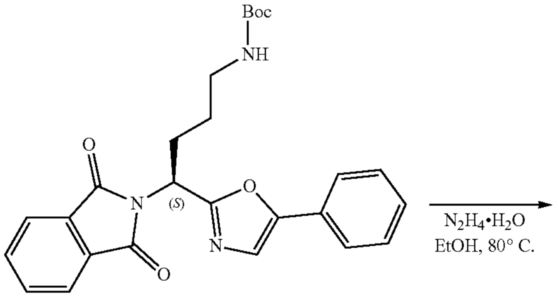

10-2

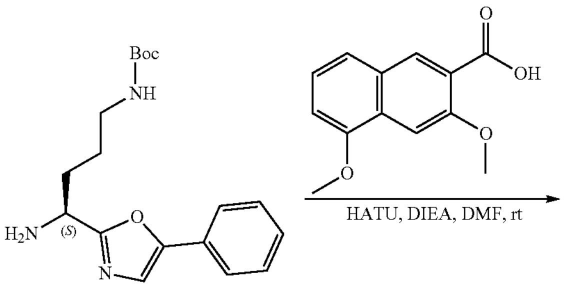

10-3

-continued

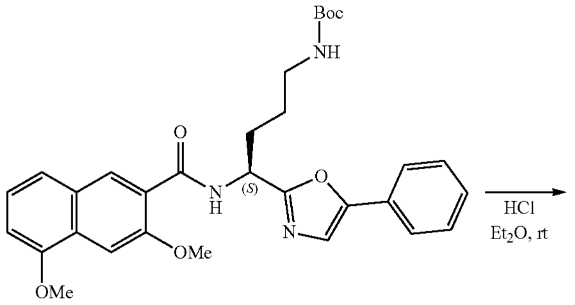

10-4

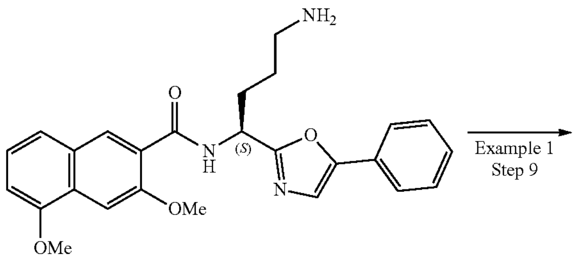

10-5

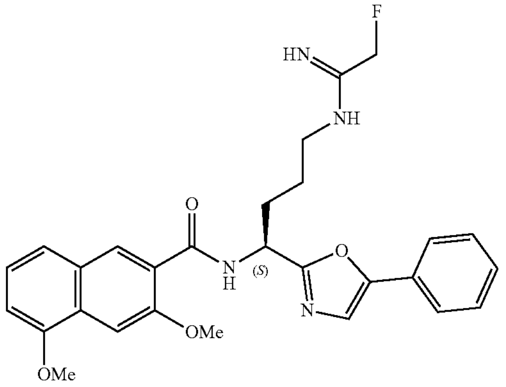

EX-10

Step 1: tert-Butyl (S)-5-(((benzyloxy)carbonyl)amino)-2-(1,3-dioxoisoindolin-2-yl)pentanoate (10-1)

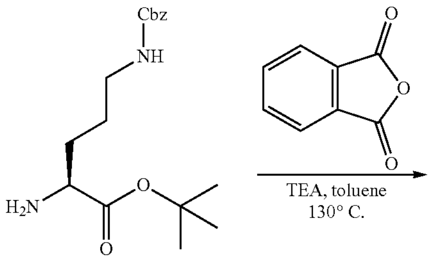

-continued

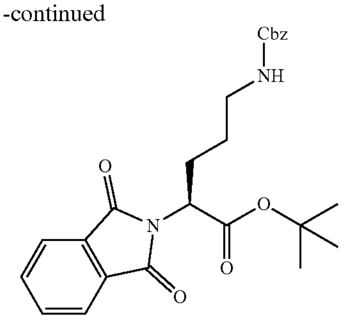

10-1

To a suspension of tert-butyl (S)-2-amino-5-(((benzyloxy) carbonyl)amino)pentanoate (5 g, 14 mmol) and phthalic anhydride (2.2 g, 15 mmol) in toluene (60 mL) at 0° C. was added TEA (1.6 g, 15 mmol).

The mixture was stirred at 130° C. for 16 hours. The reaction mixture was concentrated and diluted with ethyl acetate (150 mL), which was washed with water (50 mL), brine (50 mL) and concentrated to afford tert-butyl (S)-5-(((benzyloxy)carbonyl)amino)-2-(1,3-dioxoisoindolin-2-yl) pentanoate (10-1, 6.5 g, 93%) as a white solid. $^1H$ NMR (400 MHz, DMSO-$d_6$): δ ppm 1.34 (s, 9H), 1.35-1.45 (m, 2H), 2.00-2.14 (m, 2H), 2.93-3.06 (m, 2H), 4.70-4.82 (m, 1H), 4.97 (s, 2H), 7.19-7.40 (m, 6H), 7.85-7.99 (m, 4H). MS (ESI) m/z=474.7 [M+Na]$^+$.

Step 2: tert-Butyl (S)-(4-(1,3-dioxoisoindolin-2-yl)-4-(5-phenyloxazol-2-yl)butyl)carbamate (10-2)

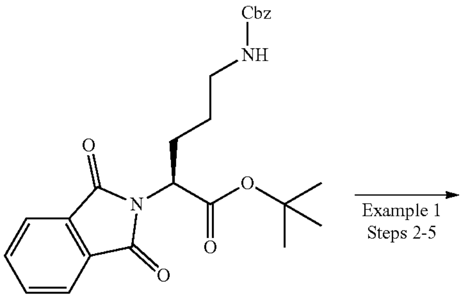

10-1

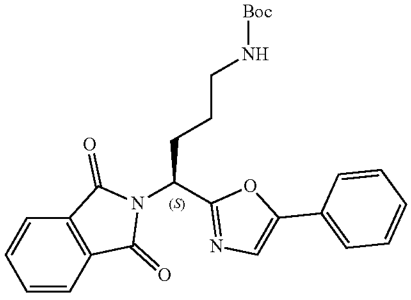

10-2 tert-Butyl (S)-(4-(1,3-dioxoisoindolin-2-yl)-4-(5-phenyloxazol-2-yl)butyl)carbamate (10-2 was synthesized from compound 10-1 similarly to Example 1, Steps 2-5. MS (ESI) m/z=461.8 [M+H]$^+$.

Step 3: tert-Butyl (S)-(4-amino-4-(5-phenyloxazol-2-yl)butyl)carbamate (10-3)

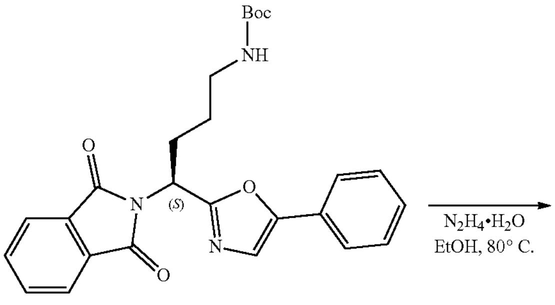

10-2

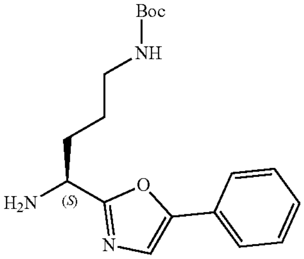

10-3

To a suspension of tert-butyl (S)-(4-(1,3-dioxoisoindolin-2-yl)-4-(5-phenyloxazol-2-yl)butyl)carbamate (10-2, 1 g, 2.2 mmol) in EtOH (20 mL) was added hydrazine hydrate (550 mg, 11 mmol). The mixture was stirred at 80° C. for 4 hours. The reaction mixture was concentrated and purified by silica gel chromatography (elution gradient: MeOH/DCM, 1/20, v/v). Pure fractions were evaporated to dryness to afford tert-butyl (S)-(4-amino-4-(5-phenyloxazol-2-yl) butyl)carbamate (10-3, 180 mg, 25%) as a brown oil. MS (ESI) m/z=331.8 [M+H]$^+$.

Step 4: tert-Butyl (S)-(4-(3,5-dimethoxy-2-naphthamido)-4-(5-phenyloxazol-2-yl)butyl)carbamate (10-4)

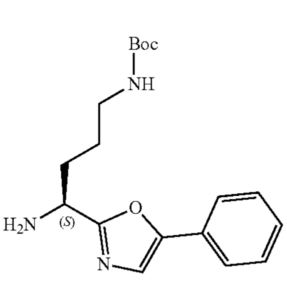

10-3

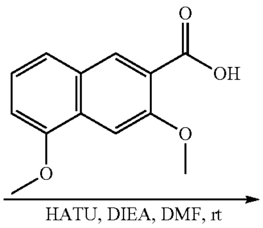

-continued

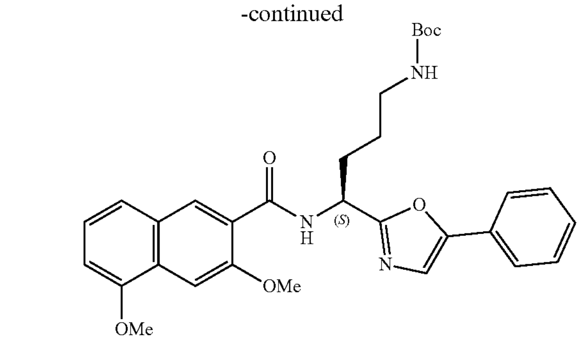

10-4

To a solution of 3,5-dimethoxy-2-naphthoic acid (125 mg, 0.54 mmol), DIEA (209 mg, 1.62 mmol) and HATU (247 g, 0.65 mmol) in DMF (10 mL) was added tert-butyl (S)-(4-amino-4-(5-phenyloxazol-2-yl)butyl)carbamate (10-3, 180 mg, 0.54 mmol). The mixture was stirred at room temperature for 16 hours. The mixture was diluted with water (50 mL) and extracted with ethyl acetate (50 mL×3). The organic phase was washed with water (30 mL), brine (30 mL) and concentrated under vacuum to give the crude product which was purified by silica gel chromatography (elution gradient: EA/PE, 2/1, v/v). Pure fractions were evaporated to dryness to afford tert-butyl (S)-(4-(3,5-dimethoxy-2-naphthamido)-4-(5-phenyloxazol-2-yl)butyl)carbamate (10-4, 200 mg, 68%) as a brown solid. MS (ESI) m/z=545.7 $[M+H]^+$.

Step 5: (S)—N-(4-Amino-1-(5-phenyloxazol-2-yl)butyl)-3,5-dimethoxy-2-naphthamide (10-5)

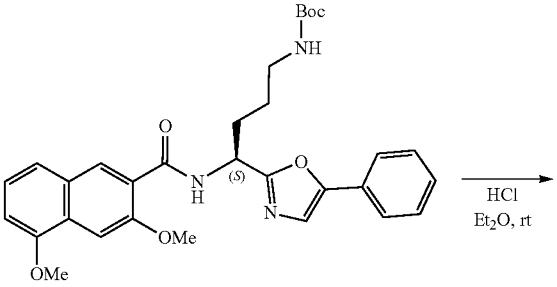

10-4

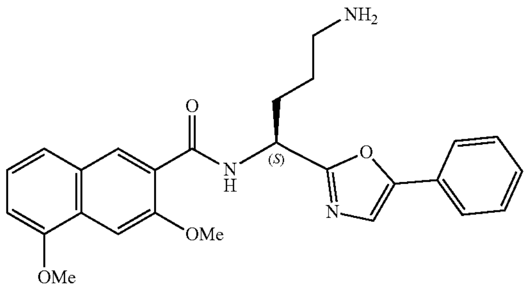

10-5

To a solution of (S)-(4-(3,5-dimethoxy-2-naphthamido)-4-(5-phenyloxazol-2-yl)butyl)carbamate (10-4, 200 mg, 0.37 mmol) in ethyl ether (10 mL) was added HCl solution (15 mL, 2N in ethyl ether). The mixture was stirred at room temperature for 3 hours. The precipitate was collected by filtration, washed with ethyl ether (20 mL), dried under vacuum to afford (S)—N-(4-amino-1-(5-phenyloxazol-2-yl)butyl)-3,5-dimethoxy-2-naphthamide (10-5, 120 mg, 74%) as an off-white solid. MS (ESI) m/z=445.8 $[M+H]^+$.

Step 6: (S)—N-(1-(5-(4-Chlorophenyl)oxazol-2-yl)-4-(2-fluoroacetimidamido)butyl)-4'-(hydroxymethyl)-[1,1'-biphenyl]-3-carboxamide (EX-10)

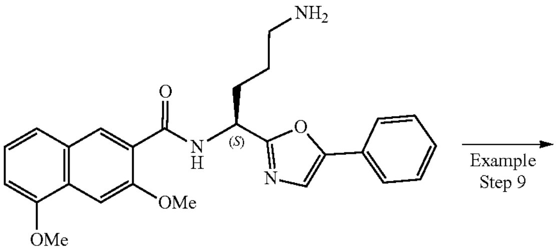

10-5

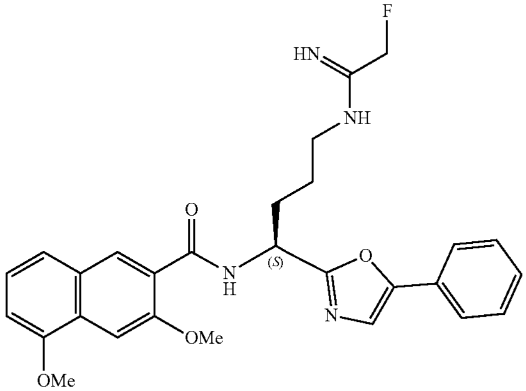

EX-10

(S)—N-(1-(5-(4-Chlorophenyl)oxazol-2-yl)-4-(2-fluoroacetimidamido)butyl)-4'-(hydroxymethyl)-[1,1'-biphenyl]-3-carboxamide (EX-10) was synthesized from (S)—N-(4-amino-1-(5-phenyloxazol-2-yl)butyl)-3,5-dimethoxy-2-naphthamide (10-5) similarly to Example 1, Step 9. $^1H$ NMR (400 MHz, DMSO-$d_6$): δ ppm 1.65-1.85 (m, 2H), 1.98-2.22 (m, 2H), 3.33-3.48 (m, 2H), 3.97 (s, 3H), 3.99 (s, 3H), 5.22-5.42 (m, 3H), 7.03 (d, J=7.6 Hz, 1H), 7.32-7.58 (m, 6H), 7.65-7.76 (m, 3H), 8.15 (s, 1H), 8.93 (d, J=8.1 Hz, 1H), 9.30 (s, 1H), 9.48 (s, 1H), 9.97 (s, 1H). MS (ESI) m/z=504.7 $[M+H]^+$.

The following examples can be prepared similarly to EX-10 using appropriate starting materials and reagents.

| EXAMPLE | NAME | STRUCTURE | MS (ESI) m/z [M + H]+ |
| --- | --- | --- | --- |
| EX-11 | (S)-N-(1-(5-Cyclopentyloxazol-2-yl)-4-(2-fluoroacetimidamido)butyl)-3,5-dimethoxy-2-naphthamide | 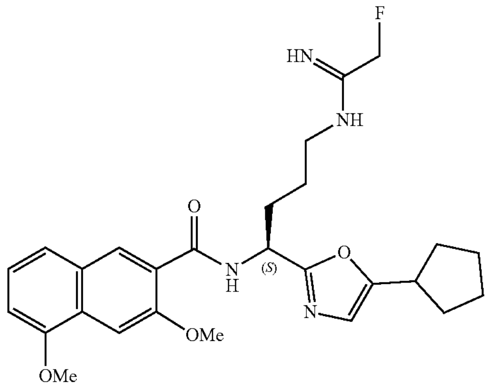 | 496.7 |
| EX-12 | (S)-N-(4-(2-fluoroacetimidamido)-1-(5-methyloxazol-2-yl)butyl)-3,5-dimethoxy-2-naphthamide | 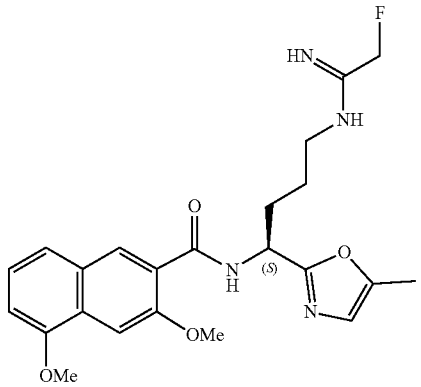 | 442.7 |
| EX-13 | (S)-N-(1-(5-(3-Chlorophenyl)oxazol-2-yl)-4-(2-fluoroacetimidamido)butyl)-3,5-dimethoxy-2-naphthamide | 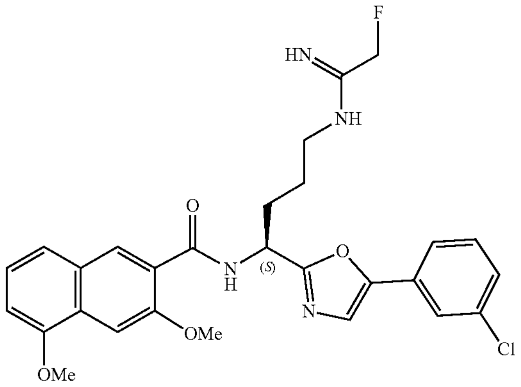 | 538.6 |
| EX-14 | (S)-N-(4-(2-Fluoroacetimidamido)-1-(5-(3-fluorophenyl)oxazol-2-yl)butyl)-3,5-dimethoxy-2-naphthamide | 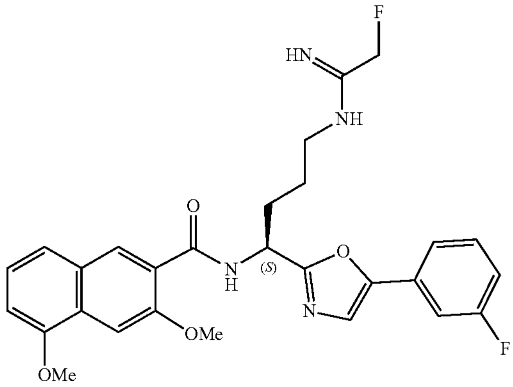 | 522.6 |

Example 15 Synthesis of (S)—N-(1-(5-(4-chlorophenyl)oxazol-2-yl)-4-(2-fluoroacetimidamido)butyl)-4'-(hydroxymethyl)-[1,1'-biphenyl]-3-carboxamide (EX-15)
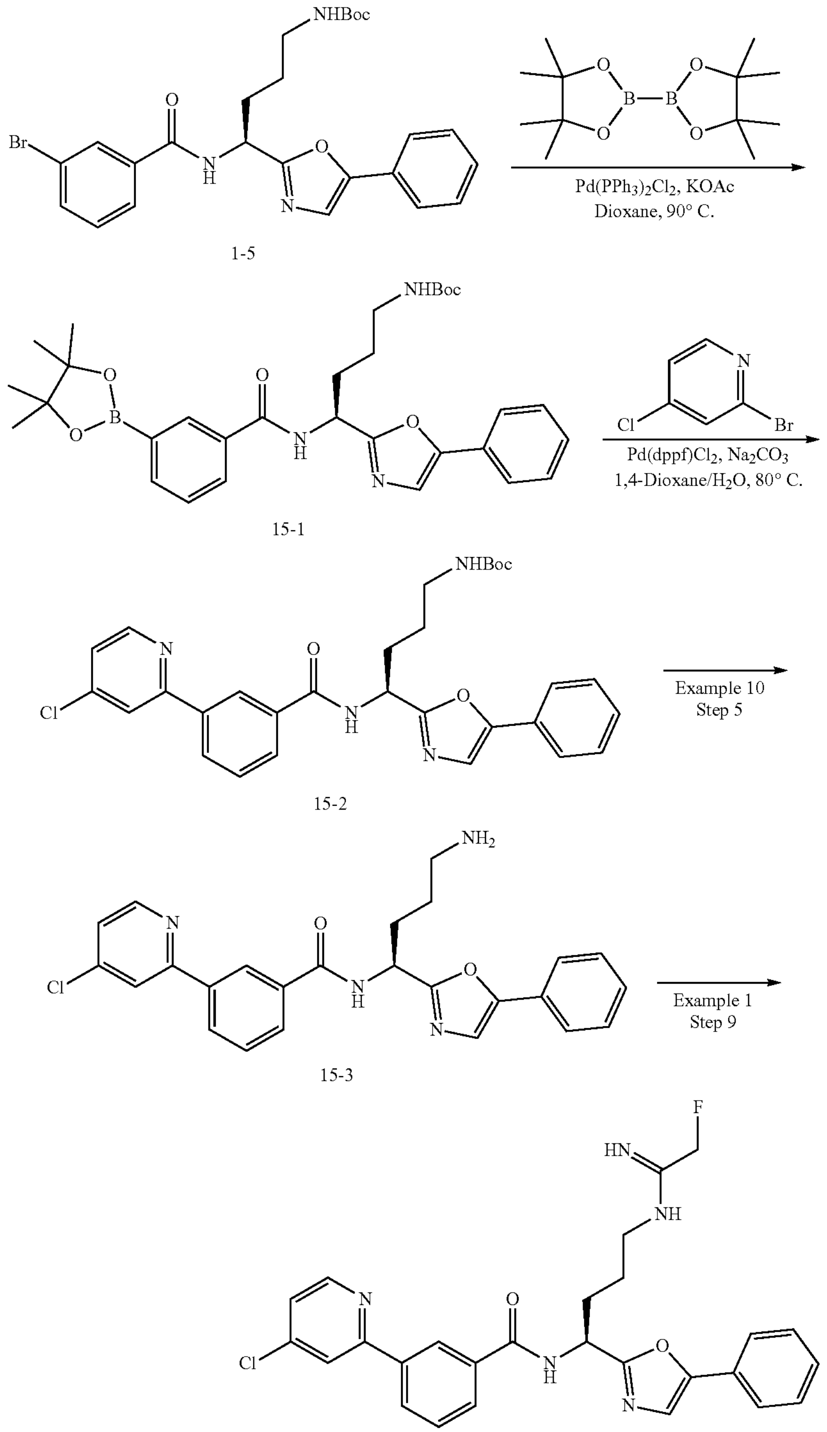
1-5
15-1
15-2
15-3
EX-15

Step 1: tert-Butyl (S)-(4-(5-phenyloxazol-2-yl)-4-(3-(4,4,5,5-tetramethyl-1,3,2-dioxaborolan-2-yl)benzamido)butyl)carbamate (15-1)

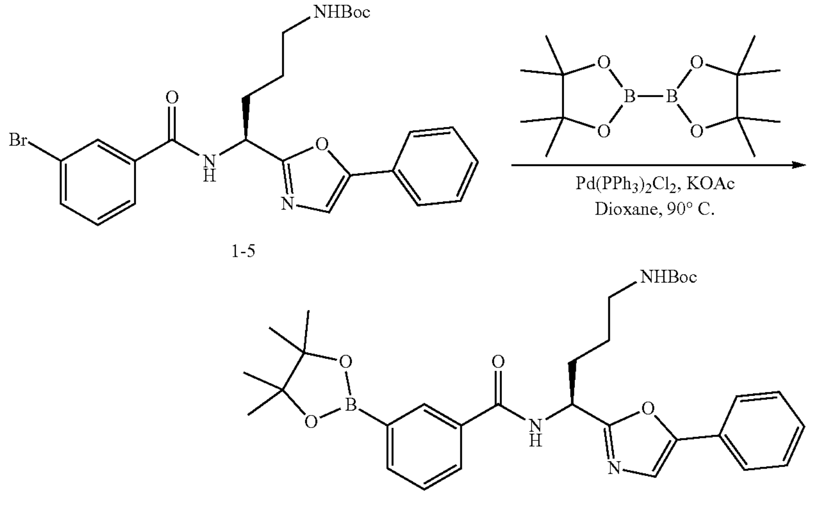

1-5

15-1

To a solution of tert-butyl N-[(4S)-4-[(3-bromophenyl)formamido]-4-(5-phenyl-1,3-oxazol-2-yl)butyl]carbamate (1-5, 3 g, 5.83 mmol), bis(pinacolato)diboron (1.77 g, 7.0 mmol), bis(triphenylphosphine)palladium(II) chloride (409 mg, 0.58 mmol) in 1,4-dioxane (50 mL) was added potassium acetate (1.71 g, 17.5 mmol). The mixture was stirred at 90° C. under $N_2$ for 3 hours. The solvent was evaporated and water (50 mL) was added. The product was extracted with ethyl acetate (100 mL×3). The organic layers were dried over anhydrous $Na_2SO_4$ and concentrated under vacuum to afford the crude product, which was purified by silica gel chromatography (elution gradient: petroleum ether/EtOAc, 20/1, v/v). Pure fractions were evaporated to dryness to afford tert-butyl (S)-(4-(5-phenyloxazol-2-yl)-4-(3-(4,4,5,5-tetramethyl-1,3,2-dioxaborolan-2-yl)benzamido)butyl)carbamate (15-1, 1.6 g, 49%) as a brown solid. MS (ESI) m/z=561.9 $[M+H]^+$.

Step 2: tert-Butyl (S)-(4-(3-(4-chloropyridin-2-yl)benzamido)-4-(5-phenyloxazol-2-yl)butyl)carbamate (15-2)

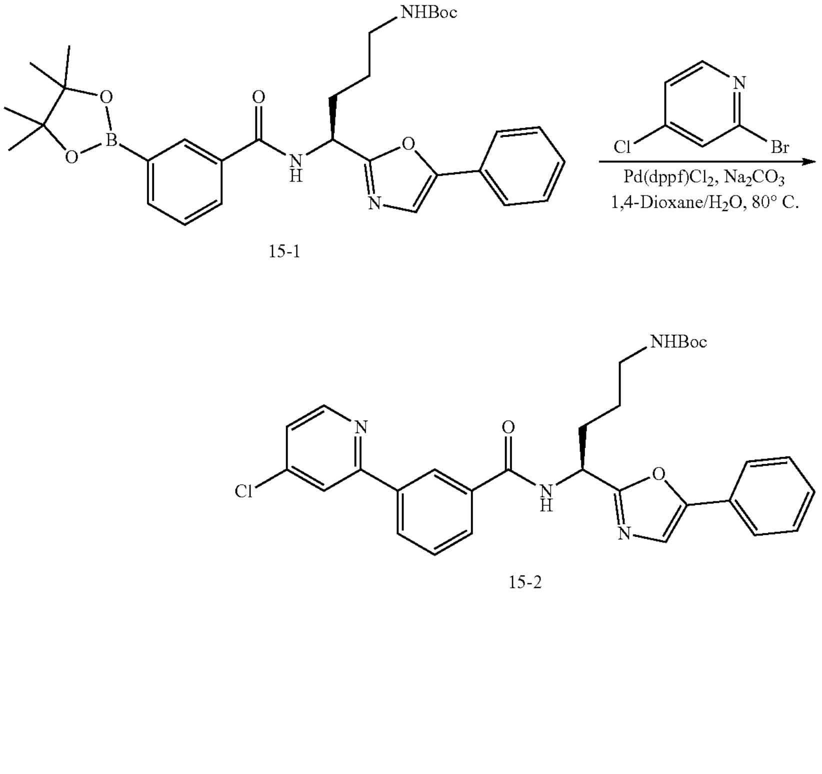 [SMILES: CC(C)(C)OC(=O)NCCC[C@H](NC(=O)c1cccc(B2OC(C)(C)C(C)(C)O2)c1)c1ncc(-c2ccccc2)o1 ; Clc1ccnc(Br)c1 ; CC(C)(C)OC(=O)NCCC[C@H](NC(=O)c1cccc(-c2cc(Cl)ccn2)c1)c1ncc(-c2ccccc2)o1]

15-1

15-2

To a solution of tert-butyl (S)-(4-(5-phenyloxazol-2-yl)-4-(3-(4,4,5,5-tetramethyl-1,3,2-dioxaborolan-2-yl)benzamido)butyl)carbamate (15-1, 1.6 g, 2.85 mmol), 2-bromo-4-chloropyridine (650 mg, 3.40 mmol), [1,1'-bis(diphenylphosphino)ferrocene]dichloropalladium (II) (208 mg, 0.28 mmol) in dioxane (20 mL) and $H_2O$ (4 mL) was added sodium carbonate (906 mg, 8.55 mmol). The mixture was stirred at 80° C. under $N_2$ for 3 hours. The solvent was evaporated and water (20 mL) was added. The product was extracted with ethyl acetate (50 mL×3). The organic layers were dried over anhydrous $Na_2SO_4$ and concentrated under vacuum to afford the crude product which was purified by silica gel chromatography (elution gradient: petroleum ether/EtOAc, 10/1, v/v). Pure fractions were evaporated to dryness to afford tert-butyl (S)-(4-(3-(4-chloropyridin-2-yl)benzamido)-4-(5-phenyloxazol-2-yl)butyl)carbamate (15-2, 1.1 g, 71%) as a yellow solid. MS (ESI) m/z=546.8 [M+H]$^+$.

Step 3: (S)—N-(4-Amino-1-(5-phenyloxazol-2-yl)butyl)-3-(4-chloropyridin-2-yl)benzamide (15-3)

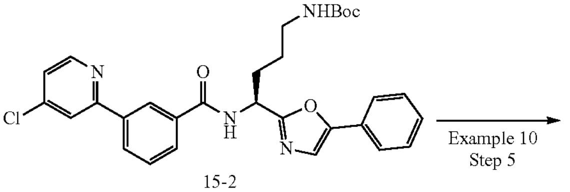

15-2

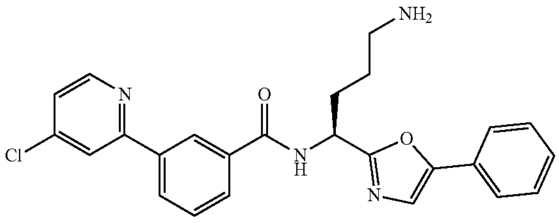

15-3

(S)—N-(4-Amino-1-(5-phenyloxazol-2-yl)butyl)-3-(4-chloropyridin-2-yl)benzamide (15-3) was synthesized from tert-butyl (S)-(4-(3-(4-chloropyridin-2-yl)benzamido)-4-(5-phenyloxazol-2-yl)butyl)carbamate (15-2) similarly to Example 10, Step 5. MS (ESI) m/z=446.8 [M+H]$^+$.

Step 4: (S)—N-(1-(5-(4-Chlorophenyl)oxazol-2-yl)-4-(2-fluoroacetimidamido)butyl)-4'-(hydroxymethyl)-[1,1'-biphenyl]-3-carboxamide (EX-15)

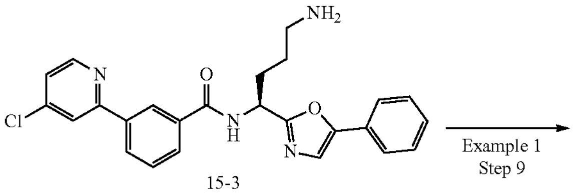

15-3

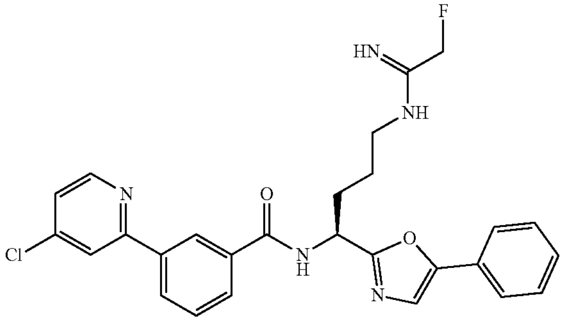

EX-15

(S)—N-(1-(5-(4-Chlorophenyl)oxazol-2-yl)-4-(2-fluoroacetimidamido)butyl)-4'-(hydroxymethyl)-[1,1'-biphenyl]-3-carboxamide (EX-15) was synthesized from (S)—N-(4-amino-1-(5-phenyloxazol-2-yl)butyl)-3-(4-chloropyridin-2-yl)benzamide (15-3) similarly to Example 1, Step 9. $^1$H NMR (400 MHz, DMSO-$d_6$): δ ppm 1.71-1.79 (m, 2H), 2.11-2.20 (m, 2H), 3.38-3.43 (m, 2H), 5.26 (s, 1H), 5.35-5.40 (m, 2H), 7.34-7.38 (m, 1H), 7.44-7.48 (m, 2H), 7.59-7.61 (m, 1H), 7.63-7.70 (m, 4H), 8.06-8.08 (m, 1H), 8.31-8.34 (m, 2H), 8.69-8.70 (m, 2H), 9.33-9.35 (m, 2H), 9.47 (s, 1H), 9.97 (s, 1H). MS (ESI) m/z=505.8 [M+H]$^+$.

Example 16 Synthesis of (S)—N-(4-(2-fluoroacetimidamido)-1-(5-phenyloxazol-2-yl)butyl)-3-(pyrrolidin-1-yl)benzamide (EX-16)

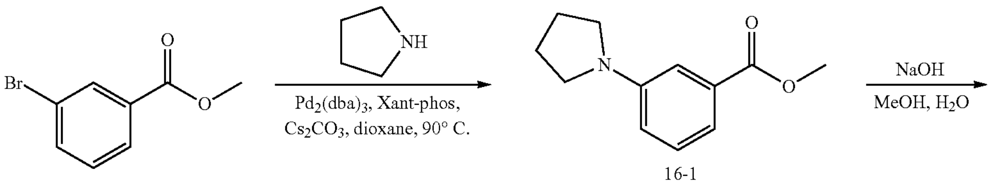

16-1

-continued

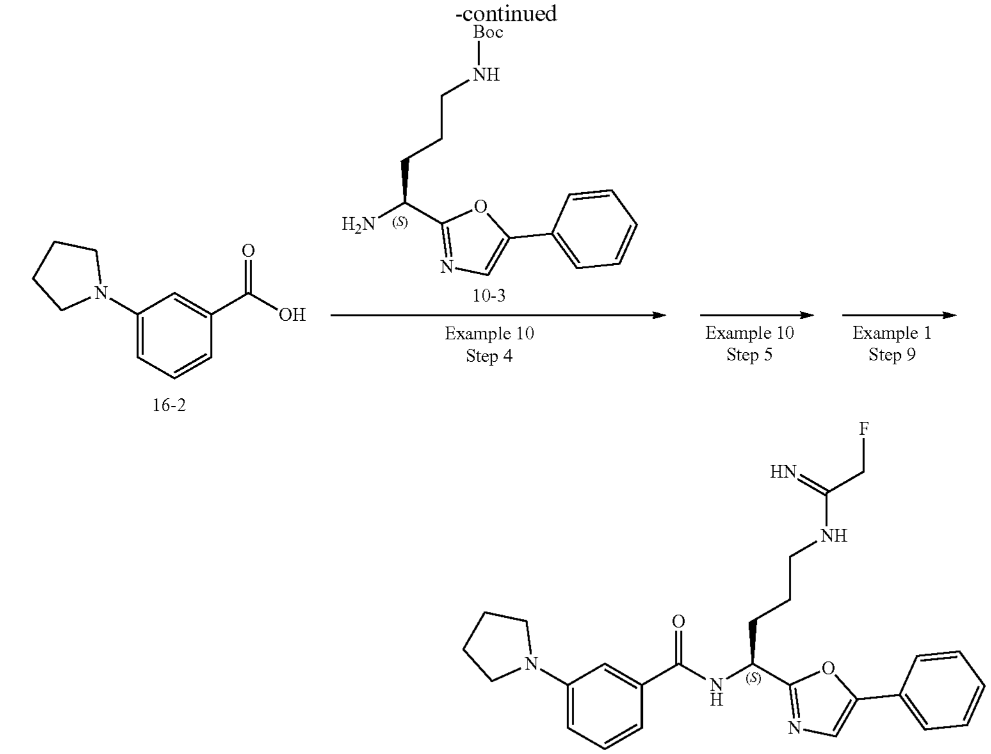

10-3

16-2

EX-16

Step 1: Methyl 3-(pyrrolidin-1-yl)benzoate (16-1)

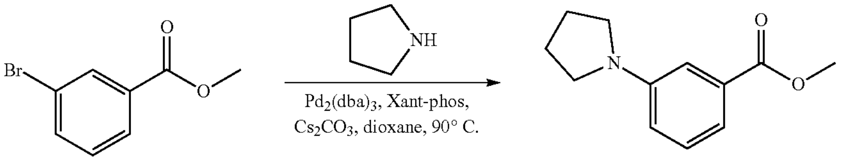

16-1

To a solution of methyl 3-bromobenzoate (1.00 g, 4.67 mmol), pyrrolidine (663 mg, 9.34 mmol), tris(dibenzylideneacetone)dipalladium (425 mg, 0.46 mmol), 4,5-bis(diphenylphosphino)-9,9-dimethylxanthene (268 mg, 0.46 mmol) in dioxane (20 mL) was added cesium carbonate (4.57 g, 14.0 mmol). The mixture was stirred at 90° C. under $N_2$ for 3 h. The solvent was evaporated and water (20 mL) was added. The product was extracted with ethyl acetate (50 mL×3). The organic layers were dried over anhydrous $Na_2SO_4$ and concentrated under vacuum to afford crude product which was purified by silica gel chromatography (elution gradient: petroleum ether/EtOAc, 3/1, v/v).

Pure fractions were evaporated to dryness to afford methyl 3-(pyrrolidin-1-yl)benzoate (16-1, 800 mg) as a yellow solid, yield: 84%. MS (ESI) m/z=206.0 $[M+H]^+$.

Step 2: 3-(Pyrrolidin-1-yl)benzoic acid (16-2)

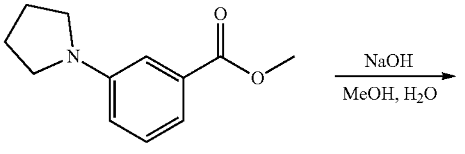

16-1

-continued

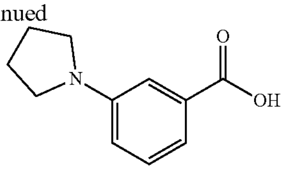

16-2

To a suspension of methyl 3-(pyrrolidin-1-yl)benzoate (16-1, 800 mg, 3.88 mmol) in MeOH (100 mL) was added sodium hydroxide (1 N, 100 mL). The mixture was stirred at room temperature for 16 h. The mixture was concentrated and adjusted pH to 5-6 with hydrochloric acid aqueous solution (2 N), then extracted with ethyl acetate (100 mL×3). The organic phase was washed with water (50 mL), brine (50 mL), and concentrated under vacuum to give 3-(pyrrolidin-1-yl)benzoic acid (16-2, 500 mg) as a yellow solid, yield: 67%. $^1H$ NMR (400 MHz, DMSO-$d_6$): δ ppm 1.95-2.00 (m, 4H), 3.23-3.33 (m, 4H), 6.75-6.77 (m, 1H), 7.07-7.08 (m, 1H), 7.16-7.18 (m, 1H), 7.24-7.28 (m, 1H), 12.71 (s, 1H). MS (ESI) m/z=192.0 $[M+H]^+$.

Step 3: (S)—N-(4-(2-fluoroacetimidamido)-1-(5-phenyloxazol-2-yl)butyl)-3-(pyrrolidin-1-yl)benzamide (EX-16)

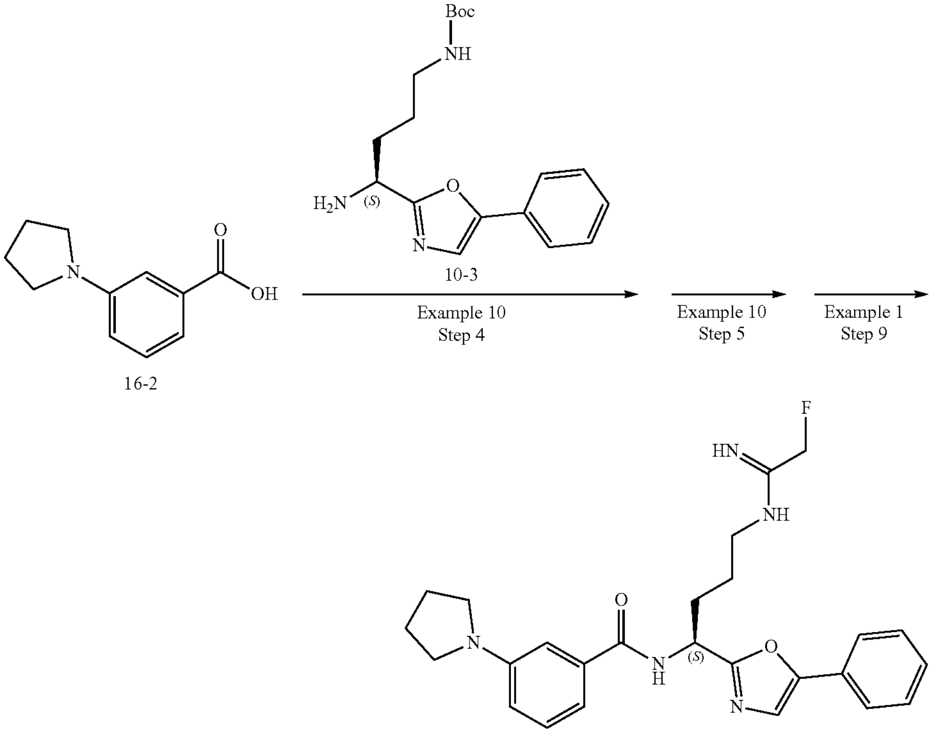

16-2
10-3
EX-16

(S)—N-(4-(2-Fluoroacetimidamido)-1-(5-phenyloxazol-2-yl)butyl)-3-(pyrrolidin-1-yl)benzamide (EX-16) was synthesized from 3-(pyrrolidin-1-yl)benzoic acid and tert-butyl (S)-(4-amino-4-(5-phenyloxazol-2-yl)butyl)carbamate (10-3) similarly to Example 10, Steps 4-5, and Example 1, Step 9, as the hydrochloride salt. $^1$H NMR (400 MHz, DMSO-$d_6$): δ ppm 1.66-1.78 (m, 2H), 1.98-2.01 (m, 4H), 2.04-2.20 (m, 2H), 3.32-3.40 (m, 6H), 5.26-5.32 (m, 2H), 5.38 (s, 1H), 6.85 (s, 1H), 7.22-7.32 (m, 3H), 7.34-7.38 (m, 1H), 7.45-7.49 (m, 2H), 7.65-7.69 (m, 3H), 9.03 (d, J=8.0 Hz, 1H), 9.34 (s, 1H), 9.49 (s, 1H), 9.99 (s, 1H). MS (ESI) m/z=464.1 $[M+H]^+$.

The following examples can be prepared similarly to EX-16 using appropriate starting materials and reagents.

| EXAMPLE | NAME | STRUCTURE | MS (ESI) m/z $[M + H]^+$ |
|---|---|---|---|
| EX-17 | (S)-N-(4-(2-Fluoroacetimidamido)-1-(5-phenyloxazol-2-yl)butyl)-2-methoxy-5-morpholinobenzamide | 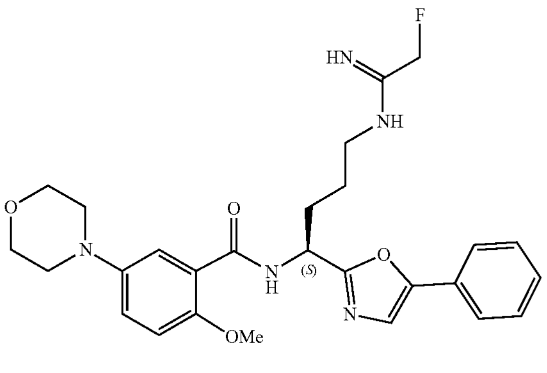 | 510.1 |

-continued

| EXAMPLE | NAME | STRUCTURE | MS (ESI) m/z $[M + H]^+$ |
|---|---|---|---|
| EX-18 | (S)-N-(4-(2-Fluoroacetimidamido)-1-(5-phenyloxazol-2-yl)butyl)-2-methoxy-5-(4-methylpiperazin-1-yl)benzamide | 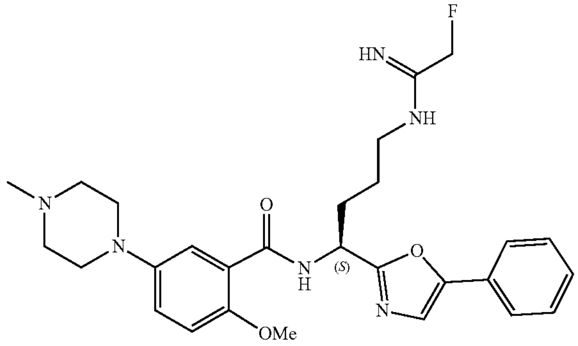 | 523.2 |

Example 19 Synthesis of (S)—N-(4-(2-fluoroacetimidamido)-1-(5-phenyloxazol-2-yl)butyl)-2,6-dimethoxybenzamide (EX-19)

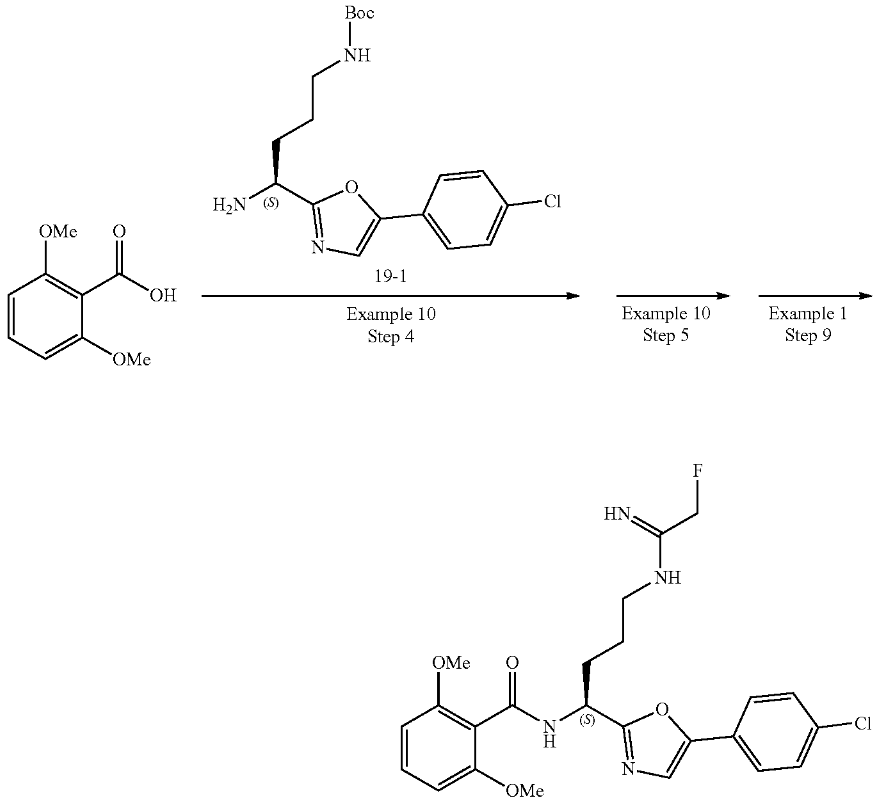

EX-19

(S)—N-(4-(2-Fluoroacetimidamido)-1-(5-phenyloxazol-2-yl)butyl)-2,6-dimethoxybenzamide (EX-19) was synthesized from 2,6-dimethoxybenzoic acid and tert-butyl (S)-(4-amino-4-(5-(4-chlorophenyl)oxazol-2-yl)butyl)carbamate (19-1, similarly prepared as 10-3 using appropriate starting materials and reagents) similarly to Example 10, Steps 4-5, and Example 1, Step 9, as the hydrochloride salt. $^1H$ NMR (400 MHz, DMSO-$d_6$): δ ppm 1.69-1.83 (m, 2H), 1.87-2.13 (m, 2H), 3.38-3.40 (m, 2H), 3.73 (s, 6H), 5.20-5.27 (m, 2H), 5.39 (s, 1H), 6.68-6.70 (m, 2H), 7.29-7.34 (m, 1H), 7.58-7.61 (m, 2H), 7.69 (s, 1H), 7.73-7.76 (m, 2H), 8.73 (d, J=8.8 Hz, 1H), 9.26 (s, 1H), 9.49 (s, 1H), 9.98 (s, 1H). MS (ESI) m/z=489.1 $[M+H]^+$.

The following examples can be prepared similarly to EX-19 using appropriate starting materials and reagents.

| EXAMPLE | NAME | STRUCTURE | MS (ESI) m/z [M + H]+ |
|---|---|---|---|
| EX-20 | (S)-N-(4-(2-Fluoroacetimidamido)-1-(5-(4-methoxyphenyl)oxazol-2-yl)butyl)-2,6-dimethoxybenzamide | 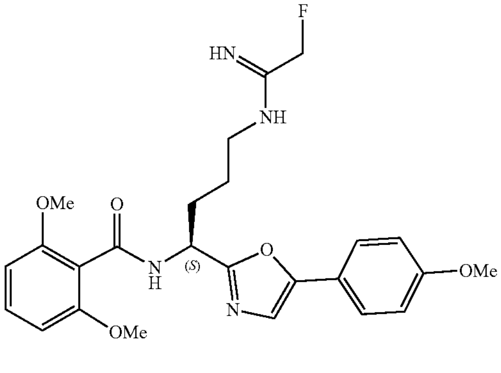 | 485.1 |
| EX-21 | (S)-N-(1-(5-(2-Chlorophenyl)oxazol-2-yl)-4-(2-fluoroacetimidamido)butyl)-2,6-dimethoxybenzamide | 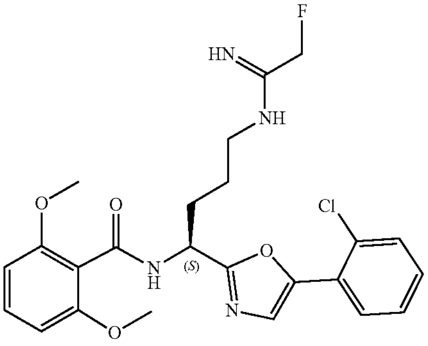 | 489.1 |
Example 22 Synthesis of (S)-2-chloro-N-(1-(5-(4-chlorophenyl)oxazol-2-yl)-4-(2-fluoroacetimidamido)butyl)-6-methoxybenzamide (EX-22)
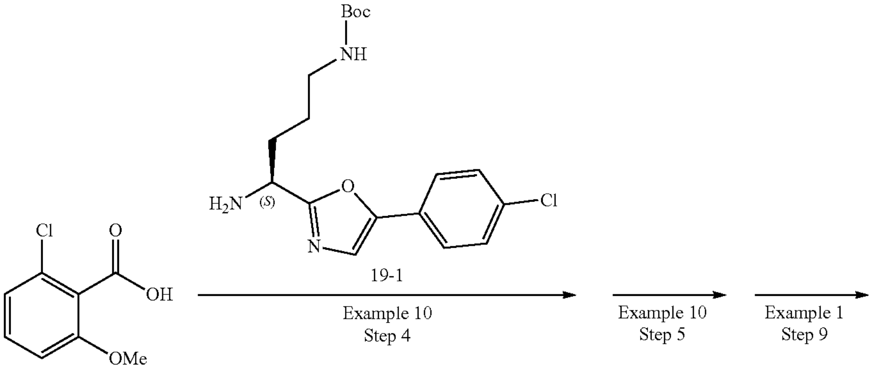

-continued

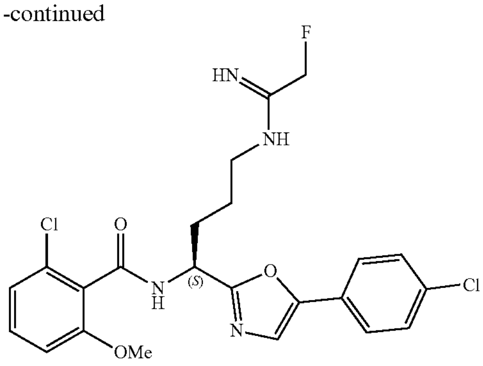

EX-22

(S)-2-Chloro-N-(1-(5-(4-chlorophenyl)oxazol-2-yl)-4-(2-fluoroacetimidamido)butyl)-6-methoxybenzamide (EX-22) was synthesized from 2-chloro-6-methoxybenzoic acid and tert-butyl (S)-(4-amino-4-(5-(4-chlorophenyl)oxazol-2-yl)butyl)carbamate (19-1) similarly to Example 10, Steps 4-5, and Example 1, Step 9, as the hydrochloride salt. $^1$H NMR (400 MHz, DMSO-$d_6$): δ ppm 1.65-2.15 (m, 4H), 3.38-3.40 (m, 2H), 3.77 (s, 3H), 5.22-5.27 (m, 2H), 5.38 (s, 1H), 7.05-7.08 (m, 2H), 7.38 (t, J=8 Hz, 1H), 7.58 (d, J=8 Hz, 2H), 7.70 (s, 1H), 7.73 (d, J=8 Hz, 2H), 9.07 (d, J=8 Hz, 1H), 9.32 (br s, 1H), 9.53 (br s, 1H), 10.04 (br s, 1H). MS (ESI) m/z=493.0 [M+H]$^+$.

The following examples can be prepared similarly to EX-16 using appropriate starting materials and reagents.

| EXAMPLE | NAME | STRUCTURE | MS (ESI) m/z [M + H]$^+$ |
|---|---|---|---|
| EX-23 | (S)-2-Chloro-N-(1-(5-(4-chlorophenyl)oxazol-2-yl)-4-(2-fluoroacetimidamido)butyl)-6-(dimethylamino)benzamide | 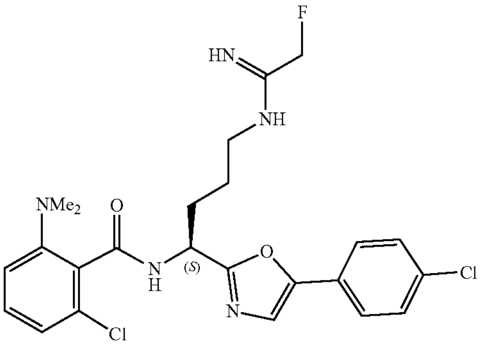 | 506.0 |
| EX-24 | (S)-2-Chloro-N-(4-(2-fluoroacetimidamido)-1-(5-(4-fluorophenyl)oxazol-2-yl)butyl)-6-methoxybenzamide | 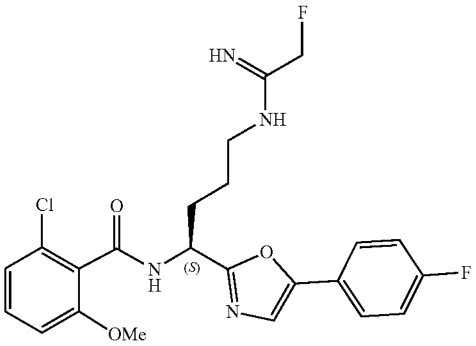 | 476.6 |

-continued

| EXAMPLE | NAME | STRUCTURE | MS (ESI) m/z [M + H]+ |
|---|---|---|---|
| EX-25 | (S)-2-Chloro-N-(1-(5-(3,5-difluorophenyl)oxazol-2-yl)-4-(2-fluoroacetimidamido)butyl)-6-methoxybenzamide | 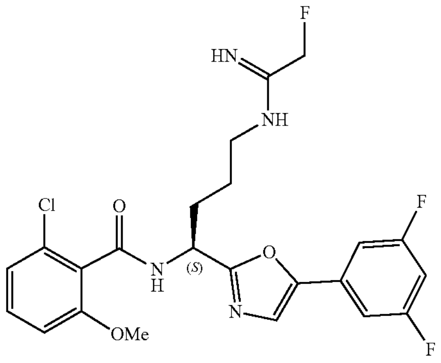 | 494.6 |
| EX-26 | (S)-2-Chloro-N-(1-(5-(2-chlorophenyl)oxazol-2-yl)-4-(2-fluoroacetimidamido)butyl)-6-methoxybenzamide | 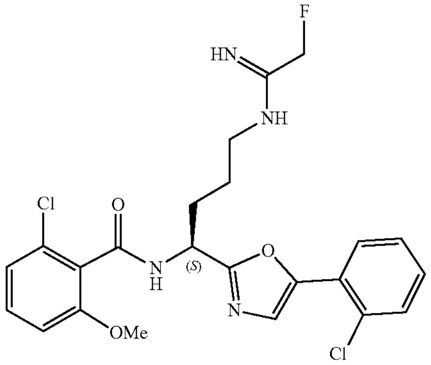 | 492.6 |
| EX-27 | (S)-2-Chloro-N-(4-(2-fluoroacetimidamido)-1-(5-(3-(trifluoromethyl)phenyl)oxazol-2-yl)butyl)-6-methoxybenzamide | 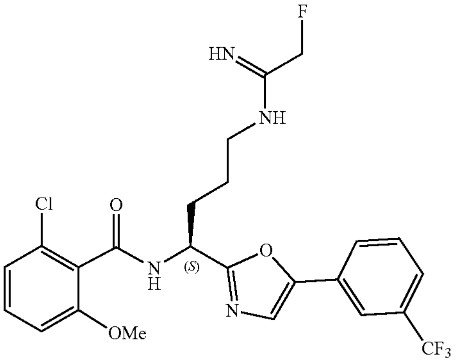 | 526.6 |
| EX-28 | (S)-2-Chloro-N-(4-(2-fluoroacetimidamido)-1-(5-(m-tolyl)oxazol-2-yl)butyl)-6-methoxybenzamide | 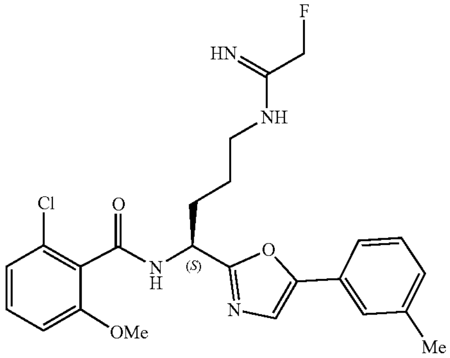 | 472.7 |

-continued

| EXAMPLE | NAME | STRUCTURE | MS (ESI) m/z [M + H]+ |
|---|---|---|---|
| EX-29 | (S)-2-Chloro-N-(1-(5-(4-(dimethylamino)phenyl)oxazol-2-yl)-4-(2-fluoroacetimidamido)butyl)-6-methoxybenzamide | 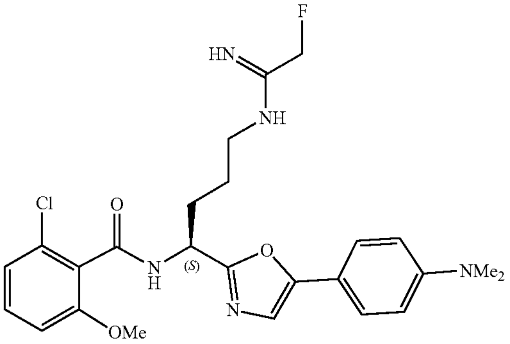 | 501.7 |
| EX-30 | (S)-2,6-Dichloro-N-(4-(2-fluoroacetimidamido)-1-(5-(4-fluorophenyl)oxazol-2-yl)butyl)benzamide | 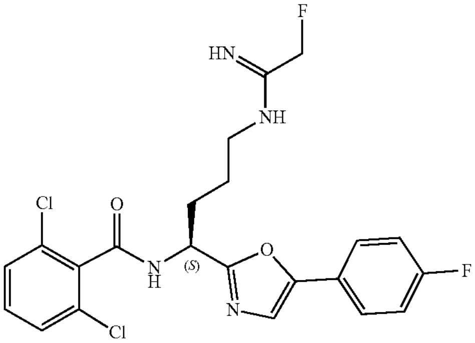 | 480.6 |
| EX-31 | (S)-2-Fluoro-N-(4-(2-fluoroacetimidamido)-1-(5-(m-tolyl)oxazol-2-yl)butyl)-6-methoxybenzamide | 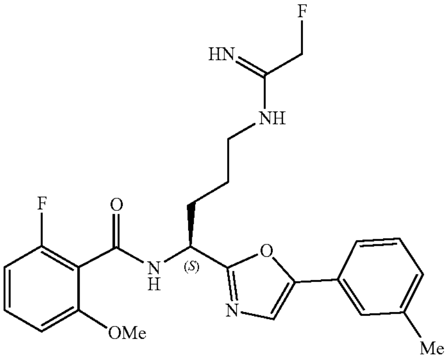 | 456.7 |
| EX-32 | (S)-2,6-Difluoro-N-(4-(2-fluoroacetimidamido)-1-(5-(m-tolyl)oxazol-2-yl)butyl)benzamide | 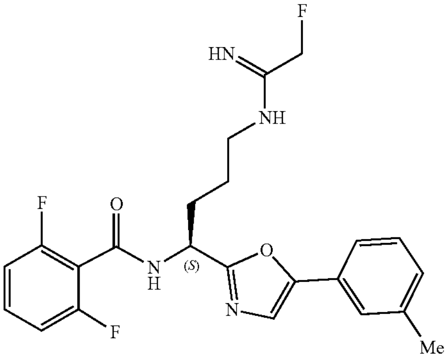 | 444.7 |

-continued
| EXAMPLE | NAME | STRUCTURE | MS (ESI) m/z [M + H]+ |
| --- | --- | --- | --- |
| EX-33 | (S)-2-Chloro-N-(1-(5-(3-chlorophenyl)oxazol-2-yl)-4-(2-fluoroacetimidamido)butyl)-6-methoxybenzamide | 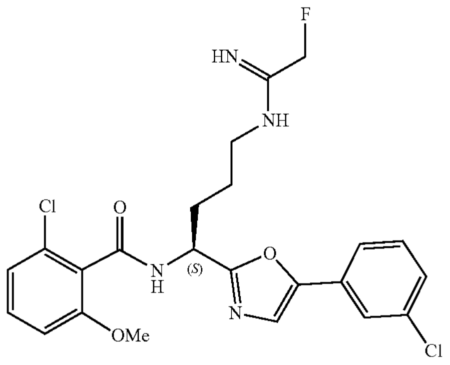 | 492.6 |
| EX-34 | (S)-N-(1-(5-(3-Chlorophenyl)oxazol-2-yl)-4-(2-fluoroacetimidamido)butyl)-5-ethynyl-2-methoxybenzamide | 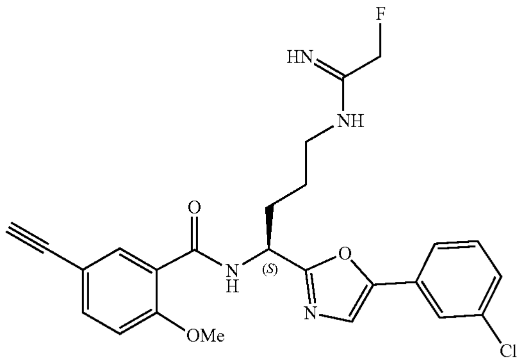 | 482.7 |
| EX-35 | (S)-2-Chloro-N-(1-(5-(3-chlorophenyl)oxazol-2-yl)-4-(2-fluoroacetimidamido)butyl)-6-fluorobenzamide | 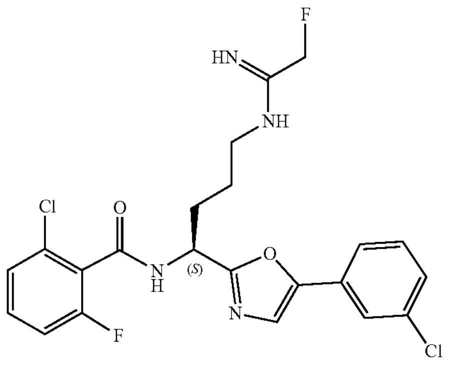 | 480.6 |

Example 36 Synthesis of (S)—N-(4-(2-fluoroacetimidamido)-1-(5-phenyloxazol-2-yl)butyl)-3-methoxy-2-naphthamide (EX-36)

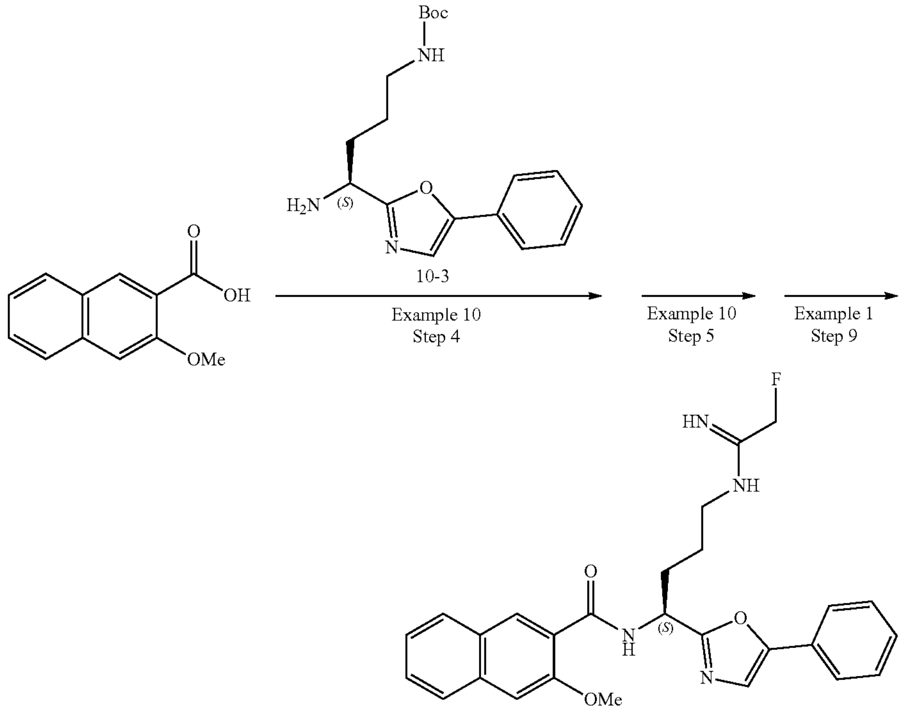

EX-36

(S)—N-(4-(2-Fluoroacetimidamido)-1-(5-phenyloxazol-2-yl)butyl)-3-methoxy-2-naphthamide (EX-36) was synthesized from 3-methoxy-2-naphthoic acid and tert-butyl (S)-(4-amino-4-(5-phenyloxazol-2-yl)butyl)carbamate (10-3) similarly to Example 10, Steps 4-5, and Example 1, Step 9, as the hydrochloride salt. $^1$H NMR (400 MHz, DMSO-$d_6$): δ ppm 1.62-1.85 (m, 2H), 1.95-2.21 (m, 2H), 3.30-3.50 (m, 2H), 3.97 (s, 3H), 5.13-5.55 (m, 3H), 7.35-7.60 (m, 7H), 7.66-7.74 (m, 3H), 7.85-8.00 (m, 2H), 8.19 (s, 1H), 8.92 (d, J=8.0 Hz, 1H), 9.29 (s, 1H), 9.47 (s, 1H), 9.96 (s, 1H). MS (ESI) m/z=474.9 [M+H]$^+$.

Example 37 Synthesis of (S)—N-(4-(2-fluoroacetimidamido)-1-(5-phenyl-1H-imidazol-2-yl)butyl)-2-methoxybenzamide (EX-37)

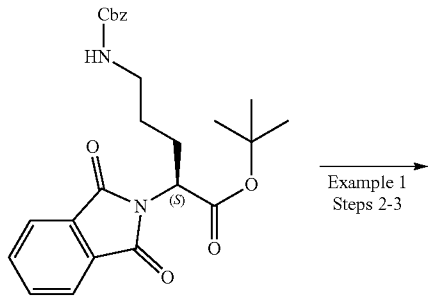

10-1

-continued

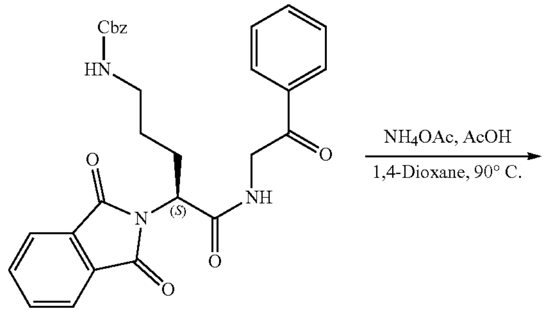

37-1

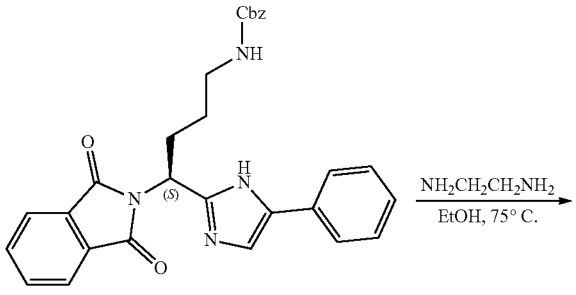

37-1

-continued

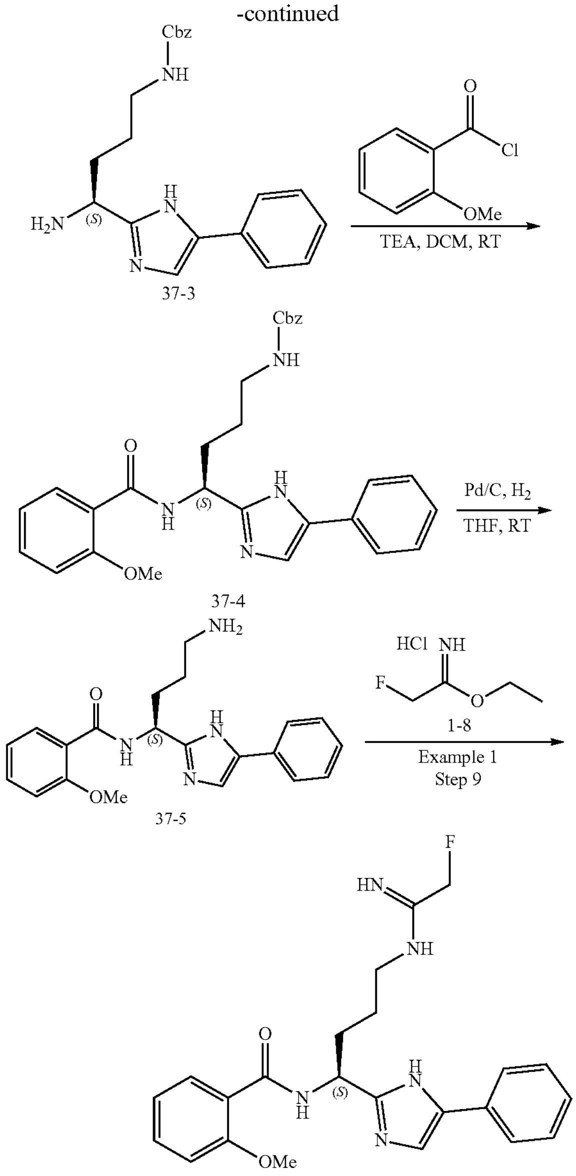

37-3

37-4

37-5

EX-37

Step 1: Benzyl (S)-(4-(1,3-dioxoisoindolin-2-yl)-5-oxo-5-((2-oxo-2-phenylethyl)amino)pentyl)carbamate (37-1)

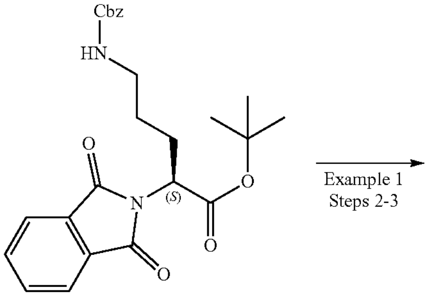

10-1

-continued

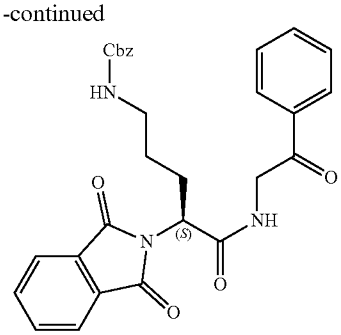

37-1

Benzyl (S)-(4-(1,3-dioxoisoindolin-2-yl)-5-oxo-5-((2-oxo-2-phenylethyl)amino)pentyl)carbamate (37-1) was prepared from compound 10-3 similarly to Example 1, Steps 2-3. $^1$H NMR (400 MHz, DMSO-$d_6$): δ ppm 1.30-1.46 (m, 2H), 2.10-2.29 (m, 2H), 2.90-3.05 (m, 2H), 4.40-4.58 (m, 1H), 4.62-4.81 (m, 2H), 4.97 (s, 2H), 7.19-7.39 (m, 6H), 7.50-7.69 (m, 3H), 7.85-8.00 (m, 6H), 8.42-8.50 (m, 1H). MS (ESI) m/z=513.8 [M+H]$^+$.

Step 2: Benzyl (S)-(4-(1,3-dioxoisoindolin-2-yl)-4-(5-phenyl-1H-imidazol-2-yl)butyl)carbamate (37-2)

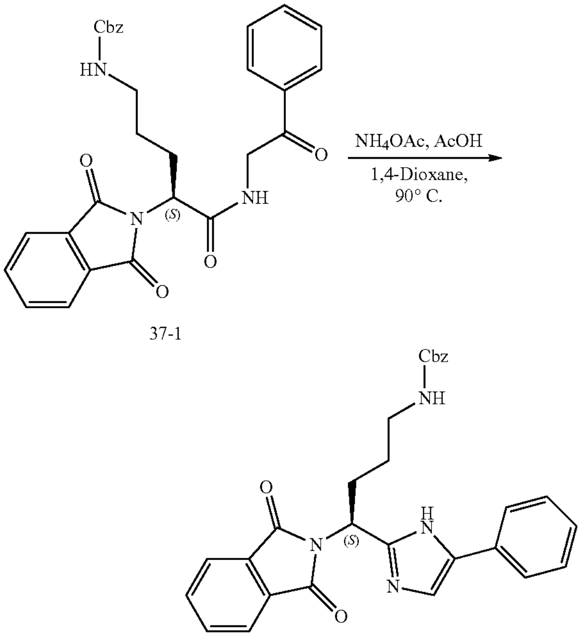

37-1

37-2

To a solution of benzyl (S)-(4-(1,3-dioxoisoindolin-2-yl)-5-oxo-5-((2-oxo-2-phenylethyl)amino)pentyl)carbamate (37-1, 9 g, 17.5 mmol), $NH_4OAc$ (27 g, 350 mmol) in 1,4-dioxane (100 mL) was added AcOH (15 mL). The mixture was stirred at 90° C. for 4 h. The reaction mixture was concentrated under vacuum and diluted with ethyl acetate (250 mL) and water (50 mL). The organic phase was washed with water (50 mL) and brine (50 mL), then concentrated under vacuum to afford the crude product which was purified by silica gel chromatography (elution gradient: petroleum ether/EA, 1/1, v/v). Pure fractions were evaporated to dryness to afford benzyl (S)-(4-(1,3-dioxoisoindolin-2-yl)-4-(5-phenyl-1H-imidazol-2-yl)butyl)carbamate (37-2, 5 g) as an off-white solid, yield: 58%. $^{1}$H NMR (400 MHz, DMSO-$d_6$): δ ppm 1.39-1.55 (m, 2H), 2.09-2.45 (m, 2H), 3.02-3.12 (m, 2H), 4.98 (s, 2H), 5.30-5.38 (m, 1H), 7.25-7.37 (m, 9H), 7.53-7.56 (m, 1H), 7.71-7.74 (m, 1H), 7.86-7.94 (m, 5H), 12.11 (s, 1H). MS (ESI) m/z=495.2 $[M+H]^+$.

Step 3: Benzyl (S)-(4-amino-4-(5-phenyl-1H-imidazol-2-yl)butyl)carbamate (37-3)

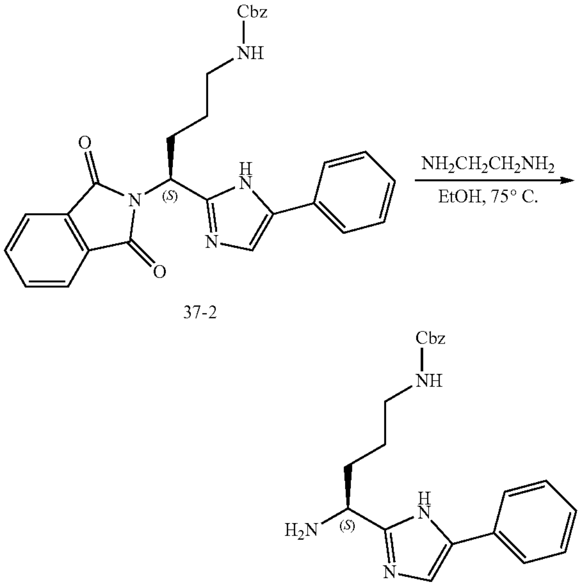

37-2

37-3

To a suspension of benzyl (S)-(4-(1,3-dioxoisoindolin-2-yl)-4-(5-phenyl-1H-imidazol-2-yl)butyl)carbamate (37-2, 3 g, 6.07 mmol) in EtOH (40 mL) was added ethylenediamine (1.82 g, 30.3 mmol). The mixture was stirred at 75° C. for 2 h. The reaction mixture was concentrated and purified by silica gel chromatography (elution gradient: MeOH/DCM, 1/10, v/v). Pure fractions were evaporated to dryness to afford benzyl (S)-(4-amino-4-(5-phenyl-1H-imidazol-2-yl)butyl)carbamate (37-3, 2 g) as a light yellow solid, yield: 90%. MS (ESI) m/z=365.2 $[M+H]^+$.

Step 4: Benzyl (S)-(4-(2-methoxybenzamido)-4-(5-phenyl-1H-imidazol-2-yl)butyl)carbamate (37-4)

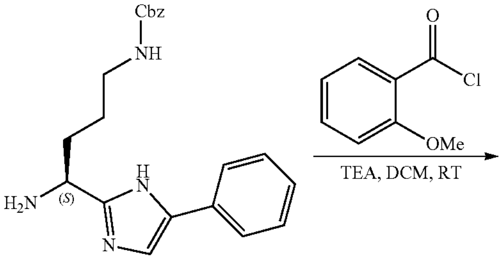

37-3

-continued

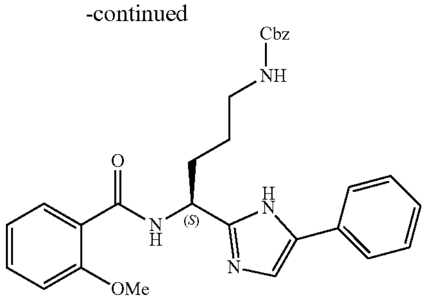

37-4

To a solution of benzyl (S)-(4-amino-4-(5-phenyl-1H-imidazol-2-yl)butyl)carbamate (37-3, 700 mg, 1.92 mmol) and TEA (580 mg, 5.76 mmol) in dichloromethane (250 mL) was added 2-methoxybenzoyl chloride (326 mg, 1.92 mmol). The mixture was stirred at room temperature for 2 h. The mixture was diluted with water (20 mL), extracted with DCM (50 mL×2). The organic phase was washed with water (100 mL), brine (100 mL) and concentrated under vacuum to give the crude product which was purified by silica gel chromatography (elution gradient: EA/PE, 2/1, v/v). Pure fractions were evaporated to dryness to afford benzyl (S)-(4-(2-methoxybenzamido)-4-(5-phenyl-1H-imidazol-2-yl)butyl)carbamate (37-4, 600 mg) as a brown solid, yield: 63%. $^{1}$H NMR (400 MHz, DMSO-$d_6$): δ ppm 1.35-1.52 (m, 2H), 1.78-1.99 (m, 2H), 2.97-3.06 (m, 2H), 3.94 (s, 3H), 4.98 (s, 2H), 5.12-5.24 (m, 1H), 7.07 (t, J=7.4 Hz, 1H), 7.14-7.22 (m, 2H), 7.24-7.37 (m, 8H), 7.48-7.58 (m, 2H), 7.75-7.93 (m, 3H), 8.75 (d, J=7.6 Hz, 1H), 12.03 (s, 1H). MS (ESI) m/z=499.2 $[M+H]^+$.

Step 5: (S)—N-(4-Amino-1-(5-phenyl-1H-imidazol-2-yl)butyl)-2-methoxybenzamide (37-5)

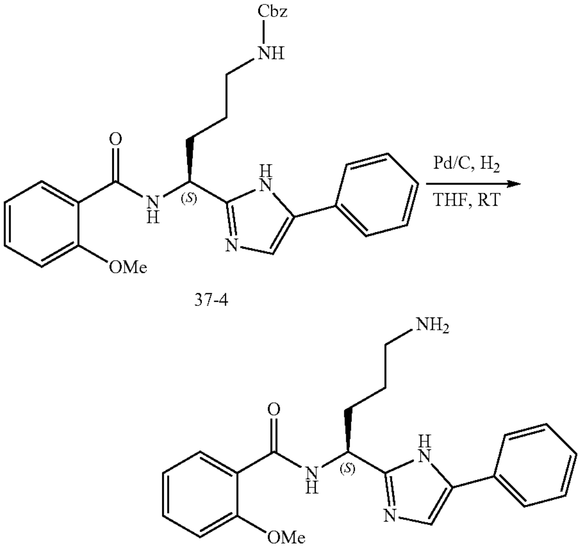

37-4

37-5

The mixture of benzyl (S)-(4-(2-methoxybenzamido)-4-(5-phenyl-1H-imidazol-2-yl)butyl)carbamate (37-4, 500 mg, 1.00 mmol) and catalytic amount of palladium on carbon in THF (30 mL) was stirred at room temperature under a hydrogen balloon for 16 h. The mixture was filtered, and the filtrate was concentrated to give (S)—N-(4-Amino-1-(5-phenyl-1H-imidazol-2-yl)butyl)-2-methoxybenzamide (37-5, 300 mg) as a pale yellow solid, yield: 82%. $^1$H NMR (400 MHz, DMSO-d6): δ ppm 1.35-1.45 (m, 2H), 1.82-2.00 (m, 2H), 3.23-3.45 (m, 2H), 3.97 (s, 3H), 5.12-5.25 (m, 1H), 7.07 (t, J=7.2 Hz, 1H), 7.14-7.24 (m, 2H), 7.35 (t, J=7.8 Hz, 2H), 7.47-7.58 (m, 2H), 7.72-7.80 (m, 2H), 7.86-7.91 (m, 1H), 8.75 (d, J=8.0 Hz, 1H). MS (ESI) m/z=365.2 [M+H]$^+$.

Step 6: (S)—N-(4-(2-Fluoroacetimidamido)-1-(5-phenyl-1H-imidazol-2-yl)butyl)-2-methoxybenzamide (EX-37)

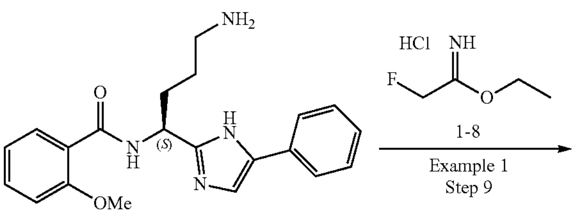

37-5

-continued

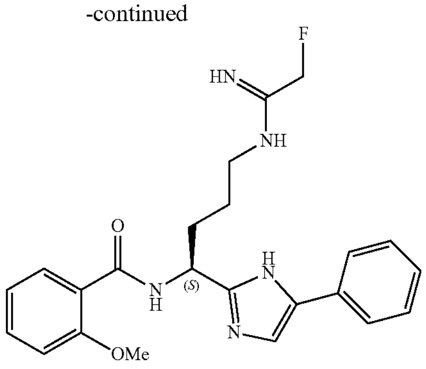

EX-37

(S)—N-(4-(2-Fluoroacetimidamido)-1-(5-phenyl-1H-imidazol-2-yl)butyl)-2-methoxybenzamide (EX-37) was synthesized from (S)—N-(4-amino-1-(5-phenyl-1H-imidazol-2-yl)butyl)-2-methoxybenzamide (37-5) as the hydrochloride salt similarly to Example 1, Step 9. $^1$H NMR (400 MHz, DMSO-$d_6$): δ ppm 1.52-1.79 (m, 2H), 2.21-2.35 (m, 2H), 3.35-3.50 (m, 2H), 3.99 (s, 3H), 5.27-5.45 (m, 2H), 5.52-5.63 (m, 1H), 7.05 (t, J=7.4 Hz, 1H), 7.19 (d, J=8.4 Hz, 1H), 7.42-7.47 (m, 1H), 7.47-7.55 (m, 3H), 7.78-7.84 (m, 1H), 7.96-8.02 (m, 2H), 8.14 (s, 1H), 8.95 (d, J=7.6 Hz, 1H), 9.37-9.58 (m, 2H), 10.00 (s, 1H), 15.07 (s, 1H), 15.64 (s, 1H). MS (ESI) m/z=424.1 [M+H]$^+$.

Example 38 (S)—N-(4-(2-fluoroacetimidamido)-1-(5-phenyloxazol-2-yl)butyl)-4-methoxy-[1,1'-biphenyl]-3-carboxamide (EX-38)

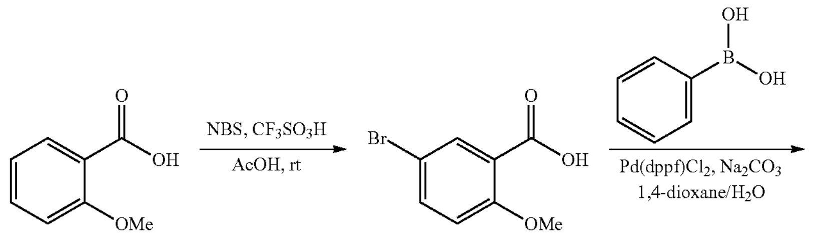

38-1

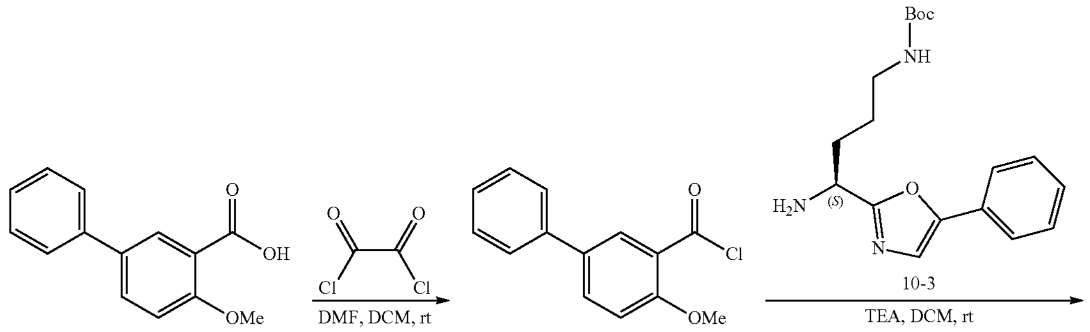

38-2

38-3

-continued

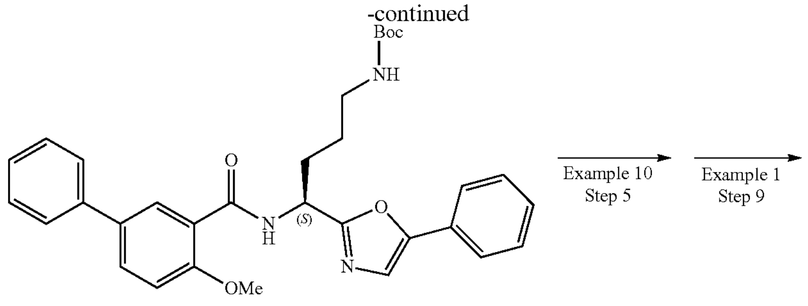

38-4

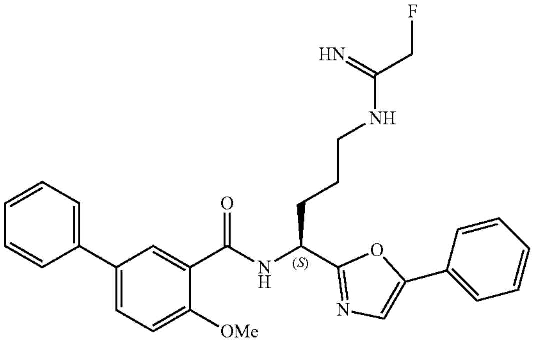

EX-38

Step 1: 5-Bromo-2-methoxybenzoic acid (38-1)

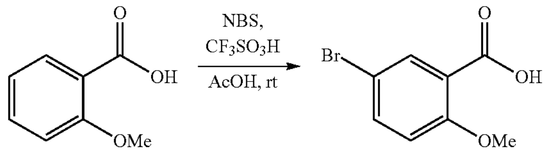

38-1

To a solution of 2-methoxybenzoic acid (5 g, 0.033 mol), NBS (5.87 g, 0.033 mol) in AcOH (80 mL) was added trifluoromethanesulfonic acid (9.87 g, 0.066 mol). The mixture was stirred at room temperature for 16 h. The mixture was concentrated and diluted with ethyl acetate (250 mL) and water (50 mL). The organic phase was washed with water (50 mL), brine (50 mL), dried and concentrated under vacuum to give 5-bromo-2-methoxybenzoic acid (38-1, 6 g) as a white solid, yield: 79%. $^1H$ NMR (400 MHz, DMSO-$d_6$): δ ppm 3.82 (s, 4H), 7.11 (d, J=8.8 Hz, 1H), 7.67 (dd, J=9.0, 2.6 Hz, 1H), 7.74 (d, J=2.4 Hz, 1H), 12.95 (s, 1H). MS (ESI) m/z=228.5, 230.5 $[M-H]^-$.

Step 2: 4-Methoxy-[1,1'-biphenyl]-3-carboxylic acid (38-2)

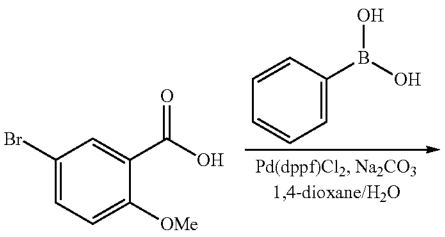

38-1

-continued

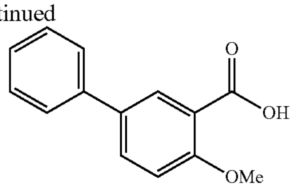

38-2

To a solution of 5-bromo-2-methoxybenzoic acid (38-1, 3 g, 13 mmol), phenylboronic acid (1.66 g, 13.6 mmol), [1,1'-bis(diphenylphosphino)ferrocene]dichloropalladium (II) (530 mg, 0.65 mmol) in dioxane (40 mL) and $H_2O$ (8 mL) was added sodium carbonate (4.13 g, 39 mmol). The mixture was stirred at 80° C. under $N_2$ for 3 h. The reaction mixture was concentrated and diluted with NaOH (0.5 N, 50 mL), then extracted with ethyl acetate (100 mL×3). The aqueous phase was adjusted pH to 5-6 with hydrochloric acid aqueous solution (1N), and then extracted with ethyl acetate (100 mL×3). The organic phase was dried over anhydrous $Na_2SO_4$ and concentrated under vacuum to afford 4-methoxy-[1,1'-biphenyl]-3-carboxylic acid (38-2, 2 g) as a pale yellow solid, yield: 67%. $^1H$ NMR (400 MHz, DMSO-$d_6$): δ ppm 3.87 (s, 3H), 7.22 (d, J=8.8 Hz, 1H), 7.31-7.39 (m, 1H), 7.42-7.50 (m, 2H), 7.61-7.67 (m, 2H), 7.81 (dd, J=8.6, 2.6 Hz, 1H), 7.90 (d, J=2.4 Hz, 1H), 12.74 (s, 1H). MS (ESI) m/z=226.7 $[M-H]^-$.

Step 3: 4-Methoxy-[1,1'-biphenyl]-3-carbonyl chloride (38-3)

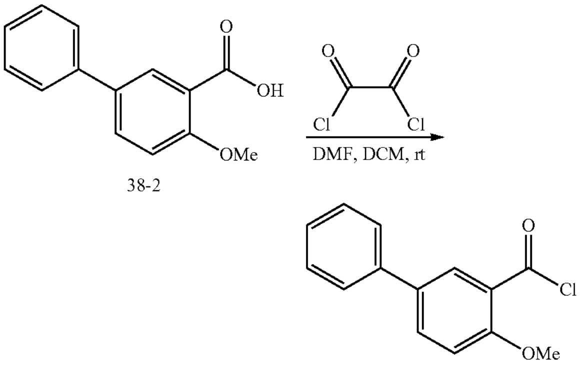

38-2

38-3

To a solution of 4-methoxy-[1,1'-biphenyl]-3-carboxylic acid (38-2, 500 mg, 2.19 mmol) in DCM (20 mL) was added oxalyl chloride (557 mg, 4.38 mmol) and DMF (0.05 mL). The mixture was stirred at room temperature for 2 h. The reaction mixture was concentrated to give 4-methoxy-[1,1'-biphenyl]-3-carbonyl chloride (38-3, 540 mg) which was used in the next step directly.

Step 4: tert-Butyl (S)-(4-(4-methoxy-[1,1'-biphenyl]-3-carboxamido)-4-(5-phenyloxazol-2-yl)butyl)carbamate (38-4)

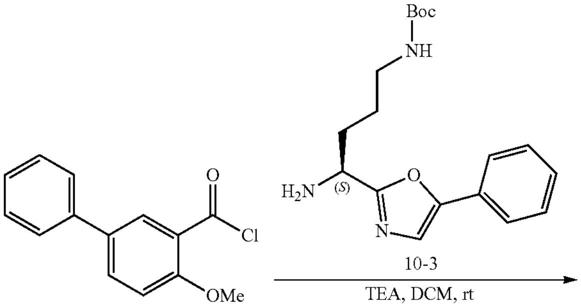

10-3

38-3

-continued

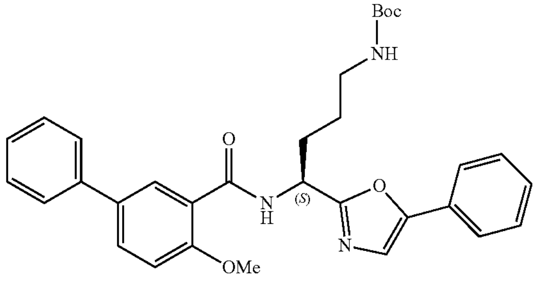

38-4

To a solution of tert-butyl (S)-(4-amino-4-(5-phenyloxazol-2-yl)butyl)carbamate (10-3, 725 mg, 2.19 mmol) and TEA (665 mg, 6.57 mmol) in DCM (20 mL) was added 4-methoxy-[1,1'-biphenyl]-3-carbonyl chloride (38-3, 540 mg, 2.19 mmol). The mixture was stirred at room temperature for 1 h. The mixture was diluted with water (20 mL), extracted with DCM (50 mL×2). The organic phase was washed with water (100 mL), brine (100 mL) and concentrated under vacuum to give the crude product which was purified by silica gel chromatography (elution gradient: EA/PE, 2/1, v/v). Pure fractions were evaporated to dryness to afford tert-butyl (S)-(4-(4-methoxy-[1,1'-biphenyl]-3-carboxamido)-4-(5-phenyloxazol-2-yl)butyl)carbamate (38-4, 600 mg) as a brown solid, yield: 50%. $^1$H NMR (400 MHz, DMSO-$d_6$): δ ppm 1.36 (s, 9H), 1.46-1.64 (m, 2H), 1.92-2.10 (m, 2H), 2.93-3.08 (m, 2H), 3.94 (s, 3H), 5.15-5.40 (m, 1H), 6.77-6.95 (m, 1H), 7.24-7.50 (m, 7H), 7.61-7.82 (m, 6H), 7.94 (d, J=2.4 Hz, 1H), 8.77 (d, J=8.0 Hz, 1H). MS (ESI) m/z=542.3 [M+H]$^+$.

Step 5: (S)—N-(4-(2-Fluoroacetimidamido)-1-(5-phenyloxazol-2-yl)butyl)-4-methoxy-[1,1'-biphenyl]-3-carboxamide (EX-38)

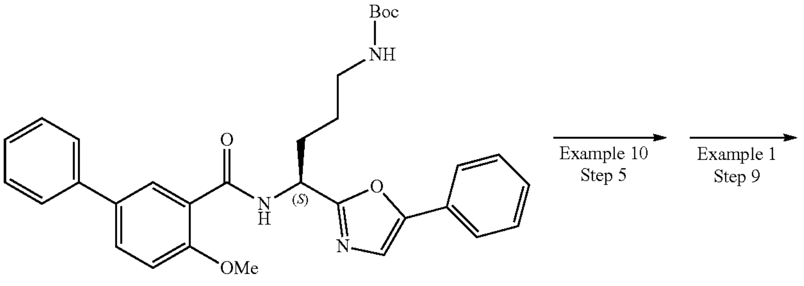

38-4

-continued

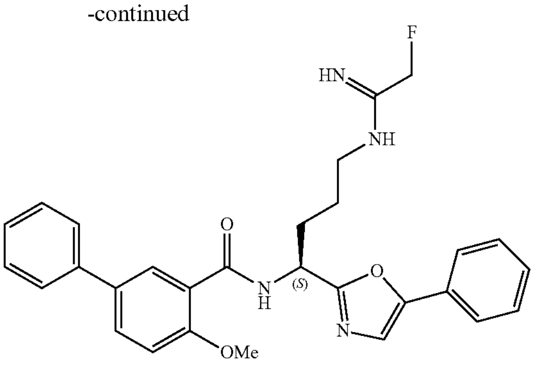

EX-38

(S)—N-(4-(2-Fluoroacetimidamido)-1-(5-phenyloxazol-2-yl)butyl)-4-methoxy-[1,1'-biphenyl]-3-carboxamide (EX-38) was synthesized from tert-butyl (S)-(4-(4-methoxy-[1,1'-biphenyl]-3-carboxamido)-4-(5-phenyloxazol-2-yl)butyl) carbamate (38-4) similarly to Example 10, Step 5 and Example 1, Step 9, as the hydrochloride salt. $^1$H NMR (400 MHz, DMSO-$d_6$): δ ppm 1.60-1.85 (m, 2H), 1.93-2.23 (m, 2H), 3.30-3.55 (m, 2H), 3.95 (s, 3H), 5.22-5.47 (m, 3H), 7.28 (d, J=8.4 Hz, 1H), 7.33-7.40 (m, 2H), 7.41-7.55 (m, 4H), 7.60-7.76 (m, 5H), 7.81 (dd, J=8.6, 2.6 Hz, 1H), 7.94 (d, J=2.4 Hz, 1H), 8.85 (d, J=8.0 Hz, 1H), 9.32 (s, 1H), 9.50 (s, 1H), 9.99 (s, 1H). MS (ESI) m/z=501.3 [M+H]$^+$.

Example 39 (S)—N-(4-(2-Fluoroacetimidamido)-1-(5-phenyloxazol-2-yl)butyl)-4-methoxy-[1,1'-biphenyl]-3-carboxamide (EX-39)

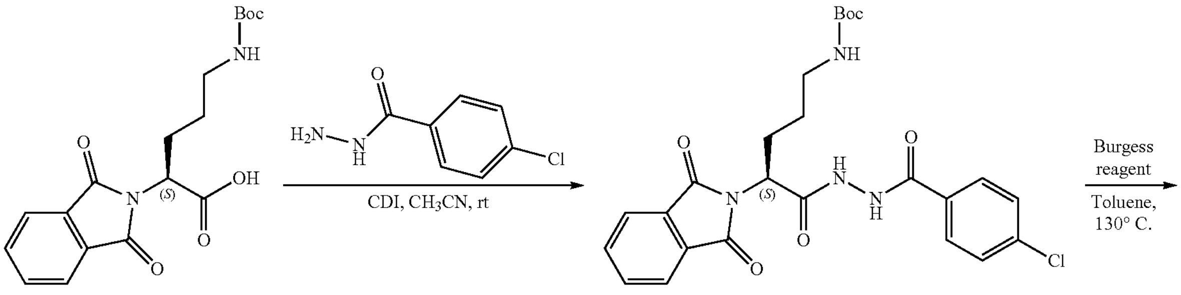

39-1

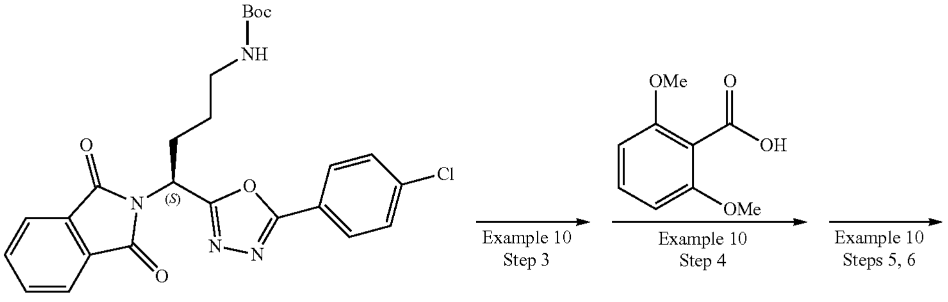

39-2

-continued

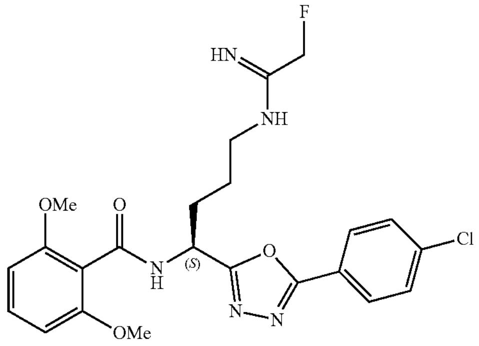

EX-39

Step 1: tert-Butyl (S)-(5-(2-(4-chlorobenzoyl)hydrazinyl)-4-(1,3-dioxoisoindolin-2-yl)-5-oxopentyl) carbamate

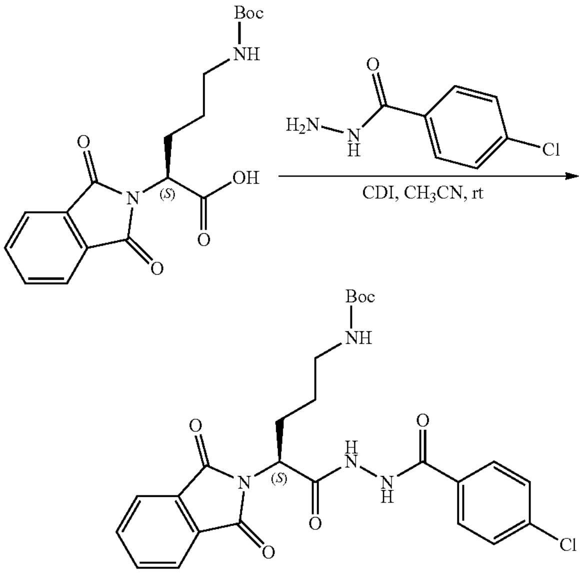

39-1

To a solution of (S)-5-((tert-butoxycarbonyl)amino)-2-(1,3-dioxoisoindolin-2-yl)pentanoic acid (3.00 g, 8.28 mmol) and 4-chlorobenzohydrazide (1.69 g, 9.94 mmol) in $CH_3CN$ (50 mL) was added carbonyldiimidazole (1.61 g, 9.94 mmol). The resulting mixture was stirred at room temperature for 16 hours. The mixture was concentrated under vacuum. The residue was diluted with water (50 mL) and extracted with ethyl acetate (100 mL×2). The organic layers were washed with brine (100 mL), dried over anhydrous $Na_2SO_4$ and concentrated under vacuum to afford crude product, which was purified by silica gel chromatography (elution gradient: petroleum ether/EA, 1/1, v/v) to afford compound 39-1 (2.0 g) as a yellow solid, yield: 46%. $^1H$ NMR (400 MHz, DMSO-$d_6$) δ ppm 10.51 (s, 1H), 10.23 (s, 1H), 7.94-7.85 (m, 6H), 7.59-7.54 (m, 2H), 6.79 (s, 1H), 4.78 (m, 1H), 2.92 (m, 2H), 2.17 (m, 2H), 1.38-1.36 (m, 2H), 1.34 (s, 9H). MS (ESI) m/z=537.0 $[M+Na]^+$.

Step 2: tert-Butyl (S)-(4-(5-(4-chlorophenyl)-1,3,4-oxadiazol-2-yl)-4-(1,3-dioxoisoindolin-2-yl)butyl) carbamate (39-2)

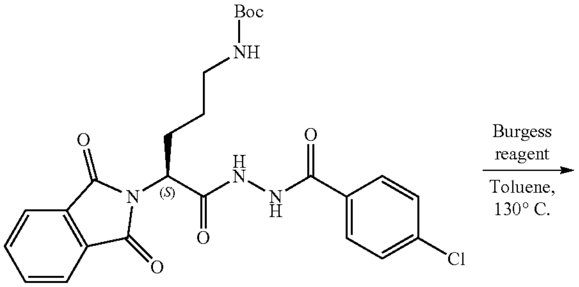

39-1

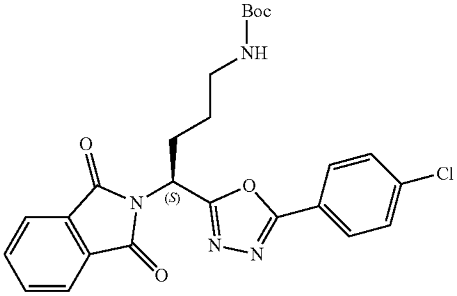

39-2

To a solution of compound 39-1 (2.00 g, 3.89 mmol) in toluene (30 mL) was added Burgess reagent (1.99 g, 7.77 mmol). The resulting mixture was stirred at 130° C. for 5 hours. The mixture was concentrated under vacuum. The residue was diluted with water (40 mL) and extracted with ethyl acetate (60 mL×3). The organic layers were washed with brine (100 mL), dried over anhydrous $Na_2SO_4$ and concentrated under vacuum to afford the crude product, which was purified by silica gel chromatography (elution gradient: petroleum ether/EA, 2/1, v/v) to afford compound 39-2 (1.0 g) as a yellow solid, yield: 51.8%. MS (ESI) m/z=497.0 $[M+H]^+$.

Step 3: (S)—N-(1-(5-(4-Chlorophenyl)-1,3,4-oxadiazol-2-yl)-4-(2-fluoroacetimidamido)butyl)-2,6-dimethoxybenzamide (EX-39)

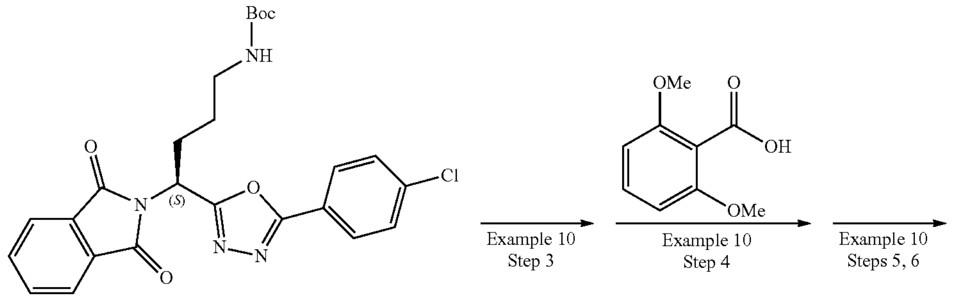

39-2

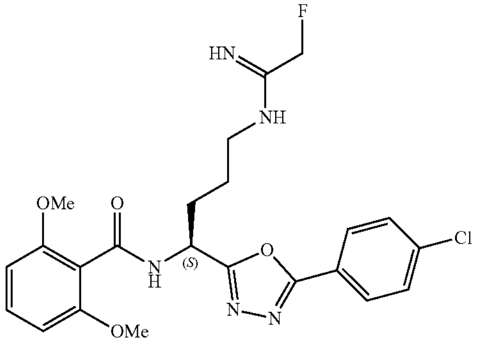

EX-39

(S)—N-(1-(5-(4-Chlorophenyl)-1,3,4-oxadiazol-2-yl)-4-(2-fluoroacetimidamido)butyl)-2,6-dimethoxybenzamide (EX-39) was synthesized from tert-butyl (S)-(4-(5-(4-chlorophenyl)-1,3,4-oxadiazol-2-yl)-4-(1,3-dioxoisoindolin-2-yl)butyl)carbamate (39-2) similarly to Example 10, Steps 3-6 replacing 3,5-dimethoxy-2-naphthoic acid with 2,6-dimethoxybenzoic acid in step 4, as the hydrochloride salt. $^1$H NMR (400 MHz, DMSO-$d_6$): δ ppm 1.73-1.83 (m, 2H), 1.95-2.14 (m, 2H), 3.38-3.39 (m, 2H), 3.71 (s, 6H), 5.26 (s, 1H), 5.33-5.37 (m, 2H), 6.69 (d, J=8.8 Hz, 2H), 7.30-7.34 (m, 1H), 7.74-7.76 (m, 2H), 8.00-8.01 (m, 2H), 8.84 (d, J=8.4 Hz, 1H), 9.20 (s, 1H), 9.42 (s, 1H), 9.88 (s, 1H). MS (ESI) m/z=490.1 $[M+H]^+$.

Example 40 (S)—N-(4-(2-Fluoroacetimidamido)-1-(5-phenyloxazol-2-yl)butyl)-4-methoxy-[1,1'-biphenyl]-3-carboxamide (EX-40)

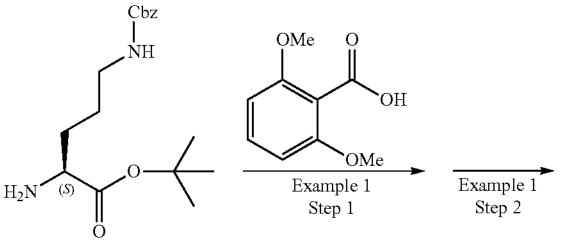

-continued

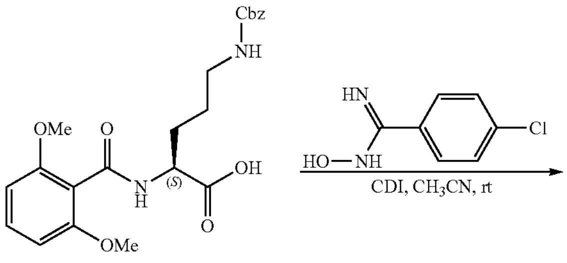

40-1

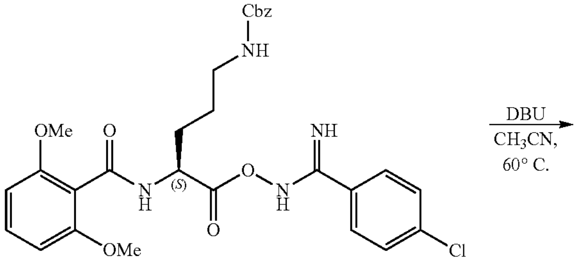

40-2

-continued

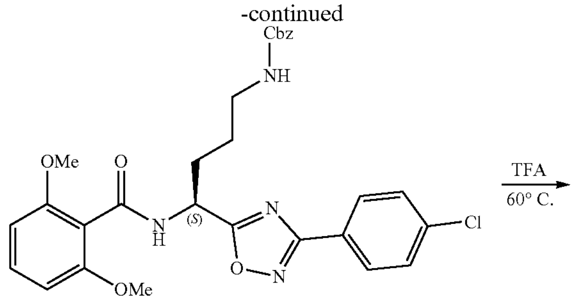

40-3

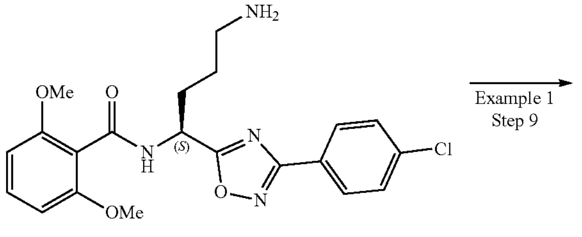

40-4

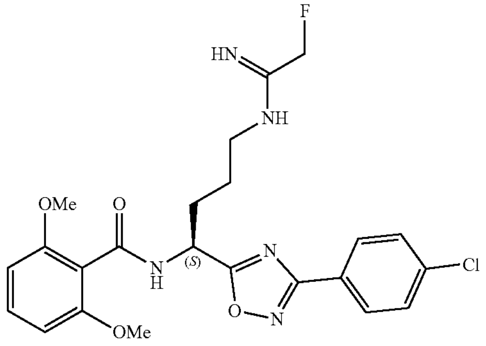

EX-40

Step 1: (S)-5-(((Benzyloxy)carbonyl)amino)-2-(2,6-dimethoxybenzamido)pentanoic acid (40-1)

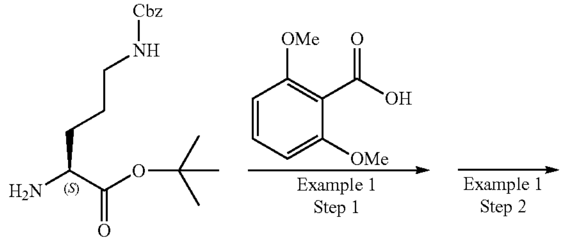

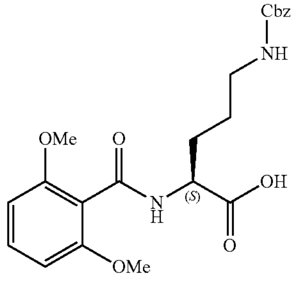

40-1

(S)-5-(((Benzyloxy)carbonyl)amino)-2-(2,6-dimethoxybenzamido)pentanoic acid (40-1) was synthesized from tert-butyl (S)-2-amino-5-(((benzyloxy)carbonyl)amino)pentanoate similarly to Example 1, Steps 1-2 replacing 3-bromobenzoic acid with 2,6-dimethoxybenzoic acid in step 1. MS (ESI) m/z=431.1 $[M+H]^+$.

Step 2: Benzyl (S)-(5-((4-chlorobenzimidamido)oxy)-4-(2,6-dimethoxybenzamido)-5-oxopentyl)carbamate (40-2)

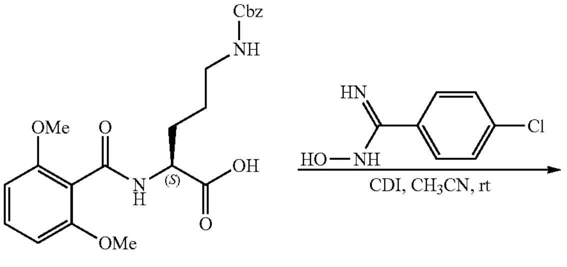

40-1

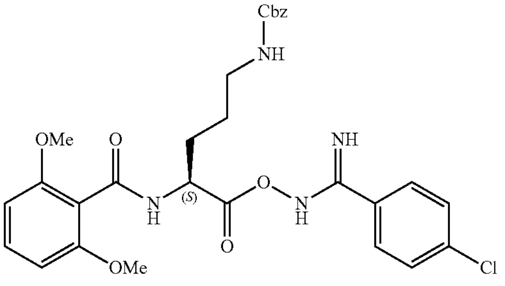

40-2

To a solution of compound 40-1 (2.00 g, 4.65 mmol) and 4-chloro-N-hydroxybenzimidamide (790 mg, 4.65 mmol) in $CH_3CN$ (50 mL) was added CDI (753 mg, 4.65 mmol). The resulting solution was stirred at room temperature for 16 hours. The resulting mixture was concentrated under vacuum. The residue was diluted with water (50 mL) and extracted with ethyl acetate (100 mL×2). The organic layers were washed with brine (100 mL), dried over anhydrous $Na_2SO_4$ and concentrated under vacuum to afford the crude product, which was purified by silica gel chromatography (elution gradient: petroleum ether/EA, 1/1, v/v) to afford compound 40-2 (1.5 g) as a yellow solid, yield: 55%.

Step 3: Benzyl (S)-(4-(3-(4-chlorophenyl)-1,2,4-oxadiazol-5-yl)-4-(2,6-dimethoxybenzamido)butyl)carbamate (40-3)

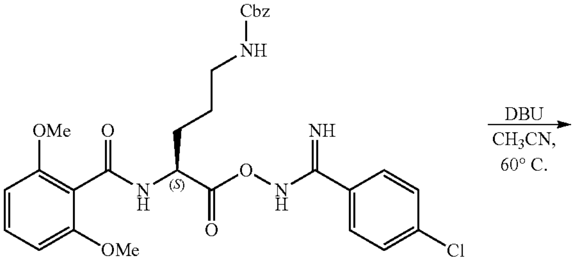

40-2

-continued

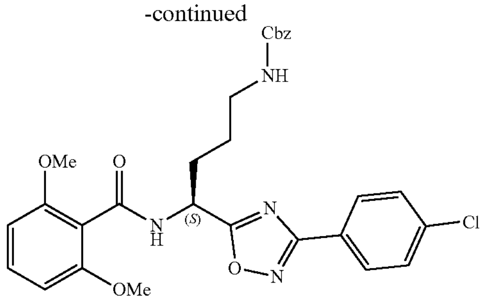

40-3

To a solution of compound 40-2 (1.5 g, 2.57 mmol) in $CH_3CN$ (10 mL) was added DBU (1.29 g, 5.15 mmol). The mixture was stirred at 60° C. for 3 hours. The mixture was concentrated under vacuum. The residue was diluted with water (50 mL) and extracted with ethyl acetate (50 mL×3). The organic layers were washed with brine (50 mL), dried over anhydrous $Na_2SO_4$ and concentrated under vacuum to afford the crude product, which was purified by silica gel chromatography (elution gradient: petroleum ether/EA, 2/1, v/v) to afford compound 40-3 (700 mg) as a yellow solid, yield: 48.2%. $^1$H NMR (400 MHz, DMSO-$d_6$) δ ppm 8.89 (d, J=8.0 Hz, 1H), 8.06-8.03 (m, 2H), 7.68-7.65 (m, 2H), 7.38-7.30 (m, 7H), 6.68 (d, J=8.4 Hz, 2H), 5.35-5.30 (m, 1H), 5.10-4.99 (m, 2H), 3.72 (s, 6H), 3.08-3.09 (m, 2H), 2.06-1.87 (m, 2H), 1.72-1.53 (m, 2H). MS (ESI) m/z=565.1 [M+H]$^+$.

Step 4: (S)—N-(4-amino-1-(3-(4-chlorophenyl)-1,2,4-oxadiazol-5-yl)butyl)-2,6-dimethoxybenzamide (40-4)

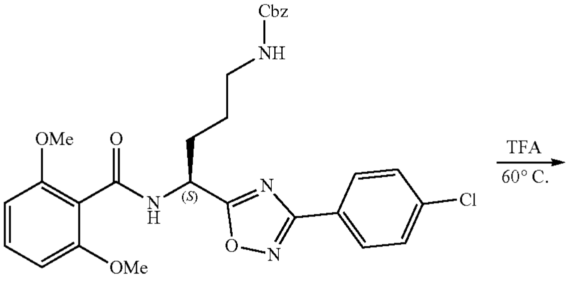

40-3

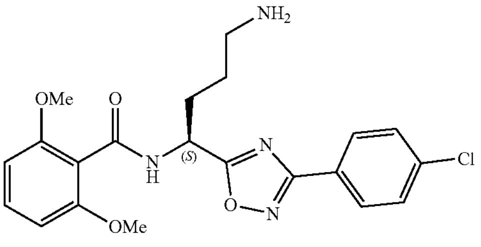

40-4

To a 25 mL round-bottom flask was placed a solution of compound 40-3 (700 g, 1.24 mmol) in TFA (5 mL). The mixture was stirred at 60° C. for 1 hour. The solvent was evaporated and diluted with water (3 mL). The mixture was adjusted with 28% ammonium hydroxide aqueous solution until pH=8 and then extracted with EtOAc (100 mL×3). The organic layers were washed with brine (100 mL), dried over $Na_2SO_4$ and evaporated in vacuo to yield compound 40-4 (350 mg) as a white solid, yield: 65.5%. MS (ESI) m/z=431.1 [M+H]$^+$.

Step 5: (S)—N-(4-(2-Fluoroacetimidamido)-1-(5-phenyloxazol-2-yl)butyl)-4-methoxy-[1,1'-biphenyl]-3-carboxamide (EX-40)

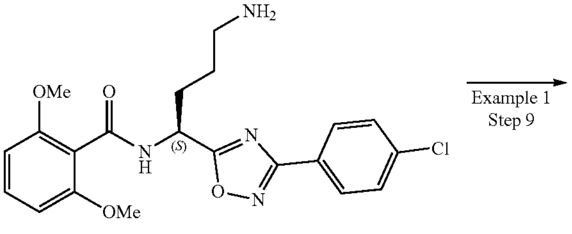

40-4

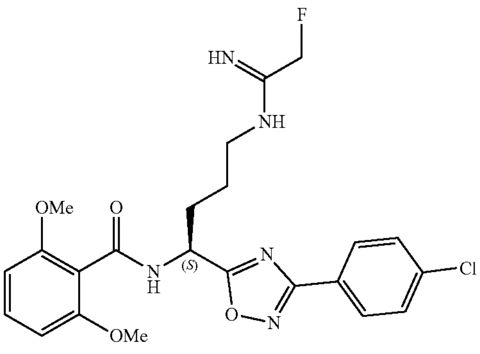

EX-40

(S)—N-(4-(2-Fluoroacetimidamido)-1-(5-phenyloxazol-2-yl)butyl)-4-methoxy-[1,1'-biphenyl]-3-carboxamide (EX-40) was synthesized from (S)—N-(4-amino-1-(3-(4-chlorophenyl)-1,2,4-oxadiazol-5-yl)butyl)-2,6-dimethoxybenzamide (40-4) similarly to Example 1, Step 9, as the hydrochloride salt. $^1$H NMR (400 MHz, DMSO-$d_6$): δ ppm 9.98 (s, 1H), 9.50 (s, 1H), 9.30 (s, 1H), 8.95 (d, J=7.6 Hz, 1H), 8.06-8.03 (m, 2H), 7.70-7.68 (m, 2H), 7.35-7.31 (m, 1H), 6.70 (d, J=8.4 Hz, 2H), 5.39-5.37 (m, 2H), 5.28 (s, 1H), 3.74 (s, 6H), 3.40-3.39 (m, 2H), 2.14-1.94 (m, 2H), 1.83-1.71 (m, 2H). MS (ESI) m/z=490.1 [M+H]$^+$.

Example 41 2-Chloro-N—((S)-4-(2-fluoroacetimidamido)-1-(5-(3-(4-(5-((3aS,4S,6aR)-2-oxohexahydro-1H-thieno[3,4-d]imidazol-4-yl)pentanamido)butanamido)phenyl)oxazol-2-yl)butyl)-6-methoxybenzamide (EX-41)
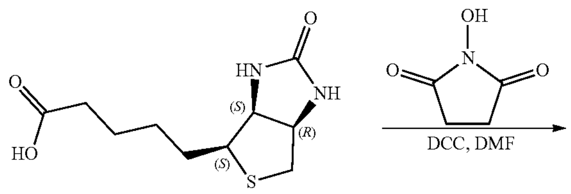
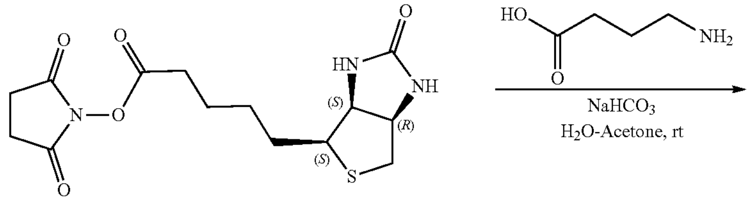
41-1
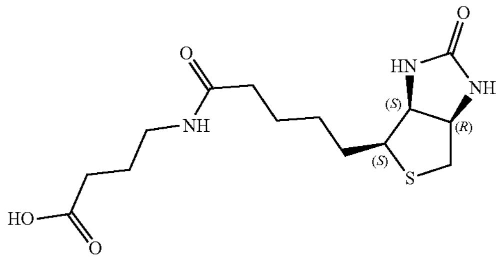
41-2
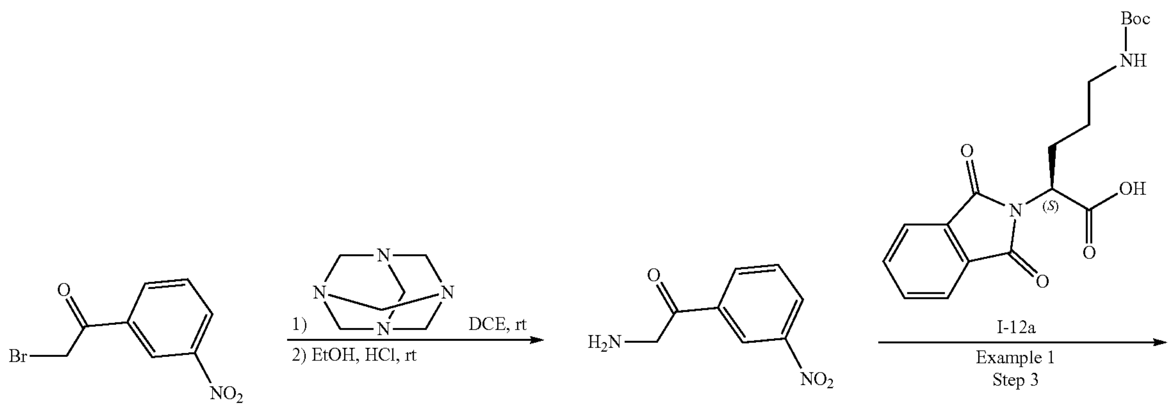
41-3
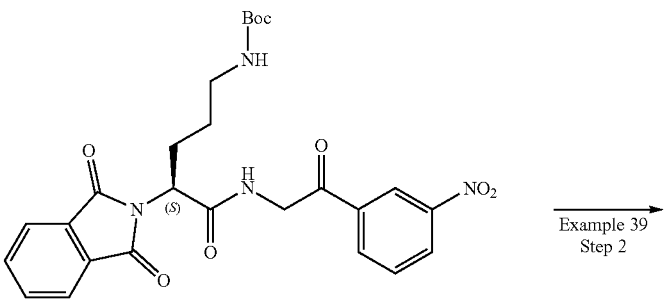
41-4

-continued
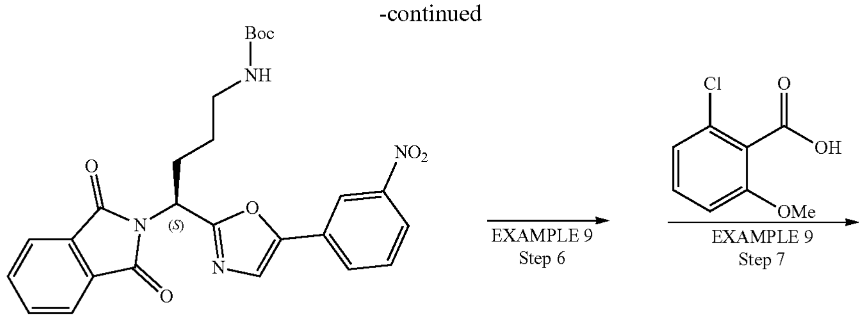
41-5
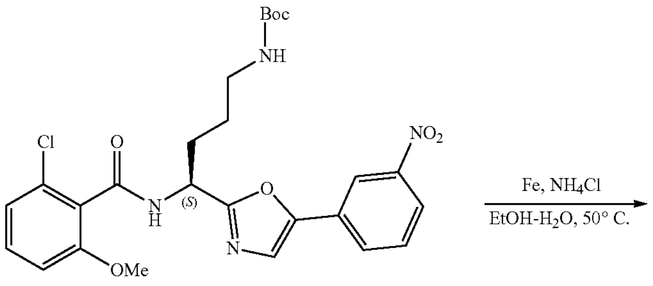
41-6
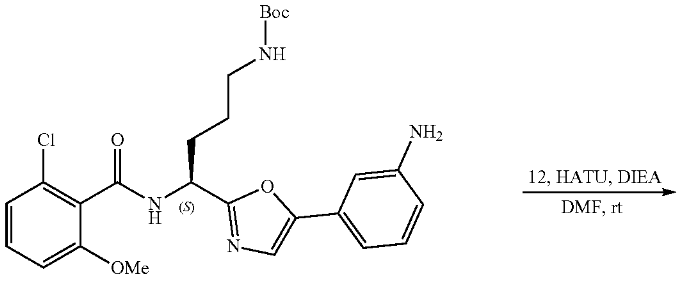
41-7
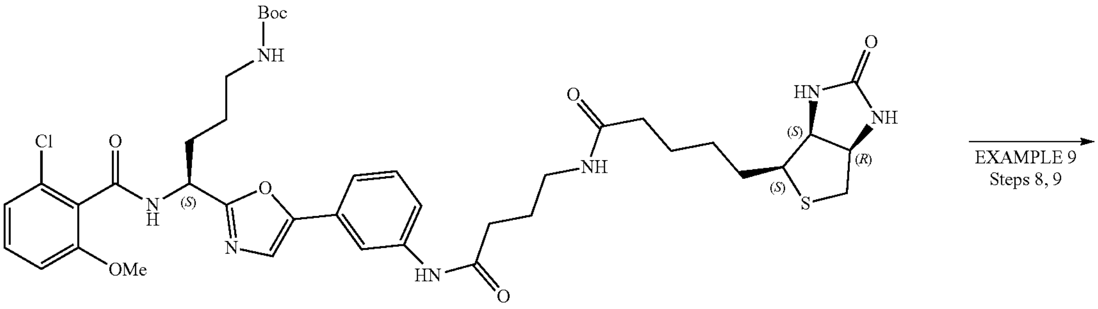
41-8
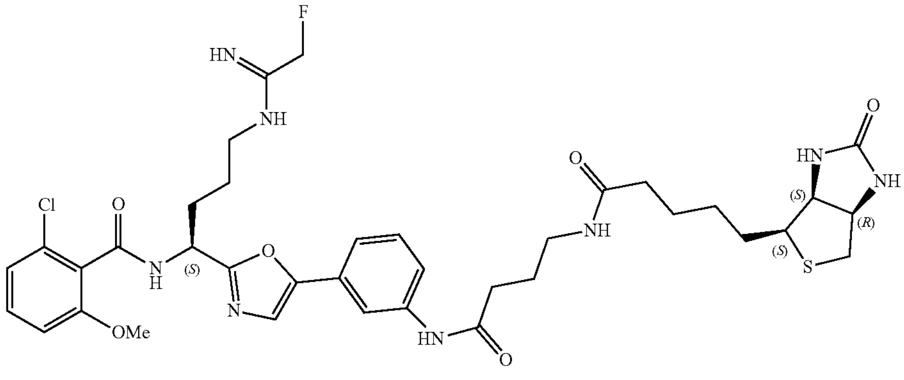
EX-41

Step 1: 2,5-Dioxopyrrolidin-1-yl 5-((3aS,4S,6aR)-2-oxohexahydro-1H-thieno[3,4-d]imidazol-4-yl)pentanoate (41-1)

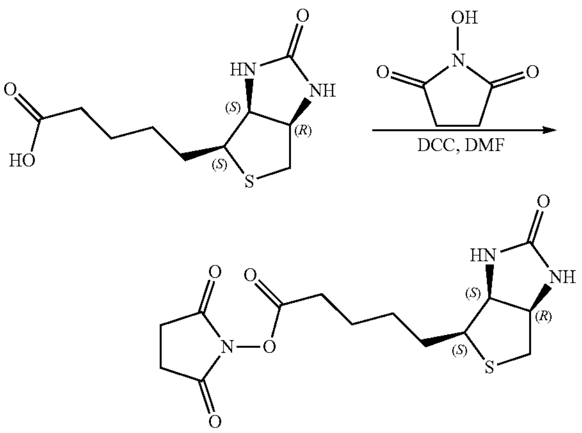

41-1

To a solution of 5-((3aS,4S,6aR)-2-oxohexahydro-1H-thieno[3,4-d]imidazol-4-yl)pentanoic acid (10 g, 41 mmol) and DCC (10.9 g, 53.2 mmol) in DMF (100 mL) was added 1-hydroxypyrrolidine-2,5-dione (4.7 g, 41 mmol). The resulting mixture was stirred at 80° C. for 12 hours. The mixture was filtered through a pad of Celite. The solvent was evaporated under reduced pressure and then $Et_2O$ (100 mL) was added. The precipitate was collected by filtration, washed with $Et_2O$ (50 mL) and dried under vacuum to afford compound 41-1 (11 g) as a white solid, yield: 79%. MS (ESI) m/z=341.8 $[M+H]^+$.

Step 2: 4-(5-((3aS,4S,6aR)-2-Oxohexahydro-1H-thieno[3,4-d]imidazol-4-yl)pentanamido)butanoic acid (41-2)

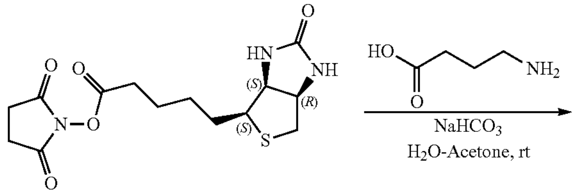

41-1

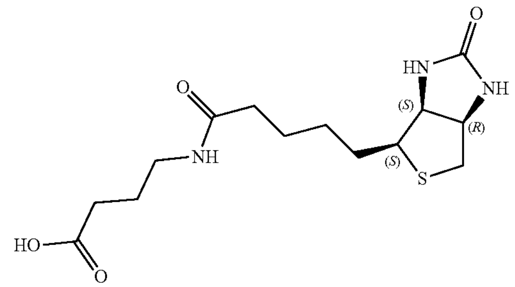

41-2

To a solution of compound 41-1 (7 g, 20 mmol) and $NaHCO_3$ (5.1 g, 61 mmol) in acetone (100 mL) and water (20 mL) was added 4-aminobutanoic acid (2.1 g, 20 mmol). The resulting mixture was stirred at room temperature for 10 hours. The solvent was evaporated under vacuum and the residue was diluted with water (20 mL). The mixture was acidified with hydrochloric acid until pH=4 and then extracted with EtOAc (100 mL×3). The organic layers were washed with brine (100 mL), dried over $Na_2SO_4$, filtered and evaporated in vacuo to yield compound 41-2 (4.5 g) as a white solid, yield: 66%. $^1H$ NMR (400 MHz, DMSO-$d_6$) δ ppm 12.04 (s, 1H), 7.81-7.79 (m, 1H), 6.44-6.37 (m, 2H), 4.32-4.29 (m, 1H), 4.14-4.11 (m, 1H), 3.12-3.01 (m, 3H), 2.84-2.80 (m, 1H), 2.59-2.56 (m, 1H), 2.22-2.19 (m, 2H), 2.08-2.03 (m, 2H), 1.66-1.57 (m, 3H), 1.51-1.25 (m, 5H). MS (ESI) m/z=329.8 $[M+H]^+$.

Step 3: 2-Amino-1-(3-nitrophenyl)ethan-1-one (41-3)

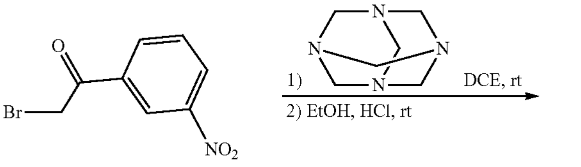

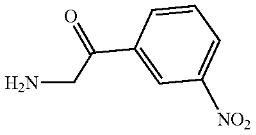

41-3

To a solution of 2-bromo-1-(3-nitrophenyl)ethan-1-one (5 g, 20 mmol) in DCE (100 mL) was added 1,3,5,7-tetraaza-adamantane (3.15 g, 22.5 mmol). The mixture was stirred at room temperature for 2 hours. The precipitate was collected by filtration, washed with DCE (50 mL) and dried under vacuum to afford the intermediate (6.5 g) as a white solid. The white solid (6.5 g, 21 mmol) was dissolved in EtOH (100 mL) and HCl (10 mL) was added. The mixture was stirred at room temperature for 2 hours. The mixture was filtered and the filtrate was evaporated under vacuum. The residue was triturated with $CH_3CN$. The precipitate was collected by filtration, washed with $CH_3CN$ (20 mL) and dried under vacuum to afford compound 41-3 hydrochloride (3 g) as a white solid, yield: 67%. MS (ESI) m/z=181.0 $[M+H]^+$.

Step 4: tert-Butyl (S)-(4-(1,3-dioxoisoindolin-2-yl)-5-((2-(3-nitrophenyl)-2-oxoethyl)amino)-5-oxopentyl)carbamate (41-4)

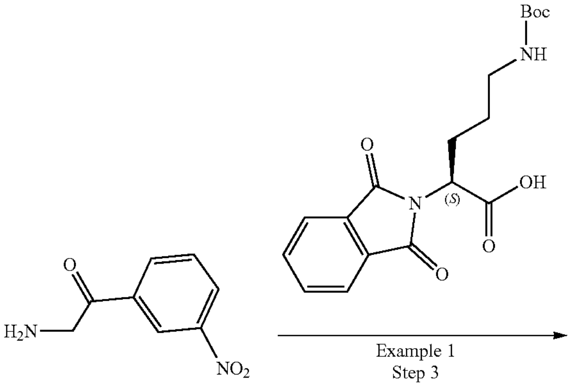

41-3

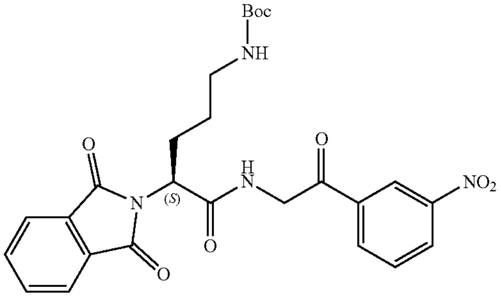

41-4 tert-Butyl (S)-(4-(1,3-dioxoisoindolin-2-yl)-5-((2-(3-nitrophenyl)-2-oxoethyl)amino)-5-oxopentyl)carbamate (41-4) was synthesized from compound 41-3 and compound (S)-5-((tert-butoxycarbonyl)amino)-2-(1,3-dioxoisoindolin-2-yl)pentanoic acid similarly to Example 1, Step 3.

Step 5: tert-Butyl (S)-(4-(1,3-dioxoisoindolin-2-yl)-4-(5-(3-nitrophenyl)oxazol-2-yl)butyl)carbamate (41-5)

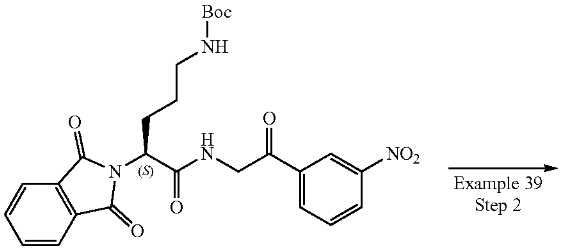

41-4

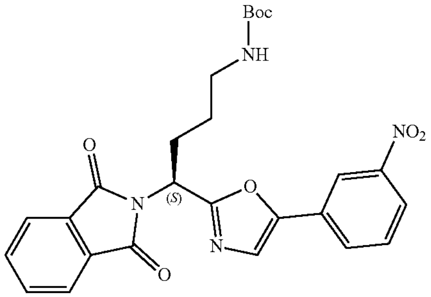

41-5 tert-Butyl (S)-(4-(1,3-dioxoisoindolin-2-yl)-4-(5-(3-nitrophenyl)oxazol-2-yl)butyl)carbamate (41-5) was synthesized from compound 41-4 similarly to Example 39, Step 2. MS (ESI) m/z=528.6 [M+Na]$^+$.

Step 6: tert-Butyl (S)-(4-(2-chloro-6-methoxybenzamido)-4-(5-(3-nitrophenyl)oxazol-2-yl)butyl)carbamate (41-6)

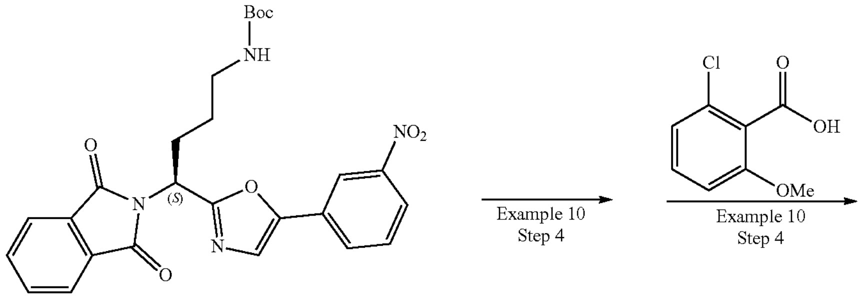

41-5

-continued

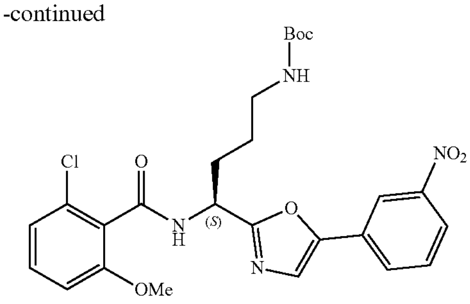

41-6 tert-Butyl (S)-(4-(2-chloro-6-methoxybenzamido)-4-(5-(3-nitrophenyl)oxazol-2-yl)butyl)carbamate (41-6) was synthesized from compound 41-5 similarly to Example 10, Steps 3-4 replacing 3,5-dimethoxy-2-naphthoic acid with 2-chloro-6-methoxybenzoic acid in step 4. MS (ESI) m/z=566.6 $[M+Na]^+$.

Step 7: tert-Butyl (S)-(4-(5-(3-aminophenyl)oxazol-2-yl)-4-(2-chloro-6-methoxybenzamido)butyl)carbamate (41-7)

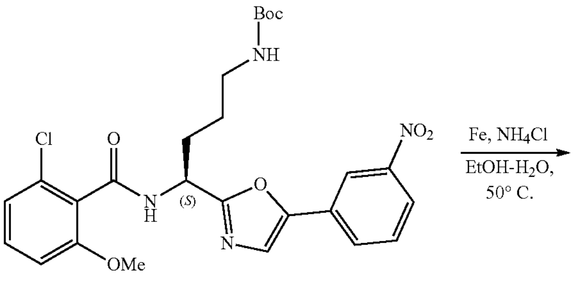

41-6

-continued

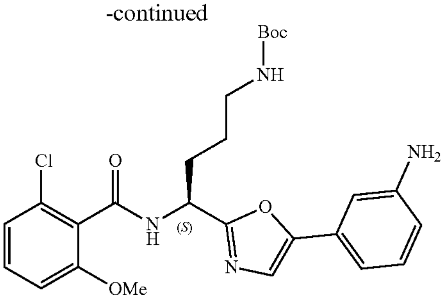

41-7

To a solution of compound 41-6 (300 mg, 0.55 mmol) in ethanol (10 mL) and water (5 mL) was added ammonium chloride (292 mg, 5.51 mmol) and iron powder (297 mg, 5.51 mmol). The mixture was stirred at 50° C. for 2 hours. The mixture was cooled to room temperature and concentrated under reduced pressure to afford the crude product which was purified by silica gel chromatography (elution gradient: DCM/MeOH, 10/1, v/v) to afford compound 41-7 (150 mg) as an off-white solid, yield: 52.9%. MS (ESI) m/z=514.7 $[M+H]^+$.

Step 8: tert-Butyl ((S)-4-(2-chloro-6-methoxybenzamido)-4-(5-(3-(4-(5-((3aS,4S,6aR)-2-oxohexahydro-1H-thieno[3,4-d]imidazol-4-yl)pentanamido)butanamido)phenyl)oxazol-2-yl)butyl)carbamate (41-8)

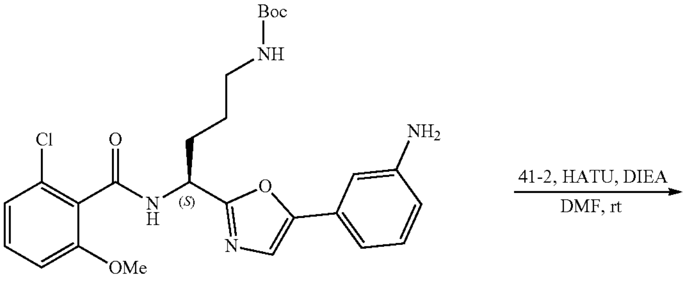

41-7

-continued

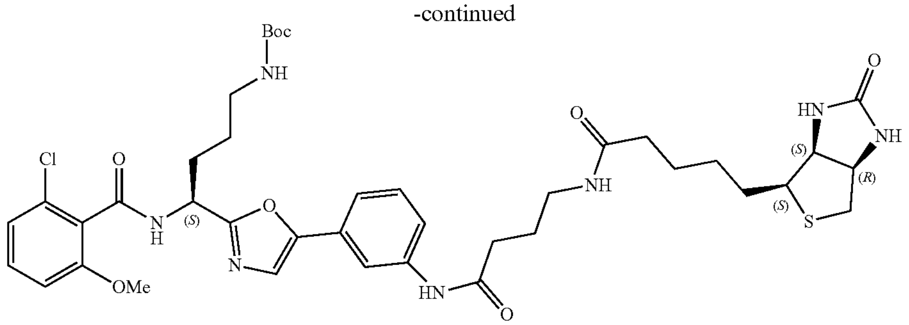

41-8

To a solution of compound 41-2 (96 mg, 0.29 mmol), DIEA (112 mg, 0.87 mmol), HATU (133 mg, 0.35 mmol) in DMF (5 mL) was added compound 41-7 (150 mg, 0.29 mmol). The resulting mixture was stirred at room temperature for 1 hour. The mixture was diluted with water (20 mL) and extracted with ethyl acetate (20 mL×3). The organic layers were washed with brine (50 mL), dried over anhydrous $Na_2SO_4$ and concentrated under vacuum to afford the crude product which was purified by silica gel chromatography (elution gradient: petroleum ether/EA, 1/2, v/v) to afford compound 41-8 (220 mg) as a white solid, yield: 91.3%. MS (ESI) m/z=825.5 $[M+H]^+$.

Step 9: 2-Chloro-N—((S)-4-(2-fluoroacetimidamido)-1-(5-(3-(4-(5-((3aS,4S,6aR)-2-oxohexahydro-1H-thieno[3,4-d]imidazol-4-yl)pentanamido)butanamido)phenyl)oxazol-2-yl)butyl)-6-methoxybenzamide (EX-41)

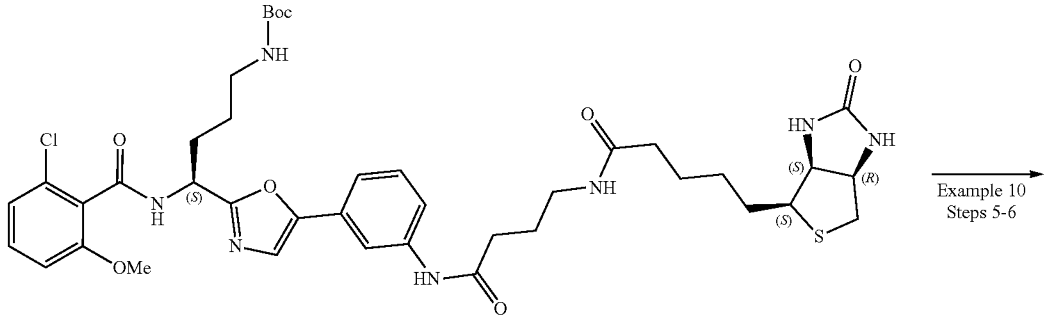

41-8

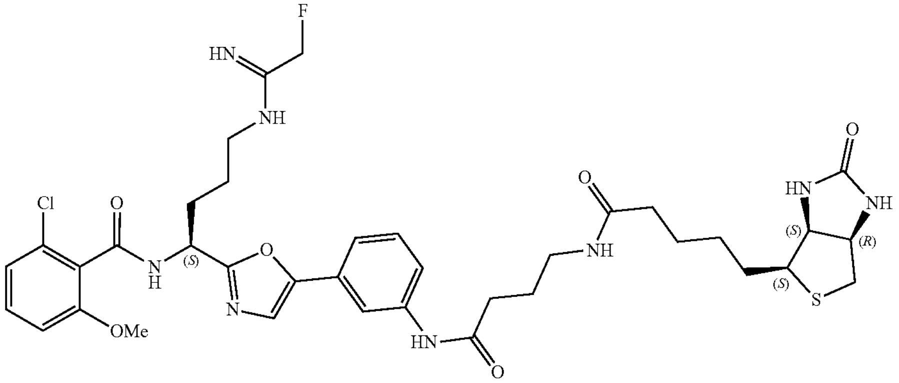

EX-41

2-Chloro-N—((S)-4-(2-fluoroacetimidamido)-1-(5-(3-(4-(5-((3aS,4S,6aR)-2-oxohexahydro-1H-thieno[3,4-d]imidazol-4-yl)pentanamido)butanamido)phenyl)oxazol-2-yl)butyl)-6-methoxybenzamide (EX-41) was synthesized from compound 41-8 similarly to Example 10, Steps 5-6, as the hydrochloride salt. $^{1}H$ NMR (400 MHz, DMSO-$d_6$): δ ppm 10.25 (s, 1H), 9.97 (s, 1H), 9.49 (s, 1H), 9.27 (s, 1H), 9.06 (d, J=8.4 Hz, 1H), 8.06 (s, 1H), 7.95-7.92 (m, 1H), 7.55-7.52 (m, 2H), 7.40-7.35 (m, 3H), 7.07-7.04 (m, 2H), 5.38 (s, 1H), 5.28-5.23 (m, 2H), 4.31-4.28 (m, 1H), 4.14-4.11 (m, 1H), 3.76 (s, 3H), 3.40-3.38 (m, 2H), 3.09-3.08 (m, 3H), 2.83-2.78 (m, 1H), 2.59-2.56 (m, 1H), 2.37-2.33 (m, 2H), 2.09-2.06 (m, 3H), 1.96-1.93 (m, 1H), 1.72-1.51 (m, 4H), 1.48-1.41 (m, 4H), 1.33-1.24 (m, 2H). MS (ESI) m/z=784.5 $[M+H]^+$.

Example 42 $N^1$-(3-(3-(((S)-1-(5-(3-Chlorophenyl)oxazol-2-yl)-4-(2-fluoroacetimidamido)butyl)carbamoyl)-4-methoxyphenoxy)propyl)-$N^5$-(15-oxo-19-((3aS,4S,6aR)-2-oxohexahydro-1H-thieno[3,4-d]imidazol-4-yl)-4,7,10-trioxa-14-azanonadecyl)glutaramide (EX-42)

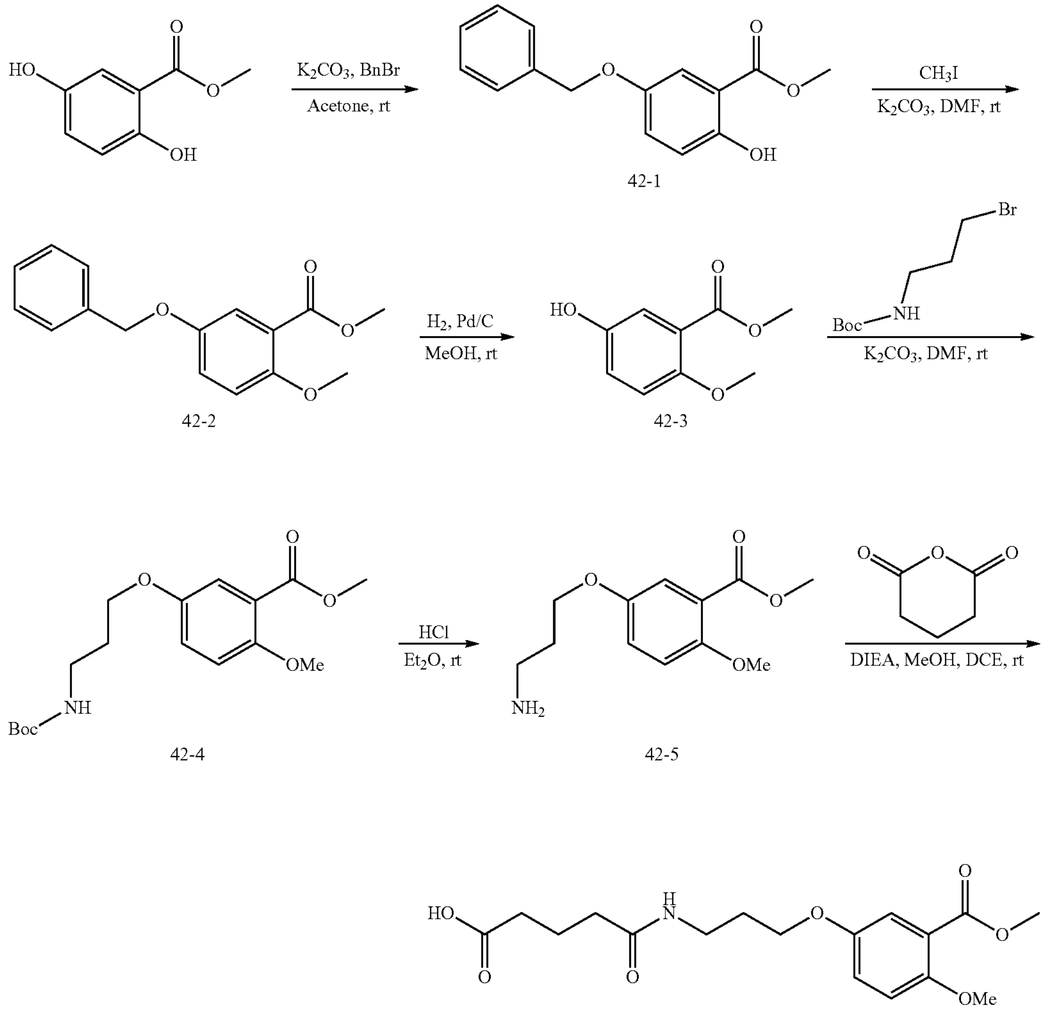

42-1

42-2

42-3

42-4

42-5

42-6

-continued
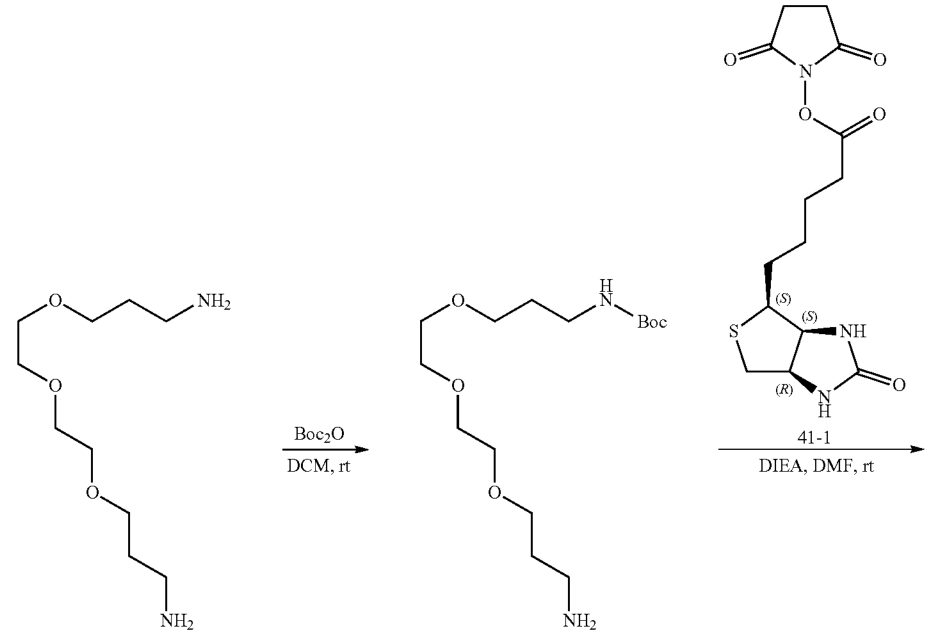
42-7
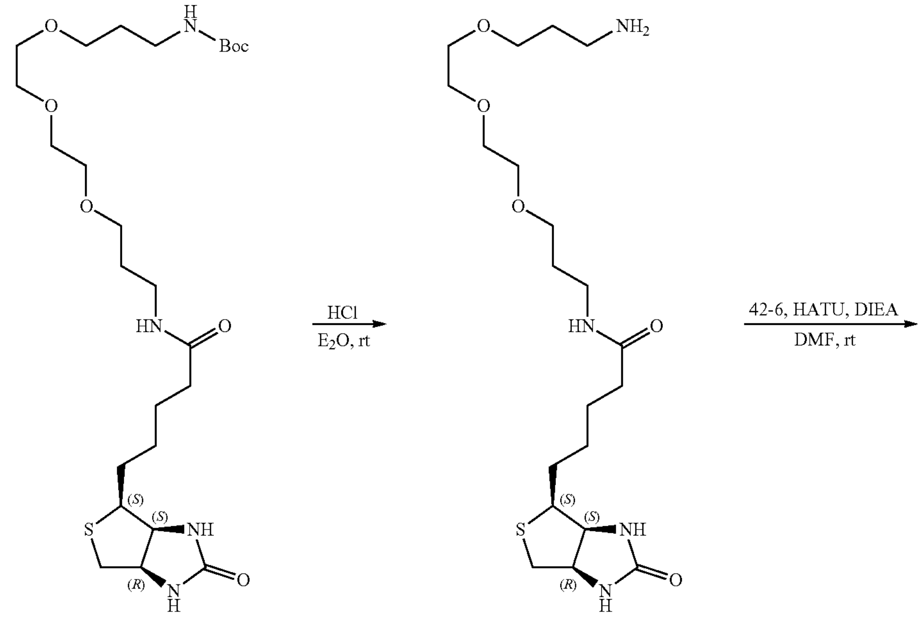
42-8
42-9

-continued
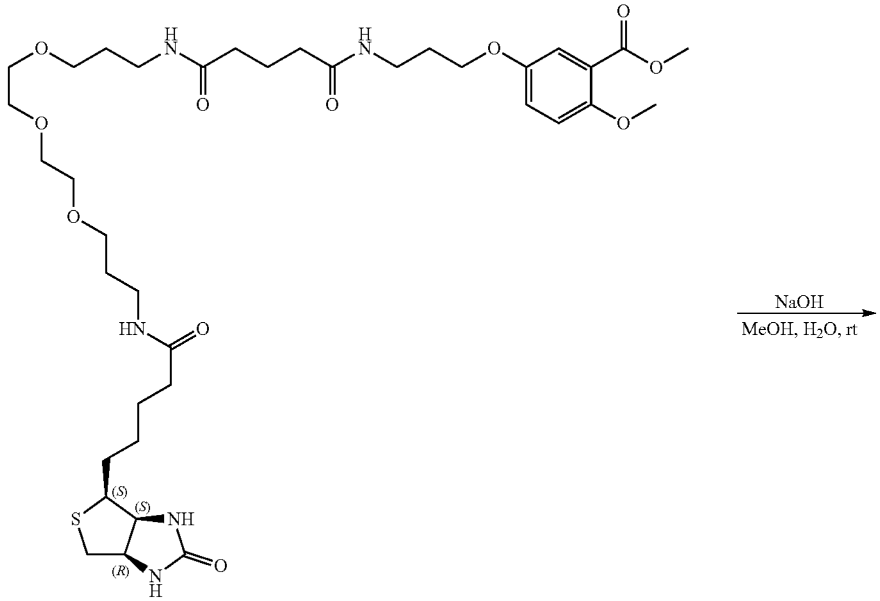
42-10
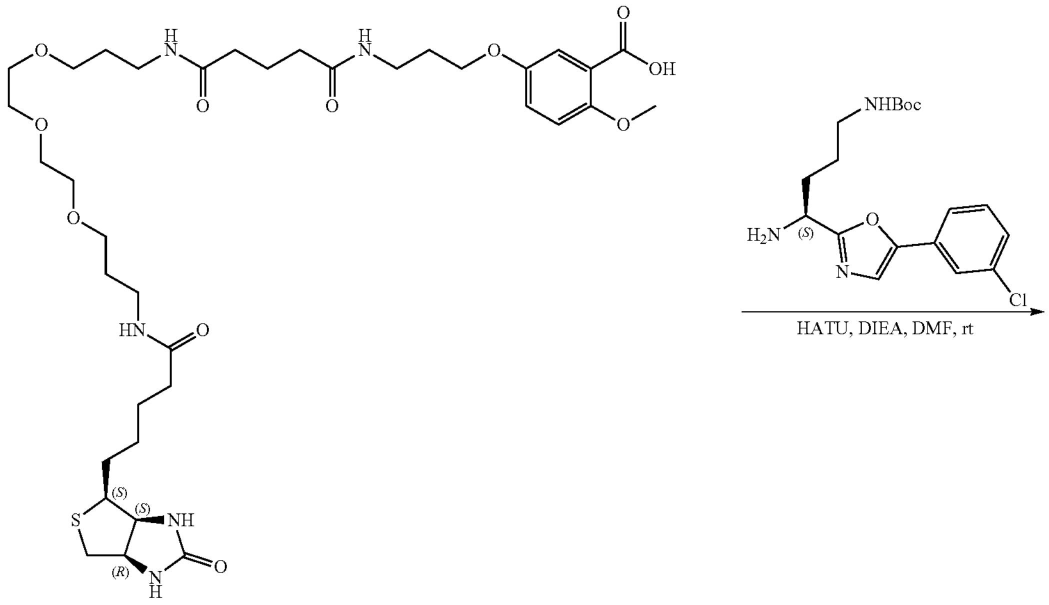
42-11

-continued
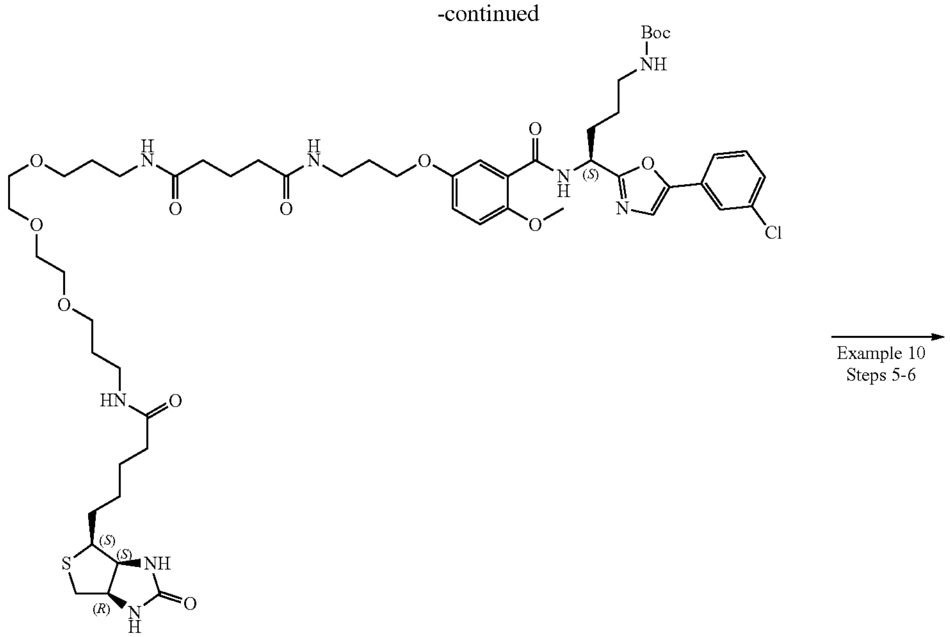
42-12
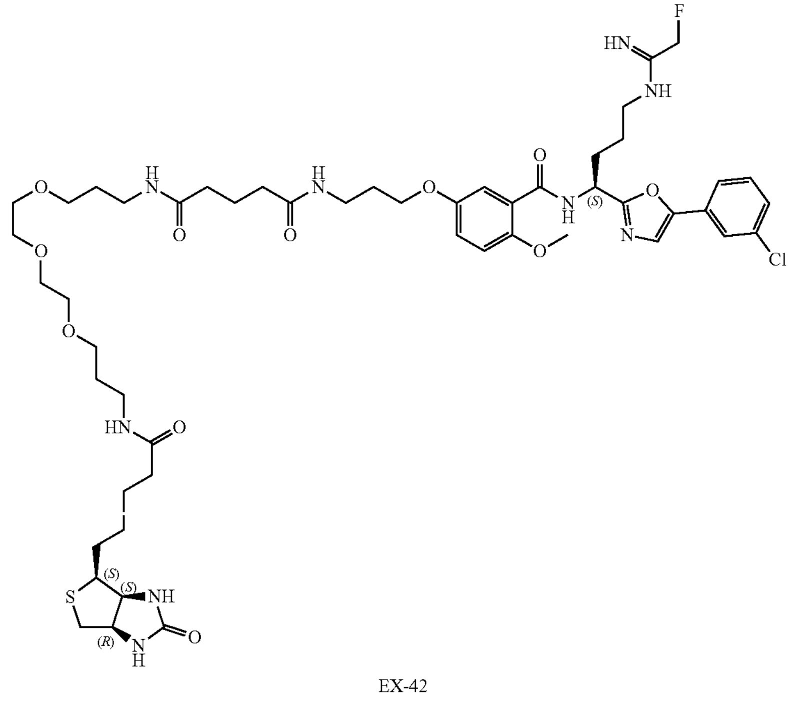
EX-42
Step 1: Methyl 5-(benzyloxy)-2-hydroxybenzoate (42-1)
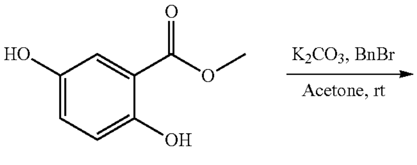
-continued
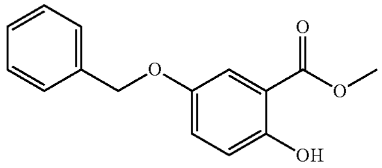
42-1
To a suspension of methyl 2,5-dihydroxybenzoate (4.5 g, 0.027 mol) and $K_2CO_3$ (7.5 g, 0.054 mol) in acetone (80 mL) was added benzyl bromide (4.4 g, 0.025 mmol). The mixture was stirred at room temperature for 16 hours. The mixture was diluted with water (150 mL) and extracted with ethyl acetate (100 mL×3). The organic phase was washed with water (100 mL) and brine (100 mL) and concentrated under vacuum to give the crude product which was purified by silica gel chromatography (elution gradient: EA/PE, 3/1, v/v) to afford compound 42-1 (4.5 g) as a white solid, yield: 65%. $^1$H NMR (400 MHz, $CDCl_3$) δ ppm 10.39 (s, 1H), 7.49-7.29 (m, 7H), 7.17-7.12 (m, 1H), 6.92 (d, J=9.1 Hz, 1H), 5.02 (s, 2H), 3.92 (s, 3H). MS (ESI) m/z=258.9 $[M+H]^+$.

Step 2: Methyl 5-(benzyloxy)-2-methoxybenzoate (42-2)

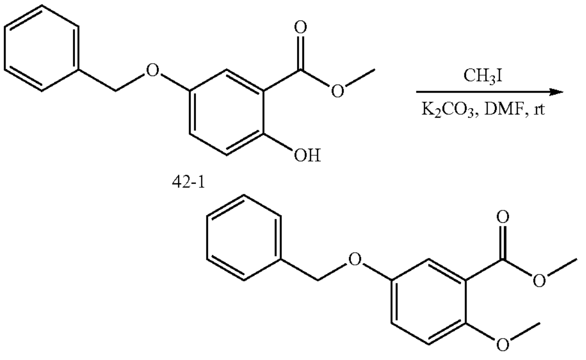

42-1

42-2

To a solution of compound 42-1 (4.5 g, 0.017 mol), $K_2CO_3$ (8.4 g, 0.061 mol) in DMF (25 mL) was added MeI (7.2 g, 0.051 mmol). The mixture was stirred at room temperature for 16 hours. The mixture was diluted with water (150 mL) and extracted with ethyl acetate (100 mL×3). The organic phase was washed with water (100 mL), brine (100 mL) and concentrated under vacuum to give the crude product which was purified by silica gel chromatography (elution gradient: EA/PE, 1/2, v/v) to afford compound 42-2 (4.2 g) as a white solid, yield: 88%. $^1$H NMR (400 MHz, DMSO-$d_6$) δ ppm 7.47-7.30 (m, 5H), 7.28-7.24 (m, 1H), 7.23-7.17 (m, 1H), 7.08 (d, J=9.1 Hz, 1H), 5.08 (s, 2H), 3.80 (s, 3H), 3.76 (s, 3H). MS (ESI) m/z=272.8 $[M+H]^+$.

Step 3: Methyl 5-hydroxy-2-methoxybenzoate (42-3)

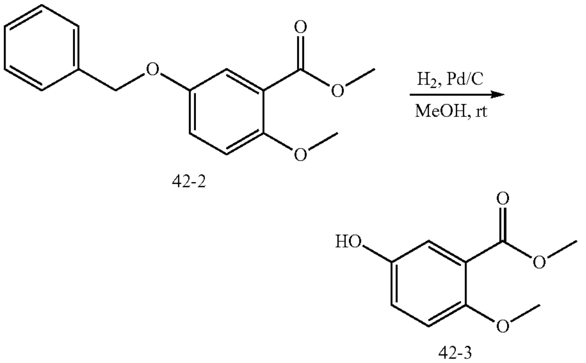

42-2

42-3

To a solution of compound 42-2 (4.2 g, 0.015 mol) in MeOH (60 mL) was added 10% Pd/C (1.6 g, 0.0015 mol). The mixture was stirred under hydrogen at room temperature for 16 hours. The mixture was filtered. The filtrate was concentrated under vacuum to afford compound 42-3 (2 g) as a white solid, yield: 71%. $^1$H NMR (400 MHz, DMSO-$d_6$) δ ppm 9.29 (s, 1H), 7.08-7.02 (m, 1H), 7.00-6.89 (m, 2H), 3.76 (s, 3H), 3.72 (s, 3H). MS (ESI) m/z=182.9 $[M+H]^+$.

Step 4: Methyl 5-(3-((tert-butoxycarbonyl)amino) propoxy)-2-methoxybenzoate (42-4)

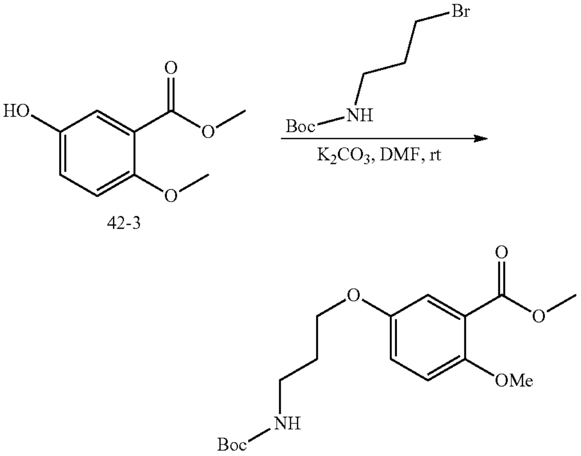

42-3

42-4

To a solution of compound 42-3 (1.0 g, 5.0 mmol) in DMF (15 mL) was added $K_2CO_3$ (1.3 g, 10.0 mol) and tert-butyl (3-bromopropyl)carbamate (1.8 g, 7.5 mmol). The mixture was stirred at room temperature for 16 h. The mixture was quenched with water (100 mL). The product was extracted with ethyl acetate (150 mL×3). The organic layers were washed with brine (100 mL), dried over anhydrous $Na_2SO_4$ and concentrated under vacuum to afford the crude product which was purified by silica gel chromatography (elution gradient: petroleum ether/EtOAc, 2/1, v/v) to afford compound 42-4 (550 mg) as a white solid, yield: 75.3%. MS (ESI) m/z=361.8 $[M+Na]^+$.

Step 5: Methyl 5-(3-aminopropoxy)-2-methoxybenzoate (42-5)

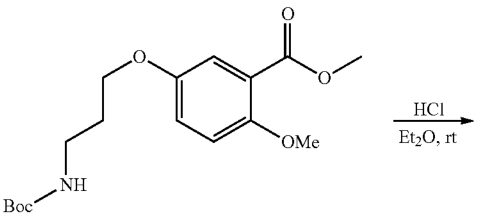

42-4

-continued

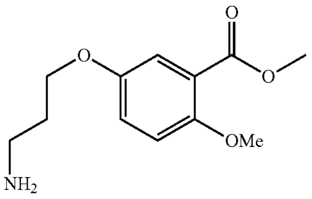

42-5

To a solution of compound 42-4 (1.4 g, 4.1 mmol) in ethyl ether (5 mL) was added hydrogen chloride solution (15 mL, 2N in ethyl ether). The mixture was stirred at room temperature for 2 h. The precipitate was collected by filtration, washed with ethyl ether (50 mL), dried under vacuum to afford compound 42-5 hydrochloride (1.0 g) as a white solid, yield: 87%. $^1$H NMR (400 MHz, DMSO-$d_6$) δ ppm 7.97 (s, 3H), 7.26-7.02 (m, 3H), 4.04 (t, J=6.1 Hz, 2H), 3.78 (s, 3H), 3.76 (s, 3H), 3.05-2.85 (m, 2H), 2.11-1.92 (m, 2H). MS (ESI) m/z=239.9 $[M+H]^+$.

Step 6: 5-((3-(4-Methoxy-3-(methoxycarbonyl)phenoxy)propyl)amino)-5-oxopentanoic acid (42-6)

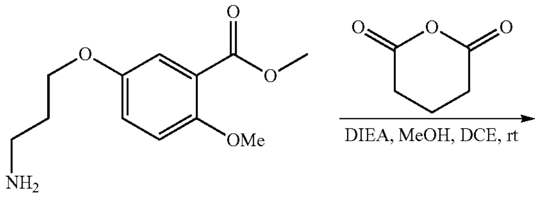

42-5

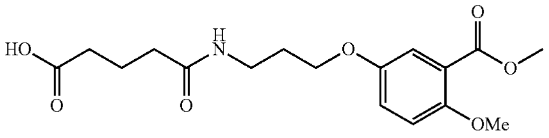

42-6

To a solution of compound 42-5 (400 mg, 1.67 mmol), dihydro-2H-pyran-2,6(3H)-dione (190 mg, 1.67 mmol) in DCE (10 mL) and MeOH (5 mL) was added DIEA (430 mg, 3.34 mmol). The resulting mixture was stirred at room temperature for 16 hours. The mixture was concentrated under vacuum to afford a crude product which was purified by silica gel chromatography (elution gradient: DCM/MeOH, 10/1, v/v) to afford compound 42-6 (450 mg) as a brown solid, yield: 87.9%. $^1$H NMR (400 MHz, DMSO-$d_6$) δ ppm 12.02 (s, 1H), 7.88 (s, 1H), 7.25-7.00 (m, 3H), 3.94 (t, J=6.2 Hz, 2H), 3.78 (s, 3H), 3.76 (s, 3H), 3.25-3.10 (m, 2H), 2.25-2.05 (m, 4H), 1.86-1.65 (m, 4H). MS (ESI) m/z=353.8 $[M+H]^+$.

Step 7: tert-Butyl (3-(2-(2-(3-aminopropoxy)ethoxy)ethoxy)propyl)carbamate (42-7)

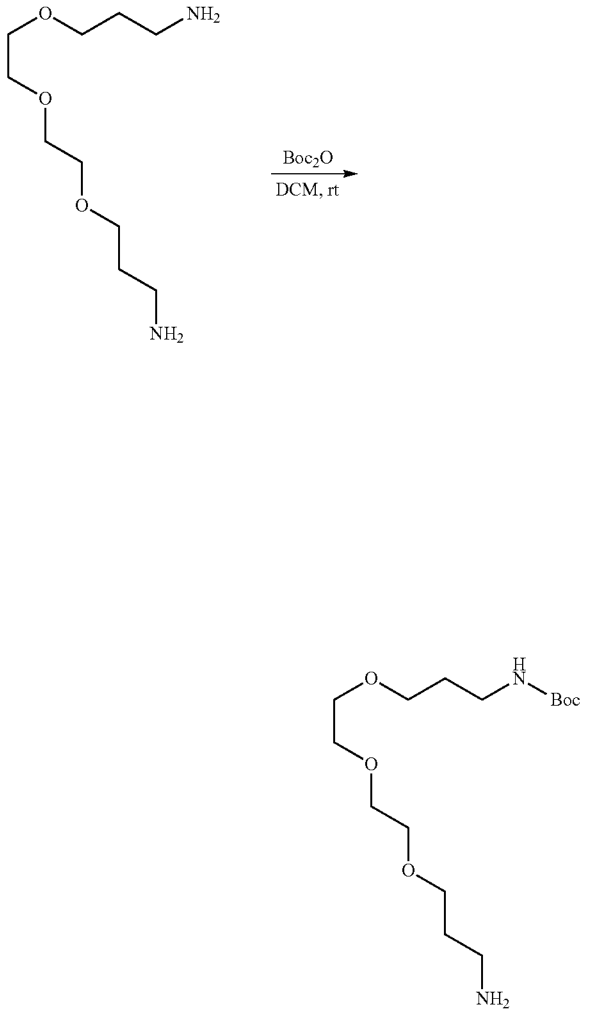

42-7

To a solution of 3,3'-((oxybis(ethane-2,1-diyl))bis(oxy))bis(propan-1-amine) (10 g, 0.045 mol) in DCM (100 mL) was added $Boc_2O$ (15 mL). The mixture was stirred at room temperature for 16 hours. The reaction mixture was concentrated and purified by silica gel chromatography (elution gradient: petroleum ether/EA, 1/3, v/v) to afford compound 42-7 (5 g) as a colorless oil, yield: 17%. $^1$H NMR (400 MHz, $CDCl_3$) δ ppm 3.76-3.49 (m, 12H), 3.32-3.16 (m, 2H), 2.81 (t, J=6.7 Hz, 2H), 1.84-1.67 (m, 4H), 1.44 (s, 9H). MS (ESI) m/z=320.9 $[M+H]^+$.

Step 8: tert-Butyl (15-oxo-19-((3aS,4S,6aR)-2-oxo-hexahydro-1H-thieno[3,4-d]imidazol-4-yl)-4,7,10-trioxa-14-azanonadecyl)carbamate (42-8)

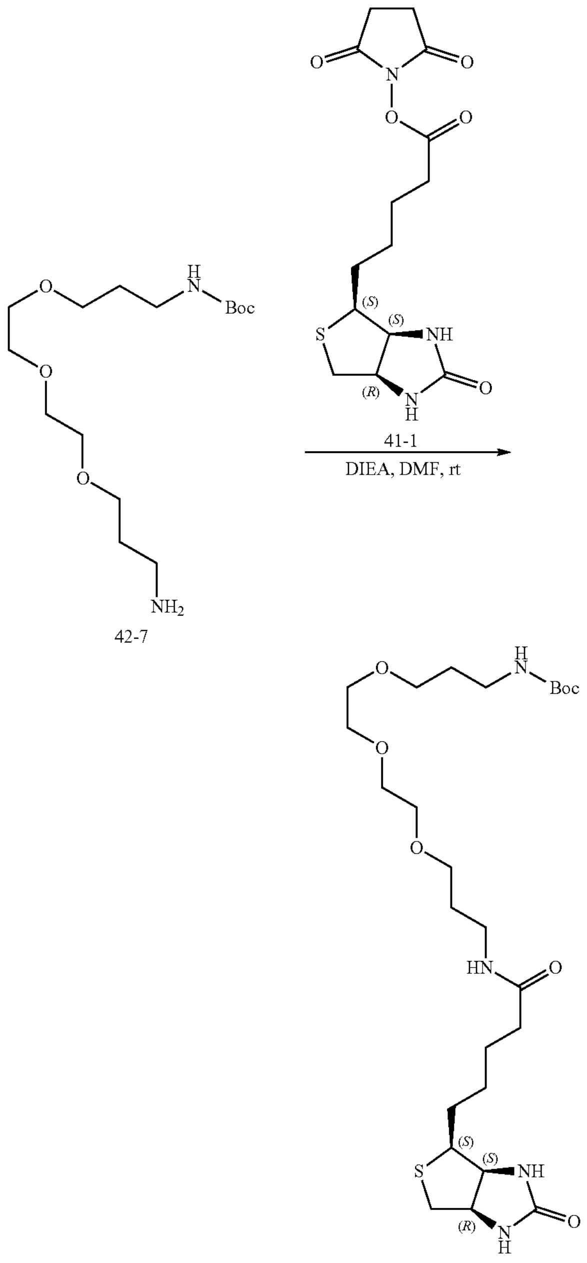

42-7

41-1

42-8

To a solution of compound 42-7 (1.2 g, 3.5 mmol) and compound 41-1 (1.1 g, 3.5 mmol) in DMF (25 mL) was added DIEA (900 mg, 7.0 mmol). The mixture was stirred at room temperature for 2 hours. The reaction mixture was concentrated and purified by silica gel chromatography (elution gradient: MeOH/DCM, 1/20, v/v) to afford compound 42-8 (1.0 g) as a light yellow solid. yield: 48%. MS (ESI) m/z=546.8 $[M+H]^+$.

Step 9: N-(3-(2-(2-(3-Aminopropoxy)ethoxy)ethoxy)propyl)-5-((3aS,4S,6aR)-2-oxohexahydro-1H-thieno[3,4-d]imidazol-4-yl)pentanamide (42-9)

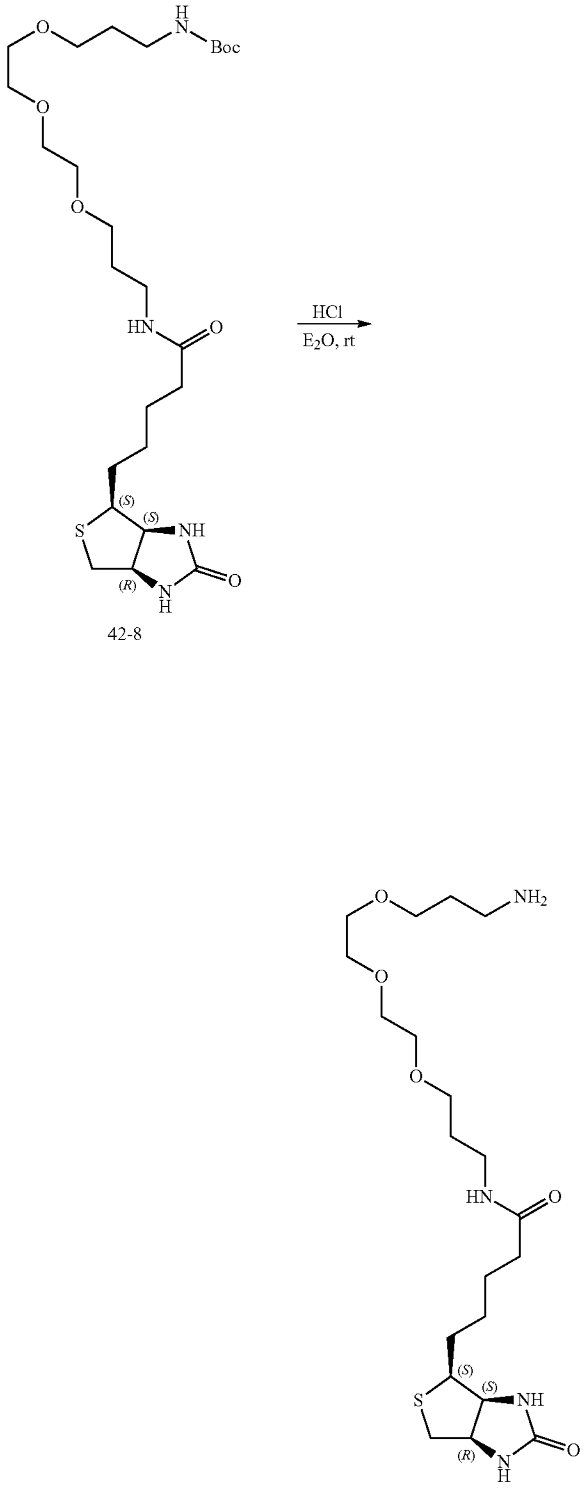

42-8

42-9

Compound 42-9 hydrochloride was prepared from compound 42-8 similarly to Step 5 above. MS (ESI) m/z=446.8 $[M+H]^+$.

Step 10: Methyl 2-methoxy-5-((5,9,25-trioxo-29-((3aS,4S,6aR)-2-oxohexahydro-1H-thieno[3,4-d]imidazol-4-yl)-14,17,20-trioxa-4,10,24-triazanonacosyl)oxy)benzoate (42-10)

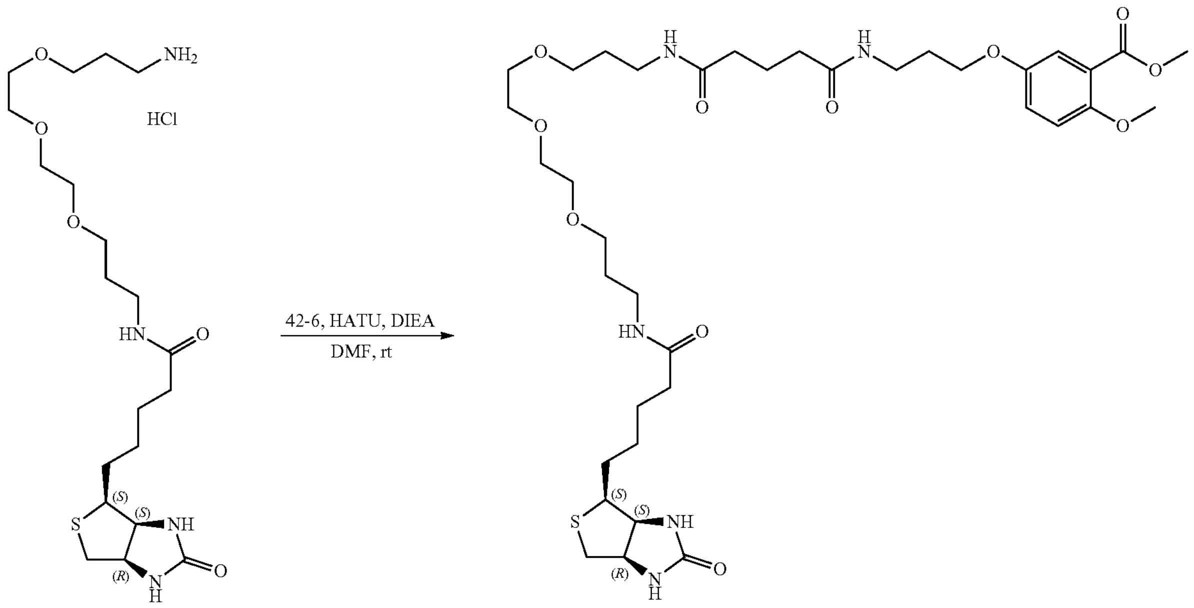

42-9 42-10

To a solution of compound 42-6 (450 mg, 1.27 mmol), DIEA (542 mg, 4.20 mmol) and HATU (760 mg, 2.00 mmol) in DMF (15 mL) was added compound 42-9 (750 mg, 1.68 mmol). The mixture was stirred at room temperature for 16 hours. The mixture was concentrated under vacuum to give the crude product which was purified by silica gel chromatography (elution gradient: DCM/MeOH, 10/1, v/v) to afford compound 42-10 (650 mg) as a brown solid, yield: 65.2%. MS (ESI) m/z=781.6 $[M+H]^+$.

Step 11: 2-Methoxy-5-((5,9,25-trioxo-29-((3aS,4S,6aR)-2-oxohexahydro-1H-thieno[3,4-d]imidazol-4-yl)-14,17,20-trioxa-4,10,24-triazanonacosyl)oxy)benzoic acid (42-11)

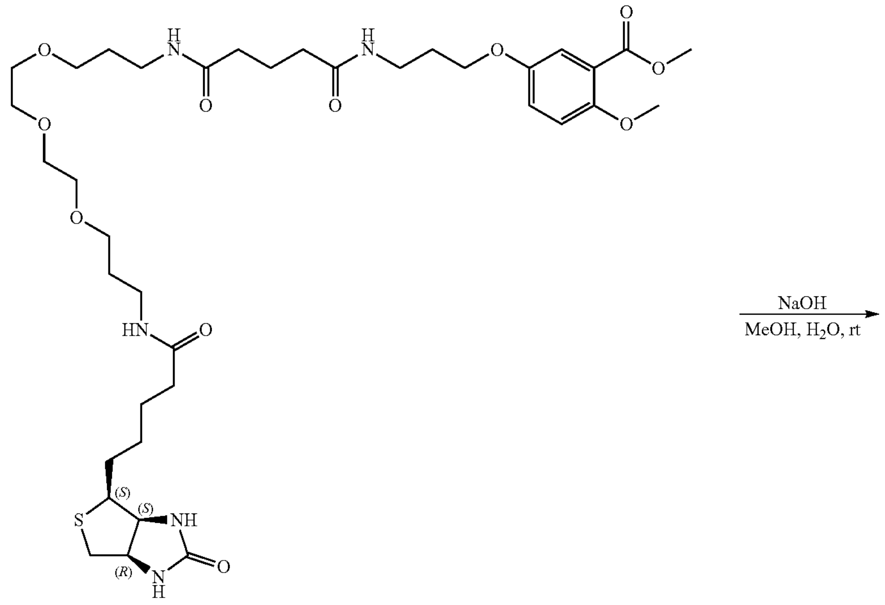

42-10

-continued

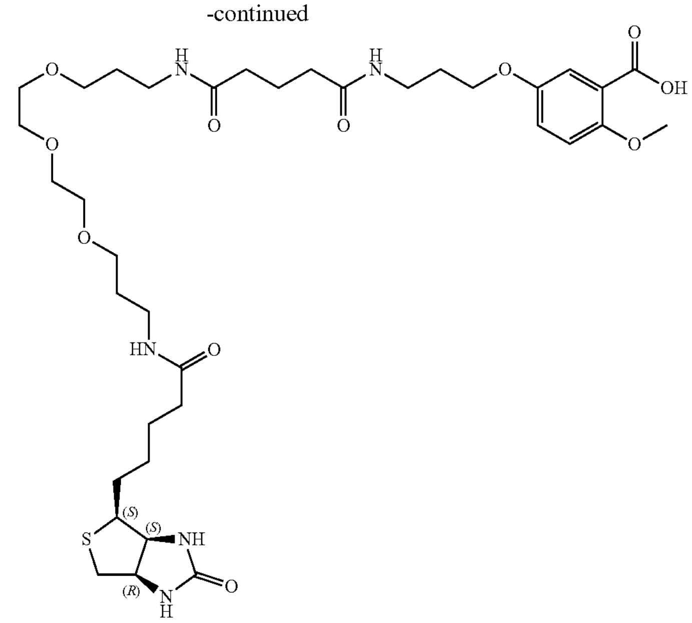

42-11

To a suspension of compound 42-10 (600 mg, 0.77 mmol) in MeOH (30 mL) was added sodium hydroxide (1 N, 25 mL). The mixture was stirred at room temperature for 16 hours. The mixture was concentrated and adjusted to pH=5-6 with hydrochloric acid aqueous solution (2N), then extracted with ethyl acetate (100 mL×3). The organic phase was washed with water (50 mL), brine (50 mL), and concentrated under vacuum to give compound 42-11 (600 mg) as a yellow solid, yield: 93.4%. MS (ESI) m/z=767.5 $[M+H]^+$.

Step 12: tert-Butyl ((S)-4-(5-(3-chlorophenyl)oxazol-2-yl)-4-(2-methoxy-5-((5,9,25-trioxo-29-((3aS,4S,6aR)-2-oxohexahydro-1H-thieno[3,4-d]imidazol-4-yl)-14,17,20-trioxa-4,10,24-triazanonacosyl)oxy)benzamido)butyl)carbamate (42-12)

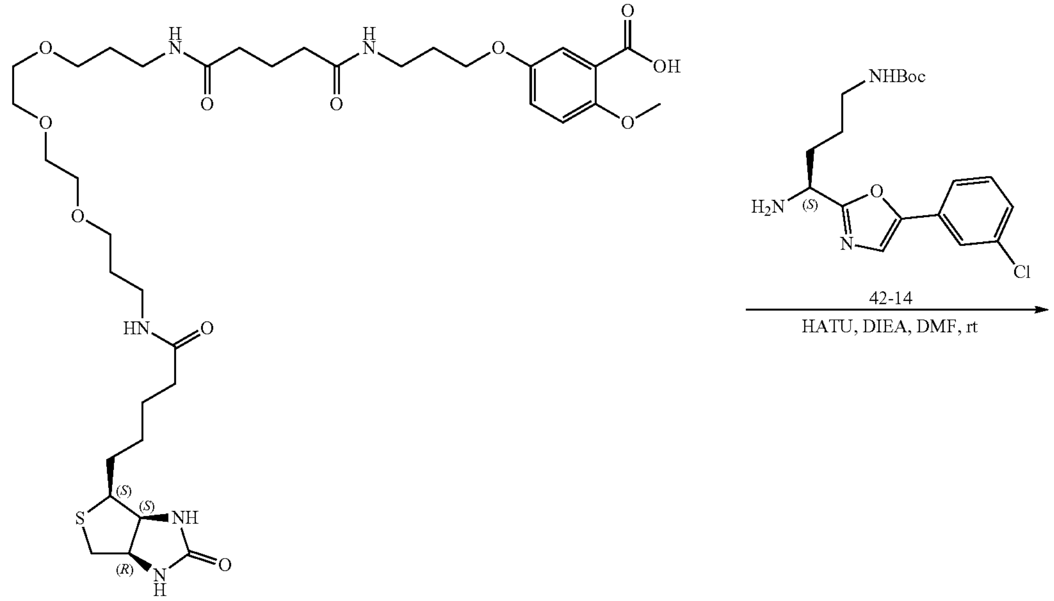

42-11

-continued

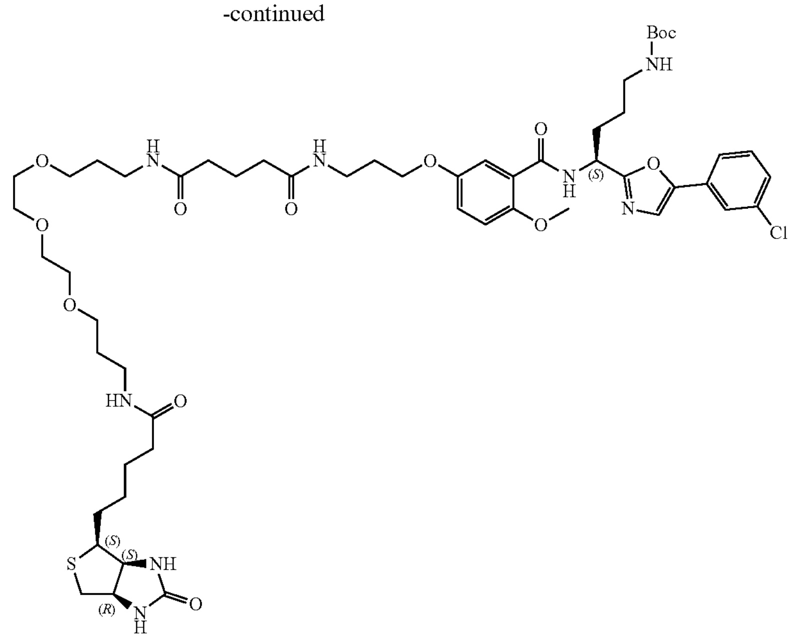

42-13

Compound 42-13 was prepared from compound 42-11 and compound 42-14 (similarly prepared as 10-3 using appropriate starting materials and reagents) similarly to Step 10 above. MS (ESI) m/z=1114.4 $[M+H]^+$.

Step 13: $N^1$-(3-(3-(((S)-1-(5-(3-Chlorophenyl)oxazol-2-yl)-4-(2-fluoroacetimidamido)butyl)carbamoyl)-4-methoxyphenoxy)propyl)-$N^5$-(15-oxo-19-((3aS,4S,6aR)-2-oxohexahydro-1H-thieno[3,4-d]imidazol-4-yl)-4,7,10-trioxa-14-azanonadecyl)glutaramide (EX-42)

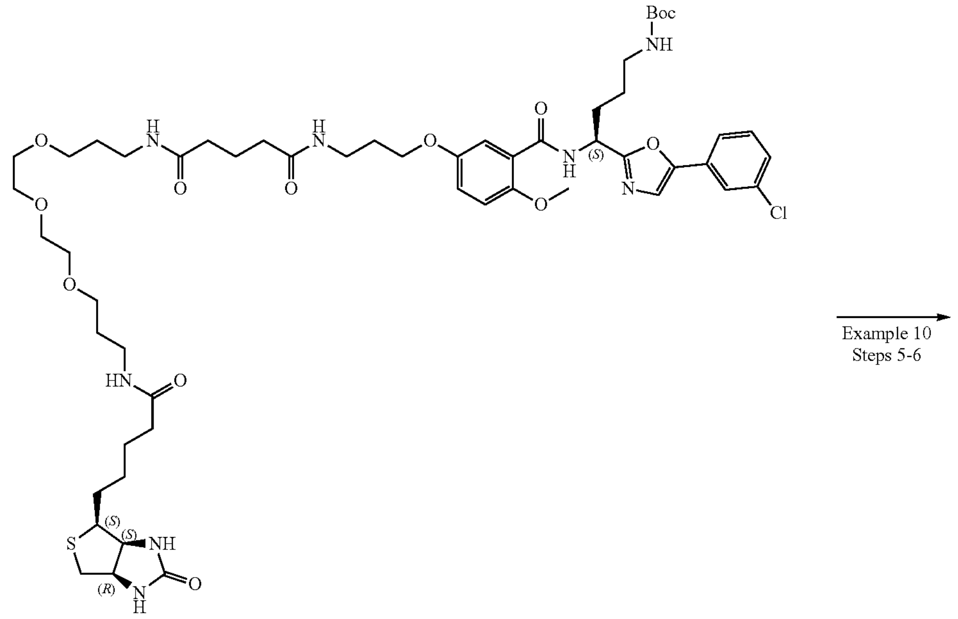

42-12

-continued

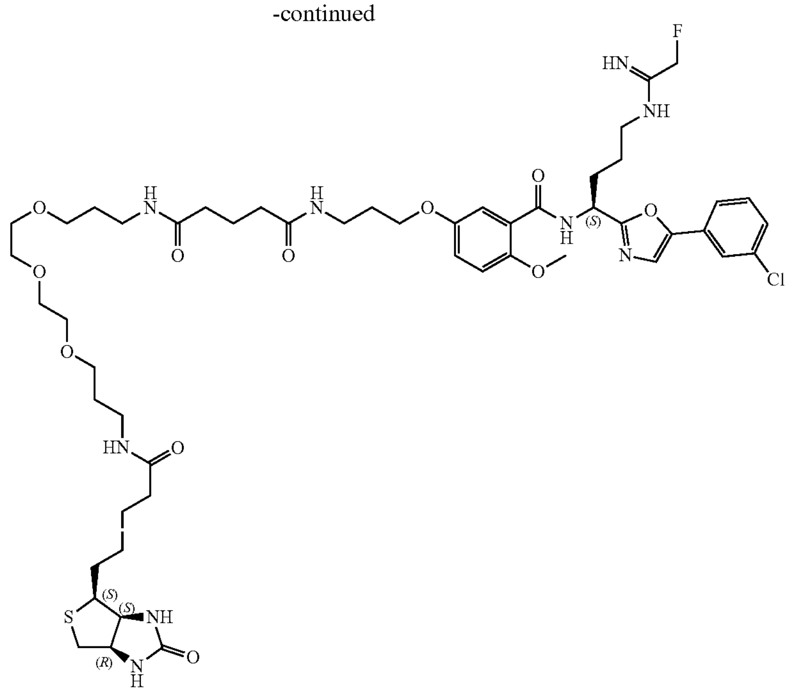

EX-42

$N^1$-(3-(3-(((S)-1-(5-(3-Chlorophenyl)oxazol-2-yl)-4-(2-fluoroacetimidamido)butyl)carbamoyl)-4-methoxyphenoxy)propyl)-$N^5$-(15-oxo-19-((3aS,4S,6aR)-2-oxohexahydro-1H-thieno[3,4-d]imidazol-4-yl)-4,7,10-trioxa-14-azanonadecyl)glutaramide (EX-42) was synthesized from compound 42-12 similarly to Example 10, Steps 5-6, as the hydrochloride salt. $^1H$ NMR (400 MHz, DMSO-$d_6$) δ ppm 10.00 (s, 1H), 9.51 (s, 1H), 9.34 (s, 1H), 8.80 (d, J=7.9 Hz, 1H), 7.97 (s, 1H), 7.84 (s, 2H), 7.79 (s, 2H), 7.70-7.63 (m, 1H), 7.52 (t, J=7.9 Hz, 1H), 7.47-7.40 (m, 1H), 7.28-7.21 (m, 1H), 7.15-7.04 (m, 2H), 5.43-5.21 (m, 3H), 4.37-4.25 (m, 1H), 4.20-4.08 (m, 1H), 4.01-3.91 (m, 2H), 3.86 (s, 3H), 3.60-3.30 (m, 14H), 3.24-2.99 (m, 7H), 2.87-2.77 (m, 1H), 2.65-2.55 (m, 1H), 2.19-1.94 (m, 8H), 1.87-1.75 (m, 2H), 1.74-1.55 (m, 9H), 1.54-1.40 (m, 3H), 1.36-1.20 (m, 2H). MS (ESI) m/z=1073.4 $[M+H]^+$.

Example 43 PAD4 Inhibition Assay

PAD4 was diluted to 75 nM in Assay Buffer (50 mM Tris-HCl, 2 mM $CaCl_2$), 2 mM DTT, 1 mM PMSF in $H_2O$) and added to wells with various concentrations of compound or DMSO vehicle in Eppendorf tubes (final volume was 100 μL). Following a 60 minute preincubation at 37° C., the reaction was initiated by the addition of 10 μL substrate (22 mM BAEE in $H_2O$) at 37° C. The reaction was stopped after 90 minutes by the addition of 25 μL $HClO_4$ (5 M), 125 μL Reagent A (10 g/L diacetyl monoxime and 15 g/L NaCl in $H_2O$) and 250 μL Reagent B (10 mg/mL antipyrine and 1.0 mg/mL $FeCl_3$ diluted in detection buffer containing 25% $H_2SO_4$, 25% $H_3PO_4$ and 50% $H_2O$) in sequence. This assay was quenched in an ice-bath for 5 minutes after boiling for 30 minutes. The citrulline formation was measured in fluorescence (κ=465 nm) on microplate reader and the $IC_{50}$ was calculated by GraphPad Prism.

The resulting $IC_{50}$ values are provided in Table 1 below.

TABLE 1

$IC_{50}$ values.

| EXAMPLE | $IC_{50}{}^a$ |
|---|---|
| EX-1 | ** |
| EX-2 | *** |
| EX-3 | ** |
| EX-4 | ** |
| EX-5 | ** |
| EX-6 | ** |
| EX-7 | *** |
| EX-8 | *** |
| EX-9 | *** |
| EX-10 | * |
| EX-11 | ** |
| EX-12 | *** |
| EX-13 | ** |
| EX-14 | ** |
| EX-15 | *** |
| EX-16 | ** |
| EX-17 | *** |
| EX-18 | ** |
| EX-19 | ** |
| EX-20 | ** |
| EX-21 | * |
| EX-22 | ** |
| EX-23 | ** |
| EX-24 | * |
| EX-25 | ** |
| EX-26 | ** |
| EX-27 | *** |
| EX-28 | ** |
| EX-29 | *** |
| EX-30 | *** |

TABLE 1-continued

| $IC_{50}$ values. | |
|---|---|
| EXAMPLE | $IC_{50}$[a] |
| EX-31 | ** |
| EX-32 | ** |
| EX-33 | ** |
| EX-35 | ** |
| EX-36 | * |
| EX-37 | *** |
| EX-38 | ** |
| EX-39 | *** |
| EX-40 | *** |
| EX-41 | ** |
| EX-42 | *** |

[a]* <200 nM;  200-500 nM; * >500 nM.

What is claimed is:

1. A compound of formula (I):

(I)

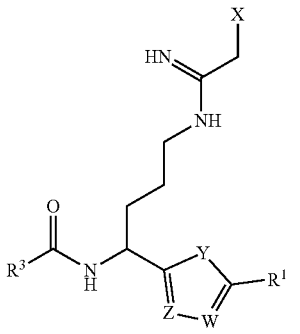

wherein,

X is halogen;

W is C—$R^2$;

Y is O;

Z is N;

$R^3$ is selected from ($C_6$-$C_{10}$) aryl, and ($C_1$-$C_9$) heteroaryl;

$R^2$ is independently selected from H, ($C_1$-$C_8$) alkyl, ($C_3$-$C_{10}$) cycloalkyl, ($C_6$-$C_{10}$) aryl, and ($C_1$-$C_9$) heteroaryl;

$R^1$ is independently selected from ($C_1$-$C_8$) alkyl, ($C_3$-$C_{10}$) cycloalkyl, ($C_6$-$C_{10}$) aryl, and ($C_1$-$C_9$) heteroaryl, provided that $R^1$ and $R^2$ are not bonded to one another by one or more chemical bonds;

when $R^1$ is ($C_3$-$C_{10}$) cycloalkyl or ($C_6$-$C_{10}$) aryl, said $R^1$ is unsubstituted or substituted with one or more substituents $R^4$, said $R^4$ is independently selected from H, halogen, ($C_1$-$C_8$) alkyl, ($C_1$-$C_8$) haloalkyl, ($C_1$-$C_8$) alkoxy, ($C_1$-$C_8$) alkylamino,

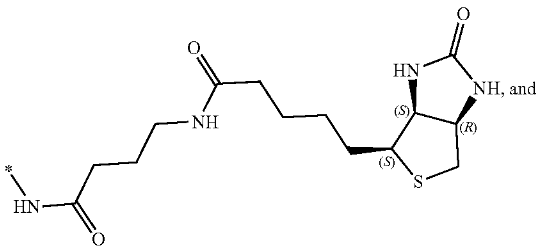

and

-continued

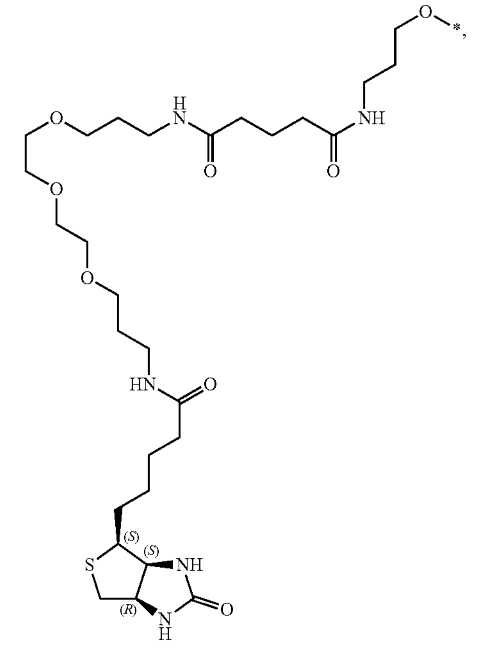

, wherein, the asterisk "*" in the structure formulas indicates the available radical ends to be connected;

when $R^3$ is ($C_6$-$C_{10}$) aryl or ($C_1$-$C_9$) heteroaryl, said $R^3$ is unsubstituted or substituted with one or more substituents $R^5$, said $R^5$ is independently selected from H, halogen, ($C_1$-$C_8$) alkyl, ($C_2$-$C_8$) alkenyl, ($C_2$-$C_8$) alkynyl, ($C_1$-$C_8$) alkoxy, ($C_1$-$C_8$) haloalkyl, ($C_1$-$C_8$) alkylamino, ($C_2$-$C_9$) heterocycloalkyl, ($C_6$-$C_{10}$) aryl, ($C_1$-$C_9$) heteroaryl,

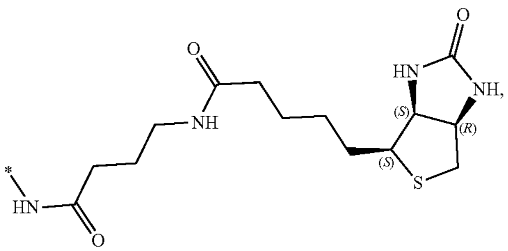

and

-continued

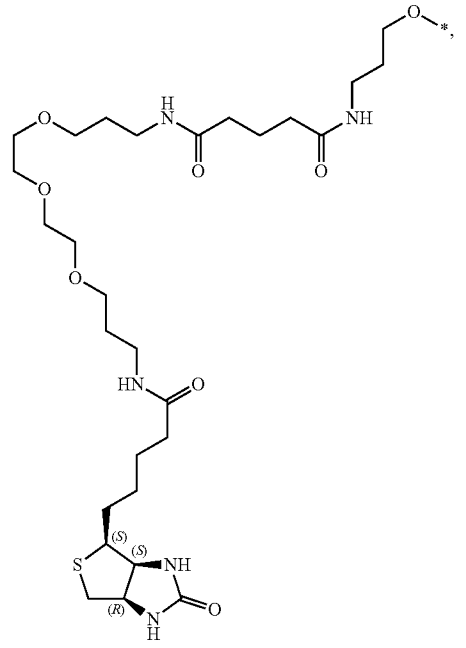

wherein, the asterisk "*" in the structure formulas indicates the available radical ends to be connected;

when $R^5$ is ($C_2$-$C_9$) heterocycloalkyl, ($C_6$-$C_{10}$) aryl or ($C_1$-$C_9$) heteroaryl, said $R^5$ is unsubstituted or substituted with one or more substituents $R^6$, said $R^6$ is independently selected from H, halogen, ($C_1$-$C_8$) alkyl, ($C_1$-$C_8$) alkoxy, ($C_1$-$C_8$) hydroxyalkyl;

or a pharmaceutically acceptable salt or solvate thereof.

2. The compound according to claim 1, wherein said $R^1$ is a phenyl.

3. The compound according to claim 1, wherein said $R^1$ is substituted with one or more substituents $R^4$, said $R^4$ is independently selected from H, halogen, ($C_1$-$C_8$) alkyl, ($C_1$-$C_8$) haloalkyl, ($C_1$-$C_8$) alkoxy, ($C_1$-$C_8$) alkylamino,

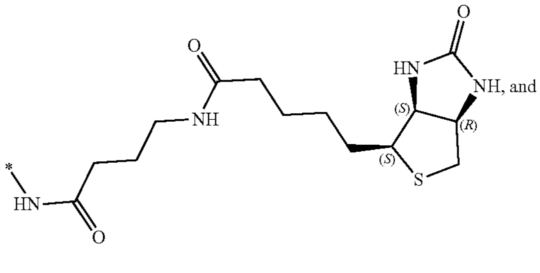

and

-continued

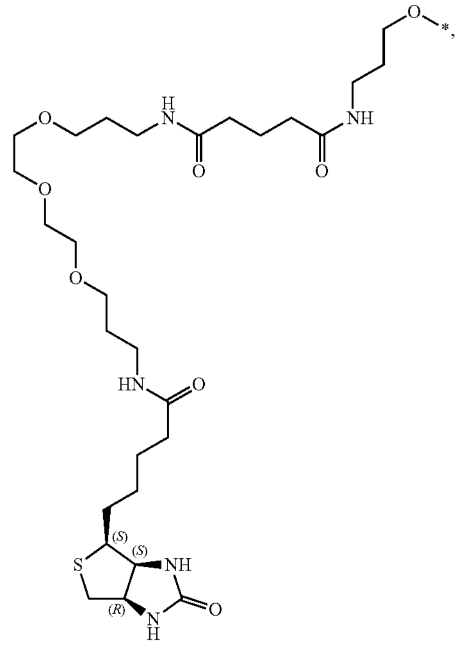

wherein, the asterisk "*" in the structure formulas indicates the available radical ends to be connected.

4. The compound according to claim 1, wherein said $R^3$ is a ($C_6$-$C_{10}$) aryl, and said $R^3$ is substituted with one or more substituents $R^5$, said $R^5$ is independently selected from H, halogen, ($C_1$-$C_8$) alkyl, ($C_2$-$C_8$) alkenyl, ($C_2$-$C_8$) alkynyl, ($C_1$-$C_8$) alkoxy, ($C_1$-$C_8$) haloalkyl, ($C_1$-$C_8$) alkylamino, ($C_2$-$C_9$) heterocycloalkyl, ($C_6$-$C_{10}$) aryl, ($C_1$-$C_9$) heteroaryl,

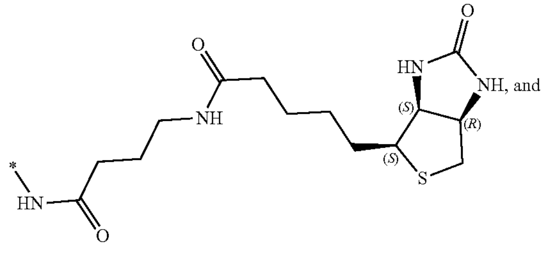

and

-continued

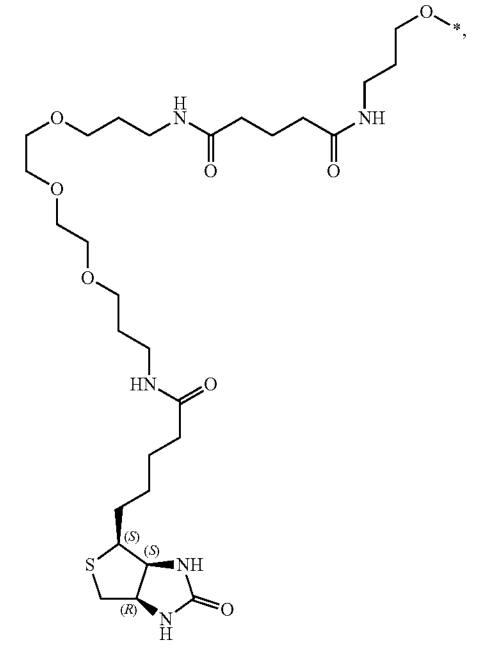

wherein, the asterisk "*" in the structure formulas indicates the available radical ends to be connected.

5. The compound according to claim 1, wherein said $R^3$ is a phenyl or naphthyl.

6. The compound according to claim 1, wherein said $R^3$ is substituted with one or more substituents $R^5$, said $R^5$ is independently selected from H, halogen, ($C_1$-$C_8$) alkyl, ($C_2$-$C_8$) alkenyl, ($C_2$-$C_8$) alkynyl, ($C_1$-$C_8$) alkoxy, ($C_1$-$C_5$) haloalkyl, ($C_1$-$C_8$) alkylamino, ($C_2$-$C_9$) heterocycloalkyl, ($C_6$-$C_{10}$) aryl, ($C_1$-$C_9$) heteroaryl,

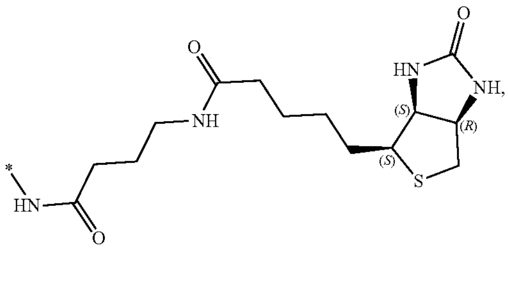

and

-continued

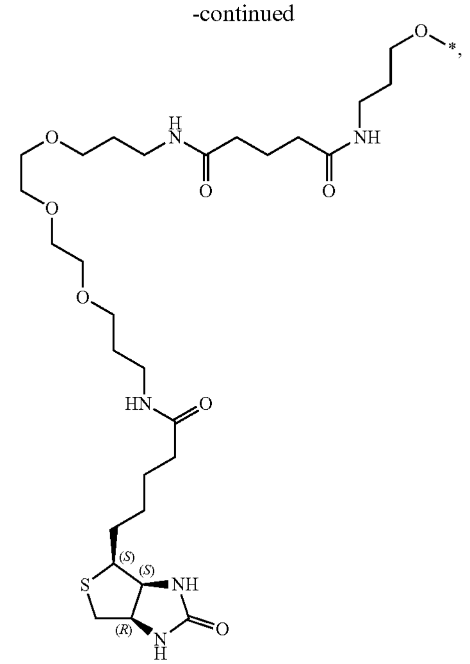

wherein, the asterisk "*" in the structure formulas indicates the available radical ends to be connected.

7. The compound according to claim 1, wherein said X is $C_1$ or F.

8. A compound of formula (II):

(II)

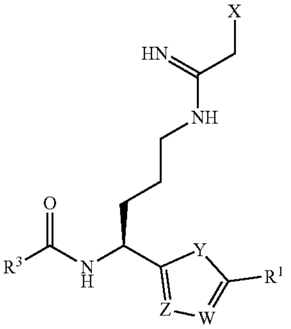

wherein,

X is halogen;

W is C—$R^2$;

Y is O;

Z is N;

$R^3$ is selected from ($C_6$-$C_{10}$) aryl, and ($C_1$-$C_9$) heteroaryl;

$R^2$ is independently selected from H, ($C_1$-$C_8$) alkyl, ($C_3$-$C_{10}$) cycloalkyl, ($C_6$-$C_{10}$) aryl, and ($C_1$-$C_9$) heteroaryl;

$R^1$ is independently selected from ($C_1$-$C_8$) alkyl, ($C_3$-$C_{10}$) cycloalkyl, ($C_6$-$C_{10}$) aryl, and ($C_1$-$C_9$) heteroaryl, provided that $R^1$ and $R^2$ are not bonded to one another by one or more chemical bonds;

when $R^1$ is ($C_3$-$C_{10}$) cycloalkyl or ($C_6$-$C_{10}$) aryl, said $R^1$ is unsubstituted or substituted with one or more substituents $R^4$, said $R^4$ is independently selected from H, halogen, ($C_1$-$C_8$) alkyl, ($C_1$-$C_8$) haloalkyl, ($C_1$-$C_8$) alkoxy, ($C_1$-$C_8$) alkylamino,

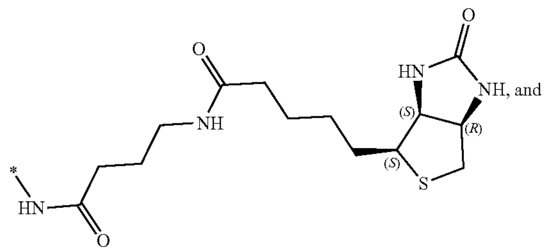
and

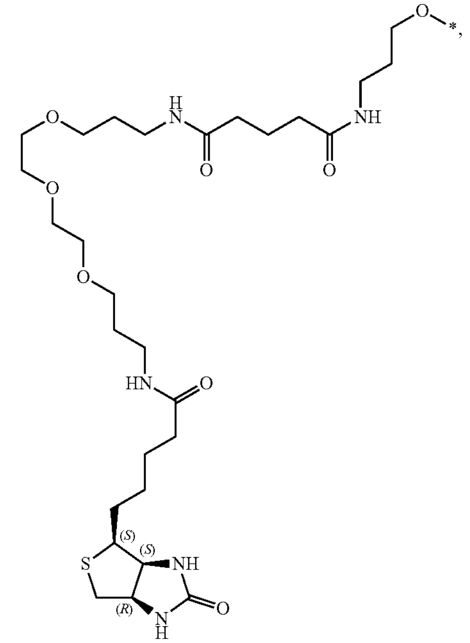
, wherein, the asterisk "*" in the structure formulas indicates the available radical ends to be connected;

when $R^3$ is ($C_6$-$C_{10}$) aryl or ($C_1$-$C_9$) heteroaryl, said $R^3$ is unsubstituted or substituted with one or more substituents $R^5$, said $R^5$ is independently selected from H, halogen, ($C_1$-$C_8$) alkyl, ($C_2$-$C_8$) alkenyl, ($C_2$-$C_8$) alkynyl, ($C_1$-$C_8$) alkoxy, ($C_1$-$C_8$) haloalkyl, ($C_1$-$C_8$) alkylamino, ($C_2$-$C_9$) heterocycloalkyl, ($C_6$-$C_{10}$) aryl, ($C_1$-$C_9$) heteroaryl

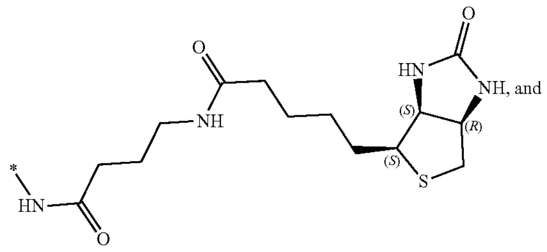
and

-continued

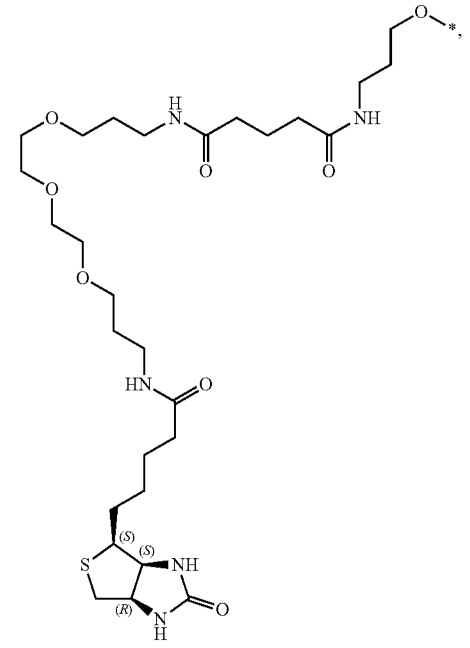
, wherein, the asterisk in the structure formulas indicates the available radical ends to be connected;

when $R^5$ is ($C_2$-$C_9$) heterocycloalkyl, ($C_6$-$C_{10}$) aryl or ($C_1$-$C_9$) heteroaryl, said $R^5$ is unsubstituted or substituted with one or more substituents $R^6$, said $R^6$ is independently selected from H, halogen, ($C_1$-$C_8$) alkyl, ($C_1$-$C_8$) alkoxy, ($C_1$-$C_8$) hydroxyalkyl;

or a pharmaceutically acceptable salt or solvate thereof.

9. The compound according to claim 8, wherein said $R^1$ is a phenyl.

10. The compound according to claim 8, wherein said $R^1$ is substituted with one or more substituents $R^4$, said $R^4$ is independently selected from H, halogen, ($C_1$-$C_8$) alkyl, ($C_1$-$C_8$) haloalkyl, ($C_1$-$C_8$) alkoxy, ($C_1$-$C_8$) alkylamino,

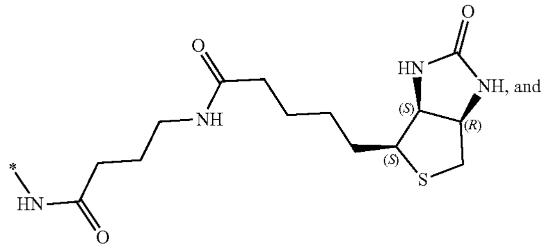
and

-continued

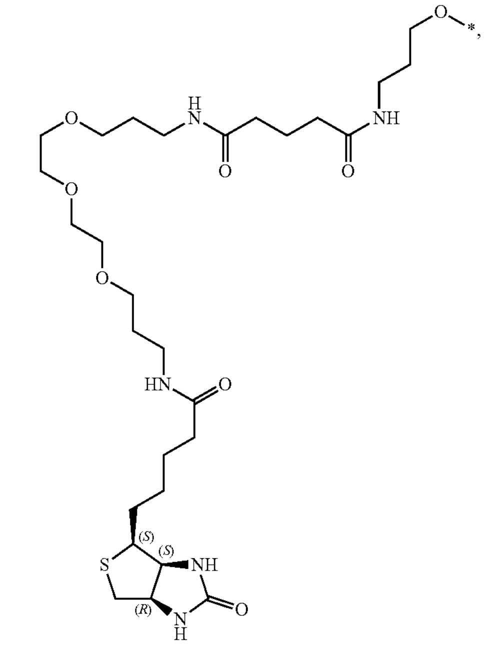

wherein, the asterisk "*" in the structure formulas indicates the available radical ends to be connected.

11. The compound according to claim 8, wherein said $R^3$ is a ($C_6$-$C_{10}$) aryl, and said $R^3$ is substituted with one or more substituents $R^5$, said $R^5$ is independently selected from H, halogen, ($C_1$-$C_8$) alkyl, ($C_2$-$C_8$) alkenyl, ($C_2$-$C_8$) alkynyl, ($C_1$-$C_8$) alkoxy, ($C_1$-$C_8$) haloalkyl, ($C_1$-$C_8$) alkylamino, ($C_2$-$C_9$) heterocycloalkyl, ($C_6$-$C_{10}$) aryl, ($C_1$-$C_9$) heteroaryl,

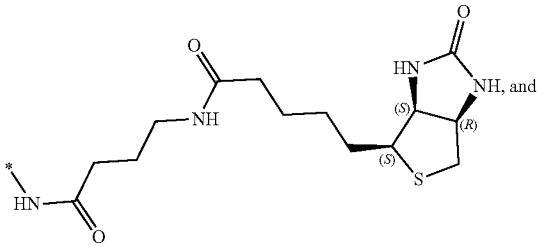

and

-continued

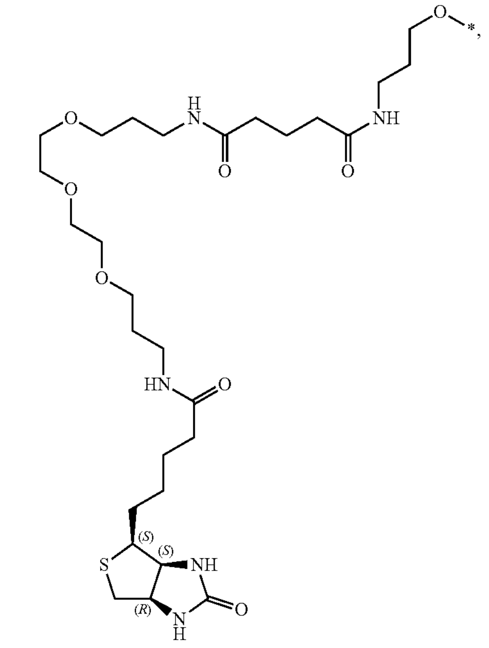

wherein, the asterisk "*" in the structure formulas indicates the available radical ends to be connected.

12. The compound according to claim 8, wherein said $R^3$ is a phenyl or naphthyl.

13. The compound according to claim 8, wherein said $R^3$ is substituted with one or more substituents $R^5$, said $R^5$ is independently selected from H, halogen, ($C_1$-$C_8$) alkyl, ($C_2$-$C_8$) alkenyl, ($C_2$-$C_8$) alkynyl, ($C_1$-$C_8$) alkoxy, ($C_1$-$C_8$) haloalkyl, ($C_1$-$C_8$) alkylamino, ($C_2$-$C_9$) heterocycloalkyl, ($C_6$-$C_{10}$) aryl, ($C_1$-$C_9$) heteroaryl,

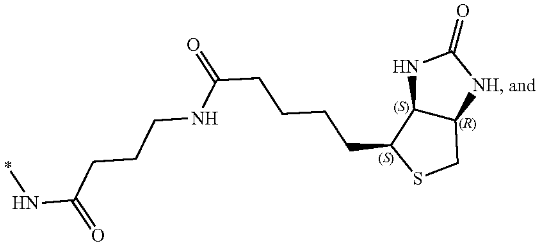

and

-continued
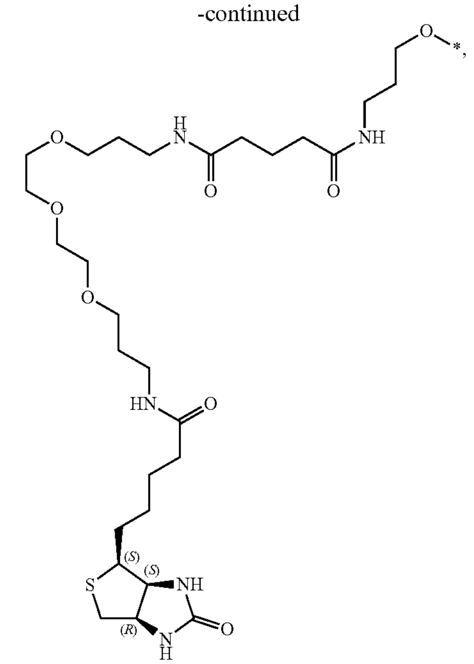
wherein, the asterisk "*" in the structure formulas indicates the available radical ends to be connected.
14. The compound according to claim 8, wherein said X is $C_1$ or F.
15. The compound according to claim 1, wherein said compound is selected from the group consisting of:
EX-1
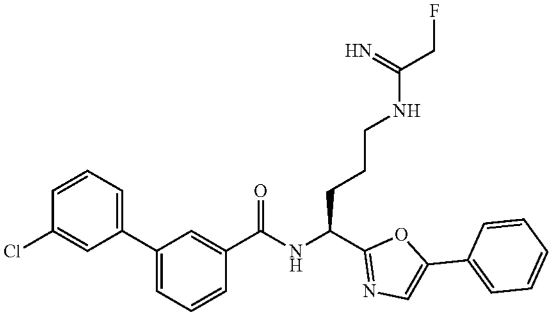
,
EX-2
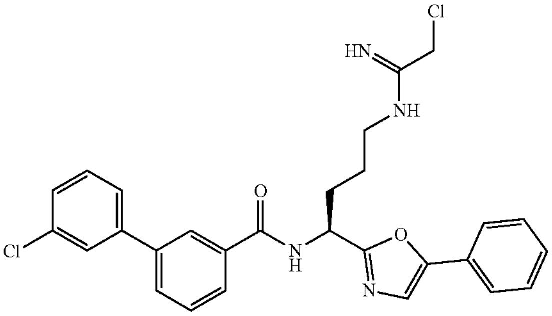
,
EX-3
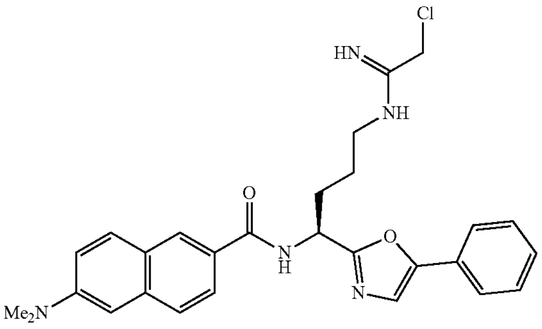
,
EX-4
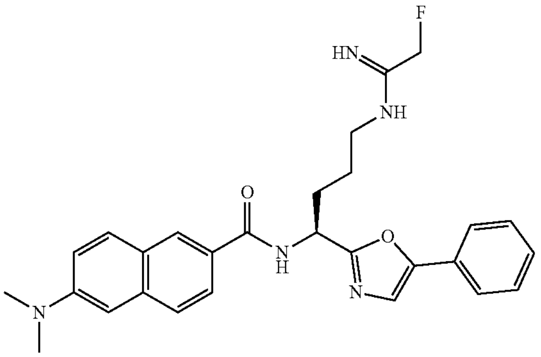
, -continued
EX-5
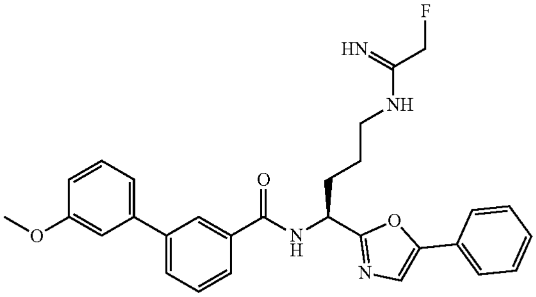
,
EX-6
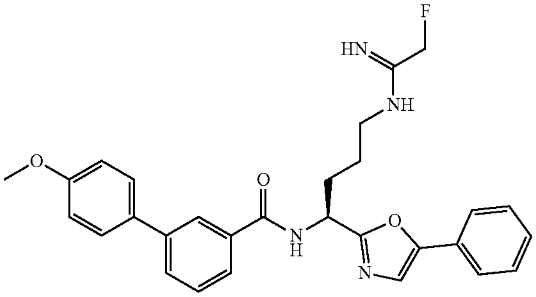
,
EX-7
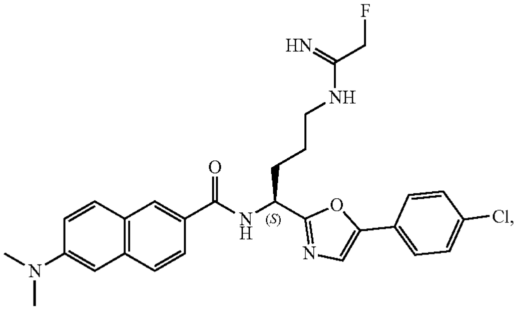
Cl,
EX-8
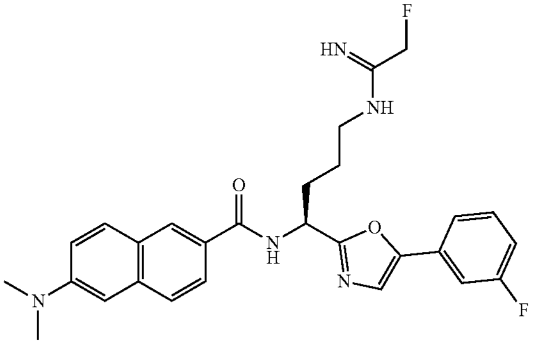
,
EX-9
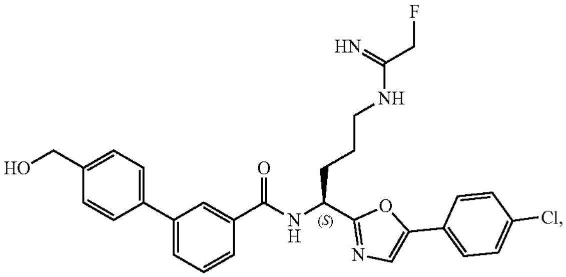
Cl,
EX-10
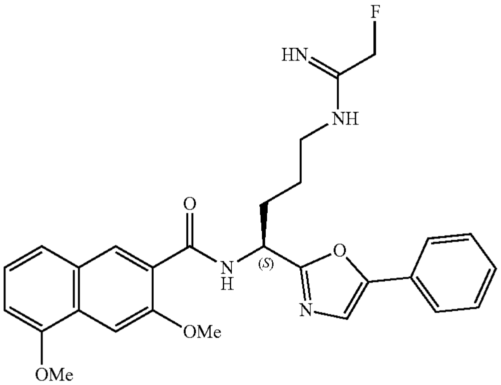
,
EX-11
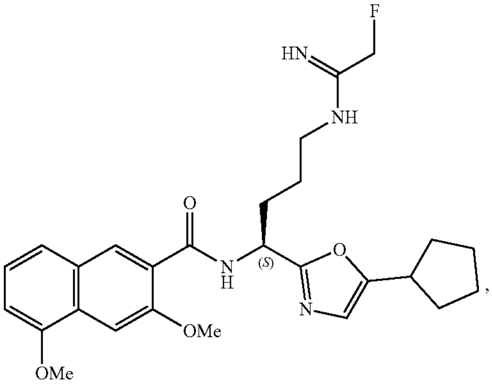
,
EX-12
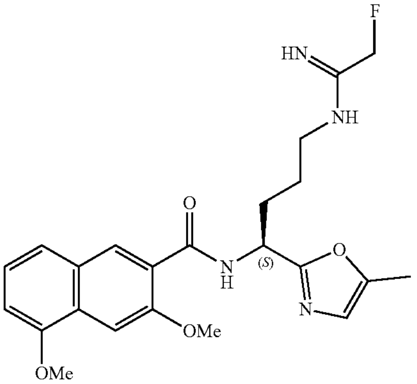
, -continued
EX-13
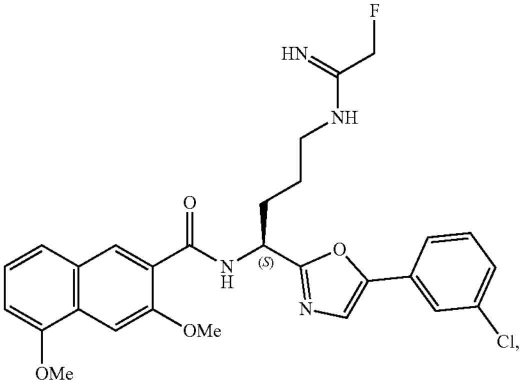
EX-14
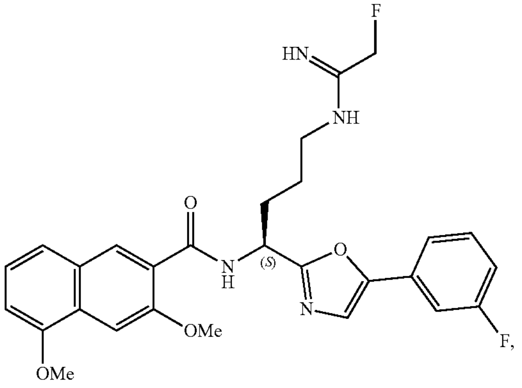
EX-15
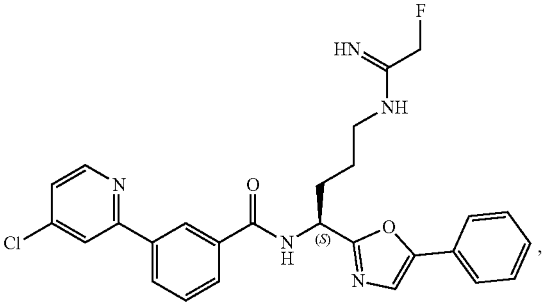
EX-16
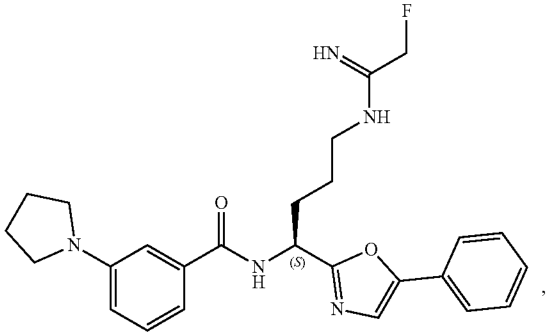
EX-17
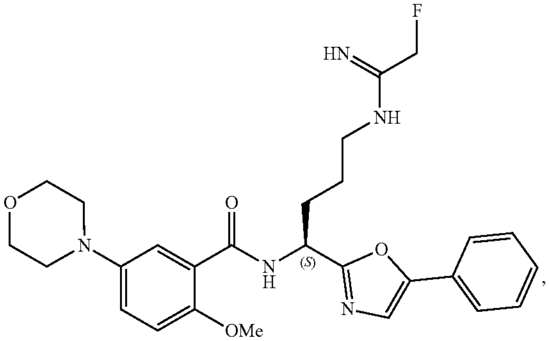
EX-18
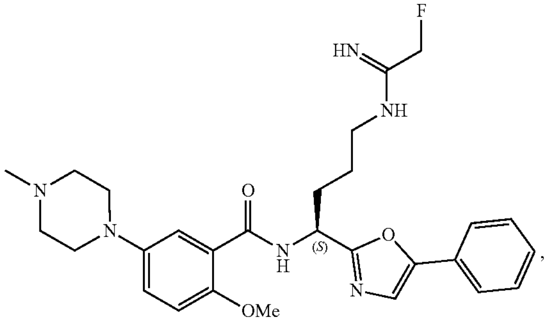
EX-19
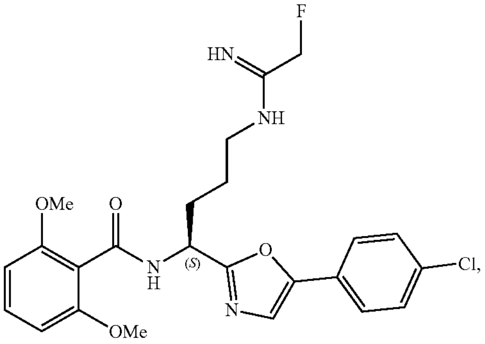
EX-20
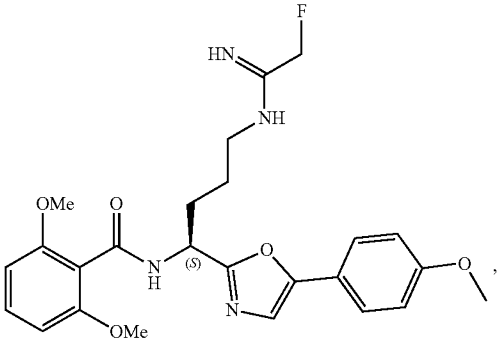

-continued
EX-21
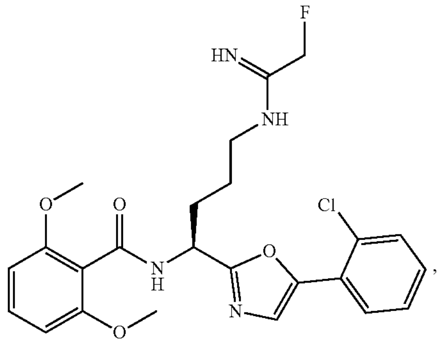
EX-22
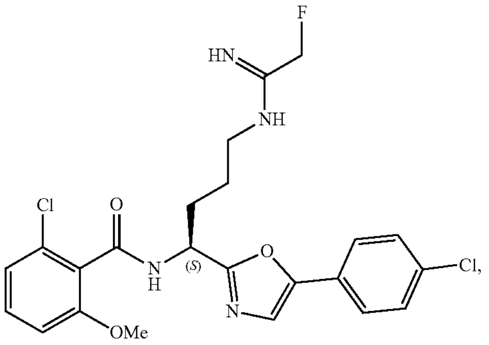
EX-23
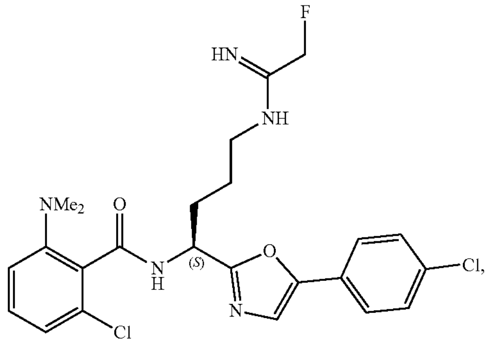
EX-24
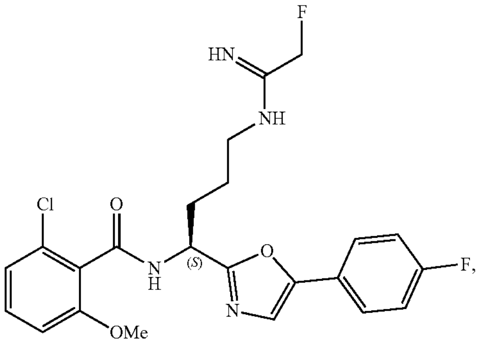
EX-25
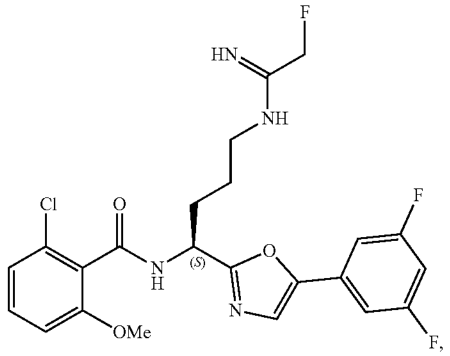
EX-26
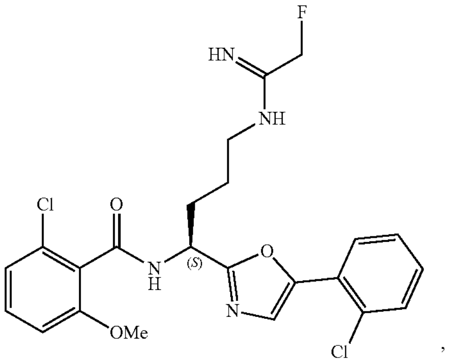
EX-27
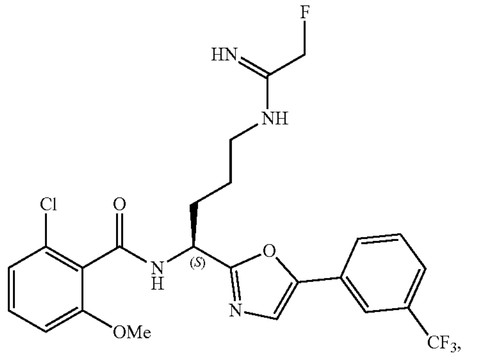
EX-28
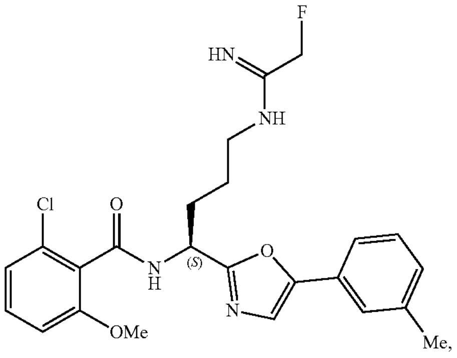

-continued
EX-29
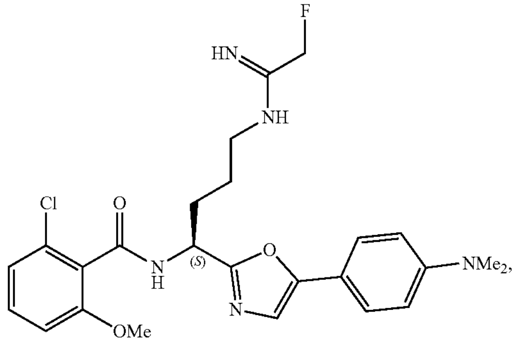
EX-30
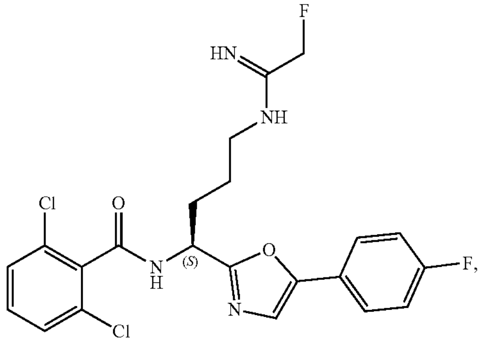
EX-31
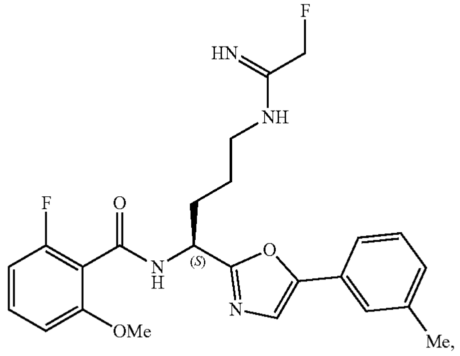
EX-32
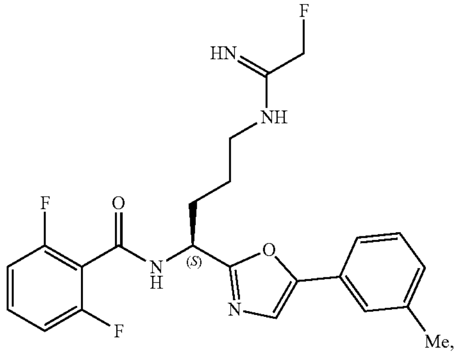
EX-33
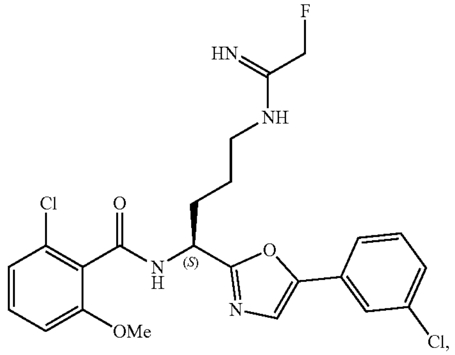
EX-34
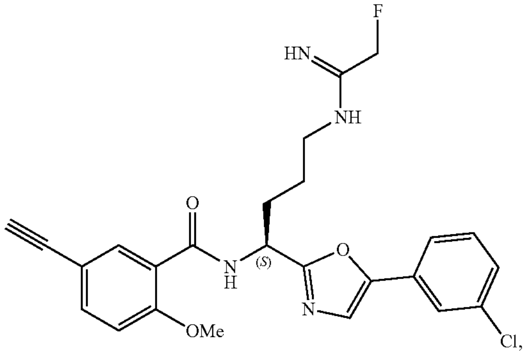
EX-35
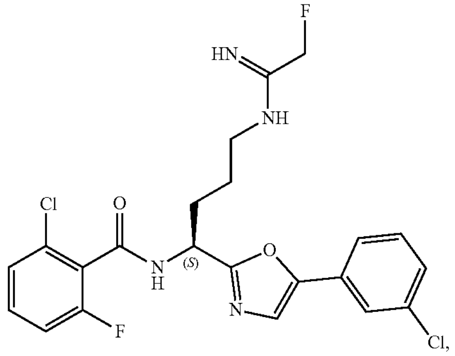
EX-36
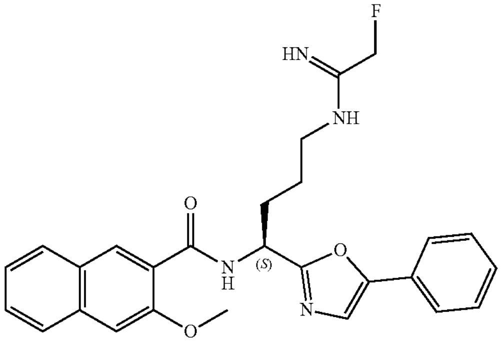
, -continued
EX-37
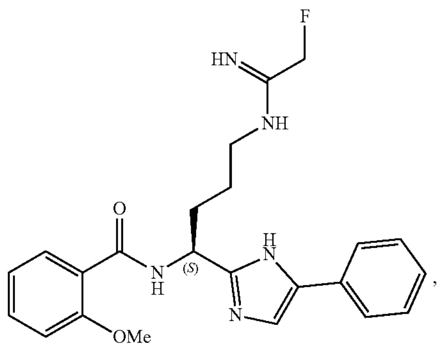
,
EX-38
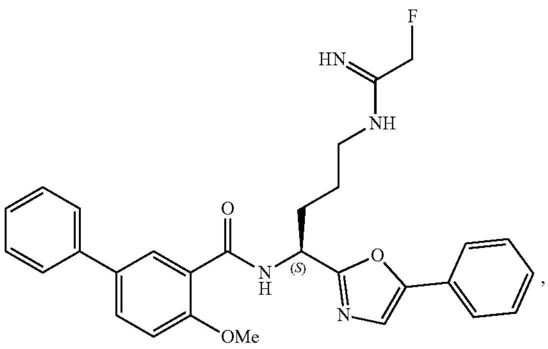
,
EX-39
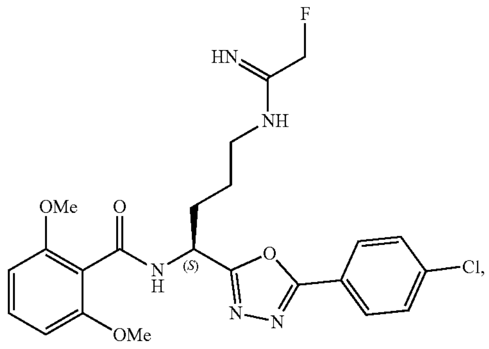
EX-40
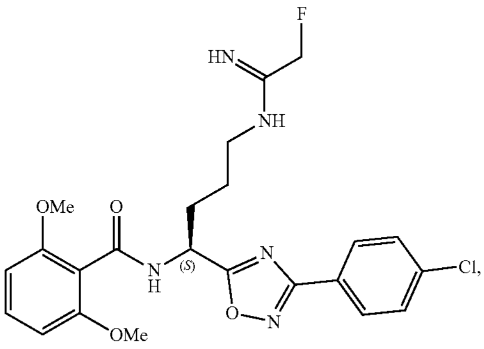
EX-41
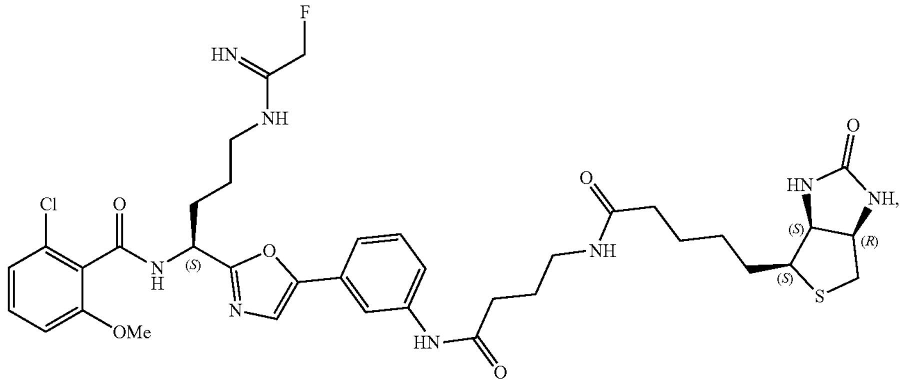
and -continued

EX-42

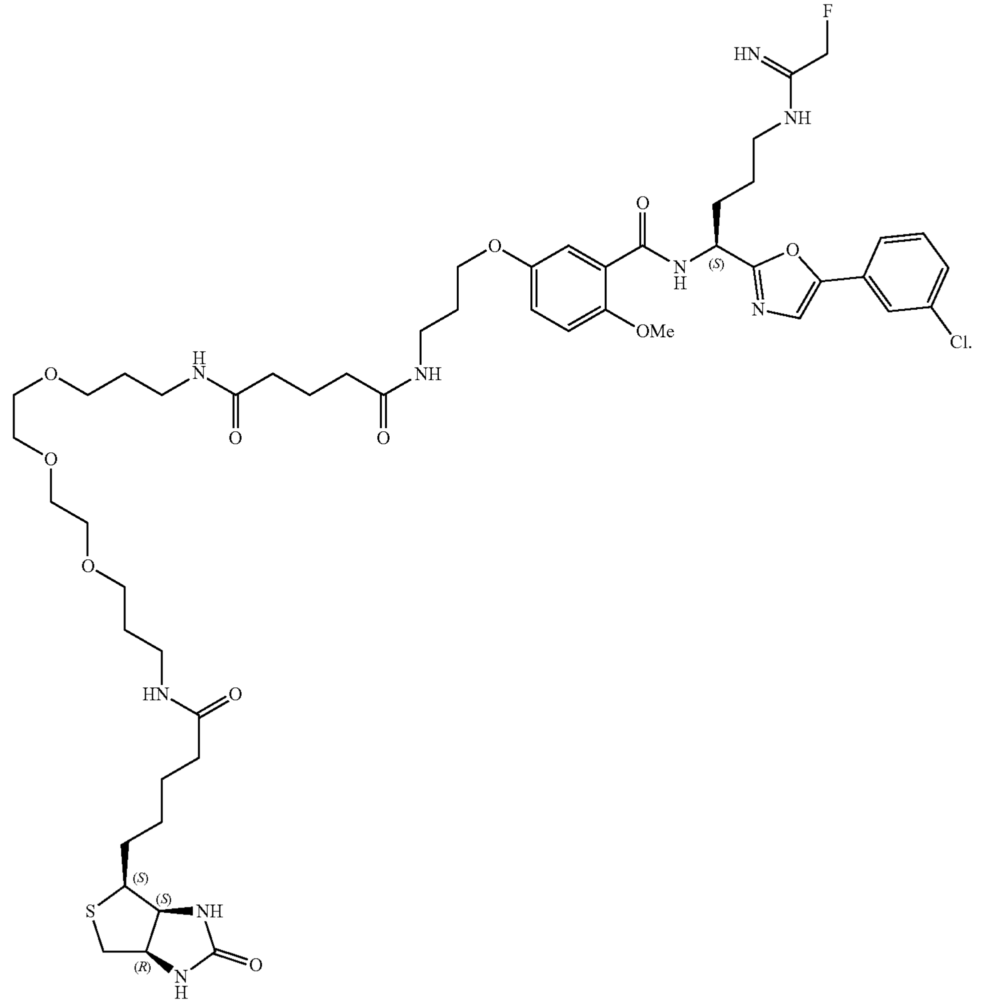

16. A composition comprising a compound according to claim 1, or a pharmaceutically acceptable salt or solvate thereof.

17. The composition according to claim 16, wherein said salt is the hydrochloride salt.

18. The composition according to claim 16, further comprising a pharmaceutically acceptable carrier.

19. The composition according to claim 16, wherein said composition comprises a therapeutically effective amount of said compound, or a pharmaceutically acceptable salt or solvate thereof.

20. The composition according to claim 16, wherein said composition is suitable for parenteral, transdermal, mucosal, nasal, buccal, sublingual, or oral administration to a patient.

21. A method of treating a disease or disorder in oncology or immunology associated with PAD, the method comprising administering to a patient a therapeutically effective amount of the compound according to claim 1, or a pharmaceutically acceptable salt, prodrug, or metabolite thereof.

22. The method according to claim 21, said disease or disorder comprises cancer and/or metastatic cancer.

23. The method according to claim 21, said disease or disorder comprises lung cancer, liver cancer, blood cancer, esophageal cancer, breast cancer, colon cancer, rheumatoid arthritis, multiple sclerosis, vasculitis, systemic lupus erythematosus, ulcerative colitis, cystic fibrosis, asthma, cutaneous lupus erythematosis, psoriasis, ischemia-reperfusion injury, and/or immune responses induced during transplant rejection.

24. The method according to claim 21, further comprising administering to the subject one or more additional therapeutics including radiotherapy, chemotherapy, cell therapy, or immune checkpoint inhibitor.

25. The method according to claim 21, further comprising administering to the subject one or more additional therapeutics including PD-1 inhibitor, PD-L1 inhibitor, CTLA-4 inhibitor, B7-H3 inhibitor, LAG3 inhibitor, TIM3 inhibitor, TIGIT inhibitor, anti-PDL1/TGFβ bispecific antibody, anti-EpCAM-CD3 bispecific antibody, and/or CD40 agonists.

26. The method according to claim 21, wherein said compound attenuates activity of a protein arginine deiminase (PAD).

27. The method according to claim 26, wherein said PAD is PAD2 or PAD4.

28. The method according to claim 26, wherein said PAD is PAD4.

29. The method according to claim 26, wherein said activity is measured by inhibition of formation of neutrophil extracellular traps (NETs).

* * * * *